(12) United States Patent
Pandit et al.

(10) Patent No.: US 10,851,428 B2
(45) Date of Patent: Dec. 1, 2020

(54) REAGENTS AND METHODS FOR ANALYSIS OF HIV

(71) Applicant: Siemens Healthcare Diagnostics Inc., Tarrytown, NY (US)

(72) Inventors: Sunil Pandit, Danville, CA (US); Arejas Uzgiris, Berkeley, CA (US); Lance Palmer, Collierville, TN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 344 days.

(21) Appl. No.: 15/757,448

(22) PCT Filed: Sep. 16, 2016

(86) PCT No.: PCT/US2016/052184
§ 371 (c)(1),
(2) Date: Mar. 5, 2018

(87) PCT Pub. No.: WO2017/049118
PCT Pub. Date: Mar. 23, 2017

(65) Prior Publication Data
US 2018/0245166 A1 Aug. 30, 2018

Related U.S. Application Data

(60) Provisional application No. 62/220,508, filed on Sep. 18, 2015.

(51) Int. Cl.
*C12P 19/34* (2006.01)
*C12Q 1/70* (2006.01)
*C07H 21/02* (2006.01)

(52) U.S. Cl.
CPC ............ *C12Q 1/703* (2013.01); *C07H 21/02* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS 6,300,056 B1 * 10/2001 Irvine .................. C12Q 1/682
435/5
2003/0158131 A1 8/2003 Aldovini 2008/0003565 A1 * 1/2008 Baptista .................. C12Q 1/70
435/5
2008/0020398 A1 1/2008 Linnen et al.
2009/0226886 A1 9/2009 Mitsuhashi
2011/0281258 A1 11/2011 Brennan et al.
2016/0244817 A1 * 8/2016 Macleod ................ C12Q 1/703

FOREIGN PATENT DOCUMENTS

| EP | 1285971 | 2/2003 |
|---|---|---|
| WO | 2012130681 | 10/2012 |
| WO | 2015048730 | 4/2015 |

OTHER PUBLICATIONS

Database accession # AQY08502 Jul. 10, 2008. (Year: 2008).*
Rychlik et al., Nucleic Acids Research 17(21), 8543-8551 (1989) (Year: 1989).*
Van Laethem K et al: "A genotypic assay for the amplification and sequencing of integrase from diverse HIV-1 group M subtypes", 1-21 Journal of Virological Methods, Elsevier by, NL, vol. 153, No. 2, Nov. 1, 2008, pp. 176-181.
Pandit S et al.,; "Development of Genotyping Assay for HIV-1 Integrase Compatible With Globally Avalibale IVD Platforms", Antiviral Therapy, vo I . 13, No. 4, Jan. 1, 2008, pp. A126-AI26.
International Search Report for PCT/US2016/052184 dated Mar. 16, 2017.
Salminen, Mo et al., Construction and Biological Characterization of Infectious Molecular 1, 5/1 Clones of HIV-1 Subtypes Band E (CRF01_AE) Generated by the Polymerase Chain Reaction, Virology. 278:1; pp. 103-110; (2000).

* cited by examiner

*Primary Examiner* — Kenneth R Horlick

(57) ABSTRACT

The present invention is based in part on the present inventors' appreciation that certain sequences within an HIV genome are more likely to successfully detect HIV across a breadth of HIV variants. The ability to detect and/or quantify the presence and/or load of HIV in a subject is important to, among other things, the diagnosis and treatment of infected individuals. The present invention is based, in part, on the discovery of oligonucleotide reagents that detectably amplify sequences from a greater breadth of HIV samples than certain prior reagents and/or that generate amplicons from HIV genomes from which certain prior reagents would not have generated amplicons. Oligonucleotide reagents as described herein provide unexpected benefits in the detection and/or quantification of the presence and/or load of HIV in a subject, and thereby in the diagnosis and treatment of HIV.

28 Claims, 7 Drawing Sheets

Specification includes a Sequence Listing.

Figure 2

| Order | Type | Sequence | # Genomes | # Groups | |
|---|---|---|---|---|---|
| 5 | for | TTTTCGGTTATTACAGAGAC | 478 | 9 | SEQ ID NO: 35 |
| 11 | for | CGGGTCTATTACAGGGAC | 16 | 0 | SEQ ID NO: 36 |
| 8 | for | GGTTATTACAGGGACAGC | 11 | 4 | SEQ ID NO: 37 |
| 13 | for | GGGTTTATTACAGAGACAGCA | 8 | 0 | SEQ ID NO: 38 |
| 2 | for | CGGGTTATTACAGGGACA | 893 | 26 | SEQ ID NO: 39 |
| 14 | probe | CTCTGGAAAGGTGAAGGGCAGTG | 5 | 1 | SEQ ID NO: 80 |
| 9 | probe | TTGGAAAGGTGAAGGGCAGTAGT | 10 | 2 | SEQ ID NO: 81 |
| 6 | probe | TACTTTGGAAGGTGAAGGGCAGT | 62 | 3 | SEQ ID NO: 82 |
| 12 | probe | CTGGAAAGGTGAAGGGCAGTTGTA | 3 | 2 | SEQ ID NO: 83 |
| 3 | probe | CTGGAAGGTGAAGGGCAGTAGT | 1319 | 42 | SEQ ID NO: 84 |
| 7 | rev | CCTGCCATTTGTTTCCAT | 15 | 0 | SEQ ID NO: 132 |
| 4 | rev | TCACCTGCCATCTGTTTT | 19 | 2 | SEQ ID NO: 133 |
| 1 | rev | CCTGCCATCTGTTTCCA | 1363 | 48 | SEQ ID NO: 134 |
| 10 | rev | TCACCTGCCATCTGTTTG | 12 | 0 | SEQ ID NO: 135 |

Figure 3

| SCR_HIV_kPCR_F | TTTTTCGGGTTTATTACAG/G | SEQ ID NO: 23 |
|---|---|---|
| SCR_HIV_kPCR_R | CCTGCCAT/TGTTTTCCA | SEQ ID NO: 129 |
| SCR_HIV_kPCR_P1_RC | /TGGAAAGGTGAAGGGGCAGTAGT | SEQ ID NO: 56 |
| SCR_HIV_kPCR_P2_RC | TCT/TGGAAAGGTGAAGGGGCAGT | SEQ ID NO: 68 |

Figure 5

| Subtype | Forward Primer 1 ATTCCCTACAATCCCCAAAG | Forward Primer 2 TACAATCCCCAAAGTCAAGGAGTAGT | Probe ACAGCAGTACAAATGGCAGTATTCAT | |
|---|---|---|---|---|
| A Cons. | ATTCCCTACAATCCCCAAAG | TACAATCCCCAAAGTCAAGGAGTAGT | ACAGCAGTACAAATGGCAGTATTCAT | |
| A1 | ATTCCCTACAATCCCCAAAG | TACAATCCCCAAAGTCAAGGAGTAGT | ACAGCAGTACAAATGGCAGTATTCAT | |
| A2 | ATTCCCTACAATCCCCAAAG | TACAATCCCCAAAGCCAAGGAGTAGT | ACAGCAGTACACATGGCAGTATCCAT | |
| A3 | ATTCCCTACAATCCCCAAAG | TACAATCCCCAAAGTCAAGGAGTAGT | ACAGCAGTACAAATGGCAGTATTCAT | |

| H Cons. | ATTCCCTACAATCCCCAAAG | TACAATCCCCAAAGTCAGGAGTAGT | ACAGCAGTACAAATGGCAGTATTCAT | |
|---|---|---|---|---|
| H1-1 | ATTCCCTACAATCCCCAAAG | TACAATCCCCAAAGCCAAGGAGTAGT | ACAGCAGTACACATGGCAGTGTTCAT | |

SEQ ID NO: 136    SEQ ID NO: 137    SEQ ID NO: 140
SEQ ID NO: 136    SEQ ID NO: 137    SEQ ID NO: 140
SEQ ID NO: 136    SEQ ID NO: 137    SEQ ID NO: 140
SEQ ID NO: 136    SEQ ID NO: 138    SEQ ID NO: 141
SEQ ID NO: 136    SEQ ID NO: 137    SEQ ID NO: 140
SEQ ID NO: 136    SEQ ID NO: 139    SEQ ID NO: 140
SEQ ID NO: 136    SEQ ID NO: 137    SEQ ID NO: 142

Figure 6

| Sample ID | CS18N13 | CS18D8 | Anti ACS20G | CS19P3 |
|---|---|---|---|---|
| 1 | -15.2% | -1.6% | -5.6% | -4.6% |
| 2 | -7.9% | -6.3% | 0.0% | 0.0% |
| 3 | 0.0% | -0.7% | 0.0% | 0.0% |
| 4 | -26.7% | -11.2% | 0.0% | 0.0% |
| 5 | -15.2% | -4.3% | 0.0% | -5.2% |
| 6 | 0.0% | -12.4% | -18.4% | -76.5% |
| 7 | -15.2% | -15.2% | -9.8% | 0.0% |
| 8 | -7.8% | -4.8% | -9.8% | 0.0% |
| 9 | 0.0% | -3.7% | 0.0% | 0.0% |
| 10 | 0.0% | -3.7% | -9.8% | 0.0% |

Selected alignments for subset of samples with potentially significant mismatches in multiple p/p's:

| | SEQ ID NO: | CS18N13 | SEQ ID NO: | CS18D8 | SEQ ID NO: | Anti-ACS20G | SEQ ID NO: | CS19P3 |
|---|---|---|---|---|---|---|---|---|
| Sample 4 | 143 | ATTCCCTACAATCCCCAAAG | 146 | TACAATCCCCAAAGTCAAGGAGTAGT | 150 | CACAATTTTAAAAGAAAAACCCG | 140 | ACAGCAAGTACAAATGCAATATATTCAT |
| | 144 | ATTCCCTACAATCCTCAAAG | 147 | TACAATCCTCAAAGTCAAGGAGTAGT | 151 | CASAATTTTAAAACAAAACCCG | 152 | ACAGAAGTATAAAATGCAATACTATTAT |
| Sample 6 | 143 | ATTCCCTACAATCCCCAAAG | 146 | TACAATCCCCAAAGTCAAGGAGTAGT | | | | |
| | | | 148 | TACAATCCCCAAAGTCAAGGGGTAGT | | | | |
| Sample 7 | 143 | ATTCCCTACAATCCCCAAAG | 146 | TACAATCCCCAAAGTCAAGGAGTAGT | | | | |
| | 145 | ATTCCCTACAATCCTCAAAG | 149 | TACAATCCTCAAAGTCATGGAGTAGT | | | | |

REAGENTS AND METHODS FOR ANALYSIS OF HIV

CROSS-REFERENCE TO RELATED APPLICATIONS

The present application claims the benefit of U.S. Provisional Application No. 62/220,508, filed Sep. 18, 2015, the entirety of which is incorporated herein by reference.

This application incorporates by reference the sequence listing which is submitted together with this application in computer readable form which has the file name 2014P20087W0 SL.txt and is 234 KB.

BACKGROUND

Human Immunodeficiency Virus (HIV) is an infectious virus associated with Acquired Immune Deficiency Syndrome (AIDS). Estimates indicate that approximately 37 million people are currently living with HIV. It is further estimated that over 5,000 people contract HIV per day, while over 1,000,000 people die as a result of infection each year. The ability to detect and/or quantify the presence and/or load of HIV in a subject is important to, among other things, the diagnosis and treatment of infected individuals. There is a need in the art for methods of detecting and/or quantifying HIV presence and/or load that captures a wide variety of variant HIV sequences.

SUMMARY

Detecting and/or quantifying the presence and/or load of HIV in a subject has proven challenging due to a number of factors. One challenging factor in the detection and/or quantification of HIV is the heterogeneity of the virus. HIV can be divided into at least two major types (HIV-1, found worldwide, and HIV-2, found largely in west Africa), while HIV-1 has been further subdivided into three subgroups (M, N, and O), and M has been still further subdivided into at least 10 subtypes (A-J). Subtypes are also able to recombine upon co-infection, resulting in yet further recombinant subtypes. Another challenging factor is that the mutation rate of HIV in vivo is extremely high. According to some studies, the estimated mutation rate of HIV is such that any single mutation conferring drug resistance should occur within a single day. The ability to detect and/or quantify the presence and/or load of HIV having a mutation associated with drug resistance can be important in diagnosis and treatment of infected individuals. For example, HIV integrase protein is a key retroviral enzyme necessary for successful replication of HIV, and is therefore an attractive drug target. However, integrase gene is highly susceptible to genetic mutations that lead to or facilitate complete or partial resistance to treatment. Despite high efficacy of integrase inhibitors in some patients, there is a low genetic barrier to resistance to certain integrase inhibitors (e.g., in that 1 or 2 mutations are capable of causing marked reduction in efficacy of certain integrase inhibitors), and resistance to any given integrase inhibitor may engender cross-resistance with one or more other integrase inhibitors. Despite these challenges, integrase inhibitors are a vital component of antiretroviral treatment for many patients.

The present invention encompasses an appreciation of the problem that various previous methods for detecting and/or quantifying the presence and/or load of HIV were not able to detect and/or quantify a sufficient or desired breadth of HIV variants. For instance, various previous methods for detecting and/or quantifying the presence and/or load of HIV were not able to detect and/or quantify HIV variants with certain mutations in integrase gene.

The VERSANT® HIV-1 RNA 1.0 Assay (kPCR) (SIEMENS®) includes primers and probes that hybridize to integrase gene of HIV-1. Without negating the general value or utility of the VERSANT® HIV-1 RNA 1.0 Assay (kPCR), the present inventors have recognized that hybridization of oligonucleotide primers utilized by the VERSANT® HIV-1 RNA 1.0 Assay (kPCR) to integrase gene is inhibited by certain mutations associated with resistance to integrase inhibitors. When such mutations are present, sensitivity and accuracy in detecting and quantifying HIV presence and/or load is significantly reduced. Another HIV-1 assay, the ABBOT® HIV-1 real-time PCR assay, is also inhibited by certain mutations associated with resistance to integrase inhibitors, leading to significant reduction in sensitivity and accuracy in detecting and quantifying HIV presence and/or load.

The present invention is based at least in part on the discovery and validation of certain oligonucleotides and kits that solve, in whole or in part, this "breadth problem." The present invention includes, among other things, reagents, kits, and methods for hybridizing, amplifying, quantifying, detecting, and/or sequencing HIV nucleic acids. Methods and compositions described herein are capable of hybridizing, amplifying, quantifying, detecting, and/or sequencing a broad range of HIV nucleic acid sequences including HIV nucleic acid sequences with a broad range of mutations in integrase gene.

At least one aspect of the present invention relates to a composition including a pair of oligonucleotide primers including a forward oligonucleotide primer and a reverse oligonucleotide primer that upon hybridization to an HIV nucleic acid molecule flank an amplicon sequence including at least 20 nucleotides of the HIV nucleic acid molecule in a region of the HIV nucleic acid molecule having at least 80% sequence identity to one of SEQ ID NOs: 12-22, the HIV nucleic acid molecule having at least 80% sequence identity with one of SEQ ID NOs: 1-11. In certain embodiments, the pair of oligonucleotide primers includes a forward oligonucleotide primer including at least 15 consecutive nucleotides of a nucleic acid sequence having at least 80% sequence identity with one of SEQ ID NOs: 23-39 and a reverse oligonucleotide primer including at least 15 consecutive nucleotides complementary to a nucleic acid sequence having at least 80% sequence identity with one of SEQ ID NOs: 40-55.

At least one aspect of the present invention relates to a composition that is an amplification reaction mixture, the composition including: an HIV nucleic acid molecule including a sequence at least 80% identical to one of SEQ ID NOs: 1-11; a forward oligonucleotide primer including at least 15 consecutive nucleotides of a nucleic acid sequence having at least 80% sequence identity with one of SEQ ID NOs: 23-39; a reverse oligonucleotide primer including at least 15 consecutive nucleotides complementary to a nucleic acid sequence having at least 80% sequence identity with one of SEQ ID NOs: 40-55; an amplicon molecule having a sequence derived from a portion of the HIV nucleic acid molecule sequence, and the sequence of the forward oligonucleotide primer or the sequence of the reverse oligonucleotide primer. In certain embodiments, such a composition further includes one or more probes including at least 15 consecutive nucleotides of a nucleic acid sequence having at least 80% sequence identity with one of SEQ ID NOs: 56-84, such that the amplicon molecule is hybridized with one or more of the probes.

Any of the above aspects or embodiments may further include one or more probes including at least 15 consecutive nucleotides of a nucleic acid sequence having at least 80% sequence identity with one of SEQ ID NOs: 56-84.

At least one aspect of the present invention relates to a kit including: a forward oligonucleotide primer including at least 15 consecutive nucleotides of a nucleic acid sequence having at least 80% sequence identity with one of SEQ ID NOs: 23-39; a reverse oligonucleotide primer including at least 15 consecutive nucleotides complementary to a nucleic acid sequence having at least 80% sequence identity with one of SEQ ID NOs: 40-55; one or more probes including at least 15 consecutive nucleotides of a nucleic acid sequence having at least 80% sequence identity with one of SEQ ID NOs: 56-84; and a positive control sample which includes an HIV nucleic acid molecule that produces an amplicon molecule when subjected to one or more amplification cycles in the presence of the forward and reverse oligonucleotide primers.

In certain embodiments of any of the above kits or compositions, the forward oligonucleotide primer includes at least 15 consecutive nucleotides of SEQ ID NO 23 and the reverse oligonucleotide primer includes at least 15 consecutive nucleotides complementary to a nucleic acid sequence having the sequence of SEQ ID NO: 40.

In certain embodiments of any of the above kits or compositions, the forward oligonucleotide primer includes the sequence of SEQ ID NO 23 and the reverse oligonucleotide primer includes a sequence complementary to the sequence of SEQ ID NO: 40.

In various embodiments of the above kits or compositions:
 a) the forward oligonucleotide primer includes at least 15 consecutive nucleotides of a nucleic acid sequence having at least 80% sequence identity with SEQ ID NO: 24 and the reverse oligonucleotide primer includes at least 15 consecutive nucleotides complementary to a nucleic acid sequence having at least 80% sequence identity with SEQ ID NO: 41;
 b) the forward oligonucleotide primer includes at least 15 consecutive nucleotides of a nucleic acid sequence having at least 80% sequence identity with SEQ ID NO: 25 and the reverse oligonucleotide primer includes at least 15 consecutive nucleotides complementary to a nucleic acid sequence having at least 80% sequence identity with SEQ ID NO: 42;
 c) the forward oligonucleotide primer includes at least 15 consecutive nucleotides of a nucleic acid sequence having at least 80% sequence identity with SEQ ID NO: 26 and the reverse oligonucleotide primer includes at least 15 consecutive nucleotides complementary to a nucleic acid sequence having at least 80% sequence identity with SEQ ID NO: 43;
 d) the forward oligonucleotide primer includes at least 15 consecutive nucleotides of a nucleic acid sequence having at least 80% sequence identity with SEQ ID NO: 27 and the reverse oligonucleotide primer includes at least 15 consecutive nucleotides complementary to a nucleic acid sequence having at least 80% sequence identity with SEQ ID NO: 44;
 e) the forward oligonucleotide primer includes at least 15 consecutive nucleotides of a nucleic acid sequence having at least 80% sequence identity with SEQ ID NO: 28 and the reverse oligonucleotide primer includes at least 15 consecutive nucleotides complementary to a nucleic acid sequence having at least 80% sequence identity with SEQ ID NO: 45;
 (f) the forward oligonucleotide primer includes at least 15 consecutive nucleotides of a nucleic acid sequence having at least 80% sequence identity with SEQ ID NO: 29 and the reverse oligonucleotide primer includes at least 15 consecutive nucleotides complementary to a nucleic acid sequence having at least 80% sequence identity with SEQ ID NO: 46;
 g) the forward oligonucleotide primer includes at least 15 consecutive nucleotides of a nucleic acid sequence having at least 80% sequence identity with SEQ ID NO: 30 and the reverse oligonucleotide primer includes at least 15 consecutive nucleotides complementary to a nucleic acid sequence having at least 80% sequence identity with SEQ ID NO: 47;
 h) the forward oligonucleotide primer includes at least 15 consecutive nucleotides of a nucleic acid sequence having at least 80% sequence identity with SEQ ID NO: 31 and the reverse oligonucleotide primer includes at least 15 consecutive nucleotides complementary to a nucleic acid sequence having at least 80% sequence identity with SEQ ID NO: 48;
 i) the forward oligonucleotide primer includes at least 15 consecutive nucleotides of a nucleic acid sequence having at least 80% sequence identity with SEQ ID NO: 32 and the reverse oligonucleotide primer includes at least 15 consecutive nucleotides complementary to a nucleic acid sequence having at least 80% sequence identity with SEQ ID NO: 49;
 j) the forward oligonucleotide primer includes at least 15 consecutive nucleotides of a nucleic acid sequence having at least 80% sequence identity with SEQ ID NO: 33 and the reverse oligonucleotide primer includes at least 15 consecutive nucleotides complementary to a nucleic acid sequence having at least 80% sequence identity with SEQ ID NO: 50; or
 k) the forward oligonucleotide primer includes at least 15 consecutive nucleotides of a nucleic acid sequence having at least 80% sequence identity with SEQ ID NO: 34 and the reverse oligonucleotide primer includes at least 15 consecutive nucleotides complementary to a nucleic acid sequence having at least 80% sequence identity with SEQ ID NO: 51.

In certain embodiments of any of the above kits or compositions, the forward oligonucleotide primer includes at least 15 consecutive nucleotides of a nucleic acid sequence having at least 80% sequence identity with one of SEQ ID NOs: 85-95 and the reverse oligonucleotide primer includes at least 15 consecutive nucleotides complementary to a nucleic acid sequence having at least 80% sequence identity with one of SEQ ID NOs: 96-106.

In certain embodiments of any of the above kits or compositions:
 a) the forward oligonucleotide primer includes at least 15 consecutive nucleotides of a nucleic acid sequence having at least 80% sequence identity with SEQ ID NO: 85 and the reverse oligonucleotide primer includes at least 15 consecutive nucleotides complementary to a nucleic acid sequence having at least 80% sequence identity with SEQ ID NO: 96;
 b) the forward oligonucleotide primer includes at least 15 consecutive nucleotides of a nucleic acid sequence having at least 80% sequence identity with SEQ ID NO: 86 and the reverse oligonucleotide primer includes at least 15 consecutive nucleotides complementary to a nucleic acid sequence having at least 80% sequence identity with SEQ ID NO: 97;
c) the forward oligonucleotide primer includes at least 15 consecutive nucleotides of a nucleic acid sequence having at least 80% sequence identity with SEQ ID NO: 87 and the reverse oligonucleotide primer includes at least 15 consecutive nucleotides complementary to a nucleic acid sequence having at least 80% sequence identity with SEQ ID NO: 98;
d) the forward oligonucleotide primer includes at least 15 consecutive nucleotides of a nucleic acid sequence having at least 80% sequence identity with SEQ ID NO: 88 and the reverse oligonucleotide primer includes at least 15 consecutive nucleotides complementary to a nucleic acid sequence having at least 80% sequence identity with SEQ ID NO: 99;
e) the forward oligonucleotide primer includes at least 15 consecutive nucleotides of a nucleic acid sequence having at least 80% sequence identity with SEQ ID NO: 89 and the reverse oligonucleotide primer includes at least 15 consecutive nucleotides complementary to a nucleic acid sequence having at least 80% sequence identity with SEQ ID NO: 100;
f) the forward oligonucleotide primer includes at least 15 consecutive nucleotides of a nucleic acid sequence having at least 80% sequence identity with SEQ ID NO: 90 and the reverse oligonucleotide primer includes at least 15 consecutive nucleotides complementary to a nucleic acid sequence having at least 80% sequence identity with SEQ ID NO: 101;
g) the forward oligonucleotide primer includes at least 15 consecutive nucleotides of a nucleic acid sequence having at least 80% sequence identity with SEQ ID NO: 91 and the reverse oligonucleotide primer includes at least 15 consecutive nucleotides complementary to a nucleic acid sequence having at least 80% sequence identity with SEQ ID NO: 102;
h) the forward oligonucleotide primer includes at least 15 consecutive nucleotides of a nucleic acid sequence having at least 80% sequence identity with SEQ ID NO: 92 and the reverse oligonucleotide primer includes at least 15 consecutive nucleotides complementary to a nucleic acid sequence having at least 80% sequence identity with SEQ ID NO: 103;
i) the forward oligonucleotide primer includes at least 15 consecutive nucleotides of a nucleic acid sequence having at least 80% sequence identity with SEQ ID NO: 93 and the reverse oligonucleotide primer includes at least 15 consecutive nucleotides complementary to a nucleic acid sequence having at least 80% sequence identity with SEQ ID NO: 104
j) the forward oligonucleotide primer includes at least 15 consecutive nucleotides of a nucleic acid sequence having at least 80% sequence identity with SEQ ID NO: 94 and the reverse oligonucleotide primer includes at least 15 consecutive nucleotides complementary to a nucleic acid sequence having at least 80% sequence identity with SEQ ID NO: 105; or
k) the forward oligonucleotide primer includes at least 15 consecutive nucleotides of a nucleic acid sequence having at least 80% sequence identity with SEQ ID NO: 95 and the reverse oligonucleotide primer includes at least 15 consecutive nucleotides complementary to a nucleic acid sequence having at least 80% sequence identity with SEQ ID NO: 106.

In certain embodiments of any of the above kits or compositions, the forward oligonucleotide primer includes no more than two mismatched nucleotides, in that no more than two nucleotides differ from the sequence of a corresponding portion of the HIV nucleic acid molecule.

In certain embodiments of any of the above kits or compositions, the reverse oligonucleotide primer includes no more than two mismatched nucleotides, in that no more than two nucleotides differ from the sequence of a corresponding portion of the HIV nucleic acid molecule.

In various embodiments of the above kits or compositions, the kit or composition includes a first probe and a second probe, the first probe including at least 15 consecutive nucleotides of a nucleic acid sequence having at least 80% sequence identity with one of SEQ ID NOs: 56-67 and the second probe including at least 15 consecutive nucleotides of a nucleic acid sequence having at least 80% sequence identity with one of SEQ ID NOs: 68-79.

In various embodiments of the above kits or compositions, the composition includes a first probe and a second probe, the first probe including at least 15 consecutive nucleotides of a nucleic acid sequence having at least 80% sequence identity with SEQ ID NO: 56 and the second probe including at least 15 consecutive nucleotides of a nucleic acid sequence having at least 80% sequence identity with SEQ ID NO: 68.

In various embodiments of the above kits or compositions, the composition includes a first probe and a second probe, the first probe including the sequence of SEQ ID NO: 56 and the second probe including the sequence of SEQ ID NO: 68. In certain such embodiments:
a) the first probe includes at least 15 consecutive nucleotides of a nucleic acid sequence having at least 80% sequence identity with SEQ ID NO: 57 and the second probe includes at least 15 consecutive nucleotides of a nucleic acid sequence having at least 80% sequence identity with SEQ ID NO: 69;
b) the first probe includes at least 15 consecutive nucleotides of a nucleic acid sequence having at least 80% sequence identity with SEQ ID NO: 58 and the second probe includes at least 15 consecutive nucleotides of a nucleic acid sequence having at least 80% sequence identity with SEQ ID NO: 70;
c) the first probe includes at least 15 consecutive nucleotides of a nucleic acid sequence having at least 80% sequence identity with SEQ ID NO: 59 and the second probe includes at least 15 consecutive nucleotides of a nucleic acid sequence having at least 80% sequence identity with SEQ ID NO: 71;
d) the first probe includes at least 15 consecutive nucleotides of a nucleic acid sequence having at least 80% sequence identity with SEQ ID NO: 60 and the second probe includes at least 15 consecutive nucleotides of a nucleic acid sequence having at least 80% sequence identity with SEQ ID NO: 72;
e) the first probe includes at least 15 consecutive nucleotides of a nucleic acid sequence having at least 80% sequence identity with SEQ ID NO: 61 and the second probe includes at least 15 consecutive nucleotides of a nucleic acid sequence having at least 80% sequence identity with SEQ ID NO: 73;
f) the first probe includes at least 15 consecutive nucleotides of a nucleic acid sequence having at least 80% sequence identity with SEQ ID NO: 62 and the second probe includes at least 15 consecutive nucleotides of a nucleic acid sequence having at least 80% sequence identity with SEQ ID NO: 74;
g) the first probe includes at least 15 consecutive nucleotides of a nucleic acid sequence having at least 80% sequence identity with SEQ ID NO: 63 and the second probe includes at least 15 consecutive nucleotides of a nucleic acid sequence having at least 80% sequence identity with SEQ ID NO: 75;

h) the first probe includes at least 15 consecutive nucleotides of a nucleic acid sequence having at least 80% sequence identity with SEQ ID NO: 64 and the second probe includes at least 15 consecutive nucleotides of a nucleic acid sequence having at least 80% sequence identity with SEQ ID NO: 76;

i) the first probe includes at least 15 consecutive nucleotides of a nucleic acid sequence having at least 80% sequence identity with SEQ ID NO: 65 and the second probe includes at least 15 consecutive nucleotides of a nucleic acid sequence having at least 80% sequence identity with SEQ ID NO: 77;

j) the first probe includes at least 15 consecutive nucleotides of a nucleic acid sequence having at least 80% sequence identity with SEQ ID NO: 66 and the second probe includes at least 15 consecutive nucleotides of a nucleic acid sequence having at least 80% sequence identity with SEQ ID NO: 78; or k) the first probe includes at least 15 consecutive nucleotides of a nucleic acid sequence having at least 80% sequence identity with SEQ ID NO: 67 and the second probe includes at least 15 consecutive nucleotides of a nucleic acid sequence having at least 80% sequence identity with SEQ ID NO: 79.

In various embodiments of the above kits or compositions, the first probe includes at least 15 consecutive nucleotides of a nucleic acid sequence having at least 80% sequence identity with one of SEQ ID NOs: 107-128.

In various embodiments of the above kits or compositions, the first probe includes at least 15 consecutive nucleotides of a nucleic acid sequence having at least 80% sequence identity with one of SEQ ID NOs: 107-117 and the second probe includes at least 15 consecutive nucleotides of a nucleic acid sequence having at least 80% sequence identity with one of SEQ ID NOs: 118-128.

In various embodiments of the above kits or compositions:

a) the first probe includes at least 15 consecutive nucleotides of a nucleic acid sequence having at least 80% sequence identity with SEQ ID NO: 107 and the second probe includes at least 15 consecutive nucleotides of a nucleic acid sequence having at least 80% sequence identity with SEQ ID NO: 118;

b) the first probe includes at least 15 consecutive nucleotides of a nucleic acid sequence having at least 80% sequence identity with SEQ ID NO: 108 and the second probe includes at least 15 consecutive nucleotides of a nucleic acid sequence having at least 80% sequence identity with SEQ ID NO: 119;

c) the first probe includes at least 15 consecutive nucleotides of a nucleic acid sequence having at least 80% sequence identity with SEQ ID NO: 109 and the second probe includes at least 15 consecutive nucleotides of a nucleic acid sequence having at least 80% sequence identity with SEQ ID NO: 120;

d) the first probe includes at least 15 consecutive nucleotides of a nucleic acid sequence having at least 80% sequence identity with SEQ ID NO: 110 and the second probe includes at least 15 consecutive nucleotides of a nucleic acid sequence having at least 80% sequence identity with SEQ ID NO: 121;

e) the first probe includes at least 15 consecutive nucleotides of a nucleic acid sequence having at least 80% sequence identity with SEQ ID NO: 111 and the second probe includes at least 15 consecutive nucleotides of a nucleic acid sequence having at least 80% sequence identity with SEQ ID NO: 122;

f) the first probe includes at least 15 consecutive nucleotides of a nucleic acid sequence having at least 80% sequence identity with SEQ ID NO: 112 and the second probe includes at least 15 consecutive nucleotides of a nucleic acid sequence having at least 80% sequence identity with SEQ ID NO: 123;

g) the first probe includes at least 15 consecutive nucleotides of a nucleic acid sequence having at least 80% sequence identity with SEQ ID NO: 113 and the second probe includes at least 15 consecutive nucleotides of a nucleic acid sequence having at least 80% sequence identity with SEQ ID NO: 124;

h) the first probe includes at least 15 consecutive nucleotides of a nucleic acid sequence having at least 80% sequence identity with SEQ ID NO: 114 and the second probe includes at least 15 consecutive nucleotides of a nucleic acid sequence having at least 80% sequence identity with SEQ ID NO: 125;

i) the first probe includes at least 15 consecutive nucleotides of a nucleic acid sequence having at least 80% sequence identity with SEQ ID NO: 115 and the second probe includes at least 15 consecutive nucleotides of a nucleic acid sequence having at least 80% sequence identity with SEQ ID NO: 126;

j) the first probe includes at least 15 consecutive nucleotides of a nucleic acid sequence having at least 80% sequence identity with SEQ ID NO: 116 and the second probe includes at least 15 consecutive nucleotides of a nucleic acid sequence having at least 80% sequence identity with SEQ ID NO: 127; or k) the first probe includes at least 15 consecutive nucleotides of a nucleic acid sequence having at least 80% sequence identity with SEQ ID NO: 117 and the second probe includes at least 15 consecutive nucleotides of a nucleic acid sequence having at least 80% sequence identity with SEQ ID NO: 128.

In various embodiments of the above kits or compositions, one or more probes, optionally one or both of the first probe and the second probe, includes no more than two mismatched nucleotides, in that no more than two nucleotides differ from the sequence of a corresponding portion of the HIV nucleic acid molecule.

At least one aspect of the present invention relates to a method including steps of: providing a nucleic acid sample from an individual who has an HIV infection or is suspected of having an HIV infection, such that the nucleic acid sample includes an HIV nucleic acid molecule; preparing an amplification reaction mixture that includes the HIV nucleic acid molecule, an amplification-dependent detectable moiety, a forward oligonucleotide primer and a reverse oligonucleotide primer, the forward oligonucleotide primer including at least 15 consecutive nucleotides of a nucleic acid sequence having at least 80% sequence identity with one of SEQ ID NOs: 23-39 and the reverse oligonucleotide primer including at least 15 consecutive nucleotides complementary to a nucleic acid sequence having at least 80% sequence identity with one of SEQ ID NOs: 40-55; subjecting the amplification reaction mixture to one or more amplification cycles, such that the HIV nucleic acid molecule in the amplification reaction mixture is amplified to produce an amplicon molecule; and detecting the amplification-dependent detectable moiety in the amplification reaction mixture during or after the one or more amplification cycles. In certain embodiments, the method further includes measuring a level of the amplification-dependent detectable moiety in the amplification reaction mixture during or after the one or more amplification cycles; and quantifying an HIV viral load for the individual based on the measured level. In certain embodiments, the HIV nucleic acid molecule is an HIV cDNA molecule. In certain embodiments, the method further includes producing the HIV cDNA molecule by reverse transcription. In certain embodiments, the amplification reaction mixture further includes one or more probes including at least 15 consecutive nucleotides of a nucleic acid sequence having at least 80% sequence identity with one of SEQ ID NOs: 56-84. In certain such embodiments, the amplification reaction mixture includes a first probe and a second probe, the first probe including at least 15 consecutive nucleotides of a nucleic acid sequence having at least 80% sequence identity with one of SEQ ID NOs: 56-67 and the second probe including at least 15 consecutive nucleotides of a nucleic acid sequence having at least 80% sequence identity with one of SEQ ID NOs: 68-79.

At least one aspect of the present invention relates to a method including steps of: providing a nucleic acid sample from an individual who has an HIV infection or is suspected of having an HIV infection, such that the nucleic acid sample includes an HIV cDNA molecule; preparing an amplification reaction mixture that includes the HIV cDNA molecule and: a forward oligonucleotide primer including at least 15 consecutive nucleotides of a nucleic acid sequence having at least 80% sequence identity with one of SEQ ID NOs: 23-39; a reverse oligonucleotide primer including at least 15 consecutive nucleotides complementary to a nucleic acid sequence having at least 80% sequence identity with one of SEQ ID NOs: 40-55; and one or more probes including at least 15 consecutive nucleotides of a nucleic acid sequence having at least 80% sequence identity with one of SEQ ID NOs: 56-84 and a detectable moiety; subjecting the amplification reaction mixture to one or more amplification cycles, such that the HIV cDNA molecule in the amplification reaction mixture is amplified to produce an amplicon molecule; measuring a level of the detectable moiety in the amplification reaction mixture during or after the one or more amplification cycles; and quantifying an HIV viral load for the individual based on the measured level. In certain embodiments, the detectable moiety is a fluorophore and the probe further includes a quencher that is capable of quenching fluorescence from the fluorophore. In certain embodiments, the method further includes producing the HIV cDNA molecule by reverse transcription. In certain embodiments, the individual has an HIV infection or is suspected of having an HIV infection that is resistant to an HIV anti-retroviral drug, e.g., an integrase inhibitor or an .HIV anti-retroviral drug is selected from raltegravir, elvitegravir, dolutegravir, globoidnan A, cabotegravir, and BMS-707035. In certain embodiments, a method as described herein is performed with at least two different nucleic acid samples from an individual undergoing treatment for an HIV infection, such that the at least two different nucleic acid samples represent different time points during the treatment, and changing the treatment if the quantified HIV viral load is increasing over time. In certain embodiments, the treatment includes administration of an HIV anti-retroviral drug and the change in treatment involves increasing the dose of the HIV anti-retroviral drug. In certain embodiments, the treatment includes administration of an HIV anti-retroviral drug and the change in treatment involves using a different HIV anti-retroviral drug or a different combination of HIV anti-retroviral drugs. In certain embodiments, a method as described herein further includes performing the method with a nucleic acid sample obtained from the individual after the treatment has changed. In certain embodiments, a method as described herein is performed with at least two different nucleic acid samples from an individual undergoing treatment for an HIV infection, such that the at least two different nucleic acid samples represent different time points during the treatment, and continuing the same treatment if the quantified HIV viral load is stable or decreasing over time.

In certain embodiments of methods described herein, the pair of oligonucleotide primers includes a forward oligonucleotide primer including at least 15 consecutive nucleotides of SEQ ID NO 23 and a reverse oligonucleotide primer including at least 15 consecutive nucleotides complementary to a nucleic acid sequence having the sequence of SEQ ID NO: 40.

In certain embodiments of methods described herein, the pair of oligonucleotide primers includes a forward oligonucleotide primer including the sequence of SEQ ID NO 23 and a reverse oligonucleotide primer including a sequence complementary to the sequence of SEQ ID NO: 40.

In certain embodiments of methods described herein:
a) the forward oligonucleotide primer includes at least 15 consecutive nucleotides of a nucleic acid sequence having at least 80% sequence identity with SEQ ID NO: 24 and the reverse oligonucleotide primer includes at least 15 consecutive nucleotides complementary to a nucleic acid sequence having at least 80% sequence identity with SEQ ID NO: 41;
b) the forward oligonucleotide primer includes at least 15 consecutive nucleotides of a nucleic acid sequence having at least 80% sequence identity with SEQ ID NO: 25 and the reverse oligonucleotide primer includes at least 15 consecutive nucleotides complementary to a nucleic acid sequence having at least 80% sequence identity with SEQ ID NO: 42;
c) the forward oligonucleotide primer includes at least 15 consecutive nucleotides of a nucleic acid sequence having at least 80% sequence identity with SEQ ID NO: 26 and the reverse oligonucleotide primer includes at least 15 consecutive nucleotides complementary to a nucleic acid sequence having at least 80% sequence identity with SEQ ID NO: 43;
d) the forward oligonucleotide primer includes at least 15 consecutive nucleotides of a nucleic acid sequence having at least 80% sequence identity with SEQ ID NO: 27 and the reverse oligonucleotide primer includes at least 15 consecutive nucleotides complementary to a nucleic acid sequence having at least 80% sequence identity with SEQ ID NO: 44;
e) the forward oligonucleotide primer includes at least 15 consecutive nucleotides of a nucleic acid sequence having at least 80% sequence identity with SEQ ID NO: 28 and the reverse oligonucleotide primer includes at least 15 consecutive nucleotides complementary to a nucleic acid sequence having at least 80% sequence identity with SEQ ID NO: 45;
f) the forward oligonucleotide primer includes at least 15 consecutive nucleotides of a nucleic acid sequence having at least 80% sequence identity with SEQ ID NO: 29 and the reverse oligonucleotide primer includes at least 15 consecutive nucleotides complementary to a nucleic acid sequence having at least 80% sequence identity with SEQ ID NO: 46;
g) the forward oligonucleotide primer includes at least 15 consecutive nucleotides of a nucleic acid sequence having at least 80% sequence identity with SEQ ID NO: 30 and the reverse oligonucleotide primer includes at least 15 consecutive nucleotides complementary to a nucleic acid sequence having at least 80% sequence identity with SEQ ID NO: 47;

h) the forward oligonucleotide primer includes at least 15 consecutive nucleotides of a nucleic acid sequence having at least 80% sequence identity with SEQ ID NO: 31 and the reverse oligonucleotide primer includes at least 15 consecutive nucleotides complementary to a nucleic acid sequence having at least 80% sequence identity with SEQ ID NO: 48;

i) the forward oligonucleotide primer includes at least 15 consecutive nucleotides of a nucleic acid sequence having at least 80% sequence identity with SEQ ID NO: 32 and the reverse oligonucleotide primer includes at least 15 consecutive nucleotides complementary to a nucleic acid sequence having at least 80% sequence identity with SEQ ID NO: 49;

j) the forward oligonucleotide primer includes at least 15 consecutive nucleotides of a nucleic acid sequence having at least 80% sequence identity with SEQ ID NO: 33 and the reverse oligonucleotide primer includes at least 15 consecutive nucleotides complementary to a nucleic acid sequence having at least 80% sequence identity with SEQ ID NO: 50; or k) the forward oligonucleotide primer includes at least 15 consecutive nucleotides of a nucleic acid sequence having at least 80% sequence identity with SEQ ID NO: 34 and the reverse oligonucleotide primer includes at least 15 consecutive nucleotides complementary to a nucleic acid sequence having at least 80% sequence identity with SEQ ID NO: 51.

In certain embodiments of methods described herein, the forward oligonucleotide primer includes at least 15 consecutive nucleotides of a nucleic acid sequence having at least 80% sequence identity with one of SEQ ID NOs: 85-95 and the reverse oligonucleotide primer includes at least 15 consecutive nucleotides complementary to a nucleic acid sequence having at least 80% sequence identity with one of SEQ ID NOs: 96-106.

In certain embodiments of methods described herein:

a) the forward oligonucleotide primer includes at least 15 consecutive nucleotides of a nucleic acid sequence having at least 80% sequence identity with SEQ ID NO: 85 and the reverse oligonucleotide primer includes at least 15 consecutive nucleotides complementary to a nucleic acid sequence having at least 80% sequence identity with SEQ ID NO: 96;

b) the forward oligonucleotide primer includes at least 15 consecutive nucleotides of a nucleic acid sequence having at least 80% sequence identity with SEQ ID NO: 86 and the reverse oligonucleotide primer includes at least 15 consecutive nucleotides complementary to a nucleic acid sequence having at least 80% sequence identity with SEQ ID NO: 97;

c) the forward oligonucleotide primer includes at least 15 consecutive nucleotides of a nucleic acid sequence having at least 80% sequence identity with SEQ ID NO: 87 and the reverse oligonucleotide primer includes at least 15 consecutive nucleotides complementary to a nucleic acid sequence having at least 80% sequence identity with SEQ ID NO: 98;

d) the forward oligonucleotide primer includes at least 15 consecutive nucleotides of a nucleic acid sequence having at least 80% sequence identity with SEQ ID NO: 88 and the reverse oligonucleotide primer includes at least 15 consecutive nucleotides complementary to a nucleic acid sequence having at least 80% sequence identity with SEQ ID NO: 99;

e) the forward oligonucleotide primer includes at least 15 consecutive nucleotides of a nucleic acid sequence having at least 80% sequence identity with SEQ ID NO: 89 and the reverse oligonucleotide primer includes at least 15 consecutive nucleotides complementary to a nucleic acid sequence having at least 80% sequence identity with SEQ ID NO: 100;

f) the forward oligonucleotide primer includes at least 15 consecutive nucleotides of a nucleic acid sequence having at least 80% sequence identity with SEQ ID NO: 90 and the reverse oligonucleotide primer includes at least 15 consecutive nucleotides complementary to a nucleic acid sequence having at least 80% sequence identity with SEQ ID NO: 101 g) the forward oligonucleotide primer includes at least 15 consecutive nucleotides of a nucleic acid sequence having at least 80% sequence identity with SEQ ID NO: 91 and the reverse oligonucleotide primer includes at least 15 consecutive nucleotides complementary to a nucleic acid sequence having at least 80% sequence identity with SEQ ID NO: 102;

h) the forward oligonucleotide primer includes at least 15 consecutive nucleotides of a nucleic acid sequence having at least 80% sequence identity with SEQ ID NO: 92 and the reverse oligonucleotide primer includes at least 15 consecutive nucleotides complementary to a nucleic acid sequence having at least 80% sequence identity with SEQ ID NO: 103;

i) the forward oligonucleotide primer includes at least 15 consecutive nucleotides of a nucleic acid sequence having at least 80% sequence identity with SEQ ID NO: 93 and the reverse oligonucleotide primer includes at least 15 consecutive nucleotides complementary to a nucleic acid sequence having at least 80% sequence identity with SEQ ID NO: 104;

j) the forward oligonucleotide primer includes at least 15 consecutive nucleotides of a nucleic acid sequence having at least 80% sequence identity with SEQ ID NO: 94 and the reverse oligonucleotide primer includes at least 15 consecutive nucleotides complementary to a nucleic acid sequence having at least 80% sequence identity with SEQ ID NO: 105; or k) the forward oligonucleotide primer includes at least 15 consecutive nucleotides of a nucleic acid sequence having at least 80% sequence identity with SEQ ID NO: 95 and the reverse oligonucleotide primer includes at least 15 consecutive nucleotides complementary to a nucleic acid sequence having at least 80% sequence identity with SEQ ID NO: 106.

In certain embodiments of methods described herein, the forward oligonucleotide primer includes no more than two mismatched nucleotides, in that no more than two nucleotides differ from the sequence of a corresponding portion of the HIV nucleic acid molecule.

In certain embodiments of methods described herein, the reverse oligonucleotide primer includes no more than two mismatched nucleotides, in that no more than two nucleotides differ from the sequence of a corresponding portion of the HIV nucleic acid molecule.

At least one aspect of the present invention relates to use of one or more probes each including at least 15 consecutive nucleotides of a nucleic acid sequence having at least 80% sequence identity with one of SEQ ID NOs: 56-84 to detect or quantify an HIV nucleic acid molecule in a nucleic acid sample from an individual who has an HIV infection or is suspected of having an HIV infection.

In certain embodiments of methods or uses described herein, the one or more probes include a first probe and a second probe, the first probe including at least 15 consecutive nucleotides of a nucleic acid sequence having at least 80% sequence identity with one of SEQ ID NOs: 56-67 and the second probe including at least 15 consecutive nucleotides of a nucleic acid sequence having at least 80% sequence identity with one of SEQ ID NOs: 68-79.

In certain embodiments of methods or uses described herein, the one or more probes include a first probe and a second probe, the first probe including at least 15 consecutive nucleotides of a nucleic acid sequence having at least 80% sequence identity with SEQ ID NO: 56 and the second probe including at least 15 consecutive nucleotides of a nucleic acid sequence having at least 80% sequence identity with SEQ ID NO: 68.

In certain embodiments of methods or uses described herein, the one or more probes include a first probe and a second probe, the first probe including the sequence of SEQ ID NO: 56 and the second probe including the sequence of SEQ ID NO: 68.

In certain embodiments of methods or uses described herein:
a) the first probe includes at least 15 consecutive nucleotides of a nucleic acid sequence having at least 80% sequence identity with SEQ ID NO: 57 and the second probe includes at least 15 consecutive nucleotides of a nucleic acid sequence having at least 80% sequence identity with SEQ ID NO: 69;
b) the first probe includes at least 15 consecutive nucleotides of a nucleic acid sequence having at least 80% sequence identity with SEQ ID NO: 58 and the second probe includes at least 15 consecutive nucleotides of a nucleic acid sequence having at least 80% sequence identity with SEQ ID NO: 70;
c) the first probe includes at least 15 consecutive nucleotides of a nucleic acid sequence having at least 80% sequence identity with SEQ ID NO: 59 and the second probe includes at least 15 consecutive nucleotides of a nucleic acid sequence having at least 80% sequence identity with SEQ ID NO: 71;
d) the first probe includes at least 15 consecutive nucleotides of a nucleic acid sequence having at least 80% sequence identity with SEQ ID NO: 60 and the second probe includes at least 15 consecutive nucleotides of a nucleic acid sequence having at least 80% sequence identity with SEQ ID NO: 72;
e) the first probe includes at least 15 consecutive nucleotides of a nucleic acid sequence having at least 80% sequence identity with SEQ ID NO: 61 and the second probe includes at least 15 consecutive nucleotides of a nucleic acid sequence having at least 80% sequence identity with SEQ ID NO: 73;
f) the first probe includes at least 15 consecutive nucleotides of a nucleic acid sequence having at least 80% sequence identity with SEQ ID NO: 62 and the second probe includes at least 15 consecutive nucleotides of a nucleic acid sequence having at least 80% sequence identity with SEQ ID NO: 74;
g) the first probe includes at least 15 consecutive nucleotides of a nucleic acid sequence having at least 80% sequence identity with SEQ ID NO: 63 and the second probe includes at least 15 consecutive nucleotides of a nucleic acid sequence having at least 80% sequence identity with SEQ ID NO: 75;

h) the first probe includes at least 15 consecutive nucleotides of a nucleic acid sequence having at least 80% sequence identity with SEQ ID NO: 64 and the second probe includes at least 15 consecutive nucleotides of a nucleic acid sequence having at least 80% sequence identity with SEQ ID NO: 76;
i) the first probe includes at least 15 consecutive nucleotides of a nucleic acid sequence having at least 80% sequence identity with SEQ ID NO: 65 and the second probe includes at least 15 consecutive nucleotides of a nucleic acid sequence having at least 80% sequence identity with SEQ ID NO: 77;
j) the first probe includes at least 15 consecutive nucleotides of a nucleic acid sequence having at least 80% sequence identity with SEQ ID NO: 66 and the second probe includes at least 15 consecutive nucleotides of a nucleic acid sequence having at least 80% sequence identity with SEQ ID NO: 78; or
k) the first probe includes at least 15 consecutive nucleotides of a nucleic acid sequence having at least 80% sequence identity with SEQ ID NO: 67 and the second probe includes at least 15 consecutive nucleotides of a nucleic acid sequence having at least 80% sequence identity with SEQ ID NO: 79.

In certain embodiments of methods or uses described herein, a first probe includes at least 15 consecutive nucleotides of a nucleic acid sequence having at least 80% sequence identity with one of SEQ ID NOs: 107-128.

In certain embodiments of methods or uses described herein, a first probe includes at least 15 consecutive nucleotides of a nucleic acid sequence having at least 80% sequence identity with one of SEQ ID NOs: 107-117 and a second probe includes at least 15 consecutive nucleotides of a nucleic acid sequence having at least 80% sequence identity with one of SEQ ID NOs: 118-128.

In certain embodiments of methods or uses described herein:
a) the first probe includes at least 15 consecutive nucleotides of a nucleic acid sequence having at least 80% sequence identity with SEQ ID NO: 107 and the second probe includes at least 15 consecutive nucleotides of a nucleic acid sequence having at least 80% sequence identity with SEQ ID NO: 118;
b) the first probe includes at least 15 consecutive nucleotides of a nucleic acid sequence having at least 80% sequence identity with SEQ ID NO: 108 and the second probe includes at least 15 consecutive nucleotides of a nucleic acid sequence having at least 80% sequence identity with SEQ ID NO: 119;
c) the first probe includes at least 15 consecutive nucleotides of a nucleic acid sequence having at least 80% sequence identity with SEQ ID NO: 109 and the second probe includes at least 15 consecutive nucleotides of a nucleic acid sequence having at least 80% sequence identity with SEQ ID NO: 120;
d) the first probe includes at least 15 consecutive nucleotides of a nucleic acid sequence having at least 80% sequence identity with SEQ ID NO: 110 and the second probe includes at least 15 consecutive nucleotides of a nucleic acid sequence having at least 80% sequence identity with SEQ ID NO: 121;
e) the first probe includes at least 15 consecutive nucleotides of a nucleic acid sequence having at least 80% sequence identity with SEQ ID NO: 111 and the second probe includes at least 15 consecutive nucleotides of a nucleic acid sequence having at least 80% sequence identity with SEQ ID NO: 122;

f) the first probe includes at least 15 consecutive nucleotides of a nucleic acid sequence having at least 80% sequence identity with SEQ ID NO: 112 and the second probe includes at least 15 consecutive nucleotides of a nucleic acid sequence having at least 80% sequence identity with SEQ ID NO: 123;

g) the first probe includes at least 15 consecutive nucleotides of a nucleic acid sequence having at least 80% sequence identity with SEQ ID NO: 113 and the second probe includes at least 15 consecutive nucleotides of a nucleic acid sequence having at least 80% sequence identity with SEQ ID NO: 124;

h) the first probe includes at least 15 consecutive nucleotides of a nucleic acid sequence having at least 80% sequence identity with SEQ ID NO: 114 and the second probe includes at least 15 consecutive nucleotides of a nucleic acid sequence having at least 80% sequence identity with SEQ ID NO: 125;

i) the first probe includes at least 15 consecutive nucleotides of a nucleic acid sequence having at least 80% sequence identity with SEQ ID NO: 115 and the second probe includes at least 15 consecutive nucleotides of a nucleic acid sequence having at least 80% sequence identity with SEQ ID NO: 126;

j) the first probe includes at least 15 consecutive nucleotides of a nucleic acid sequence having at least 80% sequence identity with SEQ ID NO: 116 and the second probe includes at least 15 consecutive nucleotides of a nucleic acid sequence having at least 80% sequence identity with SEQ ID NO: 127; or k) the first probe includes at least 15 consecutive nucleotides of a nucleic acid sequence having at least 80% sequence identity with SEQ ID NO: 117 and the second probe includes at least 15 consecutive nucleotides of a nucleic acid sequence having at least 80% sequence identity with SEQ ID NO: 128.

In certain embodiments of methods or uses described herein, one or more probes, optionally one or both of the first probe and the second probe, includes no more than two mismatched nucleotides, in that no more than two nucleotides differ from the sequence of a corresponding portion of the HIV nucleic acid molecule.

At least one aspect of the present invention relates to a container including: a forward oligonucleotide primer including at least 15 consecutive nucleotides of a nucleic acid sequence having at least 80% sequence identity with one of SEQ ID NOs: 23-39; a reverse oligonucleotide primer including at least 15 consecutive nucleotides complementary to a nucleic acid sequence having at least 80% sequence identity with one of SEQ ID NOs: 40-55; and a buffer. In certain embodiments, the forward oligonucleotide primer includes at least 15 consecutive nucleotides of SEQ ID NO 23 and the reverse oligonucleotide primer includes at least 15 consecutive nucleotides complementary to a nucleic acid sequence having the sequence of SEQ ID NO: 40. In certain embodiments, the forward oligonucleotide primer includes the sequence of SEQ ID NO 23 and the reverse oligonucleotide primer includes a sequence complementary to the sequence of SEQ ID NO: 40. In certain embodiments:

a) the forward oligonucleotide primer includes at least 15 consecutive nucleotides of a nucleic acid sequence having at least 80% sequence identity with SEQ ID NO: 24 and the reverse oligonucleotide primer includes at least 15 consecutive nucleotides complementary to a nucleic acid sequence having at least 80% sequence identity with SEQ ID NO: 41;

b) the forward oligonucleotide primer includes at least 15 consecutive nucleotides of a nucleic acid sequence having at least 80% sequence identity with SEQ ID NO: 25 and the reverse oligonucleotide primer includes at least 15 consecutive nucleotides complementary to a nucleic acid sequence having at least 80% sequence identity with SEQ ID NO: 42;

c) the forward oligonucleotide primer includes at least 15 consecutive nucleotides of a nucleic acid sequence having at least 80% sequence identity with SEQ ID NO: 26 and the reverse oligonucleotide primer includes at least 15 consecutive nucleotides complementary to a nucleic acid sequence having at least 80% sequence identity with SEQ ID NO: 43;

d) the forward oligonucleotide primer includes at least 15 consecutive nucleotides of a nucleic acid sequence having at least 80% sequence identity with SEQ ID NO: 27 and the reverse oligonucleotide primer includes at least 15 consecutive nucleotides complementary to a nucleic acid sequence having at least 80% sequence identity with SEQ ID NO: 44;

e) the forward oligonucleotide primer includes at least 15 consecutive nucleotides of a nucleic acid sequence having at least 80% sequence identity with SEQ ID NO: 28 and the reverse oligonucleotide primer includes at least 15 consecutive nucleotides complementary to a nucleic acid sequence having at least 80% sequence identity with SEQ ID NO: 45;

f) the forward oligonucleotide primer includes at least 15 consecutive nucleotides of a nucleic acid sequence having at least 80% sequence identity with SEQ ID NO: 29 and the reverse oligonucleotide primer includes at least 15 consecutive nucleotides complementary to a nucleic acid sequence having at least 80% sequence identity with SEQ ID NO: 46;

g) the forward oligonucleotide primer includes at least 15 consecutive nucleotides of a nucleic acid sequence having at least 80% sequence identity with SEQ ID NO: 30 and the reverse oligonucleotide primer includes at least 15 consecutive nucleotides complementary to a nucleic acid sequence having at least 80% sequence identity with SEQ ID NO: 47;

h) the forward oligonucleotide primer includes at least 15 consecutive nucleotides of a nucleic acid sequence having at least 80% sequence identity with SEQ ID NO: 31 and the reverse oligonucleotide primer includes at least 15 consecutive nucleotides complementary to a nucleic acid sequence having at least 80% sequence identity with SEQ ID NO: 48;

i) the forward oligonucleotide primer includes at least 15 consecutive nucleotides of a nucleic acid sequence having at least 80% sequence identity with SEQ ID NO: 32 and the reverse oligonucleotide primer includes at least 15 consecutive nucleotides complementary to a nucleic acid sequence having at least 80% sequence identity with SEQ ID NO: 49;

j) the forward oligonucleotide primer includes at least 15 consecutive nucleotides of a nucleic acid sequence having at least 80% sequence identity with SEQ ID NO: 33 and the reverse oligonucleotide primer includes at least 15 consecutive nucleotides complementary to a nucleic acid sequence having at least 80% sequence identity with SEQ ID NO: 50; or k) the forward oligonucleotide primer includes at least 15 consecutive nucleotides of a nucleic acid sequence having at least 80% sequence identity with SEQ ID NO: 34 and the reverse oligonucleotide primer includes at least 15 consecutive nucleotides complementary to a nucleic acid sequence having at least 80% sequence identity with SEQ ID NO: 51.

In certain embodiments of a container described herein, the forward oligonucleotide primer includes at least 15 consecutive nucleotides of a nucleic acid sequence having at least 80% sequence identity with one of SEQ ID NOs: 85-95 and the reverse oligonucleotide primer includes at least 15 consecutive nucleotides complementary to a nucleic acid sequence having at least 80% sequence identity with one of SEQ ID NOs: 96-106.

In certain embodiments of a container described herein:
a) the forward oligonucleotide primer includes at least 15 consecutive nucleotides of a nucleic acid sequence having at least 80% sequence identity with SEQ ID NO: 85 and the reverse oligonucleotide primer includes at least 15 consecutive nucleotides complementary to a nucleic acid sequence having at least 80% sequence identity with SEQ ID NO: 96;
b) the forward oligonucleotide primer includes at least 15 consecutive nucleotides of a nucleic acid sequence having at least 80% sequence identity with SEQ ID NO: 86 and the reverse oligonucleotide primer includes at least 15 consecutive nucleotides complementary to a nucleic acid sequence having at least 80% sequence identity with SEQ ID NO: 97;
c) the forward oligonucleotide primer includes at least 15 consecutive nucleotides of a nucleic acid sequence having at least 80% sequence identity with SEQ ID NO: 87 and the reverse oligonucleotide primer includes at least 15 consecutive nucleotides complementary to a nucleic acid sequence having at least 80% sequence identity with SEQ ID NO: 98;
d) the forward oligonucleotide primer includes at least 15 consecutive nucleotides of a nucleic acid sequence having at least 80% sequence identity with SEQ ID NO: 88 and the reverse oligonucleotide primer includes at least 15 consecutive nucleotides complementary to a nucleic acid sequence having at least 80% sequence identity with SEQ ID NO: 99;
e) the forward oligonucleotide primer includes at least 15 consecutive nucleotides of a nucleic acid sequence having at least 80% sequence identity with SEQ ID NO: 89 and the reverse oligonucleotide primer includes at least 15 consecutive nucleotides complementary to a nucleic acid sequence having at least 80% sequence identity with SEQ ID NO: 100;
f) the forward oligonucleotide primer includes at least 15 consecutive nucleotides of a nucleic acid sequence having at least 80% sequence identity with SEQ ID NO: 90 and the reverse oligonucleotide primer includes at least 15 consecutive nucleotides complementary to a nucleic acid sequence having at least 80% sequence identity with SEQ ID NO: 101;
g) the forward oligonucleotide primer includes at least 15 consecutive nucleotides of a nucleic acid sequence having at least 80% sequence identity with SEQ ID NO: 91 and the reverse oligonucleotide primer includes at least 15 consecutive nucleotides complementary to a nucleic acid sequence having at least 80% sequence identity with SEQ ID NO: 102;
h) the forward oligonucleotide primer includes at least 15 consecutive nucleotides of a nucleic acid sequence having at least 80% sequence identity with SEQ ID NO: 92 and the reverse oligonucleotide primer includes at least 15 consecutive nucleotides complementary to a nucleic acid sequence having at least 80% sequence identity with SEQ ID NO: 103;
i) the forward oligonucleotide primer includes at least 15 consecutive nucleotides of a nucleic acid sequence having at least 80% sequence identity with SEQ ID NO: 93 and the reverse oligonucleotide primer includes at least 15 consecutive nucleotides complementary to a nucleic acid sequence having at least 80% sequence identity with SEQ ID NO: 104;
j) the forward oligonucleotide primer includes at least 15 consecutive nucleotides of a nucleic acid sequence having at least 80% sequence identity with SEQ ID NO: 94 and the reverse oligonucleotide primer includes at least 15 consecutive nucleotides complementary to a nucleic acid sequence having at least 80% sequence identity with SEQ ID NO: 105; or
k) the forward oligonucleotide primer includes at least 15 consecutive nucleotides of a nucleic acid sequence having at least 80% sequence identity with SEQ ID NO: 95 and the reverse oligonucleotide primer includes at least 15 consecutive nucleotides complementary to a nucleic acid sequence having at least 80% sequence identity with SEQ ID NO: 106.

In certain embodiments a container described herein further includes a first probe including at least 15 consecutive nucleotides of a nucleic acid sequence having at least 80% sequence identity with one of SEQ ID NOs: 56-84.

In certain embodiments a container described herein further includes a second probe, the first probe including at least 15 consecutive nucleotides of a nucleic acid sequence having at least 80% sequence identity with one of SEQ ID NOs: 56-67 and the second probe including at least 15 consecutive nucleotides of a nucleic acid sequence having at least 80% sequence identity with one of SEQ ID NOs: 68-79.

In certain embodiments a container described herein further includes a second probe, the first probe including at least 15 consecutive nucleotides of a nucleic acid sequence having at least 80% sequence identity with SEQ ID NO: 56 and the second probe including at least 15 consecutive nucleotides of a nucleic acid sequence having at least 80% sequence identity with SEQ ID NO: 68.

In certain embodiments of a container described herein, the composition includes a first probe and a second probe, the first probe including the sequence of SEQ ID NO: 56 and the second probe including the sequence of SEQ ID NO: 68.

In certain embodiments a container described herein:
a) the first probe includes at least 15 consecutive nucleotides of a nucleic acid sequence having at least 80% sequence identity with SEQ ID NO: 57 and the second probe includes at least 15 consecutive nucleotides of a nucleic acid sequence having at least 80% sequence identity with SEQ ID NO: 69;
b) the first probe includes at least 15 consecutive nucleotides of a nucleic acid sequence having at least 80% sequence identity with SEQ ID NO: 58 and the second probe includes at least 15 consecutive nucleotides of a nucleic acid sequence having at least 80% sequence identity with SEQ ID NO: 70;
c) the first probe includes at least 15 consecutive nucleotides of a nucleic acid sequence having at least 80% sequence identity with SEQ ID NO: 59 and the second probe includes at least 15 consecutive nucleotides of a nucleic acid sequence having at least 80% sequence identity with SEQ ID NO: 71;
d) the first probe includes at least 15 consecutive nucleotides of a nucleic acid sequence having at least 80% sequence identity with SEQ ID NO: 60 and the second probe includes at least 15 consecutive nucleotides of a nucleic acid sequence having at least 80% sequence identity with SEQ ID NO: 72;

e) the first probe includes at least 15 consecutive nucleotides of a nucleic acid sequence having at least 80% sequence identity with SEQ ID NO: 61 and the second probe includes at least 15 consecutive nucleotides of a nucleic acid sequence having at least 80% sequence identity with SEQ ID NO: 73;

f) the first probe includes at least 15 consecutive nucleotides of a nucleic acid sequence having at least 80% sequence identity with SEQ ID NO: 62 and the second probe includes at least 15 consecutive nucleotides of a nucleic acid sequence having at least 80% sequence identity with SEQ ID NO: 74;

g) the first probe includes at least 15 consecutive nucleotides of a nucleic acid sequence having at least 80% sequence identity with SEQ ID NO: 63 and the second probe includes at least 15 consecutive nucleotides of a nucleic acid sequence having at least 80% sequence identity with SEQ ID NO: 75;

h) the first probe includes at least 15 consecutive nucleotides of a nucleic acid sequence having at least 80% sequence identity with SEQ ID NO: 64 and the second probe includes at least 15 consecutive nucleotides of a nucleic acid sequence having at least 80% sequence identity with SEQ ID NO: 76;

i) the first probe includes at least 15 consecutive nucleotides of a nucleic acid sequence having at least 80% sequence identity with SEQ ID NO: 65 and the second probe includes at least 15 consecutive nucleotides of a nucleic acid sequence having at least 80% sequence identity with SEQ ID NO: 77;

j) the first probe includes at least 15 consecutive nucleotides of a nucleic acid sequence having at least 80% sequence identity with SEQ ID NO: 66 and the second probe includes at least 15 consecutive nucleotides of a nucleic acid sequence having at least 80% sequence identity with SEQ ID NO: 78; or k) the first probe includes at least 15 consecutive nucleotides of a nucleic acid sequence having at least 80% sequence identity with SEQ ID NO: 67 and the second probe includes at least 15 consecutive nucleotides of a nucleic acid sequence having at least 80% sequence identity with SEQ ID NO: 79.

In certain embodiments of a container described herein, the first probe includes at least 15 consecutive nucleotides of a nucleic acid sequence having at least 80% sequence identity with one of SEQ ID NOs: 107-128.

In certain embodiments of a container described herein, the first probe includes at least 15 consecutive nucleotides of a nucleic acid sequence having at least 80% sequence identity with one of SEQ ID NOs: 107-117 and the second probe includes at least 15 consecutive nucleotides of a nucleic acid sequence having at least 80% sequence identity with one of SEQ ID NOs: 118-128.

In certain embodiments of a container described herein:

a) the first probe includes at least 15 consecutive nucleotides of a nucleic acid sequence having at least 80% sequence identity with SEQ ID NO: 107 and the second probe includes at least 15 consecutive nucleotides of a nucleic acid sequence having at least 80% sequence identity with SEQ ID NO: 118;

b) the first probe includes at least 15 consecutive nucleotides of a nucleic acid sequence having at least 80% sequence identity with SEQ ID NO: 108 and the second probe includes at least 15 consecutive nucleotides of a nucleic acid sequence having at least 80% sequence identity with SEQ ID NO: 119;

c) the first probe includes at least 15 consecutive nucleotides of a nucleic acid sequence having at least 80% sequence identity with SEQ ID NO: 109 and the second probe includes at least 15 consecutive nucleotides of a nucleic acid sequence having at least 80% sequence identity with SEQ ID NO: 120;

d) the first probe includes at least 15 consecutive nucleotides of a nucleic acid sequence having at least 80% sequence identity with SEQ ID NO: 110 and the second probe includes at least 15 consecutive nucleotides of a nucleic acid sequence having at least 80% sequence identity with SEQ ID NO: 121;

e) the first probe includes at least 15 consecutive nucleotides of a nucleic acid sequence having at least 80% sequence identity with SEQ ID NO: 111 and the second probe includes at least 15 consecutive nucleotides of a nucleic acid sequence having at least 80% sequence identity with SEQ ID NO: 122;

f) the first probe includes at least 15 consecutive nucleotides of a nucleic acid sequence having at least 80% sequence identity with SEQ ID NO: 112 and the second probe includes at least 15 consecutive nucleotides of a nucleic acid sequence having at least 80% sequence identity with SEQ ID NO: 123;

g) the first probe includes at least 15 consecutive nucleotides of a nucleic acid sequence having at least 80% sequence identity with SEQ ID NO: 113 and the second probe includes at least 15 consecutive nucleotides of a nucleic acid sequence having at least 80% sequence identity with SEQ ID NO: 124;

h) the first probe includes at least 15 consecutive nucleotides of a nucleic acid sequence having at least 80% sequence identity with SEQ ID NO: 114 and the second probe includes at least 15 consecutive nucleotides of a nucleic acid sequence having at least 80% sequence identity with SEQ ID NO: 125;

i) the first probe includes at least 15 consecutive nucleotides of a nucleic acid sequence having at least 80% sequence identity with SEQ ID NO: 115 and the second probe includes at least 15 consecutive nucleotides of a nucleic acid sequence having at least 80% sequence identity with SEQ ID NO: 126;

j) the first probe includes at least 15 consecutive nucleotides of a nucleic acid sequence having at least 80% sequence identity with SEQ ID NO: 116 and the second probe includes at least 15 consecutive nucleotides of a nucleic acid sequence having at least 80% sequence identity with SEQ ID NO: 127; or k) the first probe includes at least 15 consecutive nucleotides of a nucleic acid sequence having at least 80% sequence identity with SEQ ID NO: 117 and the second probe includes at least 15 consecutive nucleotides of a nucleic acid sequence having at least 80% sequence identity with SEQ ID NO: 128.

In certain embodiments of a container described herein, one or both of the first probe and the second probe includes no more than two mismatched nucleotides, in that no more than two nucleotides differ from the sequence of a corresponding portion of the HIV nucleic acid molecule.

At least one aspect of the present invention relates to a method of detecting an HIV nucleic acid in a sample, the method including: providing a nucleic acid sample from an individual who has an HIV infection or is suspected of having an HIV infection, such that the nucleic acid sample includes an HIV nucleic acid molecule; preparing an amplification reaction mixture that includes the HIV nucleic acid molecule, a forward oligonucleotide primer, and a reverse oligonucleotide primer, the forward oligonucleotide primer including at least 15 consecutive nucleotides of a nucleic acid sequence having at least 80% sequence identity with one of SEQ ID NOs: 23-39 and the reverse oligonucleotide primer including at least 15 consecutive nucleotides complementary to a nucleic acid sequence having at least 80% sequence identity with one of SEQ ID NOs: 40-55; subjecting the amplification reaction mixture to one or more amplification cycles, such that the HIV nucleic acid molecule is amplified to produce an amplicon molecule; and detecting the presence of an amplicon generated by the extension. In certain embodiments, the HIV nucleic acid molecule is an HIV cDNA molecule. In certain embodiments, the method further includes: producing the HIV cDNA molecule by reverse transcription. In certain embodiments, the amplification reaction mixture further includes one or more probes including at least 15 consecutive nucleotides of a nucleic acid sequence having at least 80% sequence identity with one of SEQ ID NOs: 56-84. In certain such embodiments, the amplification reaction mixture includes a first probe and a second probe, the first probe including at least 15 consecutive nucleotides of a nucleic acid sequence having at least 80% sequence identity with one of SEQ ID NOs: 56-67 and the second probe including at least 15 consecutive nucleotides of a nucleic acid sequence having at least 80% sequence identity with one of SEQ ID NOs: 68-79. In certain such embodiments, the first probe includes at least 15 consecutive nucleotides of a nucleic acid sequence having at least 80% sequence identity with SEQ ID NO: 56 and the second probe includes at least 15 consecutive nucleotides of a nucleic acid sequence having at least 80% sequence identity with SEQ ID NO: 68. In certain such embodiments, the first probe includes the sequence of SEQ ID NO: 56 and the second probe includes the sequence of SEQ ID NO: 68. In various embodiments:

a) the forward oligonucleotide primer includes at least 15 consecutive nucleotides of a nucleic acid sequence having at least 80% sequence identity with SEQ ID NO: 24 and the reverse oligonucleotide primer includes at least 15 consecutive nucleotides complementary to a nucleic acid sequence having at least 80% sequence identity with SEQ ID NO: 41;

b) the forward oligonucleotide primer includes at least 15 consecutive nucleotides of a nucleic acid sequence having at least 80% sequence identity with SEQ ID NO: 25 and the reverse oligonucleotide primer includes at least 15 consecutive nucleotides complementary to a nucleic acid sequence having at least 80% sequence identity with SEQ ID NO: 42;

c) the forward oligonucleotide primer includes at least 15 consecutive nucleotides of a nucleic acid sequence having at least 80% sequence identity with SEQ ID NO: 26 and the reverse oligonucleotide primer includes at least 15 consecutive nucleotides complementary to a nucleic acid sequence having at least 80% sequence identity with SEQ ID NO: 43;

d) the forward oligonucleotide primer includes at least 15 consecutive nucleotides of a nucleic acid sequence having at least 80% sequence identity with SEQ ID NO: 27 and the reverse oligonucleotide primer includes at least 15 consecutive nucleotides complementary to a nucleic acid sequence having at least 80% sequence identity with SEQ ID NO: 44;

e) the forward oligonucleotide primer includes at least 15 consecutive nucleotides of a nucleic acid sequence having at least 80% sequence identity with SEQ ID NO: 28 and the reverse oligonucleotide primer includes at least 15 consecutive nucleotides complementary to a nucleic acid sequence having at least 80% sequence identity with SEQ ID NO: 45;

f) the forward oligonucleotide primer includes at least 15 consecutive nucleotides of a nucleic acid sequence having at least 80% sequence identity with SEQ ID NO: 29 and the reverse oligonucleotide primer includes at least 15 consecutive nucleotides complementary to a nucleic acid sequence having at least 80% sequence identity with SEQ ID NO: 46;

g) the forward oligonucleotide primer includes at least 15 consecutive nucleotides of a nucleic acid sequence having at least 80% sequence identity with SEQ ID NO: 30 and the reverse oligonucleotide primer includes at least 15 consecutive nucleotides complementary to a nucleic acid sequence having at least 80% sequence identity with SEQ ID NO: 47;

h) the forward oligonucleotide primer includes at least 15 consecutive nucleotides of a nucleic acid sequence having at least 80% sequence identity with SEQ ID NO: 31 and the reverse oligonucleotide primer includes at least 15 consecutive nucleotides complementary to a nucleic acid sequence having at least 80% sequence identity with SEQ ID NO: 48;

i) the forward oligonucleotide primer includes at least 15 consecutive nucleotides of a nucleic acid sequence having at least 80% sequence identity with SEQ ID NO: 32 and the reverse oligonucleotide primer includes at least 15 consecutive nucleotides complementary to a nucleic acid sequence having at least 80% sequence identity with SEQ ID NO: 49;

j) the forward oligonucleotide primer includes at least 15 consecutive nucleotides of a nucleic acid sequence having at least 80% sequence identity with SEQ ID NO: 33 and the reverse oligonucleotide primer includes at least 15 consecutive nucleotides complementary to a nucleic acid sequence having at least 80% sequence identity with SEQ ID NO: 50; or k) the forward oligonucleotide primer includes at least 15 consecutive nucleotides of a nucleic acid sequence having at least 80% sequence identity with SEQ ID NO: 34 and the reverse oligonucleotide primer includes at least 15 consecutive nucleotides complementary to a nucleic acid sequence having at least 80% sequence identity with SEQ ID NO: 51.

In certain embodiments, of a method as described above, the forward oligonucleotide primer includes at least 15 consecutive nucleotides of a nucleic acid sequence having at least 80% sequence identity with one of SEQ ID NOs: 85-95 and the reverse oligonucleotide primer includes at least 15 consecutive nucleotides complementary to a nucleic acid sequence having at least 80% sequence identity with one of SEQ ID NOs: 96-106.

In certain embodiments, of a method as described above:

a) the forward oligonucleotide primer includes at least 15 consecutive nucleotides of a nucleic acid sequence having at least 80% sequence identity with SEQ ID NO: 85 and the reverse oligonucleotide primer includes at least 15 consecutive nucleotides complementary to a nucleic acid sequence having at least 80% sequence identity with SEQ ID NO: 96;

b) the forward oligonucleotide primer includes at least 15 consecutive nucleotides of a nucleic acid sequence having at least 80% sequence identity with SEQ ID NO: 86 and the reverse oligonucleotide primer includes at least 15 consecutive nucleotides complementary to a nucleic acid sequence having at least 80% sequence identity with SEQ ID NO: 97;

c) the forward oligonucleotide primer includes at least 15 consecutive nucleotides of a nucleic acid sequence having at least 80% sequence identity with SEQ ID NO: 87 and the reverse oligonucleotide primer includes at least 15 consecutive nucleotides complementary to a nucleic acid sequence having at least 80% sequence identity with SEQ ID NO: 98;

d) the forward oligonucleotide primer includes at least 15 consecutive nucleotides of a nucleic acid sequence having at least 80% sequence identity with SEQ ID NO: 88 and the reverse oligonucleotide primer includes at least 15 consecutive nucleotides complementary to a nucleic acid sequence having at least 80% sequence identity with SEQ ID NO: 99;

e) the forward oligonucleotide primer includes at least 15 consecutive nucleotides of a nucleic acid sequence having at least 80% sequence identity with SEQ ID NO: 89 and the reverse oligonucleotide primer includes at least 15 consecutive nucleotides complementary to a nucleic acid sequence having at least 80% sequence identity with SEQ ID NO: 100;

f) the forward oligonucleotide primer includes at least 15 consecutive nucleotides of a nucleic acid sequence having at least 80% sequence identity with SEQ ID NO: 90 and the reverse oligonucleotide primer includes at least 15 consecutive nucleotides complementary to a nucleic acid sequence having at least 80% sequence identity with SEQ ID NO: 101 g) the forward oligonucleotide primer includes at least 15 consecutive nucleotides of a nucleic acid sequence having at least 80% sequence identity with SEQ ID NO: 91 and the reverse oligonucleotide primer includes at least 15 consecutive nucleotides complementary to a nucleic acid sequence having at least 80% sequence identity with SEQ ID NO: 102;

h) the forward oligonucleotide primer includes at least 15 consecutive nucleotides of a nucleic acid sequence having at least 80% sequence identity with SEQ ID NO: 92 and the reverse oligonucleotide primer includes at least 15 consecutive nucleotides complementary to a nucleic acid sequence having at least 80% sequence identity with SEQ ID NO: 103;

i) the forward oligonucleotide primer includes at least 15 consecutive nucleotides of a nucleic acid sequence having at least 80% sequence identity with SEQ ID NO: 93 and the reverse oligonucleotide primer includes at least 15 consecutive nucleotides complementary to a nucleic acid sequence having at least 80% sequence identity with SEQ ID NO: 104;

j) the forward oligonucleotide primer includes at least 15 consecutive nucleotides of a nucleic acid sequence having at least 80% sequence identity with SEQ ID NO: 94 and the reverse oligonucleotide primer includes at least 15 consecutive nucleotides complementary to a nucleic acid sequence having at least 80% sequence identity with SEQ ID NO: 105; or k) the forward oligonucleotide primer includes at least 15 consecutive nucleotides of a nucleic acid sequence having at least 80% sequence identity with SEQ ID NO: 95 and the reverse oligonucleotide primer includes at least 15 consecutive nucleotides complementary to a nucleic acid sequence having at least 80% sequence identity with SEQ ID NO: 106.

In certain embodiments, of a method as described above, the forward oligonucleotide primer includes at least 15 consecutive nucleotides of SEQ ID NO 23 and the reverse oligonucleotide primer includes at least 15 consecutive nucleotides complementary to a nucleic acid sequence having the sequence of SEQ ID NO: 40. In certain embodiments, the forward oligonucleotide primer includes the sequence of SEQ ID NO 23 and the reverse oligonucleotide primer includes a sequence complementary to the sequence of SEQ ID NO: 40.

In certain embodiments, of a method as described above, the forward oligonucleotide primer includes no more than two mismatched nucleotides, in that no more than two nucleotides differ from the sequence of a corresponding portion of the HIV nucleic acid molecule.

In certain embodiments, of a method as described above, the reverse oligonucleotide primer includes no more than two mismatched nucleotides, in that no more than two nucleotides differ from the sequence of a corresponding portion of the HIV nucleic acid molecule.

Definitions

Primer or oligonucleotide primer, as used herein, means a nucleic acid molecule used, capable of being used, or for use in generating amplicons from a template nucleic acid molecule. A pair of oligonucleotide primers, as used herein, refers to a set of two oligonucleotide primers that are respectively complementary to a first strand and a second strand of a template double-stranded nucleic acid molecule. First and second oligonucleotide primers of a pair of oligonucleotide primers may be referred to as a "forward" oligonucleotide primer and a "reverse" oligonucleotide primer, respectively, with respect to a template nucleic acid strand, in that the forward oligonucleotide primer is capable of hybridizing with a nucleic acid strand complementary to the template nucleic acid strand, the reverse oligonucleotide primer is capable of hybridizing with the template nucleic acid strand, and the position of the forward oligonucleotide primer with respect to the template nucleic acid strand is 5' of the position of the reverse oligonucleotide primer sequence with respect to the template nucleic acid strand. It will be understood by those of skill in the art that the identification of a first and second oligonucleotide primer as forward and reverse oligonucleotide primers, respectively, is arbitrary inasmuch as these identifiers depend upon whether a given nucleic acid strand or its complement is utilized as a template nucleic acid molecule.

Amplicon or amplicon molecule, as used herein, means a nucleic acid molecule generated by transcription from a template nucleic acid molecule, or a nucleic acid molecule having a sequence complementary thereto, or a double-stranded nucleic acid including any such nucleic acid molecule. Transcription can be initiated from a primer.

HIV nucleic acid molecule, as used herein, means, a nucleic acid molecule encoding all or a portion of a genome of a human immunodeficiency virus. An HIV nucleic acid molecule may be, for example, 100 or more nucleotides or base pairs in length, e.g., at least 150, 200, 250, 500, 1,000, 2,000, 3,000, 4,000, 5,000, 6,000, 7,000, 8,000, 9,000, 10,000, 11,000, or more nucleotides or base pairs in length. An HIV nucleic acid molecule may be a single-stranded RNA molecule or any corresponding double-stranded RNA molecule, single-stranded DNA molecule, or double-stranded DNA molecule, respectfully encompassing DNA and RNA sequences complementary to a single-stranded RNA HIV nucleic acid molecule and/or nucleic acid molecules complementary thereto. Any strand of an HIV nucleic acid molecule may have at least 40%, 45%, 50%, 55%, 60%, 65%, 70%, 75%, 80%, 85%, 90%, 95%, or 100% identity to all or a portion of any known or isolated HIV genome sequence or a nucleic acid molecule complementary thereto, or may be capable of hybridizing to an isolated HIV genome sequence or a nucleic acid molecule complementary thereto.

Reverse transcription, as used herein, means a process by which a DNA sequence is generated from an RNA template.

cDNA, as used herein, means a DNA nucleic acid molecule generated from an RNA template.

Identity, as used herein, means the overall relatedness between a reference nucleic acid or amino acid sequence and one or more other nucleic acid or amino acid sequences. Identity may be expressed as a percentage. Methods for calculating percent identity are known in the art. Calculation of identity does not require that sequences be of same or similar length. Calculation of the percent identity can be performed by aligning the two sequences for optimal comparison purposes (e.g., gaps can be introduced in one or both of a first and a second nucleic acid sequences for optimal alignment and non-identical sequences can be disregarded for comparison purposes) and nucleotides at corresponding nucleotide positions can then be compared. When a position in a first sequence is occupied by the same nucleotide as the corresponding position in a second sequence, then the sequences are identical at that position. The percent identity between the two sequences is a function of the number of identical positions shared by the sequences, typically taking into account, e.g., the number and/or length of any gaps introduced for optimal alignment of the sequences. The comparison of sequences and determination of percent identity between two sequences can be accomplished using a mathematical algorithm, such as BLAST®.

Hybridization, as used herein, means formation of a double-stranded nucleic acid molecule from a first single-stranded nucleic acid molecule and a second single-stranded nucleic acid molecule by formation of hydrogen bonds between complementary nucleotides. Generally, hybridization may occur, for example, between nucleotide sequences having at least 70% complementarity, e.g., at least 75%, 80%, 85%, 90%, 91%, 92%, 93%, 94%, 95%, 96%, 97%, 98%, 99%, or 100% complementarity. Conditions under which hybridization can occur are known in the art.

Treatment, as used herein, means any administration of a therapeutic composition that partially or completely alleviates, ameliorates, relieves, inhibits, delays onset of, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

Therapeutically effective amount, as used herein, means an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular subject. Rather, a therapeutically effective amount may be that amount that provides a particular desired pharmacological response in a significant number of subjects when administered to subjects in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

Amplification, as used herein, refers to the use of a template nucleic acid molecule in combination with various reagents to generate further nucleic acid molecules from the template nucleic acid molecule, which further nucleic acid molecules may be identical to or similar to (e.g., at least 70% identical, e.g., at least 75%, 80%, 85%, 90%, 91%, 92%, 93%, 94%, 95%, 96%, 97%, 98%, 99%, or 100% identical to) a segment of the template nucleic acid molecule and/or a sequence complementary thereto.

Amplification reaction mixture or amplification reaction, as used herein, means a template nucleic acid molecule together with reagents sufficient for amplification of the template nucleic acid molecule.

HIV viral load, or HIV load, as used herein, means the presence, absence, or relative or absolute number, amount, or level of HIV genomes or representative portions thereof detected in a unit of sample. HIV viral load may be quantitative, semi-quantitative, relative, or qualitative.

BRIEF DESCRIPTION OF THE DRAWINGS

FIG. 2 shows the number of HIV-1 genomes (and HIV-1 genome groups) that perfectly matched with certain primer and probe sequences.

FIG. 3 is a chart showing the sequences of certain primers and probes of the invention.

FIG. 5 is a chart showing primers and probes of a commercially available HIV-1 viral load assay. Nucleotides mismatched as compared to certain HIV-1 subtypes are shown.

FIG. 6 is chart showing that primers and probes of a commercially available HIV-1 viral load assay have potentially significant mismatches with certain integrase resistance mutations.

DETAILED DESCRIPTION

Figure 1:
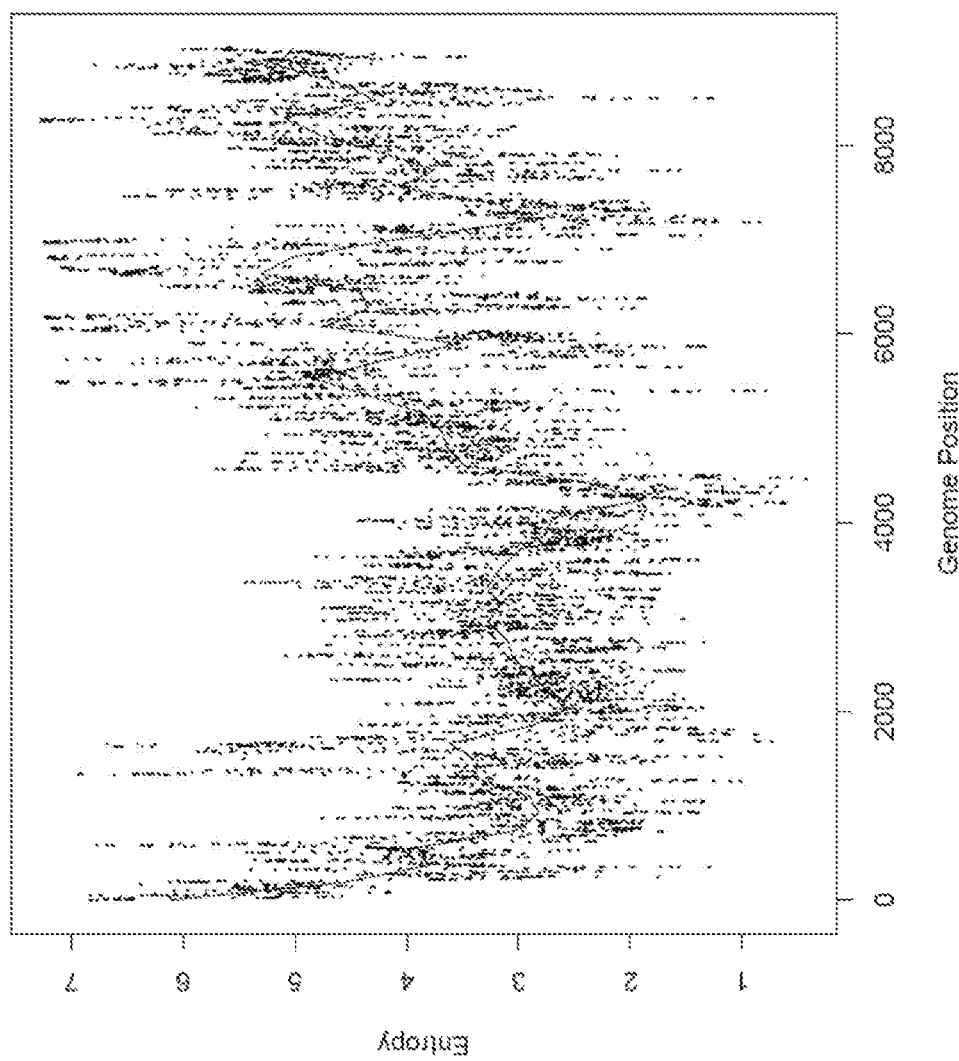
FIG. 1 is a graph showing a global minimum entropy score in the integrase gene.

The present invention is based in part on the present inventors' appreciation that certain sequences within an HIV genome are more likely to successfully detect HIV across a breadth of HIV variants. As noted previously, the ability to detect and/or quantify the presence and/or load of HIV in a subject is important to, among other things, the diagnosis and treatment of infected individuals. However, detecting and/or quantifying the presence and/or load of HIV in a subject has proven challenging due to a number of factors, including HIV heterogeneity and high rate of mutation. The present invention is based, in part, on the discovery of oligonucleotide reagents described herein that detectably amplify sequences from a greater breadth of HIV samples than certain prior reagents and/or that generate amplicons from HIV genomes from which certain prior reagents would not have generated amplicons. Thus, oligonucleotide reagents as described herein provide unexpected benefits in the detection and/or quantification of the presence and/or load of HIV in a subject, and thereby in the diagnosis and treatment of HIV.

Oligonucleotides

The present invention includes, among other things, methods and reagents for the detection and/or quantification of HIV. As is discussed above, identification of methods and reagents capable of detecting and/or quantifying HIV in a sample, and further capable of doing so across a sufficient breadth of HIV variants, requires, among other things, identification of functional oligonucleotide sequences. The present invention encompasses the identification of such oligonucleotide sequences.

In particular embodiments, the present invention encompasses, among other things, an oligonucleotide having a nucleic acid sequence having at least 80% identity (e.g., at least 80%, 85%, 90%, 95%, or 100% identity) to a sequence of between 6 and 40 base pairs selected from any one of SEQ ID NOs: 24-34 and/or an oligonucleotide having a nucleic acid sequence having at least 80% identity (e.g., at least 80%, 85%, 90%, 95%, or 100% identity) to a sequence of between 6 and 40 base pairs selected from any one of SEQ ID NOs: 41-51. In particular embodiments, the present invention encompasses, among other things, an oligonucleotide having a nucleic acid sequence having at least 80% identity (e.g., at least 80%, 85%, 90%, 95%, or 100% identity) to a sequence of between 6 and 20 base pairs selected from any one of SEQ ID NOs: 85-95 and/or an oligonucleotide having a nucleic acid sequence having at least 80% identity (e.g., at least 80%, 85%, 90%, 95%, or 100% identity) to a sequence of between 6 and 20 base pairs selected from any one of SEQ ID NOs: 96-106. In various embodiments, any of one or more oligonucleotides may be between 6 and 40 nucleotides in length, between 8 and 35 nucleotides in length, between 10 and 30 nucleotides in length, between 12 and 28 nucleotides in length, between 14 and 26 nucleotides in length, between 16 and 26 nucleotides in length, or between 18 and 24 nucleotides in length. Thus, in various embodiments, any of one or more oligonucleotides may be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In particular embodiments, the present invention encompasses, among other things, an oligonucleotide having a nucleic acid sequence having at least 80% identity (e.g., at least 80%, 85%, 90%, 95%, or 100% identity) to a sequence of between 6 and 40 base pairs selected from a 40 base pair region of any one of SEQ ID NOs: 1-11 that includes a sequence corresponding to one or more of SEQ ID NOs: 35-39 and/or an oligonucleotide having a nucleic acid sequence having at least 80% identity (e.g., at least 80%, 85%, 90%, 95%, or 100% identity) to a sequence of between 6 and 40 base pairs selected from a 40 base pair region of any one of SEQ ID NOs: 1-11 that includes a sequence corresponding to one or more of SEQ ID NOs: 52-55. In particular embodiments, the present invention encompasses, among other things, an oligonucleotide having a nucleic acid sequence having at least 80% identity (e.g., at least 80%, 85%, 90%, 95%, or 100% identity) to a sequence of between 6 and 30 base pairs selected from a 30 base pair region of any one of SEQ ID NOs: 1-11 that includes a sequence corresponding to one or more of SEQ ID NOs: 35-39 and/or an oligonucleotide having a nucleic acid sequence having at least 80% identity (e.g., at least 80%, 85%, 90%, 95%, or 100% identity) to a sequence of between 6 and 30 base pairs selected from a 30 base pair region of any one of SEQ ID NOs: 1-11 that includes a sequence corresponding to one or more of SEQ ID NOs: 52-55. Thus, in various embodiments, any of one or more oligonucleotides may be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In particular embodiments, the present invention encompasses, among other things, an oligonucleotide having a nucleic acid sequence having at least 80% identity (e.g., at least 80%, 85%, 90%, 95%, or 100% identity) to a sequence of between 6 and 40 base pairs selected from any one of SEQ ID NOs: 56-67. In particular embodiments, the present invention encompasses, among other things, an oligonucleotide having a nucleic acid sequence having at least 80% identity (e.g., at least 80%, 85%, 90%, 95%, or 100% identity) to a sequence of between 6 and 24 base pairs selected from any one of SEQ ID NOs: 107-117. In various embodiments, any of one or more oligonucleotides may be between 6 and 40 nucleotides in length, between 8 and 35 nucleotides in length, between 10 and 30 nucleotides in length, between 12 and 28 nucleotides in length, between 14 and 26 nucleotides in length, between 16 and 26 nucleotides in length, or between 18 and 24 nucleotides in length. Thus, in various embodiments, any of one or more oligonucleotides may be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In particular embodiments, the present invention encompasses, among other things, an oligonucleotide having a nucleic acid sequence having at least 80% identity (e.g., at least 80%, 85%, 90%, 95%, or 100% identity) to a sequence of between 6 and 40 base pairs selected from any one of SEQ ID NOs: 68-79. In particular embodiments, the present invention encompasses, among other things, an oligonucleotide having a nucleic acid sequence having at least 80% identity (e.g., at least 80%, 85%, 90%, 95%, or 100% identity) to a sequence of between 6 and 24 base pairs selected from any one of SEQ ID NOs: 118-128. In various embodiments, any of one or more oligonucleotides may be between 6 and 40 nucleotides in length, between 8 and 35 nucleotides in length, between 10 and 30 nucleotides in length, between 12 and 28 nucleotides in length, between 14 and 26 nucleotides in length, between 16 and 26 nucleotides in length, or between 18 and 24 nucleotides in length. Thus, in various embodiments, any of one or more oligonucleotides may be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In particular embodiments, the present invention includes, among other things, an oligonucleotide having a nucleic acid sequence according to SEQ ID NO: 23. In particular embodiments, the present invention includes, among other things, an oligonucleotide having a nucleic acid sequence complementary to SEQ ID NO: 40.

In particular embodiments, the present invention includes, among other things, an oligonucleotide having a nucleic acid sequence according to SEQ ID NO: 56.

In particular embodiments, the present invention includes, among other things, an oligonucleotide having a nucleic acid sequence according to SEQ ID NO: 68.

In particular embodiments, the present invention includes, among other things, an oligonucleotide having a nucleic acid sequence according to SEQ ID NO: 23 and an oligonucleotide having a nucleic acid sequence complementary to SEQ ID NO: 40.

In particular embodiments, the present invention includes, among other things, an oligonucleotide having a nucleic acid sequence according to SEQ ID NO: 56 and an oligonucleotide having a nucleic acid sequence according to SEQ ID NO: 68.

In particular embodiments, the present invention includes, among other things, an oligonucleotide having a nucleic acid sequence according to SEQ ID NO: 23, an oligonucleotide having a nucleic acid sequence complementary to SEQ ID NO: 40, an oligonucleotide having a nucleic acid sequence according to SEQ ID NO: 56 and an oligonucleotide having a nucleic acid sequence according to SEQ ID NO: 68.

In various embodiments of the present invention any of one or more oligonucleotides as described herein may be utilized together with any of one or more other oligonucleotides, as described herein or otherwise, to amplify DNA and/or detect amplification of DNA.

Primers

It is to be understood that the sequence of a single nucleic acid strand is representative of the provided sequence of that single nucleic acid strand, the sequence of a nucleic acid strand complementary to that single nucleic acid strand, and the sequence of a double-stranded nucleic acid molecule including a first strand having the sequence of that strand and a second strand having a sequence complementary to that strand.

In various embodiments, an oligonucleotide primer or forward oligonucleotide primer can be an oligonucleotide having a nucleic acid sequence having at least 80% identity (e.g., at least 80%, 85%, 90%, 95%, or 100% identity) to a sequence of between 6 and 40 base pairs selected from any one of SEQ ID NOs: 24-34, or from a sequence complementary thereto. In various embodiments, an oligonucleotide primer or forward oligonucleotide primer can be an oligonucleotide having a nucleic acid sequence having at least 80% identity (e.g., at least 80%, 85%, 90%, 95%, or 100% identity) to a sequence of between 6 and 20 base pairs selected from any one of SEQ ID NOs: 85-95. In various embodiments, an oligonucleotide primer or forward oligonucleotide primer can be between 6 and 40 nucleotides in length, between 8 and 35 nucleotides in length, between 10 and 30 nucleotides in length, between 12 and 28 nucleotides in length, between 14 and 26 nucleotides in length, between 16 and 26 nucleotides in length, or between 18 and 24 nucleotides in length. Thus, in various embodiments, an oligonucleotide primer or forward oligonucleotide primer can be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In various embodiments, an oligonucleotide primer or reverse oligonucleotide primer can be an oligonucleotide having a nucleic acid sequence having at least 80% identity (e.g., at least 80%, 85%, 90%, 95%, or 100% identity) to a sequence of between 6 and 40 base pairs complementary to any one of SEQ ID NOs: 41-51. In various embodiments, an oligonucleotide primer or reverse oligonucleotide primer can be an oligonucleotide having a nucleic acid sequence having at least 80% identity (e.g., at least 80%, 85%, 90%, 95%, or 100% identity) to a sequence of between 6 and 20 base pairs complementary to any one of SEQ ID NOs: 96-106, or from a sequence complementary thereto. In various embodiments, an oligonucleotide primer or reverse oligonucleotide primer can be between 6 and 40 nucleotides in length, between 8 and 35 nucleotides in length, between 10 and 30 nucleotides in length, between 12 and 28 nucleotides in length, between 14 and 26 nucleotides in length, between 16 and 26 nucleotides in length, or between 18 and 24 nucleotides in length. Thus, in various embodiments, an oligonucleotide primer or reverse oligonucleotide primer can be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In various embodiments, an oligonucleotide primer or forward oligonucleotide primer can be an oligonucleotide having a nucleic acid sequence having at least 80% identity (e.g., at least 80%, 85%, 90%, 95%, or 100% identity) to a sequence of between 6 and 40 base pairs selected from a 40 base pair region of any one of SEQ ID NOs: 1-11 that includes a sequence corresponding to one or more of SEQ ID NOs: 35-39, or from a sequence complementary thereto. In various embodiments, an oligonucleotide primer or forward oligonucleotide primer can be an oligonucleotide having a nucleic acid sequence having at least 80% identity (e.g., at least 80%, 85%, 90%, 95%, or 100% identity) to a sequence of between 6 and 30 base pairs selected from a 30 base pair region of any one of SEQ ID NOs: 1-11 that includes a sequence corresponding to one or more of SEQ ID NOs: 35-39. Thus, in various embodiments, any of one or more oligonucleotide primers or forward oligonucleotide primers may be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In various embodiments, an oligonucleotide primer or reverse oligonucleotide primer can be an oligonucleotide having a nucleic acid sequence having at least 80% identity (e.g., at least 80%, 85%, 90%, 95%, or 100% identity) to a sequence of between 6 and 40 base pairs selected from a 40 base pair region complementary to any one of SEQ ID NOs: 1-11, or a sequence complementary thereto, that includes a sequence corresponding to one or more of SEQ ID NOs: 52-55, or a sequence complementary thereto. In various embodiments, an oligonucleotide primer or reverse oligonucleotide primer can be an oligonucleotide having a nucleic acid sequence having at least 80% identity (e.g., at least 80%, 85%, 90%, 95%, or 100% identity) to a sequence of between 6 and 30 base pairs selected from a 30 base pair region complementary to any one of SEQ ID NOs: 1-11, or a sequence complementary thereto, that includes a sequence corresponding to one or more of SEQ ID NOs: 52-55, or a sequence complementary thereto. Thus, in various embodiments, any of one or more oligonucleotide primers or reverse oligonucleotide primers may be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In certain embodiments, a pair of oligonucleotide primers, including a forward primer and a reverse primer, is selected from the following, or from a pair of oligonucleotide primers complementary thereto:

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of any one of SEQ ID NOs: 23-39 or any one of SEQ ID NOs: 85-95, and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to a sequence selected from any one of SEQ ID NOs: 40-55 or any one of SEQ ID NOs: 96-106.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 23 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 40.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 24 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 41.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 25 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 42.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 26 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 43.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 27 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 44.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 28 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 45.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 29 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 46.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 30 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 47.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 31 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 48.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 32 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 49.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 33 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 50.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 34 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 51.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 85 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 96.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 86 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 97.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 87 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 98.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 88 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 99.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 89 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 100.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 90 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 101.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 91 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 102.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 92 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 103.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 93 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 104.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 94 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 105.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 95 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 106.

In various embodiments, an oligonucleotide primer or forward oligonucleotide primer can be an oligonucleotide having a nucleic acid sequence according to SEQ ID NO: 23. In various embodiments, an oligonucleotide primer or reverse oligonucleotide primer can be an oligonucleotide having a nucleic acid sequence complementary to the sequence of SEQ ID NO: 40.

In certain embodiments, a pair of oligonucleotide primers, including a forward primer and a reverse primer, includes a forward oligonucleotide primer having a nucleic acid sequence according to SEQ ID NO: 23 and a reverse oligonucleotide primer having a nucleic acid sequence complementary to the sequence of SEQ ID NO: 40.

In various embodiments a reference nucleic acid stand is a nucleic acid strand according to the sequence of any one of SEQ ID NOs: 1-11 or an HIV sequence having at least 80% identity to any one of SEQ ID NOs: 1-11 (e.g., at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity thereto), or a nucleic acid sequence complementary thereto.

Those of skill in the art will appreciate that reference to an oligonucleotide primer may refer to a single oligonucleotide primer molecule, and may also or instead refer in certain instances to a plurality of oligonucleotide primer molecules of a particular sequence or type present in a reaction.

Those of skill in the art will appreciate that it is not necessary that an oligonucleotide primer have 100% sequence identity with a template or amplicon in order to hybridize with the template or amplicon and/or participate in one or more steps of an amplification reaction with the template or amplicon. In some instances, an oligonucleotide primer may have one or more mismatches with a template or amplicon with which it hybridizes, e.g., 1 mismatch, 2 mismatches, 3 mismatches, 4 mismatches, 5 mismatches, 6 mismatches, 7 mismatches, 8 mismatches, 9 mismatches, 10 mismatches, or more mismatches. Accordingly, an oligonucleotide primer present in an amplification reaction with an amplicon or template may have no more than, e.g., 70% identity with any portion of the amplicon or template, e.g., 70% or more identity, 75% or more identity, 80% or more identity, 85% or more identity, 90% or more identity, 95% or more identity, 96% or more identity, 97% or more identity, 98% or more identity, or 99% or more identity with the template or amplicon.

In any of the various embodiments described herein, any one or more nucleotides of a nucleic acid molecule may be a natural nucleotide (A, C, G, T, or U), a synthetic nucleotide, or a modified nucleotide.

Amplicons

In particular embodiments, the present invention encompasses, among other things, an amplicon having at least 80% identity to a portion of any one of SEQ ID NOs: 1-11 that is amplified by any oligonucleotide primer or pair of oligonucleotide primers described herein. In particular embodiments, the present invention encompasses, among other things, an amplicon having at least 80% identity to a portion of the sequence of a reference strand selected from any one of SEQ ID NOs: 1-11 or to portion of the sequence of a reference strand having a sequence complementary to any one of SEQ ID NOs: 1-11, e.g., such that the amplicon includes all or a portion of the sequence of any one of SEQ ID NOs: 24-55 or all or a portion of a sequence complementary to any one of SEQ ID NOs 24-55. In various embodiments an amplicon has a sequence having at least 80% identity to all or a portion of any one of SEQ ID NOs: 12-22, or a sequence complementary thereto, wherein the portion may be 40-800, 40-700, 40-600, 40-500, 40-400, 40-300, 40-200, 40-175, 40-150, 40-125, 40-100, 40-75, or 40-50 nucleotides in length.

In certain embodiments, an amplicon is (a) a portion of any one of SEQ ID NOs: 1-22, or a sequence complementary thereto, that is or is capable of being amplified by a pair of primers selected from the following; (b) a nucleic acid complementary to a portion of any one of SEQ ID NOs: 1-22 that is or is capable of being amplified by a pair of primers selected from the following, or a double-stranded sequence comprising (a) or (b):

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of any one of SEQ ID NOs: 23-39 or any one of SEQ ID NOs: 85-95, and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to a sequence selected from any one of SEQ ID NOs: 40-55 or any one of SEQ ID NOs: 96-106.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 23 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 40.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 24 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 41.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 25 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 42.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 26 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 43.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 27 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 44.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 28 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 45.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 29 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 46.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 30 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 47.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 31 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 48.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 32 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 49.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 33 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 50.

A forward oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 34 and a reverse oligonucleotide primer including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) complementary to the sequence of SEQ ID NO: 51.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 85 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 96.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 86 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 97.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 87 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 98.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 88 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 99.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 89 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 100.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 90 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 101.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 91 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 102.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 92 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 103.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 93 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 104.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 94 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 105.

A forward oligonucleotide primer including or consisting of a sequence having at least 80% identity (e.g., at least 80%, 85%, 90%, 95%, or 100% identity) to a sequence including or consisting of 6 to 20 consecutive nucleotides (e.g., 6, 7, 8, 9, 10, 11, 12, 13, 14, 15, 16, 17, 18, 19, or 20 nucleotides) selected from the sequence of SEQ ID NO: 95 and a reverse oligonucleotide primer including or consisting of a sequence having at least 80% identity (e.g., at least 80%, 85%, 90%, 95%, or 100% identity) to a sequence including or consisting of 6 to 18 consecutive nucleotides (e.g., 6, 7, 8, 9, 10, 11, 12, 13, 14, 15, 16, 17, or 18 nucleotides) complementary to the sequence of SEQ ID NO: 106.

In various embodiments, an oligonucleotide primer or forward oligonucleotide primer can be an oligonucleotide having a nucleic acid sequence according to SEQ ID NO: 23.

In various embodiments, an oligonucleotide primer or reverse oligonucleotide primer can be an oligonucleotide having a nucleic acid sequence complementary to the sequence of SEQ ID NO: 40.

In certain embodiments, a pair of oligonucleotide primers, including a forward primer and a reverse primer, includes a forward oligonucleotide primer having a nucleic acid sequence according to SEQ ID NO: 23 and a reverse oligonucleotide primer having a nucleic acid sequence complementary to the sequence of SEQ ID NO: 40.

In various embodiments a reference nucleic acid stand is a nucleic acid strand according to the sequence of any one of SEQ ID NOs: 1-11 or an HIV sequence having at least 80% identity to any one of SEQ ID NOs: 1-11 (e.g., at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity thereto), or a nucleic acid sequence complementary thereto.

Those of skill in the art will appreciate that reference to an oligonucleotide primer may refer to a single oligonucleotide primer molecule, and may also or instead refer in certain instances to a plurality of oligonucleotide primer molecules of a particular sequence or type present in a reaction.

Those of skill in the art will appreciate that it is not necessary that an oligonucleotide primer have 100% sequence identity with a template or amplicon in order to hybridize with the template or amplicon and/or participate in one or more steps of an amplification reaction with the template or amplicon. In some instances, an oligonucleotide primer may have one or more mismatches with a template or amplicon with which it hybridizes, e.g., 1 mismatch, 2 mismatches, 3 mismatches, 4 mismatches, 5 mismatches, 6 mismatches, 7 mismatches, 8 mismatches, 9 mismatches, 10 mismatches, or more mismatches. Accordingly, an oligonucleotide primer present in an amplification reaction with an amplicon or template may have no more than, e.g., 70% identity with any portion of the amplicon or template, e.g., 70% or more identity, 75% or more identity, 80% or more identity, 85% or more identity, 90% or more identity, 95% or more identity, 96% or more identity, 97% or more identity, 98% or more identity, or 99% or more identity with the template or amplicon. In any of the various embodiments described herein, any one or more nucleotides of a nucleic acid molecule may be a natural nucleotide (A, C, G, T, or U), a synthetic nucleotide, or a modified nucleotide.

Probes

A probe or oligonucleotide probe, as described herein, is an oligonucleotide capable of hybridizing with an amplicon as described herein. A labeled probe or oligonucleotide probe is a probe associated with a detectable moiety.

A probe of the present invention may be a nucleic acid molecule that hybridizes or is capable of hybridizing with an amplicon having at least 80% identity to a portion of any one of SEQ ID NOs: 1-11 that is amplified by any oligonucleotide primer or pair of oligonucleotide primers described herein, and/or with any amplicon as described above.

In various embodiments, a probe as described herein is a nucleic acid molecule including or consisting of an oligonucleotide having a nucleic acid sequence having at least 80% identity (e.g., at least 80%, 85%, 90%, 95%, or 100% identity) to a sequence of between 6 and 40 base pairs selected from any one of SEQ ID NOs: 56-67, or from a sequence complementary thereto. In various embodiments, any of one or more oligonucleotides may be between 6 and 40 nucleotides in length, between 8 and 35 nucleotides in length, between 10 and 30 nucleotides in length, between 12 and 28 nucleotides in length, between 14 and 26 nucleotides in length, between 16 and 26 nucleotides in length, or between 18 and 24 nucleotides in length. Thus, in various embodiments, any of one or more oligonucleotides may be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In various embodiments, a probe as described herein is a nucleic acid molecule including or consisting of an oligonucleotide having a nucleic acid sequence having at least 80% identity (e.g., at least 80%, 85%, 90%, 95%, or 100% identity) to a sequence of between 6 and 24 base pairs selected from any one of SEQ ID NOs: 107-117, or from a sequence complementary thereto. In various embodiments, any of one or more oligonucleotides may be between 6 and 24 nucleotides in length, between 8 and 24 nucleotides in length, between 10 and 24 nucleotides in length, between 12 and 24 nucleotides in length, between 14 and 24 nucleotides in length, between 16 and 24 nucleotides in length, between 18 and 24 nucleotides in length, between 6 and 22 nucleotides in length, between 6 and 20 nucleotides in length, between 6 and 18 nucleotides in length, between 6 and 16 nucleotides in length, between 6 and 14 nucleotides in length, between 6 and 12 nucleotides in length, between 10 and 22 nucleotides in length, between 10 and 20 nucleotides in length, between 10 and 18 nucleotides in length, between 10 and 16 nucleotides in length, between 10 and 14 nucleotides in length, or between 10 and 12 nucleotides in length. Thus, in various embodiments, any of one or more oligonucleotides may be 6, 7, 8, 9, 10, 11, 12, 13, 14, 15, 16, 17, 18, 19, 20, 21, 22, 23, or 24 nucleotides in length.

In various embodiments, a probe as described herein is a nucleic acid molecule including or consisting of an oligonucleotide having a nucleic acid sequence having at least 80% identity (e.g., at least 80%, 85%, 90%, 95%, or 100% identity) to a sequence of between 6 and 40 base pairs selected from any one of SEQ ID NOs: 68-84, or from a sequence complementary thereto. In various embodiments, any of one or more oligonucleotides may be between 6 and 40 nucleotides in length, between 8 and 35 nucleotides in length, between 10 and 30 nucleotides in length, between 12 and 28 nucleotides in length, between 14 and 26 nucleotides in length, between 16 and 26 nucleotides in length, or between 18 and 24 nucleotides in length. Thus, in various embodiments, any of one or more oligonucleotides may be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In various embodiments, a probe as described herein is a nucleic acid molecule including or consisting of an oligonucleotide having a nucleic acid sequence having at least 80% identity (e.g., at least 80%, 85%, 90%, 95%, or 100% identity) to a sequence of between 6 and 24 base pairs selected from any one of SEQ ID NOs: 118-128, or from a sequence complementary thereto. In various embodiments, any of one or more oligonucleotides may be between 6 and 24 nucleotides in length, between 8 and 24 nucleotides in length, between 10 and 24 nucleotides in length, between 12 and 24 nucleotides in length, between 14 and 24 nucleotides in length, between 16 and 24 nucleotides in length, between 18 and 24 nucleotides in length, between 6 and 22 nucleotides in length, between 6 and 20 nucleotides in length, between 6 and 18 nucleotides in length, between 6 and 16 nucleotides in length, between 6 and 14 nucleotides in length, between 6 and 12 nucleotides in length, between 10 and 22 nucleotides in length, between 10 and 20 nucleotides in length, between 10 and 18 nucleotides in length, between 10 and 16 nucleotides in length, between 10 and 14 nucleotides in length, or between 10 and 12 nucleotides in length. Thus, in various embodiments, any of one or more oligonucleotides may be 6, 7, 8, 9, 10, 11, 12, 13, 14, 15, 16, 17, 18, 19, 20, 21, 22, 23, or 24 nucleotides in length. In various embodiments, a probe as described herein is a nucleic acid molecule having or including the sequence of SEQ ID NO: 56 or SEQ ID NO: 68, or a sequence complementary thereto.

In various instances, an amplification reaction mixture includes a single probe. In various instances, an amplification reaction mixture includes two probes. In such instances, an amplification reaction mixture may include a first probe and a second probe in accordance with the following:

A first probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 57 and a second probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 69.

A first probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 58 and a second probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 70.

A first probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 59 and a second probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 71.

A first probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 60 and a second probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 72.

A first probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 61 and a second probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 73.

A first probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 62 and a second probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 74.

A first probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 63 and a second probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 75.

A first probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 64 and a second probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 76.

A first probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 65 and a second probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 77.

A first probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 66 and a second probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 78.

A first probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 67 and a second probe including or consisting of a sequence having at least 80% identity (e.g., at least 80%, 85%, 90%, 95%, or 100% identity) to a sequence including or consisting of 6 to 40 consecutive nucleotides (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides) selected from the sequence of SEQ ID NO: 79.

A first probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 107 and a second probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 118.

A first probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 108 and a second probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 119.

A first probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 109 and a second probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 120.

A first probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 110 and a second probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 121.

A first probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 111 and a second probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 122.

A first probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 112 and a second probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 123.

A first probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 113 and a second probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 124.

A first probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 114 and a second probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 125.

A first probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 115 and a second probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 126.

A first probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 116 and a second probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 127.

A first probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 117 and a second probe including or consisting of a sequence having at least 80% identity (e.g., at least 80%, 85%, 90%, 95%, or 100% identity) to a sequence including or consisting of 6 to 24 consecutive nucleotides (e.g., 6, 7, 8, 9, 10, 11, 12, 13, 14, 15, 16, 17, 18, 19, 20, 21, 22, 23, or 24 nucleotides) selected from the sequence of SEQ ID NO: 128.

In various instances, an amplification reaction mixture includes an oligonucleotide probe having a nucleic acid sequence according to SEQ ID NO: 56.

In various instances, an amplification reaction mixture includes an oligonucleotide probe having a nucleic acid sequence according to SEQ ID NO: 68.

In various instances, an amplification reaction mixture includes two probes: a first probe that is an oligonucleotide probe having a nucleic acid sequence according to SEQ ID NO: 56 and a second probe that is an oligonucleotide probe having a nucleic acid sequence according to SEQ ID NO: 68.

Those of skill in the art will appreciate that reference to an oligonucleotide probe may refer to a single oligonucleotide probe molecule, and may also or instead refer in certain instances to a plurality of oligonucleotide probe molecules of a particular sequence or type present in a reaction.

Those of skill in the art will appreciate that it is not necessary that an oligonucleotide probe have 100% sequence identity with a template or amplicon in order to hybridize with the template or amplicon and/or facilitate detection of amplification. In some instances, an oligonucleotide probe may have one or more mismatches with a template or amplicon with which it hybridizes, e.g., 1 mismatch, 2 mismatches, 3 mismatches, 4 mismatches, 5 mismatches, 6 mismatches, 7 mismatches, 8 mismatches, 9 mismatches, 10 mismatches, or more mismatches. Accordingly, an oligonucleotide probe present in an amplification reaction with an amplicon or template may have no more than, e.g., 70% identity with any portion of the amplicon or template, e.g., 70% or more identity, 75% or more identity, 80% or more identity, 85% or more identity, 90% or more identity, 95% or more identity, 96% or more identity, 97% or more identity, 98% or more identity, or 99% or more identity with the template or amplicon.

Labeled Probes

Various methods of detecting and/or quantifying the presence and/or level of a nucleic acid sequence present in a sample as described herein may utilize a single oligonucleotide primer or a first oligonucleotide primer together with a second oligonucleotide primer, optionally in further combination with one or more probes, e.g., a single probe or a first probe together with a second probe.

In various methods of the present invention that include one or more probes, one or more probes are associated with a detectable moiety (e.g., for use in quantitative or real-time PCR). Association of an oligonucleotide probe with a detectable moiety may be direct, indirect, covalent, non-covalent, via a linker, or via association with one or more intermediary molecules.

Exemplary detectable moieties for association with an oligonucleotide probe as described herein include, without limitation, FAM®, 6-FAM (FLUORESCEIN), 6-FAM (NHS ESTER), 6-FAM (AZIDE), FLUORESCEIN DT, YAKIMA YELLOW®, VIC®, ABY®, JUN®, TET™, HEX™, JOE™, JOE™ (NHS ESTER), CY®3, CY®3.5, CY®5, CY®5.5, TAMRA™, TAMRA™ (NHS ESTER), 5-TAMRA™ (AZIDE), ROX™, ROX™ (NHS ESTER), LC RED 610, TEXAS RED®, TEXAS RED®-X (NHS ESTER), TEX 615, LC RED 640, FLUORESCEIN, BEBO, MAX, MAX (NHS ESTER), OREGON GREEN 488, OREGON GREEN 514, ATTO™ 425, ATTO™ 465, ATTO™ 488, ATTO™ 520, ATTO™ 532, ATTO™ 550, ATTO™ 565, ATTO™ RHO101, ATTO™ 590, ATTO™ 594, ATTO™ 610, ATTO™ 633, ATTO™ 647N, ATTO™ 680, ATTO™ 700, ATTO™ 740, ATTO™532 (NHS ESTER), ATTO™ 550 (NHS ESTER), ATTO™ 565 (NHS ESTER), ATTO™ RHO101 (NHS ESTER), ATTO™ 590 (NHS ESTER), ATTO™ 633 (NHS ESTER), ATTO™ 647N (NHS ESTER), TYE™ 563, TYE™ 665, TYE™ 705, ALEXA FLUOR® 488 (NHS ESTER), ALEXA FLUOR® 532 (NHS ESTER), ALEXA FLUOR® 546 (NHS ESTER), ALEXA FLUOR® 555, ALEXA FLUOR® 594 (NHS ESTER), ALEXA FLUOR® 647 (NHS ESTER), ALEXA FLUOR® 650 (NHS ESTER), ALEXA FLUOR® 750 (NHS ESTER), 5'IRDYE® 700, 5'IRDYE® 800, 5'IRDYE® 800CW (NHS ESTER), RHODAMINE GREEN™-X (NHS ESTER), RHODAMINE RED™-X (NHS ESTER), WELLRED D2 DYE, WELLRED D3 DYE, WELLRED D4 DYE, LIGHTCYCLER® 610, LIGHTCYCLER® 640 (NHS ESTER), DY 415, DY 480, DY 610, DY 649, DY 682, DY 782, DY 750 (NHS ESTER), PET®, BODIPY FL, BODIPY 530/550, BODIPY 630/650, BODIPY 650/665, BODIPY TRM-X, FITC, BODIPY R6G, CAL GOLD, CAL ORANGE, CAL RED, PULSAR-650, QUASAR-570, QUASAR 670, and NED™.

In various instances in which one or more probes includes a detectable moiety, the same probe may include a quenching moiety. Exemplary quenching moieties (e.g., for use in connection with qPCR) are known in the art. Exemplary quenching moieties include Black Hole Quencher® (e.g., BHQ®0, BHQ®1, BHQ®1-dt, BHQ®2, BHQ®3, BHQ®10), BlackBerry Quencher BBQ 650, TAMRA, Dabcyl, Dabcyl-dT, Eclipse, non-fluorescent quencher (NFQ), a G nucleotide or plurality of G nucleotides, QSY 7, QSY 9, QSY 21, QSY 35, ELLEQUENCHER, and IOWA BLACK. In various instances, a probe as described herein is double quenched. In various embodiments, a labeled oligonucleotide probe as described herein includes a detectable moiety on its 5' end and a quenching moiety on its 3' end. In various embodiments, a labeled oligonucleotide probe as described herein includes a detectable moiety on its 3' end and a quenching moiety on its 5' end.

In various embodiments, a pair of oligonucleotide probes having different nucleic acid sequences each include one detectable moiety and one quenching moiety capable of quenching the signal of the detectable moiety, wherein the detectable moiety and quenching moiety are on separate probes of the pair of oligonucleotide probes.

In various embodiments, a pair of oligonucleotide probes having different nucleic acid sequences may each include a detectable moiety and a quenching moiety, where the probes of the pair of oligonucleotide probes include different detectable moieties capable of generating different detectable signals, and the quenching moiety of each detectable probe is capable of quenching the detectable signal of the detectable moiety associated with the other probe, but is not capable of quenching the detectable signal of the detectable moiety associated with the probe with which it is associated.

In various instances, an amplification reaction mixture includes a labeled oligonucleotide probe having a nucleic acid sequence according to SEQ ID NO: 56. In various instances, an amplification reaction mixture includes a labeled oligonucleotide probe having a nucleic acid sequence according to SEQ ID NO: 68.

In various instances, an amplification reaction mixture includes two labeled oligonucleotide probes: a first labeled oligonucleotide probe having a nucleic acid sequence according to SEQ ID NO: 56 and a second labeled oligonucleotide probe having a nucleic acid sequence according to SEQ ID NO: 68.

As appreciated by those of skill in the art, the particular selection of a detectable moiety, the particular selection of a quenching moiety, and/or the pairing of a detectable moiety and a quenching moiety in an assay or probe may depend in whole or in part on the method of analysis to be used, and/or the apparatus to be used for such analysis, and/or the appropriateness of the pairing of any particular detectable moiety with any particular quenching moiety. Significant guidance regarding the use of detectable moieties, quenching moieties, assays, and/or apparatuses is found in the art.

Samples

The present invention includes the analysis of a sample to detect and/or quantify the presence and/or level of a nucleic acid sequence in a sample. In particular, the present invention includes the analysis of a sample to detect and/or quantify the presence and/or level of an HIV nucleic acid sequence in a sample. A sample can be from a subject, e.g., a human or other primate having, diagnosed as having, suspected of having, or at risk of having HIV. A sample can be from a subject, e.g., a human or other primate harboring, diagnosed as harboring, suspected of harboring, or at risk of harboring an HIV nucleic acid. A sample can be from a subject, e.g., a human or other primate having been exposed to or at risk of exposure to HIV or an HIV nucleic acid. A sample can be a sample of a tissue or bodily fluid including, without limitation, blood, a blood fraction, serum, plasma, urine, saliva, oral swab (e.g., from cheek, teeth, and/or gum), cervical smears, semen, breast milk, fetal blood, or fetal tissue.

Any sample as described herein may be used directly upon collection from a subject or may be processed prior to analysis. Processing may include, e.g., isolation or purification of RNA and/or reverse transcription of RNA, methods of which are known in the art. Methods of purifying RNA from a sample, include, without limitation organic RNA extraction, filter-based RNA extraction, column and/or centrifugation-based RNA extraction, magnetic particle-based RNA extraction, direct lysis RNA extraction, anion-exchange-based RNA extraction, and others known in the art.

Any method or step of amplification, hybridization, or sequencing described herein may include or be preceded by a step in which RNA isolated or purified from a sample is reverse-transcribed or otherwise converted to cDNA.

A sample may be said to be from a subject if that sample is directly taken from the subject or if the sample is a processed form of a sample taken from a subject, e.g., in that the sample is derived from the subject and has been subjected to, e.g., RNA extraction and/or reverse transcription of RNA.

Various samples as described herein include an HIV nucleic acid that is an HIV RNA molecule. Various samples as described herein include an HIV nucleic acid that is a complementary DNA (cDNA) molecule, generated in whole or in part by reverse transcription of an HIV RNA molecule. Any solution, mixture, or substance including a nucleic acid molecule isolated or otherwise derived from a sample as described herein may be referred to as a nucleic acid sample. Any solution, mixture, or substance including an HIV nucleic acid molecule isolated or otherwise derived from a sample as described herein may be referred to as an HIV nucleic acid sample.

Amplification and Detection, Quantification, and/or Sequencing

Various methods of detecting and/or quantifying the presence and/or level of a nucleic acid sequence present in a sample are known in the art. Such techniques can include, without limitation, methods that include amplification and/or sequencing of nucleic acid molecules, in which methods successful amplification and/or the number, concentration, or level of amplicons and/or the number, concentration, level, or presence of nucleic acids having a particular sequence (e.g., the sequence of an amplicon as described herein) is directly or indirectly detected. As appreciated by those of skill in the art, various methods of detection and/or quantification provide a quantitative of semi-quantitative result.

In various instances, a method by a which an HIV sequence or amplicon is detected and/or quantified in a sample includes an amplification reaction (e.g., a Polymerase Chain Reaction (PCR)-based amplification) in which one or more oligonucleotide primers are used to amplify a nucleic acid sequence from a template nucleic acid molecule (e.g., a reference sequence). Methods of PCR and steps thereof are well known in the art. A method of PCR can include, in some instances, steps of providing a template, contacting the template with at least (i) polymerase, (ii) free deoxynucleotides, and (iii) at least one oligonucleotide primer, and incubating the reaction. Incubation may include amplification cycles, where each cycle includes phases of (i) denaturation, (ii) annealing, and (iii) extension. Various protocols and reagents for PCR are known in the art. Various techniques for PCR are described, e.g., in: PCR: A Practical Approach, M. J. McPherson, et al., IRL Press (1991); PCR Protocols: A Guide to Methods and Applications, by Innis, et al., Academic Press (1990); and PCR Technology: Principals and Applications for DNA Amplification, H. A. Erlich, Stockton Press (1989); U.S. Pat. Nos. 4,683,195; 4,683,202; 4,800,159; 4,965,188; 4,889,818; 5,075,216; 5,079,352; 5,104,792; 5,023,171; 5,091,310; and 5,066,584, each of which is herein incorporated by reference. Various specific PCR amplification applications are available in the art (for reviews, see for example, Erlich, 1999, Rev Immunogenet., 1: 127-34; Prediger 2001, Methods Mol. Biol. 160: 49-63; Jurecic et al., 2000, Curr. Opin. Microbiol. 3: 316-21; Triglia, 2000, Methods Mol. Biol. 130: 79-83; MaClelland et al., 1994, PCR Methods Appl. 4: S66-81; Abramson and Myers, 1993, Current Opinion in Biotechnology 4: 41-47; each of which is incorporated herein by reference).

In at least some example PCR reactions, denaturing includes incubating a reaction mixture to 94° C. or higher for 15 seconds to 2 minutes; denaturing includes incubating the reaction mixture at approximately 40-60° C. for approximately 15-60 seconds; extension includes incubating the reaction mixture at a temperature in the range of 70-74° C. for approximately 1-2 minutes. A series of denaturing, annealing, and extension can be referred to as an amplification cycle. Amplification cycles can be repeated for 2 to 60 or more cycles, e.g., at least 10 cycles, 15 cycles, 20 cycles, 25 cycles, 30 cycles, 35 cycles, 40 cycles, 45 cycles, or 50 cycles, or any range therebetween In certain instances, an amplification reaction is performed with or in the presence of reagents that enable or facilitate detection of the amplification of one or more amplicons. Certain such methods are known in the art as quantitative PCR (qPCR).

In certain examples of amplification in the presence of reagents that enable or facilitate detection of amplification, amplicons, or the presence of nucleic acids having a particular sequence, one or more oligonucleotide probes are present in the amplification reaction and are labeled with (a) a detectable moiety (e.g., a fluorescent moiety) and (b) a quenching moiety capable of quenching the signal of the detectable moiety of (a). In such an amplification reaction, the signal of the detectable moiety is quenched by the quenching moiety, the two being associated with the same single oligonucleotide probe molecule (e.g., with the fluorescent moiety at the 5' end of the probe and the quenching moiety at the 3' end of the probe) and therefore in sufficiently close proximity to allow quenching. When the detectable moiety and quenching moiety are physically close to one another, the overall level of fluorescent output is low. During amplification, polymerase activity can cleave a probe that is hybridized to a template nucleic acid molecule (e.g., the original nucleic acid sequence or an amplicon produced from the original nucleic acid sequence) at a position 3' of a nascent amplicon, separating the detectable moiety from the quenching moiety. As a result, the detectable signal of the detectable moiety is no longer quenched or no longer substantially quenched by the quenching moiety associated with the single oligonucleotide probe molecule. Non-limiting examples of detectable moieties and quenching moieties are provided above. Such means of amplification may be referred to as probe-based methods. The use of a probe-based method is not exclusive of combination with other methods, such as a dye-based methods.

In certain examples of amplification in the presence of reagents that enable or facilitate detection of amplification, amplicons, or the presence of nucleic acids having a particular sequence, an intercalating dye is present in an amplification reaction. Such intercalating dyes may be referred to as amplification-dependent detectable moieties. Intercalating dyes are detectable moieties, e.g., fluorescent moieties, that become detectable or become more detectable when intercalated with or bound to double-stranded DNA. In certain such examples, a signal (or level of signal) is detectable when the dye is intercalated with or bound to double-stranded DNA. Thus, as the number of amplicons (and nucleic acids complementary thereto) increases in an amplification reaction, fluorescence (e.g., momentary, mean, median, mode, or maximum fluorescence) can increase. Such means of amplification may be referred to as dye-based methods. The use of a dye-based method is not exclusive of combination with other methods, such as a probe-based method.

Examples of intercalating dyes or amplification-dependent detectable moieties include, without limitation, ethidium bromide, proflavine, SYBR® Green (e.g, I or II), SYBR® Gold, EVAGREEN®, YO (Oxazole Yellow) and related intercalating dyes, TO (Thiazole Orange) and related intercalating dyes, PG (PicoGreen) and related intercalating dyes, indoles and related intercalating dyes, imidazoles and related intercalating dyes, Cyanine dyes, SYTO®-9, SYTO®-13, SYTO®-16, SYTO®-60, SYTO®-62, SYTO®-64, SYTO®-82, POPO™-3, TOTO®-3, BOBO-3, PO-PRO™-3, TO-PRO™-3, YO-PRO™-1, SYTOX®, YOYO™-1, YO-PRO™-1, BOXTO™, BEBO™, BETO™, and others known in the art.

In various methods of quantitative-PCR (qPCR) or real-time-PCR (kPCR), including dye-based and probe-based methods or combinations thereof, the signal generated can be used to quantitatively or semi-quantitatively determine the absolute or relative level, amount, or concentration of any of one or more amplicons or nucleic acids. In various methods of qPCR or kPCR, analysis may be non-quantitative or qualitative. Absolute quantitation is a rigorous technique for quantification. Absolute quantification can utilize the addition of external standards in every reaction to determine the absolute amount of the target nucleic acid of interest. Quantification may utilize a standard curve of external standard dilutions, which can be generated and used to determine the concentration of target. Relative quantitation requires calculation of the ratio between the amount of target template and a reference template in a sample. One approach is the comparative Ct method in which Ct value of an amplification reaction including a sample of interest is compared to a control, with or without normalization. Qualitative analysis can utilize end-point data acquired after the PCR has reached plateau phase. End-point analysis can be relative, competitive, or comparative.

In various instances of the present invention, a reaction mixture including various reagents is prepared for amplification, e.g., in a method of PCR, e.g., in a method of qPCR or kPCR. The present invention encompasses reaction mixtures including a nucleic acid from or derived from a sample (e.g., by Reverse Transcription) together with one or more primers or probes as described herein.

For example, a reaction mixture may include, without limitation, a selection of reagents according to any of the following:
  a first oligonucleotide primer as described herein and a second oligonucleotide primer as described herein, e.g., a forward oligonucleotide primer and a reverse oligonucleotide primer
  an oligonucleotide probe as described herein;
  a labeled oligonucleotide probe as described herein;

two oligonucleotide probes as described herein;
two labeled oligonucleotide probes as described herein;
a first oligonucleotide primer as described herein and a second oligonucleotide primer as described herein, e.g., a forward oligonucleotide primer and a reverse oligonucleotide primer, and an oligonucleotide probe as described herein;
a first oligonucleotide primer as described herein and a second oligonucleotide primer as described herein, e.g., a forward oligonucleotide primer and a reverse oligonucleotide primer, and a labeled oligonucleotide probe as described herein;
a first oligonucleotide primer as described herein and a second oligonucleotide primer as described herein, e.g., a forward oligonucleotide primer and a reverse oligonucleotide primer, and at least two oligonucleotide probes as described herein;
a first oligonucleotide primer as described herein and a second oligonucleotide primer as described herein, e.g., a forward oligonucleotide primer and a reverse oligonucleotide primer, and at least two labeled oligonucleotide probes as described herein;
a first oligonucleotide primer as described herein and a second oligonucleotide primer as described herein, e.g., a forward oligonucleotide primer and a reverse oligonucleotide primer, at least two oligonucleotide probes as described herein, and an intercalating dye;
a first oligonucleotide primer as described herein and a second oligonucleotide primer as described herein, e.g., a forward oligonucleotide primer and a reverse oligonucleotide primer, at least two oligonucleotide probes as described herein, and one or more of an intercalating dye, PCR buffer, water, dNTPs, and/or magnesium;
a first oligonucleotide primer as described herein and a second oligonucleotide primer as described herein, e.g., a forward oligonucleotide primer and a reverse oligonucleotide primer, at least two labeled oligonucleotide probes as described herein, and one or more of a PCR buffer, water, dNTPs, and/or magnesium.
a first oligonucleotide primer as described herein and a second oligonucleotide primer as described herein, e.g., a forward oligonucleotide primer and a reverse oligonucleotide primer, DNA polymerase, and an oligonucleotide probe as described herein;
a first oligonucleotide primer as described herein and a second oligonucleotide primer as described herein, e.g., a forward oligonucleotide primer and a reverse oligonucleotide primer, DNA polymerase, and a labeled oligonucleotide probe as described herein;
a first oligonucleotide primer as described herein and a second oligonucleotide primer as described herein, e.g., a forward oligonucleotide primer and a reverse oligonucleotide primer, DNA polymerase, and at least two oligonucleotide probes as described herein;
a first oligonucleotide primer as described herein and a second oligonucleotide primer as described herein, e.g., a forward oligonucleotide primer and a reverse oligonucleotide primer, DNA polymerase, and at least two labeled oligonucleotide probes as described herein;
a first oligonucleotide primer as described herein and a second oligonucleotide primer as described herein, e.g., a forward oligonucleotide primer and a reverse oligonucleotide primer, DNA polymerase, at least two oligonucleotide probes as described herein, and an intercalating dye;
a first oligonucleotide primer as described herein and a second oligonucleotide primer as described herein, e.g., a forward oligonucleotide primer and a reverse oligonucleotide primer, at least two oligonucleotide probes as described herein, DNA polymerase, and one or more of an intercalating dye, PCR buffer, water, dNTPs, and/or magnesium;
a first oligonucleotide primer as described herein and a second oligonucleotide primer as described herein, e.g., a forward oligonucleotide primer and a reverse oligonucleotide primer, at least two labeled oligonucleotide probes as described herein, DNA polymerase, and one or more of a PCR buffer, water, dNTPs, and/or magnesium.

In various embodiments described herein, a plurality of similar but degenerate oligonucleotide primers or probes may be present in a single reaction. Degenerate oligonucleotide primers or probes include a mixture of oligonucleotide primers or probes that differ at one or more base pairs but have at least 70% similarity to each other, e.g., at least 75%, 80%, 85%, 90%, or 95% similarity to each other. In various instances, a reaction includes oligonucleotide primers and/or probes that cumulatively include at least two, at least three, or at least four different nucleobases at a given position. Degenerate oligonucleotide probes encompass one or more nucleotide substitutions, insertions, or deletions.

In various embodiments, a first or forward oligonucleotide primer is an oligonucleotide having a nucleic acid sequence according to SEQ ID NO: 23.

In various embodiments, a second or reverse oligonucleotide primer is an oligonucleotide having a nucleic acid sequence complementary to the sequence of SEQ ID NO: 40.

In various embodiments, a first or forward oligonucleotide primer is an oligonucleotide having a nucleic acid sequence according to SEQ ID NO: 23 and a second or reverse oligonucleotide primer is an oligonucleotide having a nucleic acid sequence complementary to the sequence of SEQ ID NO: 40.

In various embodiments, an oligonucleotide probe or labeled oligonucleotide probe has a nucleic acid sequence according to SEQ ID NO: 56.

In various embodiments, an oligonucleotide probe or labeled oligonucleotide probe has a nucleic acid sequence according to SEQ ID NO: 68.

In various embodiments, two oligonucleotide probes or labeled oligonucleotide probes include an oligonucleotide probe or labeled oligonucleotide probe having a nucleic acid sequence according to SEQ ID NO: 56 and an oligonucleotide probe or labeled oligonucleotide probe having a nucleic acid sequence according to SEQ ID NO: 68.

In various embodiments, a first or forward oligonucleotide primer is an oligonucleotide having a nucleic acid sequence according to SEQ ID NO: 23, a second or reverse oligonucleotide primer is an oligonucleotide having a nucleic acid sequence complementary to the sequence of SEQ ID NO: 40, and two oligonucleotide probes or labeled oligonucleotide probes include an oligonucleotide probe or labeled oligonucleotide probe having a nucleic acid sequence according to SEQ ID NO: 56 and an oligonucleotide probe or labeled oligonucleotide probe having a nucleic acid sequence according to SEQ ID NO: 68.

Those of skill in the art will further appreciate from the present disclosure that various combinations of reagents described herein can further include any of one or more additional oligonucleotide primers, oligonucleotide primer pairs, or oligonucleotide probes, which further included reagents may or may not be known in the art.

Any amplification reaction utilizing one or more appropriate oligonucleotide primers as described herein, with or without a probe-based signal or dye-based signal, can be used to detect the presence of an HIV nucleic acid in a sample. Numerous methods of identifying the presence of an amplicon following an amplification reaction are known in the art. Certain methods include identifying that the amplicon is present following amplification and/or identifying the presence of a nucleic acid having a particular sequence following amplification, any of which methods may be quantitative, semi-quantitative, non-quantitative, or qualitative.

Identification of an amplicon following amplification (with or without a probe-based signal or dye-based signal) may be achieved by various methods known in the art, including, e.g., without limitation, gel electrophoresis methods (including without limitation, e.g., autoradiography, ethidium bromide staining, and silver staining), chromatographic separation, capillary electrophoresis hybridization analysis, comparative hybridization analysis, chromogenic hybridization (e.g., CISH), oligonucleotide hybridization analysis, microarray hybridization analysis, fluorescence hybridization analysis (e.g., FISH), Southern blot analysis, heteroduplex mobility assay (HMA), restriction fragment length polymorphism (RFLP) analysis, RNAase mismatch analysis, surface plasmon resonance analysis, and single strand conformational polymorphism (SSCP) analysis. Methods of identifying an amplicon following amplification (with or without a probe-based signal or dye-based signal) can instead or additionally include, e.g., without limitation, a mass spectrometry step utilizing, e.g., tandem mass spectrometry, matrix assisted laser desorption/ionization-time of flight (MALDI-TOF) mass spectrometry, electrospray ionization (ESI) mass spectrometry, surface-enhanced laser deorption/ionization-time of flight (SELDI-TOF) mass spectrometry, quadrupole-time of flight (Q-TOF) mass spectrometry, atmospheric pressure photoionization mass spectrometry (APPI-MS), Fourier transform mass spectrometry (FTMS), matrix-assisted laser desorption/ionization-Fourier transform-ion cyclotron resonance (MALDI-FT-ICR) mass spectrometry, and secondary ion mass spectrometry (SIMS)).

In certain embodiments, amplicons and/or nucleic acid sequences are detected and/or quantified based on hybridization to an oligonucleotide having a tag or other detectable moiety. In various such instances, nucleic acids hybridized to an oligonucleotide having a tag or other detectable moiety can be separated, isolated, or purified from other nucleic acids by, e.g., chromatography or gel electrophoresis. In various such instances, separated, isolated, or purified nucleic acids may be quantified and/or sequenced.

Identification of the presence of a nucleic acid having a particular sequence following amplification can include one or more sequencing steps. Various methods of sequencing are known in the art and include, without limitation, sequencing methods (including, without limitation, high-throughput sequencing, deep sequencing, next generation sequencing, massively parallel DNA sequencing, cycle sequencing, single-base extension sequencing, solid-phase sequencing, duplex sequencing, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, massively parallel signature sequencing (MPSS), direct sequencing, random shotgun sequencing, Sanger sequencing, targeted sequencing, exon sequencing, whole-genome sequencing, sequencing by hybridization, pyrosequencing, nanopore sequencing, Illumina Genome Analyzer platform, 454 sequencing, Solexa Genome Analyzer sequencing, SOLID® sequencing, and MS-PET sequencing), and methods utilize mass spectrometry (e.g., tandem mass spectrometry, matrix assisted laser desorption/ionization-time of flight (MALDI-TOF) mass spectrometry, electrospray ionization (ESI) mass spectrometry, surface-enhanced laser deorption/ionization-time of flight (SELDI-TOF) mass spectrometry, quadrupole-time of flight (Q-TOF) mass spectrometry, atmospheric pressure photoionization mass spectrometry (APPI-MS), Fourier transform mass spectrometry (FTMS), matrix-assisted laser desorption/ionization-Fourier transform-ion cyclotron resonance (MALDI-FT-ICR) mass spectrometry, and secondary ion mass spectrometry (SIMS)).

Thus, methods of detecting and/or quantifying the presence and/or level of a nucleic acid sequence present in a sample can include hybridization analysis, comparative hybridization analysis, chromogenic hybridization (e.g., CISH), oligonucleotide hybridization analysis, microarray hybridization analysis, fluorescence hybridization analysis (e.g., FISH), Southern blot analysis, heteroduplex mobility assay (HMA), restriction fragment length polymorphism (RFLP) analysis, RNAase mismatch analysis, surface plasmon resonance analysis, single strand conformational polymorphism (SSCP) analysis, polymerase chain reaction (PCR)-based methods (including, without limitation, quantitative PCR, real-time PCR, reverse-transcriptase-PCR analysis (RT-PCR), multiplex PCR, co-amplification at lower denaturation temperature-PCR (COLD-PCR), multiplex ligation-dependent probe amplification (MLPA), and emulsion PCR), sequencing methods (including, without limitation, high-throughput sequencing, deep sequencing, next generation sequencing, massively parallel DNA sequencing, cycle sequencing, single-base extension sequencing, solid-phase sequencing, duplex sequencing, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, massively parallel signature sequencing (MPS S), direct sequencing, random shotgun sequencing, Sanger sequencing, targeted sequencing, exon sequencing, whole-genome sequencing, sequencing by hybridization, pyrosequencing, nanopore sequencing, Illumina Genome Analyzer platform, 454 sequencing, Solexa Genome Analyzer sequencing, SOLID® sequencing, and MS-PET sequencing), and methods utilize mass spectrometry (e.g., tandem mass spectrometry, matrix assisted laser desorption/ionization-time of flight (MALDI-TOF) mass spectrometry, electrospray ionization (ESI) mass spectrometry, surface-enhanced laser deorption/ionization-time of flight (SELDI-TOF) mass spectrometry, quadrupole-time of flight (Q-TOF) mass spectrometry, atmospheric pressure photoionization mass spectrometry (APPI-MS), Fourier transform mass spectrometry (FTMS), matrix-assisted laser desorption/ionization-Fourier transform-ion cyclotron resonance (MALDI-FT-ICR) mass spectrometry, and secondary ion mass spectrometry (SIMS)), any or all of which may be used alone or in conjunction with gel electrophoresis methods (including without limitation, e.g., autoradiography, ethidium bromide staining, and silver staining), chromatographic separation, and/or capillary electrophoresis.

Kits

In various instances, the present invention includes a kit for use in detecting and/or quantifying the presence and/or level of a nucleic acid sequence present in a sample.

A kit may include, for instance, a primer capable of hybridizing to an HIV nucleic acid, two primers capable of hybridizing to an HIV nucleic acid, three or more primers capable of hybridizing to an HIV nucleic acid (e.g., 3, 4, 5, 6, 7, or 8 or more primers), a labeled probe capable of hybridizing to an HIV nucleic acid molecule at a position 3' of a position on the same HIV nucleic acid molecule to which a provided oligonucleotide primer hybridizes, two labeled probes each capable of hybridizing to an HIV nucleic acid molecule at a position 3' of a position on the same HIV nucleic acid molecule to which a provided oligonucleotide primer hybridizes, three or more labeled probes each capable of hybridizing to an HIV nucleic acid molecule at a position 3' of a position on the same HIV nucleic acid molecule to which a provided oligonucleotide primer hybridizes (e.g., 3, 4, 5, 6, 7, or 8 or more probes), an intercalating dye, free deoxynucleotides (dNTPs), polymerase, a control template sequence, water, buffer, or other reagents known for use in amplification reactions (such as magnesium, DMSO, formamide, glycerol, betaine monohydrate, Tween-20, Bovine Serum Albumin (BSA), or Tetramethyl ammonium chloride).

For example, a kit may include, without limitation, a selection of reagents according to any of the following, which reagents may be provided separately and/or separate solutions, and/or together and/or in a single solution, or in a combination thereof:

- a first oligonucleotide primer as described herein and a second oligonucleotide primer as described herein, e.g., a forward oligonucleotide primer and a reverse oligonucleotide primer
- an oligonucleotide probe as described herein;
- a labeled oligonucleotide probe as described herein;
- two oligonucleotide probes as described herein;
- two labeled oligonucleotide probes as described herein;
- a first oligonucleotide primer as described herein and a second oligonucleotide primer as described herein, e.g., a forward oligonucleotide primer and a reverse oligonucleotide primer, and an oligonucleotide probe as described herein;
- a first oligonucleotide primer as described herein and a second oligonucleotide primer as described herein, e.g., a forward oligonucleotide primer and a reverse oligonucleotide primer, and a labeled oligonucleotide probe as described herein;
- a first oligonucleotide primer as described herein and a second oligonucleotide primer as described herein, e.g., a forward oligonucleotide primer and a reverse oligonucleotide primer, and two oligonucleotide probes as described herein;
- a first oligonucleotide primer as described herein and a second oligonucleotide primer as described herein, e.g., a forward oligonucleotide primer and a reverse oligonucleotide primer, and two labeled oligonucleotide probes as described herein;
- a first oligonucleotide primer as described herein and a second oligonucleotide primer as described herein, e.g., a forward oligonucleotide primer and a reverse oligonucleotide primer, two oligonucleotide probes as described herein, and an intercalating dye;
- a first oligonucleotide primer as described herein and a second oligonucleotide primer as described herein, e.g., a forward oligonucleotide primer and a reverse oligonucleotide primer, two oligonucleotide probes as described herein, and one or more of an intercalating dye, PCR buffer, water, dNTPs, and/or magnesium;
- a first oligonucleotide primer as described herein and a second oligonucleotide primer as described herein, e.g., a forward oligonucleotide primer and a reverse oligonucleotide primer, two labeled oligonucleotide probes as described herein, and one or more of a PCR buffer, water, dNTPs, and/or magnesium.
- a first oligonucleotide primer as described herein and a second oligonucleotide primer as described herein, e.g., a forward oligonucleotide primer and a reverse oligonucleotide primer, DNA polymerase, and an oligonucleotide probe as described herein;
- a first oligonucleotide primer as described herein and a second oligonucleotide primer as described herein, e.g., a forward oligonucleotide primer and a reverse oligonucleotide primer, DNA polymerase, and a labeled oligonucleotide probe as described herein;
- a first oligonucleotide primer as described herein and a second oligonucleotide primer as described herein, e.g., a forward oligonucleotide primer and a reverse oligonucleotide primer, DNA polymerase, and at least two oligonucleotide probes as described herein;
- a first oligonucleotide primer as described herein and a second oligonucleotide primer as described herein, e.g., a forward oligonucleotide primer and a reverse oligonucleotide primer, DNA polymerase, and at least two labeled oligonucleotide probes as described herein;
- a first oligonucleotide primer as described herein and a second oligonucleotide primer as described herein, e.g., a forward oligonucleotide primer and a reverse oligonucleotide primer, DNA polymerase, at least two oligonucleotide probes as described herein, and an intercalating dye;
- a first oligonucleotide primer as described herein and a second oligonucleotide primer as described herein, e.g., a forward oligonucleotide primer and a reverse oligonucleotide primer, at least two oligonucleotide probes as described herein, DNA polymerase, and one or more of an intercalating dye, PCR buffer, water, dNTPs, and/or magnesium;
- a first oligonucleotide primer as described herein and a second oligonucleotide primer as described herein, e.g., a forward oligonucleotide primer and a reverse oligonucleotide primer, at least two labeled oligonucleotide probes as described herein, DNA polymerase, and one or more of a PCR buffer, water, dNTPs, and/or magnesium.

In various embodiments described herein, a plurality of similar but degenerate oligonucleotide primers or probes may be present in a single reagent or kit. Degenerate oligonucleotide primers or probes include a mixture of oligonucleotide primers or probes that differ at one or more base pairs but have at least 70% similarity to each other, e.g., at least 75%, 80%, 85%, 90%, or 95% similarity to each other. In various instances, a reagent or kit includes oligonucleotide primers and/or probes that cumulatively include at least two, at least three, or at least four different nucleobases at a given position. Degenerate oligonucleotide probes encompass one or more nucleotide substitutions, insertions, or deletions.

In various embodiments, a first or forward oligonucleotide primer is an oligonucleotide having a nucleic acid sequence according to SEQ ID NO: 23.

In various embodiments, a second or reverse oligonucleotide primer is an oligonucleotide having a nucleic acid sequence complementary to the sequence of SEQ ID NO: 40.

In various embodiments, a first or forward oligonucleotide primer is an oligonucleotide having a nucleic acid sequence according to SEQ ID NO: 23 and a second or reverse oligonucleotide primer is an oligonucleotide having a nucleic acid sequence complementary to the sequence of SEQ ID NO: 40.

In various embodiments, an oligonucleotide probe or labeled oligonucleotide probe has a nucleic acid sequence according to SEQ ID NO: 56.

In various embodiments, an oligonucleotide probe or labeled oligonucleotide probe has a nucleic acid sequence according to SEQ ID NO: 68.

In various embodiments, two oligonucleotide probes or labeled oligonucleotide probes include an oligonucleotide probe or labeled oligonucleotide probe having a nucleic acid sequence according to SEQ ID NO: 56 and an oligonucleotide probe or labeled oligonucleotide probe having a nucleic acid sequence according to SEQ ID NO: 68.

In various embodiments, a first or forward oligonucleotide primer is an oligonucleotide having a nucleic acid sequence according to SEQ ID NO: 23, a second or reverse oligonucleotide primer is an oligonucleotide having a nucleic acid sequence complementary to the sequence of SEQ ID NO: 40, and two oligonucleotide probes or labeled oligonucleotide probes include an oligonucleotide probe or labeled oligonucleotide probe having a nucleic acid sequence according to SEQ ID NO: 56 and an oligonucleotide probe or labeled oligonucleotide probe having a nucleic acid sequence according to SEQ ID NO: 68.

Those of skill in the art will further appreciate from the present disclosure that various reagents or kits of the present invention can include combinations of reagents described herein and can further include any of one or more additional oligonucleotide primers, oligonucleotide primer pairs, or oligonucleotide probes, which further included reagents may or may not be known in the art.

In certain instances a kit of the present invention is a kit including one or more separately packaged reagents (e.g., primers and/or probes) as described herein.

In certain instances a kit of the present invention is a kit including a single solution including one or more reagents (e.g., primers and/or probes) as described herein.

In certain instances a kit of the present invention is a kit including a single solution including one or more reagents (e.g., primers and/or probes) as described herein together with additional separately packaged reagents (e.g., primers and/or probes) as described herein.

Thus a kit of the present invention may be a be a set of separately packaged reagents or combination of reagents, optionally provided in a single housing container (e.g., a box) or plurality of housing containers (e.g., boxes).

A kit as described herein may further include instructions for use of components of the kit in detecting and/or quantifying the presence and/or level of a nucleic acid sequence present in a sample.

Applications

The present invention includes methods, reagents, and kits useful in detecting and/or quantifying the presence and/or level of a nucleic acid sequence present in a sample. A sample of the present invention may be, e.g., from a human subject, such as a human subject having, diagnosed as having, suspected of having, or at risk of having HIV.

In various instances, methods, reagents, and/or kits as described herein can be used to determine whether or not a sample contains an HIV nucleic acid, e.g., presence or absence of HIV or HIV nucleic acid in a sample.

In various instances, methods, reagents, and/or kits as described herein can be used to determine the load of HIV or HIV nucleic acid in a sample. In various instances, methods, reagents, and/or kits as described herein can be used to determine the sequence or type of HIV or HIV nucleic acid in a sample. In certain instances, methods, reagents, and/or kits as described herein can be used to monitor presence or load of HIV or HIV nucleic acid in a subject overtime, e.g., in samples from the subject. In various instances, presence or load of HIV or HIV nucleic acid is measured at each of a first time and a second time. In some instances, the first time is prior to initiation of treatment and the second time is after initiation of measurement. In some instances, the first time is at initiation of a treatment regimen and the second time is subsequent to initiation of treatment, e.g., during treatment or after conclusion of treatment. In some instances, the first time and second time are during treatment. In some instances the first time and the second time are separated by at least one day, two days, three days, four days, five days, six days, 1 week, 2 weeks, 3 weeks, 1 month, 2 months, 3 months, 4 months, 5 months, 6 months, 1 year, or more than one year.

In various instances, the sequence or type of HIV nucleic acid in a sample or subject may be used to optimize a therapeutic choice or therapeutic regimen. An decrease in HIV load between a first measure of HIV load and a subsequent second measure of HIV load may indicate that a treatment regimen is successful. In such instances, treatment can be maintained or reduced. An increase in HIV load, an insufficient or clinically insignificant decrease in HIV load, or unchanged HIV load between a first measure of HIV load and a subsequent second measure of HIV load may indicate that a treatment regimen is not successful. In such instances, treatment can be increased or otherwise modified, e.g., by the addition of one or more therapeutic agents to a treatment regimen. In exemplary instances, a therapeutic agent added to a regimen has a distinct mechanism of action from any therapeutic agent in the prior therapeutic regimen. In certain instance, failure of a treatment regimen may be due to or indicative of resistance to one or more HIV therapeutic agents. Those of skill in the art will appreciate that modification of a therapeutic regiment is generally determined by a medical practitioner after patient-specific evaluation.

In various instances, the sequence or type of HIV nucleic acids in a sample or subject may be used to identify a subject having an HIV nucleic acid sequence associated with or indicative of resistance to one or more HIV therapeutics.

In certain instances, resistance may encompass failure of a drug or therapeutic regimen (e.g., after one month, two months, three months, four months, five months, six months, or more of treatment) to reduce HIV load, as measured from a sample, in a subject as compared to HIV viral load of a comparable reference sample from the patient or as compared to a standard value. In certain instances, resistance may encompass failure of a drug or therapeutic regimen (e.g., after one month, two months, three months, four months, five months, six months, or more of treatment) to reduce or maintain HIV viral load below a level of 200 copies/ml, below a level of 300 copies/ml, below a level of 400 copies/ml, below a level of 500 copies/ml, below a level of 750 copies/ml, below a level of 1000 copies/ml, or below a level of 5,000 copies/ml.

In certain instances, resistance may encompass failure of a drug or therapeutic regimen (e.g., after one month, two months, three months, four months, five months, six months, or more of treatment) to reduce HIV RNA load, as measured from a sample, in a subject as compared to HIV RNA viral load of a comparable reference sample from the patient or as compared to a standard value. In certain instances, resistance may encompass failure of a drug or therapeutic regimen (e.g., after one month, two months, three months, four months, five months, six months, or more of treatment) to reduce or maintain HIV RNA load below a level of 200 copies/ml, below a level of 300 copies/ml, below a level of 400 copies/ml, below a level of 500 copies/ml, below a level of 750 copies/ml, below a level of 1000 copies/ml, or below a level of 5,000 copies/ml.

In certain instances, resistance may encompass failure of a drug or therapeutic regimen (e.g., after one month, two months, three months, four months, five months, six months, or more of treatment) to increase CD4+ cell count, as measured from a sample, in a subject as compared to CD4+ cell count of a comparable reference sample from the patient or as compared to a standard value. In certain instances, resistance may encompass failure of a drug or therapeutic regimen (e.g., after one month, two months, three months, four months, five months, six months, or more of treatment) to increase CD4+ cell count to or maintain CD4+ cell count above 50 CD4+ cells/W, above 100 CD4+ cells/W, above 150 CD4+ cells/W, or above 200 CD4+ cells/W.

In certain instances, resistance may encompass an infection or HIV strain characterized by HIV nucleic acids having a sequence known in the art to be associated with resistance to one or more drugs or therapeutic regimens.

In any of the various embodiments described herein, resistance to a drug or therapeutic regimen may be resistance to an integrase inhibitor or a therapeutic regimen including at least one integrase inhibitor. Examples of integrase inhibitors include, without limitation, raltegravir, elvitegravir, dolutegravir, MK-2048, GS 9137 (Gilead), globoidnan A, L-000870812, S/GSK1349572, and S/GSK1265744, with or without a pharmacokinetic (PK) booster. Mutations known to be associated with resistance to one or more integrase inhibitors include, without limitation, one or more protein mutations, HIV nucleic acid mutations, or HIV nucleic acid mutations encoding a protein mutation, known to be associated with resistance to raltegravir, e.g., T66A, E92Q, E138K, E138A, G140S, G140A, Y143R, Y143C, Y143H, Q148H, Q148R, Q148K, or N155H; one or more protein mutations, HIV nucleic acid mutations, or HIV nucleic acid mutations encoding a protein mutation, known to be associated with resistance to elvitegravir, e.g., T66I, T66A, T66K, E92Q, E138K, E138A, G140S, G140A, S147G, Q148H, Q148R, Q148K, or N155H; one or more protein mutations, HIV nucleic acid mutations, or HIV nucleic acid mutations encoding a protein mutation, known to be associated with resistance to dolutegravir, e.g., E92Q, E138K, E138A, G140S, G140A, Q148H, Q148R, or Q148K, and/or one or more protein mutations, HIV nucleic acid mutations, or HIV nucleic acid mutations encoding a protein mutation, known to be associated with resistance to integrase inhibitors including without limitation E92G, E92V, Y143K, Y143S, Y143G, Y143A, N155S, N155T, G118R, F121Y, P145S, Q146P. In various instances, such mutations as described above may be identified as primary, major, or major primary mutations in the development of integrase inhibitor resistance. Mutations known to be associated with resistance to one or more integrase inhibitors include, without limitation, one or more protein mutations, HIV nucleic acid mutations, or HIV nucleic acid mutations encoding a protein mutation, H51Y, V541, L68V, L74M, Q95K, T97A, H114Y, A128T, E138K, E138A, G140S, G140A, G140C, V151I, V151L, V151A, S153Y, S153F, E157Q, G163R, G163K, S230R, R236K, any of which may in certain instances be referred to as accessory or major accessory mutations in the development of integrase inhibitor resistance. Any of one or more mutations described herein may be indicative of, diagnostic of, or present in an HIV infection that is or may be characterized by resistance to treatment with integrase inhibitor(s). Those of skill in the art will appreciate that identification of the consensus sequence residue in identification of mutations described above is not per se substantive to the identification of any nucleotide or amino acid mutation, and is included for purposes of indicating position within and contrast against a hypothetical reference sequence, e.g., a subtype B HIV integrase consensus sequence derived from alignment of subtype B sequences (SEQ ID NO: 130). It is to be further understood by those of skill in the art that accumulation of multiple such mutations as described above will typically be associated with an increased likelihood or level of resistance to integrase inhibitor.

In various instances, the sequence or type of one or more HIV nucleic acids in a sample or subject, and/or the amino acid sequences of proteins encoded thereby, may be be used to identify a subject as resistant to one or more integrase inhibitors or as likely to be resistant to one or more integrase inhibitors. Mutations indicative of such are known in the art and are described herein above with respect to amino acid sequence mutations that may be encoded by an HIV nucleic acid. It is to be appreciated by those of skill in the art that nucleic acid mutations that would result in the described amino acid mutations are also encompassed herein. A therapeutic regiment may be prescribed accordingly.

In various instances, the sequence or type of one or more HIV nucleic acids in a sample or subject, and/or the amino acid sequences of proteins encoded thereby, may be be used to identify a subject as in need of treatment with a therapeutic regimen that excludes or does not rely solely upon one or more of raltegravir, elvitegravir, dolutegravir, MK-2048, GS 9137 (Gilead), globoidnan A, L-000870812, S/GSK1349572, S/GSK1265744, globoidnan A, cabotegravir, and BMS-707035, or any integrase inhibitor or all integrase inhibitors. Mutations indicative of such are known in the art and are described herein above with respect to amino acid sequence mutations that may be encoded by an HIV nucleic acid. It is to be appreciated by those of skill in the art that nucleic acid mutations that would result in the described amino acid mutations are also encompassed herein. A therapeutic regiment may be prescribed accordingly.

In various instances, the sequence or type of one or more HIV nucleic acids in a sample or subject, and/or the amino acid sequences of proteins encoded thereby, may be be used to identify a subject as a subject in which infection may be successfully treated by administration of a therapeutically effective dose or regimen of one or more integrase inhibitors or as a subject in which infection may likely be successfully treated by administration of a therapeutically effective dose or regimen of one or more integrase inhibitors. Absence of one or more mutations associated with resistance to integrase inhibitor treatment may be determined, as mutations associated with resistance to integrase inhibitor treatment are known in the art and are described herein above with respect to amino acid sequence mutations that may be encoded by an HIV nucleic acid. It is to be appreciated by those of skill in the art that nucleic acid mutations that would result in the described amino acid mutations are also encompassed herein. A therapeutic regiment may be prescribed accordingly.

In various instances, the sequence or type of one or more HIV nucleic acids in a sample or subject, and/or the amino acid sequences of proteins encoded thereby, may be be used to identify a subject as in need of treatment with a therapeutic regimen that includes or relies solely upon one or more of raltegravir, elvitegravir, dolutegravir, MK-2048, GS 9137 (Gilead), globoidnan A, L-000870812, S/GSK1349572, S/GSK1265744, or any integrase inhibitor or all integrase inhibitors. Absence of one or more mutations associated with resistance to integrase inhibitor treatment may be determined, as mutations associated with resistance to integrase inhibitor treatment are known in the art and are described herein above with respect to amino acid sequence mutations that may be encoded by an HIV nucleic acid. It is to be appreciated by those of skill in the art that nucleic acid mutations that would result in the described amino acid mutations are also encompassed herein. A therapeutic regiment may be prescribed accordingly.

In various instances, any of the methods, kits, and/or reagents described herein may be used to determine the presence of load of HIV in a blood sample. In certain instances, the blood sample is from a patient. In certain instances, the blood sample is present in a blood bank.

EXAMPLES

The present examples are included to illustrate at least one of the various embodiments of the present invention. The below examples are not limiting to any of the embodiments provided herein or to the scope of the present invention.

Example 1: Design of Primers and Probes for HIV-1 Viral Load Assay

An analysis of global HIV subtypes was utilized to determine the ideal hybridization region for HIV-1 assays. Based on the analysis, as implemented by Siemens inventors, the global lowest-entropy region of the HIV-1 genome (see FIG. 1) was identified for selection of primers and probes for an optimal HIV-1 viral load assay. Identification of a single lowest-entropy region for design of primers and probes from diverse HIV-1 sequences improves amplification of diverse HIV-1 sequences and reduces manufacturing cost as compared to certain other HIV-1 viral load assays.

The specific subset of possible primer and probe sequences of the present Example, targeting the integrase region, were further analyzed to avoid regions which were identified to be under mutation selection pressure due to the recently developed new class of integrase inhibitor therapy. HIV sequences derived from plasma of the first patients to experience integrase inhibitor failure were analyzed.

Primer and probe sequences were optimized to maximize the number of HIV-1 genomes (and HIV-1 genome groups) that perfectly matched the primer and probe sequences (FIG. 2).

Primer and probe sequences were additionally evaluated based on thermodynamic oligonucleotide-template hybrid melting temperature calculations, positional alignment of favorable mismatches against divergent sequences, and further features considered to maximize assay performance while minimizing assay complexity and manufacturing cost.

Figure 4:
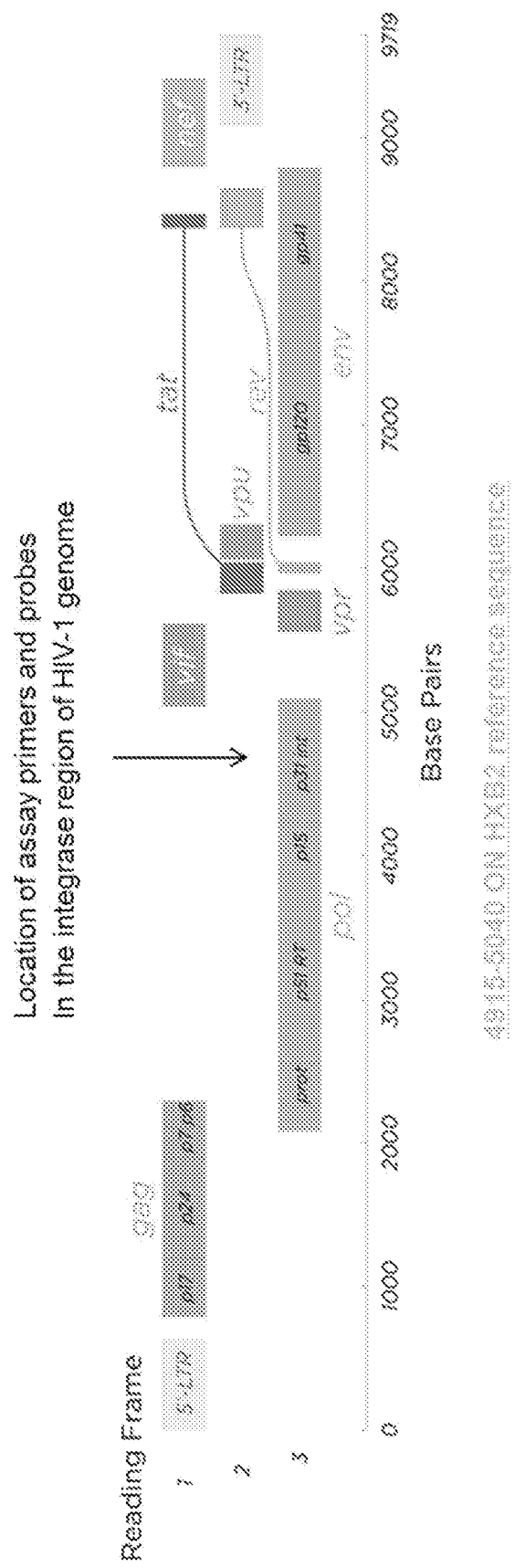
FIG. 4 is a schematic showing the region of the HIV-1 genome to which certain primers and probes of the invention correspond.

Based on the above, specific primers and probes were selected. Sequences of selected primers and probes are shown in FIG. 3. The region of the genome to which these primes and probes correspond is identified in FIG. 4.

Superiority of selected primers and probes, as compared to primers and probes of certain commercially available HIV-1 viral load assays, was confirmed by computation design analysis and laboratory testing. For instance, one commercially available HIV-1 assay was found to include primers and probes bearing significant nucleotide sequence mismatch when compared to certain HIV-1 subtypes, in particular subtypes A2 and H1 (FIG. 5). Such mismatch may lead to incorrect viral load determinations and/or non-reportable results in certain patients.

Example 2: Selected HIV-1 Assay Primers and Probes Provide Robust Assay Performance in Patient Samples To confirm performance of the assay with integrase inhibitor selected mutations, patient specimens from Raltegravir clinical trials sponsored by Merck, Inc. were analyzed by DNA sequencing. Confirmatory experiments were carried out using in vitro transcript synthetic templates matching the viral RNA sequences of the patient specimens. Results confirmed that integrase gene resistance mutations would not interfere with the new assay performance. These results contrast with certain commercially available assays, which were found to have significant mismatches that impacted assay performance detrimentally (FIG. 6).

Example 3: Selected HIV-1 Assay Primers and Probes Compare Favorably to Two Commercially Available HIV Assays In this Example, the primers and probes identified in FIG. 3 were used to assay four particular mutant integrase gene transcripts of mutant HIV-1 virus derived from integrase inhibitor experienced patient sequences. The same mutant transcripts were assayed using two commercially available assays (Siemens VERSANT® HIV-1 RNA 1.0 (kPCR) assay and Abbott REALTIME HIV-1 assay) Amplification was determined by quantitative real-time reverse transcriptase PCR.

Figure 7:
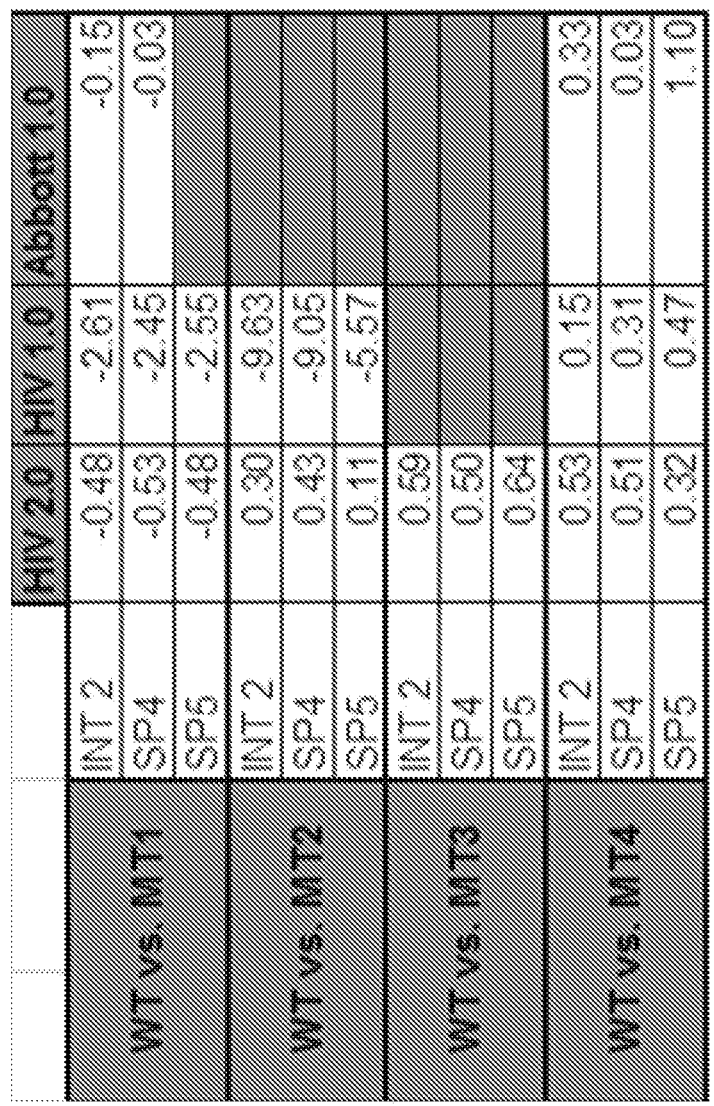
FIG. 7 is a chart which compares the amplification results of certain mutant integrase gene transcripts by primers and probes of the present invention vs. primers and probes of commercially available HIV-1 viral load assays.

Results are shown in FIG. 7. The assay utilizing the inventive primers and probes of FIG. 3 is labeled "HIV 2.0" while the Siemens VERSANT® HIV-1 RNA 1.0 (kPCR) assay and Abbott REALTIME HIV-1 assay are labeled as "HIV 1.0" and "Abbott 1.0," respectively. In each case, samples were tested at three concentrations: 1.82e6 RNA copies per mL (INT2), 1.82e4 RNA copies per mL (SP4) and 1.82e3 RNA copies per mL (SP5).

Results indicate that only the assay utilizing inventive primers and probes according to FIG. 3 performed adequately with all four mutant integrase gene transcripts derived from integrase inhibitor experienced patient sequences. In comparison, the Siemens VERSANT® HIV-1 RNA 1.0 (kPCR) assay produced high Ct results with mutants 1 and 2, and no result with mutant 3 (FIG. 7). Further, the Abbott REALTIME HIV-1 assay produced no results with mutants 2 and 3.

Sequences

I. Summary of HIV Sequences (Details in Section IV of Sequences)

This section provides a summary of selected HIV sequences that represent known and/or consensus HIV genomes. Such known genomes can be or represent templates or reference sequences encompassed by the present invention.

| SEQUENCE | BP | SEQ ID NO |
|---|---|---|
| SEQ 01_Majority | 9684 (see below) | SEQ ID NO: 1 |
| SEQ 02_Majority | 9186 (see below) | SEQ ID NO: 2 |
| SEQ A1_Majority | 9595 (see below) | SEQ ID NO: 3 |
| SEQ A2_Majority | 8980 (see below) | SEQ ID NO: 4 |
| SEQ B_Majority | 9621 (see below) | SEQ ID NO: 5 |
| SEQ C_Majority | 9611 (see below) | SEQ ID NO: 6 |
| SEQ D_Majority | 9581 (see below) | SEQ ID NO: 7 |
| SEQ F1_Majority | 8976 (see below) | SEQ ID NO: 8 |
| SEQ F2_Majority | 8574 (see below) | SEQ ID NO: 9 |
| SEQ G_Majority | 9621 (see below) | SEQ ID NO: 10 |
| SEQ NC_001802.1 | 9181 (see below) | SEQ ID NO: 11 |

II. Integrase Sequences

These sequences represent known HIV integrase sequences. Such known ingrease sequences can be or represent integrase sequences encompassed by the present invention.

| Integrase | | |
|---|---|---|
| SEQ 01_Majority | 4241-5107 | SEQ ID NO: 12 |
| SEQ 02_Majority | 4228-5094 | SEQ ID NO: 13 |
| SEQ A1_Majority | 4217-5083 | SEQ ID NO: 14 |
| SEQ A2_Majority | 3618-4484 | SEQ ID NO: 15 |
| SEQ B_Majority | 4231-5097 | SEQ ID NO: 16 |
| SEQ C_Majority | 4208-5074 | SEQ ID NO: 17 |
| SEQ D_Majority | 4235-5101 | SEQ ID NO: 18 |
| SEQ F1_Majority | 3580-4446 | SEQ ID NO: 19 |
| SEQ F2_Majority | 3426-4292 | SEQ ID NO: 20 |
| SEQ G_Majority | 4215-5081 | SEQ ID NO: 21 |
| SEQ NC_001802.1 | 3776-4642 | SEQ ID NO: 22 |

III. Oligonucleotide Primer Sequences and Oligonucleotide Probe Sequences

These sequences represent examples of forward and reverse oligonucleotide primers encompassed by the present invention and examples of oligonucleotide probes encompassed by the present invention.

```
Forward Primer Sequence
                                  SEQ ID NO: 23
TTTTCGGGTTTATTACAGRG
```

| Forward Primer Region (40 bp) | | |
|---|---|---|
| SEQ 01_Majority | 4896-4935 | SEQ ID NO: 24 |
| SEQ 02_Majority | 4883-4922 | SEQ ID NO: 25 |
| SEQ A1_Majority | 4872-4911 | SEQ ID NO: 26 |
| SEQ A2_Majority | 4273-4312 | SEQ ID NO: 27 |
| SEQ B_Majority | 4886-4925 | SEQ ID NO: 28 |
| SEQ C_Majority | 4863-4902 | SEQ ID NO: 29 |
| SEQ D_Majority | 4890-4929 | SEQ ID NO: 30 |
| SEQ F1_Majority | 4235-4274 | SEQ ID NO: 31 |
| SEQ F2_Majority | 4081-4120 | SEQ ID NO: 32 |
| SEQ G_Majority | 4870-4909 | SEQ ID NO: 33 |
| SEQ NC_001802.1 | 4431-4470 | SEQ ID NO: 34 |

```
Alternative Forward Primers
                                  SEQ ID NO: 35
TTTTCGGGTTTATTACAGAGAC

SEQ ID NO: 36
CGGGTCTATTACAGGGAC

SEQ ID NO: 37
GGTTTATTACAGGGACAGC

SEQ ID NO: 38
GGGTTTATTACAGAGACAGCA

SEQ ID NO: 39
CGGGTTTATTACAGGGACA

Reverse Primer Sequence Location
                                  SEQ ID NO: 40
TGGAAAACARATGGCAGG
```

| Reverse Primer Region (40 bp) | | |
|---|---|---|
| SEQ 01_Majority | 5042-5081 | SEQ ID NO: 41 |
| SEQ 02_Majority | 5029-5068 | SEQ ID NO: 42 |
| SEQ A1_Majority | 5018-5057 | SEQ ID NO: 43 |
| SEQ A2_Majority | 4419-4458 | SEQ ID NO: 44 |
| SEQ B_Majority | 5032-5071 | SEQ ID NO: 45 |
| SEQ C_Majority | 5009-5048 | SEQ ID NO: 46 |
| SEQ D_Majority | 5036-5075 | SEQ ID NO: 47 |
| SEQ F1_Majority | 4381-4420 | SEQ ID NO: 48 |
| SEQ F2_Majority | 4227-4266 | SEQ ID NO: 49 |
| SEQ G_Majority | 5016-5055 | SEQ ID NO: 50 |
| SEQ NC_001802.1 | 4577-4616 | SEQ ID NO: 51 |

```
Alternative Reverse Primer Sequence Locations
                                  SEQ ID NO: 52
ATGGAAAACAAATGGCAGG

SEQ ID NO: 53
AAAACAGATGGCAGGTGA

SEQ ID NO: 54
TGGAAAACAGATGGCAGG

SEQ ID NO: 55
CAAACAGATGGCAGGTGA

Probe A Sequence
                                  SEQ ID NO: 56
        GTGGAAAGGTGAAGGGGCAGTAGT
```

| Probe A Region (40 bp) | | |
|---|---|---|
| SEQ 01_Majority | 4958-4997 | SEQ ID NO: 57 |
| SEQ 02_Majority | 4945-4984 | SEQ ID NO: 58 |
| SEQ A1_Majority | 4934-4973 | SEQ ID NO: 59 |
| SEQ A2_Majority | 4335-4374 | SEQ ID NO: 60 |
| SEQ B_Majority | 4948-4987 | SEQ ID NO: 61 |
| SEQ C_Majority | 4925-4964 | SEQ ID NO: 62 |
| SEQ D_Majority | 4952-4991 | SEQ ID NO: 63 |
| SEQ F1_Majority | 4297-4336 | SEQ ID NO: 64 |
| SEQ F2_Majority | 4143-4182 | SEQ ID NO: 65 |
| SEQ G_Majority | 4932-4971 | SEQ ID NO: 66 |
| SEQ NC_001802.1 | 4493-4532 | SEQ ID NO: 67 |

```
              Probe B Sequence
                                  SEQ ID NO: 68
       TCTCTGGAAAGGTGAAGGGGCAGT
```

| Probe B Region (40 bp) | | |
|---|---|---|
| SEQ 01_Majority | 4955-4994 | SEQ ID NO: 69 |
| SEQ 02_Majority | 4942-4981 | SEQ ID NO: 70 |
| SEQ A1_Majority | 4931-4970 | SEQ ID NO: 71 |
| SEQ A2_Majority | 4332-4371 | SEQ ID NO: 72 |
| SEQ B_Majority | 4945-4984 | SEQ ID NO: 73 |
| SEQ C_Majority | 4922-4961 | SEQ ID NO: 74 |
| SEQ D_Majority | 4949-4988 | SEQ ID NO: 75 |
| SEQ F1_Majority | 4294-4333 | SEQ ID NO: 76 |
| SEQ F2_Majority | 4140-4179 | SEQ ID NO: 77 |
| SEQ G_Majority | 4929-4968 | SEQ ID NO: 78 |
| SEQ NC_001802.1 | 4490-4529 | SEQ ID NO: 79 |

Alternative Probes

SEQ ID NO: 80
CTCTGGAAAGGTGAAGGGGCAGTG

SEQ ID NO: 81
TTGGAAAGGTGAAGGGGCAGTAGT

SEQ ID NO: 82
TACTTTGGAAAGGTGAAGGGGCAGT

SEQ ID NO: 83
CTGGAAAGGTGAAGGGGCAGTTGTA

SEQ ID NO: 84
CTGGAAAGGTGAAGGGGCAGTAGT

| Forward Primer Region (20 bp) | | |
|---|---|---|
| SEQ 01_Majority | 4906-4925 | SEQ ID NO: 85 |
| SEQ 02_Majority | 4893-4912 | SEQ ID NO: 86 |
| SEQ A1_Majority | 4882-4901 | SEQ ID NO: 87 |
| SEQ A2_Majority | 4283-4302 | SEQ ID NO: 88 |
| SEQ B_Majority | 4896-4915 | SEQ ID NO: 89 |
| SEQ C_Majority | 4873-4892 | SEQ ID NO: 90 |
| SEQ D_Majority | 4900-4919 | SEQ ID NO: 91 |
| SEQ F1_Majority | 4245-4264 | SEQ ID NO: 92 |
| SEQ F2_Majority | 4091-4110 | SEQ ID NO: 93 |
| SEQ G_Majority | 4880-4899 | SEQ ID NO: 94 |
| SEQ NC_001802.1 | 4441-4460 | SEQ ID NO: 95 |

| Reverse Primer Region (18 bp) | | |
|---|---|---|
| SEQ 01_Majority | 5053-5070 | SEQ ID NO: 96 |
| SEQ 02_Majority | 5040-5057 | SEQ ID NO: 97 |
| SEQ A1_Majority | 5029-5046 | SEQ ID NO: 98 |
| SEQ A2_Majority | 4430-4447 | SEQ ID NO: 99 |
| SEQ B_Majority | 5043-5060 | SEQ ID NO: 100 |
| SEQ C_Majority | 5020-5037 | SEQ ID NO: 101 |

| Reverse Primer Region (18 bp) | | |
|---|---|---|
| SEQ D_Majority | 5047-5064 | SEQ ID NO: 102 |
| SEQ F1_Majority | 4392-4409 | SEQ ID NO: 103 |
| SEQ F2_Majority | 4238-4255 | SEQ ID NO: 104 |
| SEQ G_Majority | 5027-5044 | SEQ ID NO: 105 |
| SEQ NC_001802.1 | 4588-4605 | SEQ ID NO: 106 |

| Probe A (24 bp) | | |
|---|---|---|
| SEQ 01_Majority | 4966-4989 | SEQ ID NO: 107 |
| SEQ 02_Majority | 4953-4976 | SEQ ID NO: 108 |
| SEQ A1_Majority | 4942-4965 | SEQ ID NO: 109 |
| SEQ A2_Majority | 4343-4366 | SEQ ID NO: 110 |
| SEQ B_Majority | 4956-4979 | SEQ ID NO: 111 |
| SEQ C_Majority | 4933-4956 | SEQ ID NO: 112 |
| SEQ D_Majority | 4960-4983 | SEQ ID NO: 113 |
| SEQ F1_Majority | 4305-4328 | SEQ ID NO: 114 |
| SEQ F2_Majority | 4151-4174 | SEQ ID NO: 115 |
| SEQ G_Majority | 4940-4963 | SEQ ID NO: 116 |
| SEQ NC_001802.1 | 4501-4524 | SEQ ID NO: 117 |

| Probe B (24 bp) | | |
|---|---|---|
| SEQ 01_Majority | 4963-4986 | SEQ ID NO: 118 |
| SEQ 02_Majority | 4950-4973 | SEQ ID NO: 119 |
| SEQ A1_Majority | 4939-4962 | SEQ ID NO: 120 |
| SEQ A2_Majority | 4340-4363 | SEQ ID NO: 121 |
| SEQ B_Majority | 4953-4976 | SEQ ID NO: 122 |
| SEQ C_Majority | 4930-4953 | SEQ ID NO: 123 |
| SEQ D_Majority | 4957-4980 | SEQ ID NO: 124 |
| SEQ F1_Majority | 4302-4325 | SEQ ID NO: 125 |
| SEQ F2_Majority | 4148-4171 | SEQ ID NO: 126 |
| SEQ G_Majority | 4937-4960 | SEQ ID NO: 127 |
| SEQ NC_001802.1 | 4498-4521 | SEQ ID NO: 128 |

Reverse Primer

SEQ ID NO: 129
CCTGCCATYTGTTTTCCA

IV. HIV Sequences

These sequences represent selected known and/or consensus HIV genomes. Such known and/or consensus genomes can be or represent templates or reference sequences encompassed by the present invention. Subtype B HIV sequences are in some instances referred to or utilized as a reference HIV sequence, e.g., in the naming or identification of mutations.

INT subtype B integrase consensus amino acid sequence

SEQ ID NO: 130
FLDGIDKAQEEHEKYHSNWRAMASDFNLPPVVAKEIVASCDKCQLKGEAMHGQVD

CSPGIWQLDCTHLEGKIILVAVHVASGYIEAEVIPAETGQETAYFLLKLAGRWPVKTI

HTDNGSNFTSTTVKAACWWAGIKQEFGIPYNPQSQGVVESMNKELKKIIGQVRDQA

EHLKTAVQMAVFIHNFKRKGGIGGYSAGERIVDIIATDIQTKELQKQITKIQNFRVYY

RDSRDPLWKGPAKLLWKGEGAVVIQDNSDIKVVPRRKAKIIRDYGKQMAGDDCVA

SRQDED

Subtype B VOL consensus amino acid sequence

SEQ ID NO: 131
FFREDLAFPQGKAREFSSEQTRANSPTRRELQVWGRDNNSLSEAGADRQGTV-

SFSFPQITLWQRPLVTIKIGGQLKEALLDTGADDTVLEEMNLPGRWKPKMIGGIGGFI

-continued

KVRQYDQILIEICGHKAIGTVLVGPTPVNIIGRNLLTQIGCTLNFPISPIETVPVKLKPG

MDGPKVKQWPLTEEKIKALVEICTEMEKEGKISKIGPENPYNTPVFAIKKKDSTKWR

KLVDFRELNKRTQDFWEVQLGIPHPAGLKKKKSVTVLDVGDAYFSVPLDKDFRKYT

AFTIPSINNETPGIRYQYNVLPQGWKGSPAIFQSSMTKILEPFRKQNPDIVIYQYMDDL

YVGSDLEIGQHRTKIEELRQHLLRWGFTTPDKKHQKEPPFLWMGYELHPDKWTVQP

IVLPEKDSWTVNDIQKLVGKLNWASQIYAGIKVKQLCKLLRGTKALTEVIPLTEEAEL

ELAENREILKEPVHGVYYDPSKDLIAEIQKQGQGQWTYQIYQEPFKNLKTGKYARM

RGAHTNDVKQLTEAVQKIATESIVIWGKTPKFKLPIQKETWEAWWTEYWQATWIPE

WEFVNTPPLVKLWYQLEKEPIVGAETFYVDGAANRETKLGKAGYVTDRGRQKVVS

LTDTTNQKTELQAIHLALQDSGLEVNIVTDSQYALGIIQAQPDKSESELVSQIIEQLIKK

EKVYLAWVPAHKGIGGNEQVDKLVSAGIRKVLFLDGIDKAQEEHEKYHSNWRAMA

SDFNLPPVVAKEIVASCDKCQLKGEAMHGQVDCSPGIWQLDCTHLEGKIILVAVHVA

SGYIEAEVIPAETGQETAYFLLKLAGRWPVKTIHTDNGSNFTSTTVKAACWWAGIKQ

EFGIPYNPQSQGVVESMNKELKKIIGQVRDQAEHLKTAVQMAVFIHNFKRKGGIGGY

SAGERIVDIIATDIQTKELQKQITKIQNFRVYYRDSRDPLWKGPAKLLWKGEGAVVIQ

DNSDIKVVPRRKAKIIRDYGKQMAGDDCVASRQDED

SEQ 01_Majority

SEQ ID NO: 1
TGGATGGGCTAATTTACTCCAAGAAAAGACAAGAGATCCTTGACTTATGGGTCTA

TAATACACAAGGCTTCTTCCCTGATTGGCAAAACTACACACCAGGGCCAGGGATC

AGATACCCACTGTGTTTTGGATGGTGCTTCAAGCTAGTACCAGTTGACCCAAGAG

AAGTAGAGGAGGACAACAAAGGAGAAAACAACTGCCTGTTACACCCCATGAGCC

AGCATGGAATAGATGACGAAGAAAGAAGTGCTGATGTGGAAGTTTGACAGTG

CCCTAGCACGAAAACACATAGCCCGAGAACTGCATCCAGAGTACTATAAAGACT

GCTGACAAAGAAGTTTCTAACCAGGACTTCCGCTGGGGACTTTCCAGGGGAGGT

GTGGCCGGGGCGGAGTTGGGGAGTGGCTAACCCTCAGATGCTGCATAAAAGCAG

CCGCTTTTCGCTTGTACTGGGTCTCTCTTGTTAGACCAGGTCGAGCCCGGGAGCTC

TCTGGCTAGCAAGGGAACCCACTGCTTAAAGCCTCAATAAAGCTTGCCTTGAGTG

CTTAAAGTGGTGTGTGCCCGTCTGTGTTAGGACTCTGGTAACTAGAGATCCCTCA

GACCACTCTAGACTGAGTAAAAATCTCTAGCAGTGGCGCCCGAACAGGGACTTG

AAAGCGAAAGTTAATAGGGACTCGAAAGCGAAAGTTCCAGAGAAGTTCTCTCGA

CGCAGGACTCGGCTTGCTGAGGTGCACACAGCAAGAGGCGAGAGCGGCGACTGG

TGAGTACGCCAAATTTTGACTAGCGGAGGCTAGAAGGAGAGAGATGGGTGCGAG

AGCGTCAGTATTAAGTGGGGGAAAATTAGATGCATGGGAAAAAATTCGGTTACG

GCCAGGGGGAAAGAAAAAATATAGGATGAAACATTTAGTATGGGCAAGCAGAG

AGTTAGAAAGATTCGCACTTAACCCTGGCCTTTTAGAAACAGCAGAAGGATGTC

AACAAATAATAGAACAGTTACAGTCAACTCTCAAGACAGGATCAGAAGAACTTA

AATCATTATTTAATACAGTAGCAACCCTCTGGTGCGTACACCAAAGGATAGAGGT

AAAAGACACCAAGGAAGCTTTAGATAAAATAGAGGAAGTACAAAATAAGAGCC

AGCAAAAGACACAGCAGGCAGCAGCTGGCACAGGAAGCAGCAGCAAAGTCAGC

CAAAATTACCCTATAGTGCAAAATGCACAAGGGCAAATGGTACATCAGCCTTTAT

-continued

```
CACCTAGAACTTTGAATGCATGGGTGAAAGTAGTAGAAGAAAAGGGTTTTAACC

CAGAAGTAATACCCATGTTCTCAGCATTATCAGAGGGAGCCACCCCACAAGATTT

AAATATGATGCTAAATATAGTGGGGGGACACCAGGCAGCAATGCAAATGTTAAA

AGAAACCATCAATGAGGAAGCTGCAGAATGGGATAGGGTACACCCAGTACATGC

AGGGCCTATTCCACCAGGCCAGATGAGGGAACCAAGGGGAAGTGACATAGCAG

GAACTACTAGTACCCTTCAAGAACAAATAGGATGGATGACAAACAATCCACCTA

TCCCAGTGGGAGACATCTATAAAAGGTGGATAATCCTGGGATTAAATAAAATAG

TAAGAATGTATAGCCCTGTTAGCATTTTGGACATAAGACAAGGGCCAAAAGAAC

CCTTCAGAGACTATGTAGATAGGTTCTATAAAACTCTCAGAGCGGAACAAGCTAC

ACAGGAGGTAAAAAACTGGATGACAGAAACCTTGCTAGTCCAAAATGCGAATCC

AGACTGTAAGTCCATTTTAAAAGCATTAGGAACAGGAGCTACATTAGAAGAAAT

GATGACAGCATGCCAGGGAGTGGGAGGACCTAGCCATAAAGCAAGGGTTTTGGC

TGAGGCAATGAGCCAAGCACAACATGCAAATATAATGATGCAGAGAGGCAATTT

TAAGGGCCAGAAAAGAATTAAGTGCTTCAACTGTGGCAAAGAAGGACACCTAGC

CAGAAATTGCAGGGCCCCTAGAAAAAAGGGTTGTTGGAAATGTGGGAAGGAAG

GACATCAAATGAAAGACTGCACTGAGAGACAGGCTAATTTTTTAGGGAAAATTT

GGCCTTCCAACAAGGGAAGGCCGGGGAATTTTCCTCAGAGCAGACCAGAGCCAA

CAGCCCCACCAGCAGAAAACTGGGGGATGGGGAAGAGATAACCTCCTTACNGA

AGCAGGAGCAGAAAGACAAGGAACATCCTCCTCCTTTAGTTTCCCTCAAATCACT

CTTTGGCAACGACCCCTTGTCACAGTAAAAATAGGAGGACAGCTGAAAGAAGCT

CTATTAGATACAGGAGCAGATGATACAGTATTAGAAGATATAAATTTGCCAGGA

AAATGGAAACCAAAAATGATAGGGGGAATTGGAGGTTTTATCAAGGTAAGGCAA

TATGATCAGATACTTATAGAAATTTGTGGAAAAAAGGCTATAGGTACAGTATTAG

TAGGACCTACACCTGTCAACATAATTGGACGAAATATGTTGACTCAGATTGGTTG

TACTTTAAATTTCCCAATTAGTCCTATTGACACTGTACCAGTAACATTAAAGCCA

GGAATGGATGGACCAAAGGTTAAACAGTGGCCATTGACAGAAGAAAAATAAA

AGCATTAACAGAAATTTGTAAAGAGATGGAAGAGGAAGGAAAAATCTCAAAAA

TTGGGCCTGAAAATCCATACAATACTCCAGTATTTGCTATAAAGAAAAAGGACA

GCACCAAATGGAGGAAATTAGTAGATTTCAGAGAGCTCAATAAAAGAACTCAGG

ACTTTTGGGAAGTTCAATTAGGAATACCGCATCCAGCAGGTTTAAAAAAGAAAA

AATCAGTAACAGTACTAGATGTGGGAGATGCATATTTTTCAGTTCCTTTAGATGA

AAGCTTTAGAAAGTATACTGCATTCACCATACCTAGTATAAACAATGAGACACCA

GGAATCAGATATCAGTACAATGTGCTGCCACAGGGATGGAAAGGATCACCGGCA

ATATTCCAGAGTAGCATGACAAAAATCTTAGAGCCCTTTAGAATAAAAAATCCA

GAAATGGTTATCTATCAATACATGGATGACTTGTATGTAGGATCTGATTTAGAAA

TAGGGCAGCACAGAACAAAAATAGAGGAGCTAAGAGCTCATCTATTGAGCTGGG

GATTTACTACACCAGACAAAAAGCATCAGAAGGAACCTCCATTCCTTTGGATGG

GATATGAACTCCATCCTGACAGATGGACAGTCCAGCCTATAGAACTGCCAGAAA

AAGACAGCTGGACTGTCAATGATATACAGAAATTAGTGGGAAAACTAAATTGGG

CAAGTCAAATTTATGCAGGGATTAAGGTAAAGCAACTGTGTAAACTCCTCAGGG

GAGCTAAAGCACTAACAGACATAGTACCACTGACTGAAGAAGCAGAATTAGAGT
```

```
TGGCAGAGAACAGGGAGATTCTAAAAACCCCTGTGCATGGAGTATATTATGACC
CATCAAAAGACTTAGTAGCAGAAGTACAGAAACAAGGGCAGGACCAATGGACA
TATCAAATTTATCAAGAGCCATTTAAAAATCTAAAAACAGGAAAATATGCCAGA
AAAAGGTCTGCTCACACTAATGATGTAAGACAATTAACAGAAGTGGTGCAAAAA
ATAGCCACAGAAAGCATAGTAATATGGGGAAAGACCCCTAAATTTAGACTACCC
ATACAAAGAGAAACATGGGAAACATGGTGGATGGAGTATTGGCAGGCTACCTGG
ATTCCTGAATGGGAGTTTGTTAATACCCCTCCTCTAGTAAAATTATGGTACCAATT
AGAAAAAGACCCCATAGTAGGAGCAGAGACTTTCTATGTAGATGGGGCAGCTAG
TAGGGAGACTAAGCTAGGAAAAGCAGGGTATGTCACTGACAGAGGAAGACAAA
AGGTAGTTTCCCTAACTGAGACAACAAATCAAAAGACTGAATTACATGCGATCC
ATTTAGCCTTGCAGGATTCAGGATCAGAAGTAAATATAGTAACAGACTCACAAT
ATGCATTAGGAATCATTCAGGCACAACCAGACAGGAGTGAATCAGAAGTAGTCA
ACCAAATAATAGAGGAGCTAATAAAAAAGGAAAAAGTCTACCTGTCATGGGTAC
CAGCACACAAGGGGATTGGAGGAAATGAACAAGTAGATAAATTAGTCAGTTCAG
GAATCAGGAAGGTGCTATTTTTAGATGGGATAGATAAGGCTCAAGAAGAACATG
AAAGATATCACAGCAATTGGAGAACAATGGCTAGTGATTTTAATTTGCCACCTAT
AGTAGCAAAGGAAATAGTAGCCAACTGTGATAAATGTCAACTAAAAGGGGAAGC
TATGCATGGACAAGTAGACTGTAGTCCAGGGATATGGCAATTAGATTGCACACA
TCTAGAAGGAAAAGTCATCCTGGTAGCAGTCCACGTGGCCAGTGGATATATAGA
AGCAGAAGTTATCCCAGCAGAAACAGGACAGGAGACAGCATACTTTCTGCTAAA
ATTAGCAGGAAGATGGCCAGTAAAAGTAATACACACAGACAACGGTAGCAATTT
CACCAGCGCTGCAGTTAAAGCAGCCTGTTGGTGGGCCAATGTCCGACAGGAATTT
GGGATCCCCTACAATCCCCAAAGTCAAGGAGTAGTAGAATCTATGAATAAGGAA
TTAAAGAAAATCATAGGGCAGGTAAGAGAGCAAGCTGAACACCTTAAGACAGCA
GTACAAATGGCAGTATTCATTCACAATTTTAAAAGAAAAGGGGGGATTGGGGGG
TACAGTGCAGGGGAAAGAATAATAGACATAATAGCAACAGACATACAAACTAA
AGAATTACAAAAACAAATTACAAAAATTCAAAATTTTCGGGTTTATTACAGGGA
CAGCAGAGACCCAATTTGGAAAGGACCAGCAAAACTACTCTGGAAAGGTGAAGG
GGCAGTAGTAATACAAGACAATAGTGATATAAAAGTAGTACCAAGAAGAAAAG
CAAAGATCATTAGGGATTATGGAAAACAGATGGCAGGTGATGATTGTGTGGCAG
GTAGACAGGATGAGGATTAGAACATGGAACAGTTTAGTAAAACATCATATGTAT
ATCTCAAAGAAAGCTAAAAAGTGGTTTTATAGACATCATTATGAAAGCCAGCAT
CCAAAGGTAAGTTCAGAAGTACATATCCCACTAGGAGAGGCTAGATTAGTAATA
AGAACATATTGGGGTCTGCAGACAGGAGAAAAGGACTGGCAATTGGGTCATGGA
GTCTCCATAGAATGGAGGCAGAGAAAATATAGCACACAAATAGATCCTGACCTA
GCAGACCAACTGATTCATCTACAATATTTTGACTGTTTTTCAGACTCTGCCATAAG
GAAAGCCATATTAGGACAAGTAGTTAGACGTAGGTGTGAATATCCATCAGGACA
TAACAAGGTAGGATCCCTACAATATTTGGCACTGAAAGCATTAACAACACCAAA
AAGGATAAGGCCACCTCTGCCTAGTGTTAAGAAATTAACAGAAGATAGATGGAA
CAAGCCCCAGAAGATCAGGGGCCACAGAGAGAACCCTACAATGAATGGACATTA
```

-continued

```
GAACTGTTAGAGGAGCTTAAAAATGAAGCTGTTAGACATTTTCCTAGGCCCTGGC

TCCATGGCTTAGGACAGTACATCTATAACAATTATGGGGATACTTGGGAAGGGGT

TGAAGCTATAATAAGAATTTTGCAACAACTACTGTTTGTTCATTTCAGAATTGGG

TGTCAACATAGCAGAATAGGCATTATACCAGGGAGAAGAGGCAGGAATGGAGCC

GGTAGATCCTAACCTAGAGCCCTGGAATCATCCGGGAAGTCAGCCTACAACTGCT

TGTAGCAAGTGTTACTGTAAAATATGTTGCTGGCATTGCCAACTATGCTTTCTGA

AAAAAGGCTTAGGCATCTCCTATGGCAGGAAGAAGCGGAAGCACCGACGAGGA

ACTCCTCAGAGCAGTAAGGATCATCAAAATCCTATACCAGAGCAGTAAGTAANA

AGTATATGTAATGTCACCTTTGGAAATTAGTGCAATAGTAGGACTGATAGTAGCG

CTAATCTTAGCAATAGTAGTGTGGACTATAGTAGCTATAGAATTTAAGAAAATAC

TAAGGCAAAGAAAAATAGACAGGTTAGTTAAGAGAATAAGAGAAAGAGCAGAA

GACAGTGGAAATGAGAGTGAAGGAGACACAGATGAATTGGCCAAACTTGTGGA

AATGGGGACTTTGATCCTTGGGTTGGTGATAATTTGTAGTGCCTCAGACAACTT

GTGGGTTACAGTTTATTATGGGGTTCCTGTGTGGAGAGATGCAGATACCACCCTA

TTTTGTGCATCAGATGCCAAAGCACATGAGACAGAAGTGCACAATGTCTGGGCC

ACACATGCCTGTGTACCCACAGACCCCAACCCACAAGAAATACACCTGGAAAAT

GTAACAGAAAATTTTAACATGTGGAAAAATAACATGGTAGAGCAGATGCAGGAG

GATGTAATCAGTTTATGGGATCAAAGTCTAAAGCCATGTGTAAAGTTAACTCCTC

TCTGCGTTACTTTAAATTGTACCAATGCTAATTTGACCAATGTCAATAACACAAC

CAATGTCTCTAACATAATAGGAAATATAACAGATGAAGTAAGAAACTGTTCTTTT

AATATGACCACAGAACTAAGAGATAAGAAGCAGAAGGTCCATGCACTTTTTTAT

AAGCTTGATATAGTACAAATTGANAATAAAATAGTAGTGAGTATAGGTTAATAA

ATTGTAATACTTCAGTCATTAAGCAGGCTTGTCCAAAGATATCCTTTGATCCAATT

CCTATACATTATTGTACTCCAGCTGGTTATGCGATTTTAAAGTGTAATGATAAGA

ATTTCAATGGGACAGGGCCATGTAAAAATGTCAGCTCAGTACAATGCACACATG

GAATTAAGCCAGTGGTATCAACTCAATTGCTGTTAAATGGCAGTCTAGCAGAAG

AAGAGATAATAATCAGATCTGAAAATCTCACAAACAATGCCAAAACCATAATAG

TGCACCTTAATAAATCTGTAGAAATCAATTGTACCAGACCCTCCAACAATACAAG

AACAAGTATAACTATAGGACCAGGACAAGTATTCTATAGAACAGGAGACATAAT

AGGAGATATAAGAAAAGCATATTGTGAGATTAATGGAACAAAATGGAATGAAGT

TTTAAAACAGGTAACTGAAAAATTAAAAGAGCACTTTAATAATAAGACAATAAT

CTTTCAACCACCCTCAGGAGGAGATCTAGAAATTACAATGCATCATTTTAATTGT

AGAGGGGAATTTTTCTATTGCAATACAACANAACTGTTTAATAATACTTGCNTAN

GAAATNNAANCAGGAGGGGTGTAATGGCACTATCACACTTCCATGCAAGATAAA

GCAAATTATAAACATGTGGCAGGGAGCAGGACAAGCAATGTATGCTCCTCCCAT

CAGTGGAANAATTAATTGTGTATCAAATATTACAGGAATACTATTGACAAGAGA

TGGTGGTGCTAATAATACGAATAACGAGACCTTCAGACCTGGAGGAGGAAATAT

AAAGGACAATTGGAGAAGTGAATTATATAAATATAAAGTAGTACAAATTGAACC

ACTAGGAATAGCACCCACCAGGGCAAAGAGAAGAGTGGTGGAGAGAGAAAAAA

GAGCAGTGGGAATAGGAGCTATGATCTTTGGGTTCTTAGGAGCAGCAGGAAGCA

CTATGGGCGCGGCGTCAATAACGCTGACGGTACAGGCCAGACAATTATTGTCTG
```

-continued

GTATAGTGCAACAGCAAAGCAATTTGCTGAGGGCTATAGAGGCGCAGCAGCATC

TGTTGCAACTCACAGTCTGGGGCATTAAACAGCTCCAGGCAAGAGTCCTGGCTGT

GGAAAGATACCTAAAGGATCAAAAGTTCCTAGGACTTTGGGGCTGCTCTGGAAA

AATCATCTGCACCACTGCTGTGCCCTGGAACTCCACTTGGAGTAATAAATCTTTT

GAAGAGATTTGGAACAACATGACATGGATAGAATGGGAGAGAGAAATTAGCAA

TTACACAAACCAAATATATGAGATACTTACAGAATCGCAGAACCAGCAGGACAG

GAATGAAAAGGATTTGTTAGAATTGGATAAATGGGCAAGTCTGTGGAATTGGTTT

GACATAACAAATTGGCTGTGGTATATAAAAATATTTATAATGATAGTAGGAGGTT

TAATAGGTTTAAGAATAATTTTTGCTGTGCTTTCTATAGTAAATAGAGTTAGGCA

GGGATACTCACCTTTGTCTTTCCAGACCCCTACCCATCATCAGAGGGAACCCGAC

AGACCCGAAAGAATCGAAGAAGGAGGTGGCGAGCAAGGCAGAGACAGATCCGT

GCGATTAGTGAGCGGATTCTTAGCACTTGCCTGGGACGATCTACGGAGCCTGTGC

CTCTTCAGCTACCACCGCTTGAGAGACTTCATCTTGATTGCAGCGAGGACTGTGG

AACTTCTGGGACACAGCAGTCTCAAGGGACTGAGACGGGGGTGGGAAGGCCTCA

AATATCTGGGGAATCTTCTGTTATATTGGGGCCAGGAACTAAAAATTAGTGCTAT

TTCTTTGCTTGATGCTACAGCAATAGCAGTAGCGGGGTGGACAGATAGGGTTATA

GAAGTAGCACAAGGAGCTTGGAGAGCCATTCTCCACATACCTAGAAGAATCAGA

CAGGGCTTAGAAAGGGCTTTGCTATAACATGGGAGGCAAGTGGTCAAAAAGTAG

CATAGTGGGATGGCCTCAGGTCAGGGAAAGAATAAAGCAAACTCCTCCAGCAGC

AGAAGGAGTAGGAGCAGTATCTCAAGATCTAGATAAACATGGAGCAGTAACAAG

TAGTAATATGAATAATGCTGATTGTGTCTGGCTGAGAGCACAAGAGGAAGAGGA

GGTAGGCTTTCCAGTCAGGCCGCAGGTACCTCTAAGACCAATGACTTATAAGGG

AGCTTTTGATCTTAGCTTCTTTTTAAAAGAAAAGGGGGACTGGATGGGCTAATT

TACTCCAAGAAAAGACAAGAGATCCTTGACTTATGGGTCTATAATACACAAGGC

TTCTTCCCTGATTGGCAAAACTACACACCAGGGCCAGGGATCAGATACCCACTGT

GTTTTGGATGGTGCTTCAAGCTAGTACCAGTTGACCCAAGAGAAGTAGAGGAGG

ACAACAAAGGAGAAAACAACTGCCTGTTACACCCCATGAGCCAGCATGGAATAG

AGGACGAAGAAAGAGAAGTGCTGATGTGGAAGTTTGACAGTGCCCTAGCACGAA

AACACATAGCCCGAGAACTGCATCCAGAGTACTATAAAGACTGCTGACAAAGAA

GTTTCTAACTAGGACTTCCGCTGGGGACTTTCCAGGGGAGGTGTGGCCGGGGCGG

AGTTGGGGAGTGGCTAACCCTCAGATGCTGCATAAAAGCAGCCGCTTTTCGCTTG

TACTGGGTCTCTCTTGTTAGACCAGGTCGAGCCCGGGAGCTCTCTGGCTAGCAAG

GGAACCCACTGCTTAAAGCCTCAATAAAGCTTGCCTTGAGTGCTTAAAGTGGTGT

GTGCCCGTCTGTGTTAGGACTCTGGTAACTA

SEQ 02_Majority

SEQ ID NO: 2

TGGNTNNNNTAATTTACTCCAAGAAAAGACAAGAGATCCTTGATCTGTGGGTCTA

TNACACACAAGGATTCTTCCCAGATTGGCAGAACTACACACCAGGNCCAGGGNN

TAGNTNCCCACTGACCTTTGGGTGGTGCTTCAAACTAGTACCANTGGATCCAGNA

GAGATAGAGNAAGCCAATGAAGNAGAGAACAACNGNTTATTACANCCCATCTGN

CAGCATGGAATGGAGGACGAAGANAGAGAAGTGCTGGTCTGGANNTTTGACAGT

-continued

```
NNCCTGGCANTNANACACATNGCTCGAGAGANNCATCCGGAGNNNTACAAAGA
CTGCTGACACAGAANTTGCTGACANGGGACTTTCCGCTGGGGACTTTCCGNGGG
AGGNGTNNNNTGGGAGGAGTTGGGGAGTGGCTAGCCCTCANATGCTGCATATAA
GCAGCTGCTTCTCGCCTGTACTGGGTCTCTCTTGCTAGACCAGATCTGAGCCTGG
GAGCTCTCTGGCTAGCNGGGGAACCCACTGCTTAAGCCTCAATAAAGCTTGCCTT
GAGTGCTTCAAGTAGTGTGTGCCCGTCTGTTGTGTGACTCTGGTAACTAGAGATC
CCTCAGACCACTCTAGACTGTGTAAAAATCTCTAGCAGTGGCGCCCGAACAGGG
ACTTGNAGNTAATAGGGACTCGAAAGCGAAAGTTCCAGAGAAGATCTCTCGACG
CAGGGACTCGGCTTGCTGAGGTGCACACAGCAAGAGGCGAGAGCGGCGACTGGT
GAGTACGCCAAATTTTGACTAGCGGAGGCTAGAAGGAGAGAGATGGGTGCGAGA
GCGTCAGTATTAAGTGGGGGAAAATTAGATGCATGGGAGAAAATTCGGTTAAGG
CCAGGGGGAAAGAAAAAATATAGACTAAAACATCTAGTATGGGCAAGCAGGGA
GCTGGAAAGATTCGCACTTAACCCTGGCCTTTTAGAAACAGCAGAAGGATGTCA
ACAAATAATGGAACAGTTACAATCAACTCTCAAGACAGGATCAGAAGAACTTAA
ATCATTATTTAATACAATAGCAACCCTTTGGTGCGTACATCAAAGGATAGACATA
AAAGACACCAAGGAAGCCTTAGATAAAATAGAGGAAATACAAAATAAGAGCAA
GCAAAAGACACAGCAGGCAGCAGCTGCCACAGGAAGCAGCAGCCAAAATTACC
CTATAGTGCAAAATGCACAAGGGCAAATGACACATCAGACCATGTCACCTAGGA
CTTTGAATGCATGGGTGAAGGTAATAGAAGAAAAGGCTTTCAGCCCAGAAGTAA
TACCCATGTTTTCAGCATTATCAGAGGGAGCCACCCCACAAGATTTAAATATGAT
GCTAAACATAGTGGGGGACACCAGGCAGCAATGCAGATGTTAAAAGATACCAT
CAATGAGGAAGCTGCAGAATGGGACAGGGTACATCCAGTACATGCAGGGCCTAT
TCCACCAGGCCAGATGAGGGAACCAAGGGGAAGTGACATAGCAGGAACTACTA
GTACCCTTCAAGAACAAATAGGATGGATGACAAGCAATCCACCTATCCCAGTGG
GAGAAATCTATAAAAGATGGATAATCCTGGGATTAAATAAAATAGTAAGAATGT
ATAGCCCTGTCAGCATTTTGGACATAAGACAAGGGCCAAAAGAACCCTTTAGAG
ATTATGTAGATAGGTTCTTTAAAACTTTGAGAGCTGAACAAGCTACGCAGGAGGT
AAAAAACTGGATGACAGAAACCTTGCTGGTCCAAAATGCGAATCCAGACTGTAA
GTCCATTTTAAGAGCATTAGGACCAGGGGCTACATTAGAAGAAATGATGACAGC
ATGTCAGGGAGTGGGAGGACCTGGCCATAAAGCAAGGGTTTTGGCTGAGGCAAT
GAGTCAAGTACAACAGGCCAACATAATGATGCAGAGAGGCAATTTTAGGGGCCA
GAGAACAATAAAGTGTTTCAACTGTGGCAAAGAAGGACACCTAGCCAGAAATTG
CAAGGCCCCTAGGAAAAGGGGCTGTTGGAAATGTGGGAAGGAAGGACACCAAA
TGAAAGACTGTACTGAGAGACAGGCTAATTTTTTAGGGAAAATTTGGCCTTCCAG
CAAGGGGAGGCCAGGAAATTTTCCTCAGAGCAGACCGGAACCAACAGCCCCACC
AGCAGAGAGCTTTGGGATGGGGAAGAGATAACCTCCTCTCCGAAGCAGGAACC
GAGGGACAAGGGACTATATCCTCCTTTAACTTCCCTCAAATCACTCTTTGGCAAC
GACCCTTAGTCACAGTAAGAATAGGGGGACAGCTAATAGAAGCCCTATTAGACA
CAGGAGCAGATGATACAGTATTAGAAGAAATAAATTTACCAGGAAAATGGAAAC
CAAAAATGATAGGGGGAATTGGAGGTTTTATCAAAGTAAGACAGTATGATCAGA
TACTTATAGAAATTTGTGGAAAAAAGGCCATAGGTACAGTATTAGTAGGACCTA
```

-continued

```
CACCTGTCAACATAATTGGACGAAATATGTTGACTCAGATTGGTTGTACTTTAAA

TTTTCCAATTAGTCCTATTGAAACTGTGCCAGTAAAATTAAAGCCAGGAATGGAT

GGCCCAAAGGTTAAACAATGGCCATTGACAGAAGAAAAAATAAAAGCATTAACA

GAAATTTGTACAGATGGAAAAGGAAGGAAAAATTTCAAAAATTGGGCCTGAA

AATCCATACAATACTCCAGTATTTGCCATAAAGAAAAAGATAGTACTAAATGG

AGAAAATTAGTAGATTTCAGAGAACTCAATAAGAGAACTCAAGACTTCTGGGAG

GTCCAATTAGGAATACCTCATCCCGCGGGATTAAAAAAGAAAAAATCAGTAACA

GTACTAGATGTGGGGGATGCATATTTTTCAGTTCCCTTAGATAAAGACTTTAGAA

AGTATACTGCATTCACTATACCTAGTGTAAATAATGAGACACCAGGGATTAGATA

TCAGTACAATGTGCTTCCACAGGGATGGAAAGGATCACCAGCAATATTTCAGGC

AAGCATGACAAAAATCTTAGAGCCCTTTAGAACAAAAAATCCAGAGATAGTGAT

CTACCAATATATGGATGATTTATATGTAGGATCTGACTTAGAGATAGGGCAGCAT

AGAGCAAAAATAGAGGAGTTGAGAGAACATCTACTGAGATGGGGATTTACCACA

CCAGACAAAAAACATCAGAAAGAACCTCCATTTCTTTGGATGGGATATGAACTC

CATCCTGACAAATGGACAGTCCAGCCTATACAGCTGCCAGAAAAAGACAGCTGG

ACTGTCAATGATATACAGAAATTAGTGGGAAAACTAAATTGGGCAAGTCAGATT

TATGCAGGAATTAAAGTAAAGCAACTGTGTAAACTCCTCAGGGGAGCCAAAGCA

CTAACAGATATAGTAACACTGACTGAGGAAGCAGAATTAGAATTGGCAGAGAAC

AGGGAAATTCTAAAAGAACCTGTACATGGAGTATATTATGACCCANCAAAAGAC

TTAGTAGCAGAAATACAGAAACAAGGGCAAGACCAATGGACATATCAAATTTAT

CAAGAGCCATTTAAAAATCTAAAAACAGGAAAATATGCAAAAAAGAGGTCTGCC

CACACTAATGATGTAAAACAATTAACAGAGGTAGTGCAAAAAGTGGCTACAGAA

AGCATAGTAATATGGGGAAAGACCCCTAAATTTAGACTACCCATACAAAGAGAA

ACATGGGAAGCATGGTGGATGGAGTATTGGCAGGCTACCTGGATTCCTGAATGG

GAGTTTGTCAATACCCCTCCTCTAGTAAAATTATGGTACCAGTTAGAGAAAGACC

CCATAGTAGGAGCAGAAACTTTCTATGTAGATGGGGCAGCTAATAGGGAGACTA

AGCTAGGAAAAGCAGGGTATGTCACTGACAGAGGAAGACAAAAGGTTGTTTCCC

TAACTGAGACAACAAATCAAAAGACTGAATTACATGCAATTCATCTAGCCTTGCA

GGATTCAGGATCAGAAGTAAATATAGTAACAGACTCACAGTATGCATTAGGAAT

CATTCAGGCACAACCAGACAGGAGTGAATCAGAGTTAGTCAATCAAATAATAGA

GAAGCTAATAGAAAAGGACAAAGTCTACCTGTCATGGGTACCAGCACACAAAGG

GATTGGAGGAAATGAACAAGTAGATAAATTAGTCAGTAATGGAATCAGGAAAGT

ACTATTTTTAGATGGCATAGATAAAGCCCAAGAAGAGCATGAAAGATATCACAG

CAATTGGAGAGCAATGGCTAGTGATTTTAATCTGCCACCTATAGTAGCAAAAGA

AATAGTGGCCAGCTGTGATAAATGTCAGCTAAAAGGGGAAGCCATGCATGGACA

AGTAGACTGTAGTCCAGGAATATGGCAATTAGATTGTACACATTTAGAAGGAAA

AATTATCCTGGTAGCAGTCCATGTAGCCAGTGGCTATATAGAAGCAGAAGTTATC

CCAGCAGAAACAGGACAGGAGACAGCATACTTTATATTAAAATTAGCAGGAAGA

TGGCCAGTGAAAGTAATACACACAGACAATGGCAGCAATTTCACCAGTGCTGCA

GTAAAGGCAGCATGTTGGTGGGCAAATGTCACACAAGAATTTGGAATTCCCTAC
```

-continued

```
AATCCCCAAAGCCAAGGAGTAGTGGAATCTATGAATAAAGAATTAAAGAAAATT

ATAGGGCAGGTCAGGGATCAAGCTGAACACCTTAAGACAGCAGTACAGATGGCA

GTATTCATTCACAATTTTAAAAGAAAAGGGGGATTGGGGGGTACAGTGCAGGG

GAAAGAATAATAGACATAATAGCATCAGATATACAAACTAAAGAACTACAAAAA

CAAATTACAAAAATTCAAAATTTTCGGGTTTATTACAGGGACAGCAGAGACCCC

ATTTGGAAAGGACCAGCAAAACTACTCTGGAAAGGTGAAGGGGCAGTAGTAATA

CAGGACAATAGTGATATAAAGGTAGTACCAAGAAGAAAAGCAAAAATCATTAA

GGATTATGGAAAACAGATGGCAGGTGATGATTGTGTGGCAGGTAGACAGGATGA

GGATTAGAACATGGAACAGTTTAGTAAAACATCATATGTATATCTCTAAGAAAG

CTAAGAATTGGTTTTATAGACATCACTATGAAAGTAGGCATCCAAAAGTAAGTTC

AGAAGTACACATCCCACTAGGGGATGCTAGATTAGTAGTAAGAACATATTGGGG

TCTGCATACAGGAGAAAGAGACTGGCACTTGGGTCATGGGGTCTCCATAGAATG

GAAGCAGAGAAGATATAGCACACAAATAGATCCTGACCTAGCAGACCAACTGAT

TCACCTGCATTATTTTGACTGTTTTTCAGAATCTGCCATAAGGAAAGCCATATTAG

GACAAGTAGTTAGACCTAGGTGTGAATATCAAGCAGGACATAATAAGGTAGGAT

CGCTACAATATTTGGCACTGAAAGCATTAGTAACACCAACAAGGACAAAGCCAC

CTTTGCCTAGTGTTAAGAAGTTAGCAGAAGACAGATGGAACAAGCCCCAGAAGA

CCAGGGGCCACAGAGGGAGCCGTTCAATGAATGGACACTAGAACTGTTAGAAGA

GCTTAAACATGAAGCTGTTAGACATTTTCCTAGGCCATGGCTCCATGGATTAGGA

CAACATATCTATGAAACATATGGGGATACTTGGGAAGGGGTTGAAGCTATAATA

AGAATTTTGCAACAACTACTGTTTGTTCATTTCAGAATTGGGTGTCAACATAGCA

GAATAGGCATTATTCGAGGGAGAAGAGGCAGGAATGGAGCCGGTAGATCCTAGC

CTAGAGCCCTGGAACCACCCGGGAAGTCAGCCTACAACTGCTTGTAGCAATTGTT

ACTGTAAAAAATGCTGCTGGCATTGCCAATTNTGCTTTCTGAACAAGGGCTTAGG

CATCTCCTATGGCAGGAAGAAGCGGAGACGCCGACGAGGAACTCCTCAGAGCCG

TCAGGATCATCAAAATCCTGTACCAAAGCAGTGAGTAGTAATAATTAGTATATGT

GATGCAATCTTTAGAAATAGCTGCAATAGTAGGACTAGTAGTAGCATTCATAGCA

GCCATAGTTGTGTGGACCATAGTATTTATAGAATATAGGAAAATAAGGAAACAG

AAGAAAATAGACAGGTTACTTGATAGAATAAGAGAAAGAGCAGAAGATAGTGG

CAATGAGAGTGATGGGGATACAGAGGAATTATCCACTCTTATGGAGATGGGGTA

TGATGATATTTTGGATAATGATAATTTGTAATGCTGAAAATTTGTGGGTCACGGT

CTACTATGGGGTACCTGTGTGGAGAGACGCAGAGACCACCCTATTTTGTGCATCA

GATGCTAAAGCATATGATACAGAAGCACATAATGTCTGGGCTACACATGCCTGT

GTACCCACAGACCCTAACCCACAAGAAATACATTTGGAAAATGTAACAGAAAAG

TTTAACATGTGGAAAAATAACATGGTAGAGCAGATGCATGAAGATATAATTAGT

CTATGGGACCAAAGCCTAAAGCCATGTGTAAAGTTAACCCCTCTCTGCGTTACTT

TAGATTGTCATAACNTCAACAGCAACAACAGCAACAATATCTANTGACATGAAA

GGGGAAATAAAAAACTGCTCTTTCAATATGACCACAGAACTAAGAGATAAGAAA

CAGAAAGTGTATGCACTTTTTTATAGACTTGATGTAGTACAAATTAATGAAATA

ATAATAGTCAGTATAGGTTAATAAATTGTAATACCTCAGCCATTACACAGGCTTG

TCCAAAGGTATCCTTTGAGCCAATTCCCATACATTATTGTGCCCCAGCTGGTTTTG
```

```
CAATTCTAAAGTGTAATGATAAGAAGTTCAATGGAACAGGGCCATGCAAGAATG

TCAGCACAGTACAATGCACACATGGAATCAAGCCAGTAGTATCAACTCAACTGC

TGTTAAATGGCAGTCTAGCAGAAGAAGAGGTAGTGATTAGATCTGAAAATATCA

CAAACAATGCCAAAACCATAATAGTACAGTTGGATAAGCCTGTAAAAATTAATT

GTACCAGACCTAGCAACAATACAAGAAAAAGTGTACGTATAGGACCAGGACAAA

CATTCTATGCAACAGGTGACATAATAGGGGATATAAGACAAGCACATTGTAATG

TCAGTAGAACAGAATGGAATAAAACTTTACAACAGGTAGCTACACAATTAAGGA

AGTACTTTAAGAATACAACAATAATCTTTGCTAACTCCTCAGGAGGGGATTTAGA

AATTACAACACATAGTTTTAATTGTGGAGGAGAATTTTTCTATTGCAATACATCA

GAACTGTTTAATAGCACTTGGAATAATAATACTANCAACACNAACAACACAAAG

GCAAATGACACTATAACTCTCCAATGCAGAATAAAGCAAATTGTAAATATGTGG

CAGAGAGTAGGACAAGCAATGTATGCCCCTCCCATCCAAGGAGTAATAAGGTGT

GAATCAAACATTACAGGACTACTATTAACAAGAGATGGAGGGAATAATAATAGT

ACAAATGAGACATTCAGGCCTGGAGGAGGAGATATGAGGGACAATTGGAGAAG

TGAATTATATAAGTATAAAGTAGTAAAAATTGAACCACTAGGTGTAGCACCCAC

CCATGCAAAAGAAGAGTGGTGGAGAGAGAAAAAAGAGCAGTTGGACTGGGAG

CTGTCTTCCTTGGGTTCTTAGGAGCAGCAGGAAGCACTATGGGCGCGGCGTCAAT

AACGCTGACGGTACAGGCCAGACAATTATTGTCTGGTATAGTGCAACAGCAGAG

CAATTTGCTGAGGGCTATAGAGGCTCAACAACATCTGTTGAAACTCACGGTCTGG

GGCATTAAACAGCTCCAGGCAAGAGTCCTGGCTCTGGAAAGATACCTAAAGGAT

CAACAGCTCCTAGGAATTTGGGGCTGCTCTGGAAAACTCATCTGCACCACTACTG

TGCCCTGGAACTCTAGTTGGAGTAATAAAACTTATAATGACATATGGGATAACAT

GACCTGGCTGCAATGGGATAAAGAAATTAGCAATTACACAGACATAATATATAA

TCTAATTGAAGAATCGCAGAACCAGCAGGAAAAGAATGAACAAGACTTATTGGC

ATTGGACAAGTGGGCAAGTCTGTGGAATTGGTTTGACATAACAAATTGGCTATGG

TATATAAAAATATTTATAATGATAGTAGGAGGTTTGATAGGTTTAAGAATAGTTT

TTGCTGTGCTTACTATAATAAATAGAGTTAGGCAGGGATACTCACCTTTGTCATT

CCAGACCCTTACCCACCACCAGAGGGAACCCGACAGGCCCGAAAGAATCGAAGA

AGGAGGTGGCGAGCAAGACAGAGACAGATCCGTGCGATTAGTGAGCGGATTCTT

AGCACTTGCCTGGGACGATCTGCGGAGCCTGTGCCTCTTCAGCTACCACCGATTG

AGAGACTTTGTCTTGATTGCAGCGAGGNCTGTGGAACTTCTGGGACACAGCAGTC

TCAAGGGACTGAGACTGGGGTGGGAAGCCCTCAAATATCTGGGGAATCTTCTAT

CATACTGGGGTCAGGAACTAAAGAATAGTGCTATTAATTTGCTTGATACAATAGC

AATAGCAGTAGCTAACTGGACAGATAGAGTTATAGAAATAGGACAAAGAGCTGG

TAGAGCTATTCTTAACATACCTAGAAGAATCAGACAGGGCNTNGAAAGGGCTTT

GCTATAACATGGGTGGCAAGTGGTCAAAAAGCAGCATAGTGGGATGGCCTCAGG

TTAGGGAAAGAATAAGACAAACCCCTCCAGCAGCAACAGGAGTAGGAGCAGCA

TCTCAAGATTTAGATAGACATGGAGCAATCACAAGCAGTAATACAGCAGCTACT

AATGCTGATTGTGCCTGGCTGGAAGCACAAGAGGAAGAGGAGGTAGGCTTTCCA

GTCAGGCCGCAGGTACCTTTGAGACCAATGACTTATAAGGCAGCTGTCGATCTCA
```

-continued

GCCACTTTTTAAAAGAAAAGGGGGGACTGGATGGGTTAATTTACTCCAAGAAAA

GACAAGAGATCCTTGATCTGTGGGTCTATCACACACAAGGATTCTTCCCAGATTG

GCAGAACTACACACCAGGGCCAG

SEQ A1_Majority

SEQ ID NO: 3

TGGATGGGTTAATTTACTCCAGGAAAAGACAAGAAATCCTTGATCTGTGGGTCTA

CAACACACAAGGCTACTTCCCTGATTGGCAGAATTACACACCAGGGCCAGGGAT

CAGATTCCCACTAACATTTGGATGGTGCTTCAAGCTAGTACCAGTTGATCCAGAT

GAAGTAGAAAAGGCTACTGAGGGAGAGAACAACAGCCTATTACACCCTATAAGC

CAACATGGAATGGATGATGAAGAAAGAGAAACATTAATGTGGAAGTTTGACAGC

CGCCTGGCACTTACACACAGAGCCCGAGAGCTGCATCCGGAGTTCTACAAAGAC

TGCTGACACAGAAGTTGCTGACAGGGACTTTCCGCTGGGGACTTTCCAGGGGAG

GTGTGGTTTGGGCGGAGTNGGGGAGTGGCTAACCCTCAGATGCTGCATATAAGC

AGCTGCTTTTCGCCTGTACTGGGTCTCTCTTGTTAGACCAGATCGAGCCTGGGAG

CTCTCTGGCTAGCTAGGGAACCCACTGCTTAAGCCTCAATAAAGCTTGCCTTGAG

TGCTTNAAGTAGTGTGTGCCCGTCTGTTGTNTGACTCTGGTAACTAGAGATCCCT

CAGACCACTCTAGACNGTGTAAAAATCTCTAGCAGTGGCGCCCGAACAGGGACT

CGAAAGCGAAAGTTCCAGAGAAGTTCTCTCGACGCAGGACTCGGCTTGCTGAGG

TGCACACAGCAAGAGGCGAGAGCGGCGACTGGTGAGTACGCCAATTTTTGACTA

GCGGAGGCTAGAAGGAGAGAGATGGGTGCGAGAGCGTCAGTATTAAGTGGGGG

AAAATTAGATGCATGGGAGAAAATTCGGTTAAGGCCAGGGGGAAAGAAAAAAT

ATAGACTGAAACATCTAGTATGGGCAAGCAGGGAGCTGGAAAGATTTGCACTTA

ACCCTAGCCTTTTAGAAACAGCAGAAGGATGTCAACAAATAATGGAACAGTTAC

AACCAGCTCTCAAGACAGGAACAGAAGAACTTAGATCATTATTTAATACAGTAG

CAACCCTCTATTGTGTACATCAACGGATAGATGTAAAAGACACCAAGGAAGCTC

TAGATAAAATAGAGGAAATACAAAATAAGAGCAAGCAAAAGACACAACAGGCA

GCAGCTGACACAGGAAACAGCAGCAAGGTCAGCCAAAATTACCCTATAGTGCAA

AATGCACAAGGGCAAATGATACACCAGTCCTTGTCACCTAGGACTTTGAATGCAT

GGGTAAAAGTAATAGAAGAAAAGGCTTTCAGCCCAGAAGTAATACCCATGTTCT

CAGCATTATCAGAAGGAGCCACCCCACAAGATTTAAATATGATGCTGAACATAG

TGGGGGGACACCAGGCAGCTATGCAAATGTTAAAAGATACCATCAATGAGGAAG

CTGCAGAATGGGACAGGTTACATCCAGTACATGCAGGGCCTATTCCACCAGGCC

AGATGAGAGAACCAAGGGGAAGTGACATAGCAGGAACTACTAGTACCCCTCAAG

AACAAATAGGATGGATGACAGGCAACCCACCTATCCCAGTGGGAGACATCTATA

AAAGATGGATAATCCTGGGATTAAATAAAATAGTAAGAATGTATAGCCCTGTTA

GCATTTGGATATAAAACAAGGGCCAAAAGAACCCTTCAGAGATTATGTAGATA

GGTTCTTTAAAACTCTCAGAGCTGAGCAAGCTACACAGGAGGTAAAAGGTTGGA

TGACAGAAACATTACTGGTCCAAAATGCAAATCCAGATTGTAAGTCCATTTTAAG

AGCATTAGGAGCAGGGGCTACATTAGAAGAAATGATGACAGCATGCCAGGGAGT

GGGAGGACCCGGCCATAAAGCAAGGGTTTTGGCTGAGGCAATGAGTCAAGTACA

ACATACAAACATAATGATGCAGAGAGGCAATTTTAGGGGCCAGAAAAGGATTAA

GTGTTTCAACTGTGGCAAAGAAGGACACCTAGCCAGAAATTGCAGGGCCCCTAG

-continued

```
GAAAAAGGGCTGTTGGAAATGTGGGAAGGAGGGACACCAAATGAAAGACTGCA

CTGAAAGACAGGCTAATTTTTTAGGGAAAATTTGGCCTTCCAGCAAGGGGAGGC

CAGGAAATTTTCCTCAGAGCAGACCGGAGCCAACAGCCCCACCAGCAGAGATCT

TTGGGATGGGGGAAGAGATAGCCTCCCCTCCGAAGCAGGAGCAGAAAGACAGG

GAACAGGCCCCACCTTTAGTTTCCCTCAAATCACTCTTTGGCAACGACCCCTTGT

CACAGTAAGAATAGGGGGACAGCTAAAAGAAGCTCTATTAGATACAGGAGCAG

ATGATACAGTATTAGAAGACATAAATTTGCCAGGAAAATGGAAACCAAAAATGA

TAGGGGGAATTGGAGGTTTCATCAAGGTAAAACAGTATGATCAGATACTTATAG

AAATTTGTGGAAAAAAGGCTATAGGTACAGTATTAGTAGGACCTACACCTGTCA

ACATAATTGGAAGAAATATGTTGACCCAGATTGGTTGTACTTTAAATTTCCCAAT

TAGTCCTATTGAGACTGTACCAGTAAAATTAAAGCCAGGAATGGATGGCCCAAA

GGTTAAACAATGGCCATTGACAGAAGAAAAAATAAAAGCATTAACAGAAATTTG

TACAGAGATGGAAAAGGAAGGAAAAATTTCAAAAATTGGGCCTGAAAATCCATA

CAATACTCCAATATTTGCTATAAAGAAAAAAGATAGCACTAAATGGAGGAAATT

AGTAGATTTCAGAGAGCTCAATAAAAGAACTCAAGACTTTTGGGAAGTTCAATT

AGGAATACCGCATCCAGCGGGCCTAAAAAAGAAAAAATCAGTAACAGTACTAGA

TGTGGGGGACGCATATTTTTCAGTTCCTTTAGATGAAAGCTTTAGAAAGTATACT

GCATTCACCATACCTAGTACAAACAATGAGACACCAGGAATCAGGTATCAGTAC

AATGTGCTTCCACAGGGATGGAAAGGATCACCGGCAATATTCCAGAGTAGCATG

ACAAAAATCTTAGAGCCCTTTAGATCAAAAAATCCAGAAATAATTATCTATCAAT

ACATGGATGACTTGTATGTAGGATCTGATTTAGAAATAGGGCAGCATAGAACAA

AAATAGAAGAGTTAAGAGCTCATCTATTGAGCTGGGGATTTACTACACCAGACA

AAAAGCATCAGAAAGAACCTCCATTTCTTTGGATGGGATATGAACTCCATCCTGA

CAAGTGGACAGTCCAGCCTATAGAGCTGCCAGAAAAAGAAAGCTGGACTGTCAA

TGATATACAGAAATTAGTGGGAAAACTAAATTGGGCAAGTCAAATTTATGCAGG

GATTAAAGTAAAGCAATTGTGTAAACTCCTCAGGGGAGCCAAAGCACTAACAGA

TATAGTAACATTGACTGAGGAAGCAGAATTAGAATTGGCAGAGAACAGGGAGAT

TCTAAAAGACCCTGTGCATGGAGTATATTATGACCCATCAAAAGACTTAATAGCA

GAAATACAGAAACAAGGGCAAGACCAATGGACATATCAAATTTATCAAGAGCCA

TTTAAAAATCTAAAAACAGGAAAATATGCAAGAAAAAGGTCTGCTCACACTAAT

GATGTAAAACAATTAGCAGAAGTGGTGCAAAAGGTGGTCATGGAAAGCATAGTA

ATATGGGGAAAGACTCCTAAATTTAAACTACCCATACAAAAGAAACATGGGAA

ACATGGTGGATGGACTATTGGCAGGCTACCTGGATTCCTGAATGGGAGTTTGTCA

ATACCCCTCCTCTAGTAAAATTATGGTACCAGTTAGAGAAAGACCCCATAGTAGG

AGCAGAGACTTTCTATGTAGATGGGGCAGCCAATAGGGAGACTAAGCTAGGAAA

AGCAGGGTATGTCACTGACAGAGGAAGACAAAAGGTTGTTTCCCTAACTGAGAC

AACAAATCAAAAGACTGAACTACATGCAATCCATCTAGCCTTGCAGGATTCAGG

ATCAGAAGTAAACATAGTAACAGACTCACAGTATGCATTAGGAATCATTCAGGC

ACAACCAGACAGGAGTGAATCAGAGTTAGTCAATCAAATAATAGAGAAGCTAAT

AGGAAAGGACAAAGTCTACCTGTCATGGGTACCAGCACACAAAGGAATTGGAGG
```

-continued

```
AAATGAACAAGTAGATAAATTAGTCAGTTCTGGAATCAGGAAGGTGCTATTTTTA
GATGGGATAGATAAAGCTCAAGAAGAACATGAAAGATATCACAGCAATTGGAG
AGCAATGGCTAGTGATTTTAATCTGCCACCTATAGTAGCAAAGGAAATAGTAGCC
AGCTGTGATAAATGTCAGCTAAAAGGGGAAGCCATGCATGGACAAGTAGACTGC
AGTCCAGGGATATGGCAATTAGATTGCACACATCTAGAAGGAAAAGTAATTCTG
GTAGCAGTCCATGTAGCCAGTGGCTATATAGAAGCAGAAGTTATCCCAGCAGAA
ACAGGACAGGAGACAGCATACTTTCTACTAAAATTAGCAGGAAGATGGCCAGTA
AAAGTAGTACACACAGACAATGGCAGCAATTTCACCAGCGCTGCATTTAAAGCA
GCCTGTTGGTGGGCAAATATCCAACAGGAATTTGGGATTCCCTACAATCCCCAAA
GTCAAGGAGTAGTGGAATCTATGAATAAGGAATTAAAGAAAATCATAGGGCAGG
TAAGAGAGCAAGCTGAACACCTTAAAACAGCAGTACAAATGGCAGTATTCATTC
ACAATTTTAAAAGAAAAGGGGGGATTGGGGGGTACAGTGCAGGGGAAAGAATA
ATAGACATAATAGCAACAGACATACAAACTAAAGAATTACAAAAACAAATTACA
AAAATTCAAAATTTTCGGGTTTATTACAGGGACAGCAGAGATCCAATTTGGAAA
GGACCAGCAAAACTACTCTGGAAAGGTGAAGGGGCAGTAGTAATACAGGACAAT
AGTGATATAAAGGTAGTACCAAGAAGAAAAGCAAAGATCATTAGGGATTATGGA
AAACAGATGGCAGGTGATGATTGTGTGGCAGGTAGACAGGATGAGGATTAGAAC
ATGGAACAGTTTAGTAAAACATCATATGTATGTCTCAAAGAAAGCTAAAGATTG
GTTTTATAGACATCACTATGAAAGCAGGCATCCAAAAGTAAGTTCAGAAGTACA
CATCCCACTAGGGGATGCTAGATTAGTAGTAAGAACATATTGGGGTCTGCATACA
GGAGAAAAAGACTGGCACTTGGGTCATGGGGTCTCCATAGAATGGAGGCTAAAA
AGATATAGCACACAAATAGATCCTGACCTGGCAGACCAACTAATTCATCTGCATT
ATTTTGACTGTTTTTCAGACTCTGCCATAAGGAAAGCCATATTAGGACAAGTAGT
TAGCCCTAGGTGTGAATATCAAACAGGACATAACAAGGTAGGATCTCTACAATA
TTTAGCACTGAAAGCATTAGTAACACCAACAAAGACAAAGCCACCTTTGCCTAGT
GTTAGGAAATTAACAGAGGATAGATGGAACAAGCCCCAGAAGACCAGGGGCCC
CAGAGGGAGCCATACAATGAATGGATGTTAGAACTGTTAGAAGATCTTAAGCAT
GAAGCTGTTAGACATTTTCCTAGGCCATGGCTTCATGGATTAGGACAACATATCT
ATAACACCTATGGGGATACTTGGGAAGGAGTTGAAGCTATAATAAGAATTTTGC
AACAACTACTGTTTGTTCATTTCAGAATTGGGTGCCAACATAGCAGAATAGGCAT
TATTCGAGGGAGAAGAGTCAGGGATGGATCCGGTAGATCCTAACCTAGAGCCCT
GGAACCATCCGGGAAGTCAGCCTACAACTCCTTGTAGCAAGTGTTACTGTAAAA
AGTGTTGCTATCATTGCCAAGTTTGCTTTCTGAACAAAGGCTTAGGCATCTCCTAT
GGCAGGAAGAAGCGGAGACAGCGACGAGGAACTCCTCAAAGCAGTAAGGATCA
TCAAAATCCTATACCAAAGCAGTAAGTATTAGTAATTAGTATATGTAATGCCTCC
TTTGGAAATCTGTGCAATAGTAGGACTGATAGTAGCGCTAATCCTAGCAATAGTT
GTGTGGACTATAGTAGGTATAGAATATAAGAAATTGCTAAAGCAAAGAAAAATA
GACAGGTTAATTGAGAGAATAAGAGAAAGAGCAGAAGACAGTGGCAATGAGAG
TGATGGGGATACAGAGGAATTGTCAACACTTATTGAGATGGGGAACTATGATCTT
GGGGATGATAATAATCTGTAGTGCTGCAGAAAACTTGTGGGTTACTGTCTACTAT
GGGGTACCTGTGTGGAAAGATGCAGAGACCACCTTATTTTGTGCATCAGATGCTA
```

```
AAGCATATGAGACAGAAGTGCATAATGTCTGGGCTACACATGCCTGTGTAC CCA
CAGACCCCAACCCACAAGAAATACATTTGGAAAATGTGACAGAAGAGTTTAACA
TGTGGAAAAATAACATGGTAGAGCAGATGCATACAGATATAATCAGTCTATGGG
ACCAAAGCCTAAAGCCATGTGTAAAGTTAACCCCTCTCTGCGTTACTTTAAATTG
TAGCAATGTCAACATCAACAACANCAACACAATATCACCAATAACATGAAAGAA
GAAATAAAAAACTGCTCTTTCAATATGACCACAGAACTAAGGGATAAGAAACAG
AAAGTATATTCACTTTTTTATAGACTTGATGTAGTACAAATTAATGAAANTAATA
GTAATAGTAGTGAGTATAGATTAATAAATTGTAATACCTCAGCCATTACACAGGC
TTGTCCAAAGGTATCCTTTGAGCCAATTCCCATACATTATTGTGCCCCAGCTGGTT
TTGCGATCCTAAAGTGTAAGGATAAGGAGTTCAATGGAACAGGGCCATGCAAGA
ATGTCAGCACAGTACAATGCACACATGGAATCAAGCCAGTAGTATCAACTCAAC
TGCTGTTAAATGGCAGTCTAGCAGAAGAAGAGGTAATAATTAGATCTGAAAATA
TCACAAACAATGCCAAAACCATAATAGTACAACTTACCAAGCCTGTAAAAATTA
ATTGTACCAGACCTAACAACAATACAAGAAAAAGTATACGTATAGGACCAGGAC
AAGCATTCTATGCAACAGGTGACATAATAGGGGATATAAGACAAGCACATTGTA
ATGTCAGTAGATCAGAATGGAATAAAACTTTACAAAAGGTAGCTAAACAATTAA
GAAAATACTTTAAGAACAAAACAATAATCTTTACTAACTCCTCAGGAGGGGATCT
AGAAAATTACAACACATAGTTTTAATTGTGGAGGAGAATTTTTCTATTGTAATACA
TCAGGCCTGTTTAATAGCACTTGGAATAANAACANTAACNAGACAAATAGCACG
GAGTCAAATGACACTATAACTCTCCCATGCAGAATAAAGCAAATTATAAATATGT
GGCAGAGAGCAGGACAAGCAATGTATGCCCCTCCCATCCAAGGAGTAATAAGGT
GTGAATCAAACATTACAGGACTACTATTAACAAGAGATGGTGGGAATAATAACA
GTACAAATGAAACCTTCAGACCTGGAGGAGGAGATATGAGGGACAATTGGAGAA
GTGAATTATATAAGTATAAAGTAGTAAAAATTGAACCACTAGGAGTAGCACCCA
CCAGGGCAAAGAGAAGAGTGGTGGAGAGAGAAAAAAGAGCAGTTGGAATAGGA
GCTGTCTTCCTTGGGTTCTTAGGAGCAGCAGGAAGCACTATGGGCGCGGCGTCAA
TAACGCTGACGGTACAGGCCAGACAATTATTGTCTGGCATAGTGCAACAGCAAA
GCAATTTGCTGAGGGCTATAGAGGCTCAACAGCATCTGTTGAAACTCACGGTCTG
GGGCATTAAACAGCTCCAGGCAAGAGTCCTGGCTGTGGAAAGATACCTAAAGGA
TCAACAGCTCCTAGGAATTTGGGGCTGCTCTGGAAAACTCATCTGCACCACTAAT
GTGCCCTGGAACTCTAGTTGGAGTAATAAATCTCAGAATGAGATATGGGATAAC
ATGACCTGGCTGCAATGGGATAAAGAAATTAGCAATTACACACACATAATATAT
AATCTAATTGAAGAATCGCAGAACCAGCAGGAAAAGAATGAACAAGACTTATTG
GCATTGGACAAGTGGGCAAATCTGTGGAATTGGTTTGACATATCAAACTGGCTGT
GGTATATAAAAATATTTATAATGATAGTAGGAGGCTTAATAGGATTAAGAATAG
TTTTTGCTGTGCTTTCTATAATAAATAGAGTTAGGCAGGGATACTCACCTTTGTCG
TTTCAGACCCATACCCCAAACCCAAGGGGTCTCGACAGGCCCGGAAGAATCGAA
GAAGAAGGTGGAGAGCAAGGCAGAGACAGATCGATTCGATTAGTGAGCGGATTC
TTAGCACTTGCCTGGGACGATCTGCGGAGCCTGTGCCTCTTCAGCTACCACCGCT
TGAGAGACTTCATCTTGATTGCAGCGAGGACTGTGGAACTTCTGGGACACAGCA
```

-continued

```
GTCTCAAGGGGTTGAGACTGGGGTGGGAAGGCCTCAAGTATCTGTGGAATCTCCT

GTTATATTGGGGTCGGGAACTAAAAATTAGTGCTATTAATTTGNTTGATACCATA

GCAATAGCAGTAGCTGGCTGGACAGATAGGGTTATAGAAATAGGACAAAGAATT

GGTAGAGCTATTCTCCACATACCTAGAAGAATCAGACAGGGCTTAGAAAGGGCT

TTGCTATAACATGGGTGGCAAGTGGTCAAAAAGTAGCATAGTGGGATGGCCTGA

GGTTAGGGAAAGAATAAGACGAACTCCTCCAGCAGCAACAGGAGTAGGAGCAG

TATCTCAAGATTTAGATAAACATGGAGCAGTCACAAGCAGTAATATAAATCACC

CTAGTTGCGCCTGGCTGGAAGCGCAAGAGGAAGAGGAGGTAGGCTTTCCAGTCA

GGCCACAAGTACCTCTAAGACCAATGACTTACAAGGGAGCTCTGGATCTCAGCC

ACTTTTTAAAAGAAAAGGGGGGACTGGATGGGTTAATTTACTCCAGGAAAAGAC

AAGAAATCCTTGATCTGTGGGTCTACCACACACAAGGCTACTTCCCTGATTGGCA

GAATTACACACCAGGGCCAGGGATCAGATACCCCACTAACATTTGGATGGTGCTTC

AAGCTAGTACCAGTTGATCCAGATGAAGTAGAGAAGGCTACTGAGGGAGAGAAC

AACAGCCTATTACACCCTATATGCCAACATGGAATGGATGATGAGGAGAGAGAA

GTATTAATGTGGAAGTTTGACAGCCGCCTGGCACTAAAACACAGAGCCCAAGAG

CTGCATCCGGAGTTCTACAAAGACTGCTGACACAGAAGTTGCTGACAGGGACTTT

CCGCTGGGGACTTTCCAGGGGAGGTGTGGTTTGGGCGGAGTTGGGGAGTGGCTA

ACCCTCAGATGCTGCATATAAGCAGCTGCTTTTCGCCTGTACTGGGTCTCTCTTGT

TAGACCAGATCGAGCCTGGGAGCTCTCTGGCTAGCGAGGGAACCCACTGCT
```

SEQ A2_Majority

SEQ ID NO: 4

```
TTGAAAAGCGAAAGTAACAGGGACTNNNNGAANGCGANAGTNCCAGNGNAGT

TCTCTCGACGCANGACTCGGCTTGCTGAGGTGCACACGGCAAGAGGCGAGNNGC

GNCGNCTGGTGAGTACGCCTAANATTTTTGACTAGCNGAGGCTAGAAGGAGAGA

GATGGGTGCGAGAGCGTCANTATTNAGCGGNGGAAAATTAGANGCTTGGGAGAA

AATTCGGTTAAGGCCAGGGGGAAAGAAAAAATATAGACTGAAACATTTNGTATG

GGCAAGCAGGGAGCTGGANAAATTCTCAATNAACCCNNGCCTTTTAGAAACANN

ANNNGGATGTAGACNAATANTNNGGCANTTACAACCAGCTCTCNANACAGGAAC

AGAAGAACTTANATCATTATATAATACANTAGNAGTCCTCTACTNNGTNCATCAA

ANGNTAGANGTAAAAGACACCAAGGAAGCTCTAGATAAAATAGAGGAAGAACA

AAACAACAGAANNNNNNNACACAGCANGCAGCAGCTGACACAGGNANCAGCA

GCNNNNNNNNNNNNNNNNNNNNNNNCAGTCAAAATTACCCTATAGTGCAAAAT

GCACAAGGGCAAATGGTACACCAGGCCNTATCACCTAGGACTTTGAATGCATGG

GTCAAAGTAGTAGAAGAAAAGGCTTTCAGCCCAGAAGTAATACCCATGTTTACA

GCATTATCAGAAGGAGCCACCCCACAAGACTTAAATACTATGCTAAACACAGTG

GGGGGACATCAAGCAGCTATGCAAATGTTAAAAGATACCATCAATGAGGAAGCT

GCAGAATGGGACAGGNTACATCCAGTACATGCAGGGCCTATTCCACCAGGCCAG

ATGAGAGAACCAAGGGGAAGTGACATAGCAGGAACTACTAGTACCCTTCAGGAA

CAAATAGGATGGATGACCAGCAACCCACCTATCCCAGTGGGAGAAATCTATAAA

AGATGGATAATCCTGGGATTAAATAAAATAGTAAGAATGTATAGCCCTGTCAGC

ATTTTGGACATAAGACAAGGGCCAAAAGAACCCTTTAGAGACTATGTAGATAGG

TTCTTTAAAACTCTCAGAGCTGAGCAAGCTACACAGGAGGTAAAAAACTGGATG
```

-continued

ACAGACACCTTGCTGGTCCAAAATGCGAACCCAGATTGTAAATCCATCTTGAGAG

CATTAGGACCAGGGGCTACATTAGAAGAAATGATGACAGCATGTCAGGGAGTGG

GAGGACCCGGCCATAAAGCAAGGGTTTTGGCTGAAGCAATGAGCCAAGTACAAA

ATACAANTNCAAACATAATGATGCAGAGAGGCAATTTTAGGGGTCAAAAAAGAA

TTAAGTGTTTCAACTGTGGCAAGGAAGGACACCTAGCCAGAAATTGCAGGGCCC

CTAGGAAAAAGGGCTGCTGGAAATGTGGGAAGGAAGGACATCAAATGAAAGAC

TGCACTGAGAGACAGGCTAATTTTTTAGGGAAAATTTGGCCTTCCAACAAAGGG

AGGCCAGGAAATTTTCCTCAGAGCAGAACAGAGCCAACAGCCCCACCAGCAGAG

NACTTNNGAATGGGGGAAGAGATAACCTCCTCNCTGAAGCAGGANNNNANCAG

GGAACCGTACACTCCTGCAATTTCCCTCAAATCACTCTTTGGCAACGACCTCTTGT

CACAGTAAAAATAGAAGGACAGCTAAGAGAAGCTCTATTAGATACAGGAGCAG

ATGATACAGTGTTAGAAGACATAAATTTGCCAGGAAAATGGAAACCAAAAATGA

TAGGGGGAATTGGAGGTTTTATCAAAGTAAGACAATATGATCAGATAGCTATAG

AAATTTGTGGAAAAAGGGCCATAGGTACAGTATTAGTAGGACCTACACCTGTCA

ACATAATTGGAAGAAATATGTTGGTTCAGCTTGGTTGTACTTTAAATTTTCCAATT

AGTCCTATTGAAACTGTACCAGTAAAATTAAAGCCAGGAATGGATGGTCCAAAG

GTTAAACAATGGCCATTGACAGAAGAAAAAATAAAAGCATTAACAGAAATTTGT

AAAGAAATGGAAAAGGAAGGAAAAATTTCAAAAATTGGGCCTGAAAATCCATA

CAACACTCCAGTGTTTGCTATAAAGAAAAAAGACAGCACTAAATGGAGAAAATT

AGTAGATTTCAGAGAACTCAATAAGAGAACTCAAGACTTCTGGGAAGTTCAGTT

AGGAATACCACATCCAGCAGGATTAAAAAAGAAAAAATCAGTAACAGTACTAGA

TGTGGGGACGCATATTTTTCCGTTCCCTTACATGAAGACTTCAGAAAATATACT

GCATTCACCATACCTAGTATAAACAATGAGACACCAGGAATTAGGTATCAGTAC

AATGTACTTCCACAGGGATGGAAAGGATCACCAGCAATATTCCAGAGTAGCATG

ACAAAAATCTTAGAGCCCTTTAGATCAAAAAATCCAGAGATGGTCATCTACCAAT

ACATGGATGACTTGTATGTAGGATCTGATTTAGAAATAGGTCAGCATAGAGCAA

AAATAGAGGAATTAAGGGCTCATTTATTAAGATGGGGATTTACTACACCAGACA

AAAAACATCAGAAAGAACCTCCATTTCTTTGGATGGGATATGAGCTTCATCCTGA

CAAATGGACAGTCCAGCCTATAAAGCTGCCAGAAAAAGACAGCTGGACTGTCAA

TGATATACAGAAATTAGTAGGAAAGTTAAATTGGGCAAGTCAGATTTATGCAGG

GATTAAAGTAAAGCAACTGTGTAAACTCCTTAGAGGAACCAAAGCACTAACAGA

CATAGTAACACTGACTAAAGAAGCAGAATTAGAATTGGAAGAGAACAGGGAGA

TTCTAAAAACCCTGTACATGGGGTATACTATGACCCATCAAAAGACTTAATAGC

AGAAATACAGAAACAAGGGCAAGACCAATGGACATATCAAATTTATCAAGAACC

ATTTAAAAATCTAAAAACAGGGAAATATGCAAAAAGGAAGTCCACCCACACTAA

TGATGTAAAACAATTAACAGAAGCAGTACAAAAAATAGCCATAGAAAGCATAGT

AATATGGGGAAAGACTCCTAAATTTAGATTACCCATACAAAAAGAAACATGGGA

GACATGGTGGACGGAGTATTGGCAGGCTACCTGGATTCCTGAGTGGGAGTTTGTC

AATACCCCTCCTCTAGTAAAACTATGGTACCAGTTAGAAACAGAACCCATAGCA

GGAGCAGAAACTTTCTATGTAGATGGGGCAGCTAATAGAGAGACTAAACTAGGA

```
AAGGCAGGGTATGTCACTGACAGAGGAAGACAAAAAATTGTCTCCCTGACGGAG

ACAACAAATCAAAAGACTGAATTACATGCAATCTATTTGGCTTTACAGGATTCAG

GATTAGAAGTNAACATAGTNACAGATTCACAGTATGCATTAGGAATCATTCANG

CACAACCAGATAGGAGTGAATCAGAGTTAGTCAATCAAATAATAGAAAAGTTAA

TAGAAAAGGAAAGGGTCTACCTGTCATGGGTACCAGCACACAAAGGGATTGGAG

GAAATGAACAGGTAGANAAATTAGTCAGTTCTGGAATCAGGAAAGTGNTATTTT

TAGATGGGATAGATAAGGCTCAAGAAGAACATGAAAGATATCACAGNAATTGGA

GAGCAATGGCTCATGACTTTAATCTGCCACCTATAGTAGCAAAAGAAATAGTAG

CTAGCTGTGATAAATGTCAGCTAAAAGGGGAAGCCATGCATGGACAAGTAGACT

GTAGTCCAGGAATATGGCAACTAGATTGCACACATCTAGAAGGAAAAGTTATCC

TGGTAGCAGTCCATGTAGCCAGTGGCTATATAGAAGCAGAAGTCATNCCAGCAG

ANACAGGACAGGAAACAGCATACTTTATATTAAAANTAGCAGGAAGATGGCCAG

TAAAAGTAATACATACAGACAATGGGCCCAATTTCACCAGTGCAACAGTTAAGG

CAGCCTGTTGGTGGGCAGGTGTCCAACANGAATTTGGGATTCCCTACAATCCCCA

AAGTCAAGGAGTAGTGGAATCTATGAATAAAGAATTAAAGAAAATCATAGGGCA

GGTAAGAGATCAAGCTGAACACCTTAAGACAGCAGTACAAATGGCAGTATTCAT

NCACAATTTTAAAAGAAAAGGGGGGATTGGGGGATACAGTGCAGGGGAAAGAA

TAATAGACATAATAGCAACAGATATACAAACTAAAGAATTACAAAAACAAATTA

TAAAAATTCAAAATTTTCGGGTTTATTACAGGGACAGCAGAGATCCAATTTGGAA

AGGACCAGCAAAACTCCTNTGGAAAGGTGAAGGGGCAGTAGTAATACAAGACA

ATAGTGATATAAAGGTAGTACCAAGAAGAAAAGCAAAGATCATTAGGGATTATG

GAAAACAGATGGCAGGTGATGATTGTGTGGCAGGTAGACAGGATGAGGATTAGA

ACATGGAACAGTTTAGTAAAACATCATATGTATNTTTCAANGAAAGCTAAAGAN

TGGTTCTATAGACATCACTATGAAAGCAGACATCCAAGAGTAAGTTCAGAAGTA

CACATCCCGCTAGGGGAGGCTAGATTAATAGTAAGAACATATTGGGGTCTGCAC

CCAGGAGAAAAAGACTGGCACTTGGGTCATGGGGTCTCCATAGAATGGAGGCAG

AAAAGGTATAGTACACAAATAGACCCTGATCTGGCAGACCATCTAATCCATCTGT

ATTATTTTGACTGTTTTTCAGAATCTGCCATAAGGAAAGCCATATTAGGAGAAAT

AGTTAGTCCTAGGTGTGAATATCAAGCAGGACATAACAAGGTAGGNTCTCTGCA

ATATTTGGCATTGAAAGCATTAGTAGCTNCAACAAGGNCAAAGCCACCTTTGCCT

AGTGTTAGGAAATTAGTAGAGGATAGATGGAACAAGCCCCAGAAGACCAGGGG

CCACNGAGGGAGCCANACAATGAATGGGTGTTAGAACTGTTAGAGGAGCTCAAG

CAGGAAGCTGTTAGACATTTCCCTAGGCAGTGGCTACATGGCCTAGGACAACAT

ATCTATAATACCTATGGGGATACTTGGGAAGGAGTTGAAGCTATAATAAGAACT

NTGCAACAACTACTGTTTGTCCATTTCAGAATTGGGTGCCAACATAGCAGNATAG

GCATTATTCGAAGAAGAAGAGTAAGGGATGGAGCCAGTAGACCCTAAANTAGAG

CCCTGGAACCATCCGGGAAGNCAGCCTAAAACTGCTTGTANCAAGTGNTATTGT

AAAAAGTGTTGCTATCATTGCCANNTGTGCTTTCTAAACAAAGGCTTAGGCATCT

CCTATGGCAGGAAGAAGCGGAGACCCCGACGAGGACCTNCTCANAGCANTAAG

GATCATCAAAATCCTNTACCAAAGCAGTAAGTAGTAGTAATTAATATATGTAATG

TTACCTTTAGCAATATTGNCAATAGTAGGACTGNTAGTAGCATTAATCTTAGCAA
```

```
TAGTTGTATGGACTATAGTATTTATAGAATATAGGAANATTAAGAAGCAAAGGA
AAATAGACTGGTTAATCAANAGAATAAGTGAAAGAGCAGAAGACAGTGGCAAT
GAGAGTGATGGGGACACAGAGGAATTNTCANCACTTGTGGNGATGGGGAATCTT
GATTTTNGGGATGNTAATAATGTGTAAAGCTACAGATTTGTGGGTCACAGTATAC
TATGGAGTACCTGTGTGGAAAGATGCAGATACCACCCTATTTTGTGCATCAGATG
CTAAAGCATATGATACAGAAGNGCATAATGTCTGGGCCACACATGCCTGTGTAC
CCACAGACCCCAACCCACAAGAAGTAAACCTGGAAAATGTAACAGAAGATTTTA
ACATGTGGAAAAATAACATGGTAGAGCAGATGCATGAAGATATAATCAGTCTAT
GGGATCAAAGCCTAAAGCCATGTGTAAAATTAACCCCTCTCTGCGTCACTTTAAA
TTGTAGCAATGCCAACACCANTANCACCAATNNNNNNNNNNNNNNNAGCACTGAA
GAAATAAAAAACTGCTCTTACAATATTACCACAGAACTAAGAGATAAAACACAG
AAAGTCTATTCACTGTTTTATAAACTTGATGTAGTACAACTTAATGAANNAATAN
NACAAGTAGTAATACTCNGTATAGACTAATAAATTGTAATACCTCAGCCATCACA
CAAGCTTGTCCAAAGGTATCCTTTGAGCCAATTCCTATACATTATTGTGCCCCAG
CTGGTTTTGCGATTCTAAAGTGTAAGGATCCGAGATTCAATGGAACAGGGTCATG
CAATAATGTTAGCTCAGTACAATGTACACATGGAATTANGCCAGTAGCATCAACT
CAACTGCTGTTGAATGGCAGTCTAGCAGAAGGAGAGGTAATGATTAGATCTGAA
AATATTACAAACAATGCCAAAAACATAATAGTACAGTTTAATAAACCTGTACCA
ATTACTTGTATCAGACCCAACAACAATACAAGAAAAAGTATACGCTTTGGACCA
GGACAAGCCTTCTATACAAATGACATAATAGGGGATATAAGACAAGCACATTGT
AATATCAACAAAACANAATGGAATGCCACTTTACAAAAGGTAGCTGAACAATTA
AGAGAACACTTCCCTAATAAAACAATAATCTTTACTAACTCCTCAGGAGGGGACC
TAGAAATTACAACACATAGTTTTAATTGTGGAGGAGAATTTTTCTATTGCAATAC
AACAGGCCTGTTTAATAGCACATGGNNGATANNGGCACCANNCANNAGAATNNC
ACGGAGACAAATGGAANTATAACNCTCCCATGCAGAATAAAACAAATTATAAAC
ATGTGGCAGAGAGTAGGACGAGCAATGTATGCCCCTCCCATTGCAGGAGTAATA
AAGTGTACATCAAACATTACAGGAATAATATTGACAAGAGATGGTGGGAANAAC
AGNANTAATGAGACCTTCAGACCTGGAGGAGGAGATATGAGGGACAATTGGAG
AAGTGAATTATATAAGTATAAAGTAGTAAAAATTGAACCACTAGGAGTAGCACC
CACCAGGGCAAAGAGAAGAGTGGTGGAGAGAGAAAAAAGAGCAGTTGGANTGG
GAGCTGTTTTCCTTGGGTTCTTGGGAGCAGCAGGAAGCACTATGGGCGCGGCGTC
AATAACGCTGACGGTACAGGCCAGACAATTATTGTCTGGCATAGTGCAACAGCA
AAGCAATTTGCTGAAGGCTATAGAGGCTCAACAGCATCTGTTGAAACTCACAGTC
TGGGGCATTAAACAGCTCCAGGCAAGAGTCCTGGCTCTGGAAAGATACCTACAG
GATCAACAGCTCCTGGGAATTTGGGGCTGCTCTGGAAAACTCATCTGCGCCACTA
CTGTGCCCTGGAACTCTAGTTGGAGTAATAAGACTCAGGAGGAGATTTGGAACA
ACATGACCTGGTTGCAATGGGATAAAGAAATTAGCAATTACACAAACATAATAT
ATANGCTACTTGAAGAATCGCAGAACCAGCAGGAAAAGAATGAACAAGACTTAT
TGGCATTAGACAAATGGGCAAATTTGTGGAATTGGTTTAACATAACAAACTGGCT
GTGGTATATAAGAATATTTATAATGATAGTAGGAGGCTTGATAGGATTAAGAAT
```

-continued

```
AGTTATTGCTATAATTTCTGTAGTAAATAGAGTTAGGCAGGGATACTCACCTTTG

TCATTTCAGATCCCTACCCCAAACCCAGAGGGTCTCGACAGGCCCGGAAGAATC

GAAGAAGGAGGTGGAGAGCAAGGCAGAGACAGATCGATTCGATTAGTGAGCGG

ATTCTTNGCACTTGCCTGGGACGACCTACGGAGCCTGTGCCTCTTCAGCTACCAC

CGCTTGAGAGATTGCATCTTGATTGCAGCGAGGACTGTGGAACTTCTGGGACACA

GCAGTCTCAAGGGACTGAGACTGGGGTGGGAAGGCCTCAAANATCTGTGGAATC

TTCTGNTATATTGGGGTCGGGAATTGAAGAATAGTGCTATTAGNTTACTTGATAC

CATAGCAGTAGCAGTAGCTGAGTGGACAGATAGGGTTATAGAAATAGGACAAAG

AGCTTGCAGAGCTATTCTCAACATACCTAGAAGAATCAGACAGGGCTTCGAAAG

GGCTTTACTATAAAATGGGGGGCAAGTGGTCAAAAAGNACCATAGTGGGATGGC

CTGCTATTAGGGAGAGAATGAGAAGAACTCCTCCAGCAGCAGAAGGAACAAGAC

CAACTCCTCCAGCAGCAGAAGGAGTAGGAGCAGTGTCTCAAGATTTAGCTACAC

ATGGAGCAGTCACAAGCAGTAATACAGCAGCTAATAATCCTGATTGCGCCTGGG

TGGAAGCGCAAGAAGAGGAGGAAGTAGGCTTCCCAGTCAGGCCACAGGTACCTT

TAAGGCCAATGACCTTCAAGGGAGCTTTTGATCTCAGCCACTTTTTAAAAGAAAA

GGGGGGACTGGATGGGTTAATTTACTCCCAGAAAAGACAAGACATCCTTGATCT

GTGGGTCTACAACNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNN

NNNNNNNNN

SEQ B_Majority
                                                SEQ ID NO: 5
CTGGAAGGGCTAATTTACTCCCAAAAAAGACAAGATATCCTTGATCTGTGGGTCT

ACCACACACAAGGCTACTTCCCTGATTGGCAGAACTACACACCAGGGCCAGGGA

TCAGATATCCACTGACCTTTGGATGGTGCTTCAAGCTAGTACCAGTTGAGCCAGA

GAAGGTAGAAGAGGCCAATGAAGGAGAGAACAACAGCTTGTTACACCCTATGAG

CCNGCATGGGATGGATGACCCGGAGAAAGAAGTGTTAGTGTGGANGTTTGACAG

CCGCCTAGCATTTCATCACATGGCCCGAGAGCTGCATCCGGAGTACTACAAGNA

CTGCTGACATCGAGCTTTCTACAAGGGACTTTCCGCTGGGGACTTTCCAGGGAGG

CGTGGCCTGGGCGGGACTGGGGAGTGGCGAGCCCTCAGATGCTGCATATAAGCA

GCTGCTTTTTGCCTGTACTGGGTCTCTCTGGTTAGACCAGATCTGAGCCTGGGAG

CTCTCTGGCTANCTAGGGAACCCACTGCTTAAGCCTCAATAAAGCTTGCCTTGAG

TGCTTCAAGTAGTGTGTGCCCGTCTGTTGTGTGACTCTGGTAACTAGAGATCCCTC

AGACCCTTTTAGTCAGTGTGGAAAATCTCTAGCAGTGGCGCCCGAACAGGGACTT

GAAAGCGAAAGTGAAACCAGAGGAGCTCTCTCGACGCAGGACTCGGCTTGCTGA

AGCGCGCACGGCAAGAGGCGAGGGGCGGCGACTGGTGAGTACGCCAAAAATTTT

GACTAGCGGAGGCTAGAAGGAGAGAGATGGGTGCGAGAGCGTCAGTATTAAGC

GGGGGAGAATTAGATAGATGGGAAAAAATTCGGTTAAGGCCAGGGGGAAAGAA
```

-continued

```
AAAATATAAATTAAAACATATAGTATGGGCAAGCAGGGAGCTAGAACGATTCGC

AGTTAATCCTGGCCTGTTAGAAACATCAGAAGGCTGTAGACAAATACTGGGACA

GCTACAACCATCCCTTCAGACAGGATCAGAAGAACTTAGATCATTATATAATACA

GTAGCAACCCTCTATTGTGTGCATCAAAGGATAGAGGTAAAAGACACCAAGGAA

GCTTTAGAGAAGATAGAGGAAGAGCAAAACAAAAGTAAGAAAAAAGCACAGCA

AGCAGCAGCTGACACAGGAAACAGCAGCCAGGTCAGCCAAAATTACCCTATAGT

GCAGAACCTCCAGGGGCAAATGGTACATCAGGCCATATCACCTAGAACTTTAAA

TGCATGGGTAAAAGTAGTAGAAGAGAAGGCTTTCAGCCCAGAAGTAATACCCAT

GTTTTCAGCATTATCAGAAGGAGCCACCCCACAAGATTTAAACACCATGCTAAAC

ACAGTGGGGGGACATCAAGCAGCCATGCAAATGTTAAAAGAGACCATCAATGAG

GAAGCTGCAGAATGGGATAGATTGCATCCAGTGCATGCAGGGCCTATTGCACCA

GGCCAGATGAGAGAACCAAGGGGAAGTGACATAGCAGGAACTACTAGTACCCTT

CAGGAACAAATAGGATGGATGACAAATAATCCACCTATCCCAGTAGGAGAAATC

TATAAAAGATGGATAATCCTGGGATTAAATAAAATAGTAAGAATGTATAGCCCT

ACCAGCATTCTGGACATAAGACAAGGACCAAAGGAACCCTTTAGAGACTATGTA

GACCGGTTCTATAAAACTCTAAGAGCCGAGCAAGCTTCACAGGAGGTAAAAAAT

TGGATGACAGAAACCTTGTTGGTCCAAAATGCGAACCCAGATTGTAAGACTATTT

TAAAAGCATTGGGACCAGCAGCTACACTAGAAGAAATGATGACAGCATGTCAGG

GAGTGGGAGGACCCGGCCATAAAGCAAGAGTTTTGGCTGAAGCAATGAGCCAAG

TAACAAATTCAGCTACCATAATGATGCAGAGAGGCAATTTTAGGAACCAAAGAA

AGACTGTTAAGTGTTTCAATTGTGGCAAAGAAGGGCACATAGCCAAAAATTGCA

GGGCCCCTAGGAAAAAGGGCTGTTGGAAATGTGGAAAGGAAGGACACCAAATG

AAAGATTGTACTGAGAGACAGGCTAATTTTTTAGGGAAGATCTGGCCTTCCCACA

AGGGAAGGCCAGGGAATTTTCTTCAGAGCAGACCAGAGCCAACAGCCCCACCAG

AAGAGAGCTTCAGGTTTGGGGAAGAGACAACAACTCCCTCTCAGAAGCAGGAGC

CGATAGACAAGGAACTGTATCCTTTAGCTTCCCTCAGATCACTCTTTGGCAACGA

CCCCTCGTCACAATAAAGATAGGGGGGCAACTAAAGGAAGCTCTATTAGATACA

GGAGCAGATGATACAGTATTAGAAGAAATGAATTTGCCAGGAAGATGGAAACCA

AAAATGATAGGGGGAATTGGAGGTTTTATCAAAGTAAGACAGTATGATCAGATA

CTCATAGAAATCTGTGGACATAAAGCTATAGGTACAGTATTAGTAGGACCTACAC

CTGTCAACATAATTGGAAGAAATCTGTTGACTCAGATTGGTTGCACTTTAAATTT

TCCCATTAGTCCTATTGAAACTGTACCAGTAAAATTAAAGCCAGGAATGGATGGC

CCAAAAGTTAAACAATGGCCATTGACAGAAGAAAAAATAAAAGCATTAGTAGAA

ATTTGTACAGAAATGGAAAAGGAAGGGAAAATTTCAAAAATTGGGCCTGAAAAT

CCATACAATACTCCAGTATTTGCCATAAAGAAAAAAGACAGTACTAAATGGAGA

AAATTAGTAGATTTCAGAGAACTTAATAAGAGAACTCAAGACTTCTGGGAAGTT

CAATTAGGAATACCACATCCCGCAGGGTTAAAAAAGAAAAAATCAGTAACAGTA

CTGGATGTGGGTGATGCATATTTTTCAGTTCCCTTAGATAAAGACTTCAGGAAGT

ATACTGCATTTACCATACCTAGTATAAACAATGAGACACCAGGGATTAGATATCA

GTACAATGTGCTTCCACAGGGATGGAAAGGATCACCAGCAATATTCCAAAGTAG
```

-continued

```
CATGACAAAAATCTTAGAGCCTTTTAGAAAACAAAATCCAGACATAGTTATCTAT

CAATACATGGATGATTTGTATGTAGGATCTGACTTAGAAATAGGGCAGCATAGA

ACAAAAATAGAGGAACTGAGACAACATCTGTTGAGGTGGGGATTTACCACACCA

GACAAAAAACATCAGAAAGAACCTCCATTCCTTTGGATGGGTTATGAACTCCATC

CTGATAAATGGACAGTACAGCCTATAGTGCTGCCAGAAAAAGACAGCTGGACTG

TCAATGACATACAGAAGTTAGTGGGAAAATTGAATTGGGCAAGTCAGATTTATG

CAGGGATTAAAGTAAAGCAATTATGTAAACTCCTTAGGGGAACCAAAGCACTAA

CAGAAGTAGTACCACTAACAGAAGAAGCAGAGCTAGAACTGGCAGAAAACAGG

GAGATTCTAAAAGAACCAGTACATGGAGTGTATTATGACCCATCAAAAGACTTA

ATAGCAGAAATACAGAAGCAGGGGCAAGGCCAATGGACATATCAAATTTATCAA

GAGCCATTTAAAAATCTGAAAACAGGAAAGTATGCAAGAATGAGGGGTGCCCAC

ACTAATGATGTAAAACAATTAACAGAGGCAGTGCAAAAAATAGCCACAGAAAGC

ATAGTAATATGGGGAAAGACTCCTAAATTTAAACTACCCATACAAAAAGAAACA

TGGGAAGCATGGTGGACAGAGTATTGGCAAGCCACCTGGATTCCTGAGTGGGAG

TTTGTCAATACCCCTCCCTTAGTGAAATTATGGTACCAGTTAGAGAAAGAACCCA

TAGTAGGAGCAGAAACTTTCTATGTAGATGGGGCAGCTAATAGGGAGACTAAAT

TAGGAAAAGCAGGATATGTTACTGACAGAGGAAGACAAAAAGTTGTCTCCCTAA

CTGACACAACAAATCAGAAGACTGAGTTACAAGCAATTCATCTAGCTTTGCAGG

ATTCGGGATTAGAAGTAAACATAGTAACAGACTCACAATATGCATTAGGAATCA

TTCAAGCACAACCAGATAAAAGTGAATCAGAGTTAGTCAGTCAAATAATAGAGC

AGTTAATAAAAAAGGAAAAGGTCTACCTGGCATGGGTACCAGCACACAAAGGAA

TTGGAGGAAATGAACAAGTAGATAAATTAGTCAGTGCTGGAATCAGGAAAGTAC

TATTTTTAGATGGAATAGATAAGGCCCAAGAAGAACATGAGAAATATCACAGTA

ATTGGAGAGCAATGGCTAGTGATTTTAACCTGCCACCTGTAGTAGCAAAAGAAA

TAGTAGCCAGCTGTGATAAATGTCAGCTAAAAGGAGAAGCCATGCATGGACAAG

TAGACTGTAGTCCAGGAATATGGCAACTAGATTGTACACATTTAGAAGGAAAAG

TTATCCTGGTAGCAGTTCATGTAGCCAGTGGATATATAGAAGCAGAAGTTATTCC

AGCAGAGACAGGGCAGGAAACAGCATACTTTCTCTTAAAATTAGCAGGAAGATG

GCCAGTAAAAACAATACATACAGACAATGGCAGCAATTTCACCAGTACTACGGT

TAAGGCCGCCTGTTGGTGGGCGGGATCAAGCAGGAATTTGGCATTCCCTACAAT

CCCCAAAGTCAAGGAGTAGTAGAATCTATGAATAAAGAATTAAAGAAAATTATA

GGACAGGTAAGAGATCAGGCTGAACATCTTAAGACAGCAGTACAAATGGCAGTA

TTCATCCACAATTTTAAAAGAAAAGGGGGGATTGGGGGGTACAGTGCAGGGGAA

AGAATAGTAGACATAATAGCAACAGACATACAAACTAAAGAATTACAAAAACA

AATTACAAAAATTCAAAATTTTCGGGTTTATTACAGGGACAGCAGAGATCCACTT

TGGAAAGGACCAGCAAAGCTTCTCTGGAAAGGTGAAGGGGCAGTAGTAATACAA

GATAATAGTGACATAAAAGTAGTGCCAAGAAGAAAAGCAAAGATCATTAGGGAT

TATGGAAAACAGATGGCAGGTGATGATTGTGTGGCAAGTAGACAGGATGAGGAT

TAGAACATGGAAAAGTTTAGTAAAACACCATATGTATATTTCAAGGAAAGCTAA

GGGATGGTTTTATAGACATCACTATGAAAGCACTCATCCAAGAATAAGTTCAGA

AGTACACATCCCACTAGGGGATGCTAAATTGGTAATAACAACATATTGGGGTCTG
```

```
CATACAGGAGAAAGAGACTGGCATTTGGGTCAGGGAGTCTCCATAGAATGGAGG

AAAAAGAGATATAGCACACAAGTAGACCCTGACCTAGCAGACCAACTAATTCAT

CTGTATTANTTTGATTGTTTTTCAGAATCTGCTATAAGAAATGCCATATTAGGACA

TATAGTTAGTCCTAGGTGTGAATATCAAGCAGGACATAACAAGGTAGGATCTCTA

CAGTACTTGGCACTAGCAGCATTAATAACACCAAAAAAGATAAAGCCACCTTTG

CCTAGTGTTACGAAACTGACAGAGGATAGATGGAACAAGCCCCAGAAGACCAAG

GGCCACAGAGGGAGCCATACAATGAATGGACACTAGAGCTTTTAGAGGAGCTTA

AGAGTGAAGCTGTTAGACATTTTCCTAGGATATGGCTCCATGGCTTAGGACAACA

TATCTATGAAACTTATGGGGATACTTGGGCAGGAGTGGAAGCCATAATAAGAAT

TCTGCAACAACTGCTGTTTATTCATTTCAGAATTGGGTGTCAACATAGCAGAATA

GGCATTACTCGACAGAGGAGAGCAAGAAATGGAGCCAGTAGATCCTAGACTAGA

GCCCTGGAAGCATCCAGGAAGTCAGCCTAAGACTGCTTGTACCAATTGCTATTGT

AAAAAGTGTTGCTTTCATTGCCAAGTTTGTTTCATAACAAAAGGCTTAGGCATCT

CCTATGGCAGGAAGAAGCGGAGACAGCGACGAAGAGCTCCTCAAGACAGTCAG

ACTCATCAAGTTTCTCTATCAAAGCAGTAAGTAGTACATGTAATGCAATCTTTAC

AAATATTAGCAATAGTAGCATTAGTAGTAGCAGCAATAATAGCAATAGTTGTGT

GGACCATAGTATTCATAGAATATAGGAAAATATTAAGACAAAGAAAAATAGACA

GGTTAATTGATAGAATAAGAGAAAGAGCAGAAGACAGTGGCAATGAGAGTGAA

GGGGATCAGGAAGAATTATCAGCACTTGTGGAGATGGGGCACCATGCTCCTTGG

GATGTTGATGATCTGTAGTGCTGCAGAAAAATTGTGGGTCACAGTCTATTATGGG

GTACCTGTGTGGAAAGAAGCAACCACCACTCTATTTTGTGCATCAGATGCTAAAG

CATATGATACAGAGGTACATAATGTTTGGGCCACACATGCCTGTGTACCCACAGA

CCCCAACCCACAAGAAGTAGTATTGGAAAATGTGACAGAAAATTTTAACATGTG

GAAAAATAACATGGTAGAACAGATGCATGAGGATATAATCAGTTTATGGGATCA

AAGCCTAAAGCCATGTGTAAAATTAACCCCACTCTGTGTTACTTTAAATTGCACT

GATTTGAAGAATACTACTAATACTNTATACTACTAGTAGTAGTGGGAAAAGAT

GGAGAAAGGAGAAATAAAAAACTGCTCTTTCAATATCACCACAAGCATAAGAGA

TAAGGTGCAGAAAGAATATGCACTTTTTTATAAACTTGATGTAGTACCAATAGAT

AATAATAATACTAGCTATAGGTTGATAAGTTGTAACACCTCAGTCATTACACAGG

CCTGTCCAAAGGTATCCTTTGAGCCAATTCCCATACATTATTGTGCCCCGGCTGGT

TTTGCGATTCTAAAGTGTAATGATAAGAAGTTCAATGGAACAGGACCATGTACA

AATGTCAGCACAGTACAATGTACACATGGAATTAGGCCAGTAGTATCAACTCAA

CTGCTGTTAAATGGCAGTCTAGCAGAAGAAGAGGTAGTAATTAGATCTGACAAT

TTCACGGACAATGCTAAAACCATAATAGTACAGCTGAATGAATCTGTAGAAATT

AATTGTACAAGACCCAACAACAATACAAGAAAAAGTATACATATAGGACCAGGG

AGAGCATTTTATACAACAGGAGAAATAATAGGAGATATAAGACAAGCACATTGT

AACATTAGTAGAGCAAAATGGAATAACACTTTAAAACAGATAGTTAAAAAATTA

AGAGAACAATTTGGGAATAAAACAATAGTCTTTAATCAATCCTCAGGAGGGGAC

CCAGAAATTGTAATGCACAGTTTTAATTGTGGAGGGGAATTTTTCTACTGTAATA

CAACACAACTGTTTAATAGTACTTGGATAATANTANTAATAGTACTAATAATACT
```

-continued

```
GAAGGAAATGAAACTATCACACTCCCATGCAGAATAAAACAAATTATAAACATG

TGGCAGGAAGTAGGAAAAGCAATGTATGCCCCTCCCATCAGAGGACAAATTAGA

TGTTCATCAAATATTACAGGGCTGCTATTAACAAGAGATGGTGGTNAATAACAAC

AACGAGACCGAGATCTTCAGACCTGGAGGAGGAGATATGAGGGACAATTGGAG

AAGTGAATTATATAAATATAAAGTAGTAAAAATTGAACCATTAGGAGTAGCACC

CACCAAGGCAAAGAGAAGAGTGGTGCAGAGAGAAAAAAGAGCAGTGGGAATAG

GAGCTATGTTCCTTGGGTTCTTGGGAGCAGCAGGAAGCACTATGGGCGCAGCGTC

AATGACGCTGACGGTACAGGCCAGACAATTATTGTCTGGTATAGTGCAACAGCA

GAACAATTTGCTGAGGGCTATTGAGGCGCAACAGCATCTGTTGCAACTCACAGTC

TGGGGCATCAAGCAGCTCCAGGCAAGAGTCCTGGCTGTGGAAAGATACCTAAAG

GATCAACAGCTCCTGGGGATTTGGGGTTGCTCTGGAAAACTCATTTGCACCACTG

CTGTGCCTTGGAATGCTAGTTGGAGTAATAAATCTCTGGATGAGATTTGGAATAA

CATGACCTGGATGGAGTGGGAAAGAGAAATTGACAATTACACAAGCTTAATATA

CACCTTAATTGAAGAATCGCAGAACCAACAAGAAAAGAATGAACAAGAATTATT

GGAATTGGATAAATGGGCAAGTTTGTGGAATTGGTTTGACATAACAAACTGGCT

GTGGTATATAAAAATATTCATAATGATAGTAGGAGGCTTGGTAGGTTTAAGAATA

GTTTTTGCTGTACTTTCTATAGTGAATAGAGTTAGGCAGGGATACTCACCATTATC

GTTTCAGACCCGCCTCCCAGCCCCGAGGGGACCCGACAGGCCCGAAGGAATCGA

AGAAGAAGGTGGAGAGAGAGACAGAGACAGATCCGGTCGATTAGTGAATGGAT

TCTTAGCACTTATCTGGGACGACCTGCGGAGCCTGTGCCTCTTCAGCTACCACCG

CTTGAGAGACTTACTCTTGATTGTAACGAGGATTGTGGAACTTCTGGGACGCAGG

GGGTGGGAAGCCCTCAAATATTGGTGGAATCTCCTGCAGTATTGGAGTCAGGAA

CTAAAGAATAGTGCTGTTAGCTTGCTCAATGCCACAGCTATAGCAGTAGCTGAGG

GGACAGATAGGGTTATAGAAGTAGTACAAAGAGCTTATAGAGCTATTCTCCACA

TACCTANAAGAATAAGACAGGGCTTGGAAAGGGCTTTGCTATAAGATGGGTGGC

AAGTGGTCAAAACGTAGTGTGGGTGGATGGCCTACTGTAAGGGAAAGAATGAGA

CGAGCTGAGCCAGCAGCAGATGGGGTGGGAGCAGTATCTCGAGACCTGGAAAAA

CATGGAGCAATCACAAGTAGCAATACAGCAGCTACTAATGCTGATTGTGCCTGG

CTAGAAGCACAAGAGGAGGAGGAGGTGGGTTTTCCAGTCAGACCTCAGGTACCT

TTAAGACCAATGACTTACAAGGCAGCTGTAGATCTTAGCCACTTTTTAAAAGAAA

AGGGGGGACTGGAAGGGCTAATTTACTCCCAAAAAAGACAAGATATCCTTGATC

TGTGGGTCTACCACACACAAGGCTACTTCCCTGATTGGCAGAACTACACACCAGG

GCCAGGGATCAGATATCCACTGACCTTTGGATGGTGCTTCAAGCTAGTACCAGTT

GAGCCAGAGAAGGTAGAAGAGGCCAATGAAGGAGAGAACAACAGCTTGTTACA

CCCTATGAGCCTGCATGGGATGGATGACCCGGAGAAAGAAGTGTTAGTGTGGAA

GTTTGACAGCCGCCTAGCATTTCATCACATGGCCCGAGAGCTGCATCCGGAGTAC

TACAAGAACTGCTGACATCGAGCTTTCTACAAGGGACTTTCCGCTGGGGACTTTC

CAGGGAGGCGTGGCCTGGGCGGGACTGGGGAGTGGCGAGCCCTCAGATGCTGCA

TATAAGCAGCTGCTTTTTGCCTGTACTGGGTCTCTCTGGTTAGACCAGATCTGAGC

CTGGGAGCTCTCTGGCTANCTAGGGAACCCACTGCTTAAGCCTCAATAAAGCTTG

CCTTGAGTGCTTA
```

-continued

SEQ C_Majority
SEQ ID NO: 6
TGGAAGGGTTAATTTACTCCAAGAAAAGGCAAGAGATCCTTGATTTGTGGGTCTA

TCACACACAAGGCTACTTCCCTGATTGGCAAAACTACACACCGGGACCAGGGGT

CAGATATCCACTGACCTTTGGATGGTGCTTCAAGCTAGTGCCAGTTGACCCAAGG

GAAGTAGAAGAGGCCAACGAAGGAGAAGACAACTGTTTGCTACACCCTATGAGC

CAGCATGGAATGGAGGATGAAGACAGAGAAGTATTAAATGGAAGTTTGACAGT

CNGCTAGCACGCAGACACATGGCCCGCGAGCTACATCCGGAGTATTACAAAGAC

TGCTGACACAGAAGGGACTTTCCGCTGGGACTTTCCACTGGGGCGTTCCAGGAGG

TGTGGTCTGGGCGGGACTGGGGAGTGGTCAACCCTCAGATGCTGCATATAAGCA

GCTGCTTTTCGCCTGTACTGGGTCTCTCTAGGTAGACCAGATCTGAGCCTGGGAG

CTCTCTGGCTATCTAGGGAACCCACTGCTTAAGCCTCAATAAAGCTTGCCTTGAG

TGCTCTAAGTAGTGTGTGCCCGTCTGTTGTGTGACTCTGGTAACTAGAGATCCCTC

AGACCCTTTTTGGTAGTGTGGAAAATCTCTAGCAGTGGCGCCCGAACAGGGACTT

GAAAGCGAAAGTAAGACCAGAGGAGATCTCTCGACGCAGGACTCGGCTTGCTGA

AGTGCACTCGGCAAGAGGCGAGAGCGGCGGCTGGTGAGTACGCCAAATTTTATT

TGACTAGCGGAGGCTAGAAGGAGAGAGATGGGTGCGAGAGCGTCAATATTAAG

AGGGGGAAAATTAGATAAATGGGAAAAAATTAGGTTAAGGCCAGGGGGAAAGA

AACACTATATGCTAAAACACCTAGTATGGGCAAGCAGGGAGCTGGAAAGATTTG

CACTTAACCCTGGCCTTTTAGANACATCAGAAGGCTGTAAACAAATAATAAAAC

AGCTACAACCAGCTCTTCAGACAGGAACAGAGGAACTTAGATCATTATACAACA

CAGTAGCAACTCTCTATTGTGTACATGAAAAGATAGAGGTACGAGACACCAAGG

AAGCCTTAGACAAGATAGAGGAAGAACAAACAAAAGTCAGCAAAAAACACAG

CAGGCAAAAGCGGCTGACGGAAAGGTCAGTCAAAATTATCCTATAGTGCAGAAT

CTCCAAGGGCAAATGGTACACCAGGCCATATCACCTAGAACTTTGAATGCATGG

GTAAAAGTAATAGAGGAGAAGGCTTTTAGCCCAGAGGTAATACCCATGTTTACA

GCATTATCAGAAGGAGCCACCCCACAAGATTTAAACACCATGTTAAATACAGTG

GGGGGACATCAAGCAGCCATGCAAATGTTAAAAGATACCATCAATGAGGAGGCT

GCAGAATGGGATAGATTACATCCAGTACATGCAGGGCCTATTGCACCAGGCCAA

ATGAGAGAACCAAGGGGAAGTGACATAGCAGGAACTACTAGTACCCTTCAGGAA

CAAATAGCATGGATGACAAGTAACCCACCTATTCCAGTGGGAGACATCTATAAA

AGATGGATAATTCTGGGGTTAAATAAAATAGTAAGAATGTATAGCCCTGTCAGC

ATTTTGGACATAAAACAAGGGCCAAAGGAACCCTTTAGAGACTATGTAGACCGG

TTCTTTAAAACTTTAAGAGCTGAACAAGCTACACAAGATGTAAAAAATTGGATG

ACAGACACCTTGTTGGTCCAAAATGCGAACCCAGATTGTAAGACCATTTTAAGAG

CATTAGGACCAGGGGCTACATTAGAAGAAATGATGACAGCATGTCAGGGAGTGG

GAGGACCTGGCCACAAAGCAAGAGTGTTGGCTGAGGCAATGAGCCAAGCAAAC

AATACAAACATAATGATGCAGAGAAGCAATTTTAAAGGCCCTAAAAGAATTGTT

AAATGTTTCAACTGTGGCAAGGAAGGGCACATAGCCAGAAATTGCAGGGCC CCT

AGGAAAAAAGGCTGTTGGAAATGTGGAAAGGAAGGACACCAAATGAAAGACTG

TACTGAGAGGCAGGCTAATTTTTTAGGGAAAATTTGGCCTTCCCACAAGGGGAG

-continued

```
GCCAGGGAATTTCCTTCAGAACAGACCAGAGCCAACAGCCCCACCAGCAGAGAG
CTTCAGGTTCGAGGAGACAACCCCCGCTCCGAAGCAGGAGCCGAAAGACAGGGA
ACCCTTAACTTCCCTCAAATCACTCTTTGGCAGCGACCCCTTGTCTCAATAAAGT
AGGGGGCCAGATAAAGGAGGCTCTCTTAGACACAGGAGCAGATGATACAGTATT
AGAAGAAATAAATTTGCCAGGAAAATGGAAACCAAAAATGATAGGAGGAATTG
GAGGTTTTATCAAAGTAAGACAGTATGATCAAATACTTATAGAAATTTGTGGAAA
AAAGGCTATAGGTACAGTATTAGTAGGACCTACACCTGTCAACATAATTGGAAG
AAATATGTTGACTCAGCTTGGATGCACACTAAATTTTCCAATTAGTCCCATTGAA
ACTGTACCAGTAAAATTAAAGCCAGGAATGGATGGCCCAAAGGTTAAACAATGG
CCATTGACAGAAGAGAAAATAAAAGCATTAACAGCAATTTGTGAAGAAATGGAG
AAGGAAGGAAAAATTACAAAAATTGGGCCTGAAAATCCATATAACACTCCAGTA
TTTGCCATAAAAAAGAAGGACAGTACTAAGTGGAGAAAATTAGTAGATTTCAGG
GAACTCAATAAAAGAACTCAAGACTTTTGGGAAGTTCAATTAGGAATACCACAC
CCAGCAGGGTTAAAAAAGAAAAAATCAGTGACAGTACTGGATGTGGGGGATGCA
TATTTTTCAGTTCCTTTAGATGAAGGCTTCAGGAAATATACTGCATTCACCATACC
TAGTATAAACAATGAAACACCAGGGATTAGATATCAATATAATGTGCTTCCACA
GGGATGGAAAGGATCACCAGCAATATTCCAGAGTAGCATGACAAAAATCTTAGA
GCCCTTTAGAGCACAAAATCCAGAAATAGTCATCTATCAATATATGGATGACTTG
TATGTAGGATCTGACTTAGAAATAGGGCAACATAGAGCAAAAATAGAGGAGTTA
AGAGAACATCTATTAAAGTGGGGATTTACCACACCAGACAAGAAACATCAGAAA
GAACCCCCATTTCTTTGGATGGGGTATGAACTCCATCCTGACAAATGGACAGTAC
AGCCTATACAGCTGCCAGAAAAGGATAGCTGGACTGTCAATGATATACAGAAGT
TAGTGGGAAAATTAAACTGGGCAAGTCAGATTTACCCAGGGATTAAAGTAAGGC
AACTTTGTAAACTCCTTAGGGGGGCCAAAGCACTAACAGACATAGTACCACTAA
CTGAAGAAGCAGAATTAGAATTGGCAGAGAACAGGGAAATTCTAAAAGAACCA
GTACATGGAGTATATTATGACCCATCAAAAGACTTGATAGCTGAAATACAGAAA
CAGGGGCATGACCAATGGACATATCAAATTTACCAAGAACCATTCAAAAATCTG
AAAACAGGGAAGTATGCAAAAATGAGGACTGCCCACACTAATGATGTAAAACAG
TTAACAGAGGCAGTGCAAAAAATAGCCATGGAAAGCATAGTAATATGGGGAAA
GACTCCTAAATTTAGACTACCCATCCAAAAAGAAACATGGGAGACATGGTGGAC
AGACTATTGGCAAGCCACCTGGATTCCTGAGTGGGAGTTTGTTAATACCCCTCCC
CTAGTAAAATTATGGTACCAGCTGGAGAAAGAACCCATAGCAGGAGCAGAAACT
TTCTATGTAGATGGAGCAGCTAATAGGGAAACTAAAATAGGAAAAGCAGGGTAT
GTTACTGACAGAGGAAGGCAGAAAATTGTTTCTCTAACTGAAACAACAAATCAG
AAGACTGAATTACAAGCAATTCAGCTAGCTTTGCAAGATTCAGGATCAGAAGTA
AACATAGTAACAGACTCACAGTATGCATTAGGAATCATTCAAGCACAACCAGAT
AAGAGTGAATCAGAGTTAGTCAACCAAATAATAGAACAATTAATAAAAAAGGAA
AGGGTCTACCTGTCATGGGTACCAGCACATAAAGGAATTGGAGGAAATGAACAA
GTAGATAAATTAGTAAGTAGTGGAATCAGGAAAGTGCTGTTTCTAGATGGAATA
GATAAGGCTCAAGAAGAGCATGAAAAGTATCACAGCAATTGGAGAGCAATGGCT
AGTGAGTTTAATCTGCCACCCATAGTAGCAAAAGAAATAGTAGCTAGCTGTGAT
```

-continued

```
AAATGTCAGCTAAAAGGGGAAGCCATACATGGACAAGTAGACTGTAGTCCAGGG

ATATGGCAATTAGATTGTACACATTTAGAAGGAAAAATCATCCTGGTAGCAGTCC

ATGTAGCCAGTGGCTACATAGAAGCAGAGGTTATCCCAGCAGAAACAGGACAAG

AAACAGCATACTATATACTAAAATTAGCAGGAAGATGGCCAGTCAAAGTAATAC

ATACAGACAATGGCAGTAATTTCACCAGTGCTGCAGTTAAGGCAGCCTGTTGGTG

GGCAGGTATCCAACAGGAATTTGGAATTCCCTACAATCCCCAAAGTCAGGGAGT

AGTAGAATCCATGAATAAAGAATTAAAGAAAATCATAGGGCAGGTAAGAGATCA

AGCTGAGCACCTTAAGACAGCAGTACAAATGGCAGTATTCATTCACAATTTTAAA

AGAAAAGGGGGGATTGGGGGGTACAGTGCAGGGGAAAGAATAATAGACATAAT

AGCAACAGACATACAAACTAAAGAATTACAAAAACAAATTATAAAAATTCAAAA

TTTTCGGGTTTATTACAGAGACAGCAGAGACCCTATTTGGAAAGGACCAGCCAA

ACTACTCTGGAAAGGTGAAGGGGCAGTAGTAATACAAGATAATAGTGACATAAA

GGTAGTACCAAGGAGGAAAGCAAAAATCATTAAGGACTATGGAAAACAGATGG

CAGGTGCTGATTGTGTGGCAGGTAGACAGGATGAAGATTAGAACATGGAATAGT

TTAGTAAAGCACCATATGTATATTTCAAGGAGAGCTAATGGATGGTTTTACAGAC

ATCATTATGAAAGCAGACATCCAAAAGTAAGTTCAGAAGTACACATCCCATTAG

GGGANGCTAGATTAGTAATAAAAACATATTGGGGTTTGCAAACAGGAGAAAGAG

ATTGGCATTTGGGTCATGGAGTCTCCATAGAATGGAGATTGAGAAGATATAGCA

CACAAGTAGACCCTGGCCTGGCAGACCAGCTAATTCATATGCATTATTTTGATTG

TTTTGCAGACTCTGCCATAAGAAAAGCCATATTAGGACACATAGTTATTCCTAGG

TGTGACTATCAAGCAGGACATAATAAGGTAGGATCTCTACAATACTTGGCACTGA

CAGCATTGATAAAACCAAAAAAGATAAAGCCACCTCTGCCTAGTGTTAGGAAAT

TAGTAGAGGATAGATGGAACAAGCCCCAGAAGACCAGGGGCCGCAGAGGGAAC

CATACAATGAATGGACACTAGAGCTTCTAGAGGAACTCAAGCAGGAAGCTGTCA

GACACTTTCCTAGACCATGGCTCCATAGCTTAGGACAATATATCTATGAAACCTA

TGGGGATACTTGGACAGGAGTTGAAGCTATAATAAGAATACTGCAACAACTACT

GTTTATTCATTTCAGAATTGGGTGCCAGCATAGCAGAATAGGCATTTTGCGACAG

AGAAGAGCAAGAAATGGAGCCAGTAGATCCTAACCTAGAGCCCTGGAACCATCC

AGGAAGTCAGCCTAAAACTGCTTGTAATAAGTGCTATTGTAAACACTGTAGCTAT

CATTGTCTAGTTTGCTTTCAGACAAAAGGCTTAGGCATTTCCTATGGCAGGAAGA

AGCGGAGACAGCGACGAAGCGCTCCTCCAAGCAGTGAGGATCATCAAAATCCTA

TATCAAAGCAGTAAGTATATGTAATGTTAGATTTACTAGCAAGAGTAGATTATAG

ATTAGGAGTAGGAGCATTGATAGTAGCACTAATCATAGCAATAGTTGTGTGGAC

CATAGTATATATAGAATATAGGAAATTGTTAAGACAAAGAAAAATAGACTGGTT

AATTAAAAGAATTAGGGAAAGAGCAGAAGACAGTGGCAATGAGAGTGAGGGGG

ATACTGAGGAATTGTCAACAATGGTGGATATGGGGCATCTTAGGCTTTTGGATGT

TAATGATTTGTAATGTGGTGGGGAACTTGTGGGTCACAGTCTATTATGGGGTACC

TGTGTGGAAAGAAGCAAAAACTACTCTATTCTGTGCATCAGATGCTAAAGCATAT

GAGAAAGAAGTGCATAATGTCTGGGCTACACATGCCTGTGTACCCACAGACCCC

AACCCACAAGAAATAGTTTTGGAAAATGTAACAGAAAATTTTAACATGTGGAAA
```

-continued

```
AATGACATGGTGGATCAGATGCATGAGGATATAATCAGTTTATGGGATCAAAGC

CTAAAGCCATGTGTAAAGTTGACCCCACTCTGTGTCACTTTAAACTGTACAAATG

TTAATATTACTAATAATAATAAACAATAATAACATGAATGAAGAAATAAAAAAT

TGCTCTTTCAATATAACCACAGAAATAAGAGATAAGAAACAGAAAGTGTATGCA

CTTTTTTATAGACTTGATATAGTACCACTTAATGAGAATAACAATTCTAGTGAGT

ATAGATTAATAAATTGTAATACCTCAACCATAACACAAGCCTGTCCAAAGGTCTC

TTTTGACCCAATTCCTATACATTATTGTGCTCCAGCTGGTTATGCGATTCTAAAGT

GTAATAATAAGACATTCAATGGGACAGGACCATGCAATAATGTCAGCACAGTAC

AATGTACACATGGAATTAAGCCAGTGGTATCAACTCAACTACTGTTAAATGGTAG

CCTAGCAGAAGAAGAGATAATAATTAGATCTGAAAATCTGACAAACAATGTCAA

AACAATAATAGTACATCTTAATGAATCTGTAGAAATTGTGTGTACAAGACCCAAC

AATAATACAAGAAAAAGTATAAGGATAGGACCAGGACAAACATTCTATGCAACA

GGAGACATAATAGGAGACATAAGACAAGCACATTGTAACATTAGTGAAGATAAA

TGGAATAAAACTTTACAAAAGGTAAGTAAAAAATTAAAAGAACACTTCCCTAAT

AAAACAATAAAATTTGAACCATCCTCAGGAGGGGACCTAGAAATTACAACACAT

AGCTTTAATTGTAGAGGAGAATTTTTCTATTGCAATACATCAAAACTGTTTAATA

GTACATACAANAATAATACTAATAATAATACAAATTCAACCATCACACTCCCATG

CAGAATAAAACAAATTATAAACATGTGGCAGGAGGTAGGACGAGCAATGTATGC

CCCTCCCATTGCAGGAAACATAACATGTAAATCAAATATCACAGGACTACTATTG

ACACGTGATGGAGGAAAAAAAAATAATAACACAGAGATATTCAGACCTGGAGG

AGGAGATATGAGGGACAATTGGAGAAGTGAATTATATAAATATAAAGTGGTAGA

AATTAAGCCATTGGGAGTAGCACCCACTGAGGCAAAAAGGAGAGTGGTGGAGA

GAGAAAAAAGAGCAGTGGGAATAGGAGCTGTGTTCCTTGGGTTCTTGGGAGCAG

CAGGAAGCACTATGGGCGCGGCGTCAATAACGCTGACGGTACAGGCCAGACAAT

TGTTGTCTGGTATAGTGCAACAGCAAAGCAATTTGCTGAGGGCTATAGAGGCGC

AACAGCATATGTTGCAACTCACGGTCTGGGGCATTAAGCAGCTCCAGACAAGAG

TCCTGGCTATAGAAAGATACCTAAAGGATCAACAGCTCCTAGGGATTTGGGGCT

GCTCTGGAAAACTCATCTGCACCACTGCTGTGCCTTGGAACTCCAGTTGGAGTAA

TAAATCTCAAGAAGATATTTGGGATAACATGACCTGGATGCAGTGGGATAGAGA

AATTAGTAATTACACAGACACAATATACAGGTTGCTTGAAGACTCGCAAACCA

GCAGGAAAAAAATGAAAAAGATTTATTAGCATTGGACAGTTGGAAAAATCTGTG

GAATTGGTTTGACATAACAAATTGGCTGTGGTATATAAAAATATTCATAATGATA

GTAGGAGGCTTGATAGGTTTAAGAATAATTTTTGCTGTGCTCTCTATAGTGAATA

GAGTTAGGCAGGGATACTCACCTTTGTCGTTTCAGACCCTTACCCCAAACCCGAG

GGGACCCGACAGGCTCGGAAGAATCGAAGAAGAAGGTGGAGAGCAAGACAGAG

ACAGATCCATTCGATTAGTGANCGGATTCTTAGCACTTGCCTGGGACGATCTGCG

GAGCCTGTGCCTCTTCAGCTACCACCGATTGAGAGACTTCATATTGGTGGCAGCG

AGAGCAGTGGAACTTCTGGGACGCAGCAGTCTCAGGGGACTACAGAGGGGGTGG

GAAGCCCTTAAGTATCTGGGAAGTCTTGTGCAGTATTGGGGTCTGGAGCTAAAAA

AGAGTGCTATTAGTCTGCTTGATACCATAGCAATAGCAGTAGCTGAAGGAACAG

ATAGGATTATAGAATTAATACAAAGAATTTGTAGAGCTATCCGCAACATACCTAG
```

-continued

```
AAGAATAAGACAGGGCTTTGAAGCAGCTTTGCTATAAAATGGGGGGCAAGTGGT

CAAAAAGCAGTATAGTTGGATGGCCTGCTGTAAGAGAAAGAATAAGAAGAACTG

AGCCAGCAGCAGAGGGAGTAGGAGCAGCGTCTCAAGACTTAGATAAACATGGA

GCACTTACAAGCAGCAACACAGCCACCAATAATGCTGATTGTGCCTGGCTGGAA

GCACAAGAGGAGGAAGAAGAAGTAGGCTTTCCAGTCAGACCTCAGGTGCCTTTA

AGACCAATGACTTATAAGGGAGCATTCGATCTCAGCTTCTTTTTAAAAGAAAAGG

GGGGACTGGAAGGGTTAATTTACTCTAAGAAAAGGCAAGAGATCCTTGATTTGT

GGGTCTATCACACACAAGGCTACTTCCCTGATTGGCAAAACTACACACCGGGAC

CAGGGGTCAGATATCCACTGACCTTTGGATGGTGCTTCAAGCTAGTGCCAGTTGA

CCCAAGGGAAGTAGAAGAGGCCAACGAAGGAGAAAACAACTGTTTGCTACACCC

TATGAGCCAGCATGGAATGGAGGATGAAGACAGAGAAGTATTAAAGTGGAAGTT

TGACAGTAGCCTAGCACGCAGACACATGGCCCGCGAGCTACATCCGGAGTATTA

CAAAGACTGCTGACACAGAAGGGACTTTCCGCTGGGACTTTCCACTGGGCGTTC

CAGGAGGTGTGGTCTGGGCGGGACTGGGAGTGGTCAACCCTCAGATGCTGCATA

TAAGCAGCTGCTTTTCGCCTGTACTGGGTCTCTCTAGGTAGACCAGATCTGAGCC

TGGGAGCTCTCTGGCTATCTAGGGAACCCACTGCTTAAGCCTCAATAAAGCTTGC

CTTGAGTGCTCTA

SEQ D_Majority
                                                    SEQ ID NO: 7
ATTATGGAAGGGCTAATTTGGTCNNAAAGAAGACAAGANATCCTTGATCTTTGG

GTCTACCACACACAAGGCTTCTTCCCTGATTGGCAAAACTACACACCAGGGCCAG

GGATTAGATATCCACTGACCTTTGGATGGTGCTTCGAGCTAGTACCAGTTGATCC

AGAGGAGGTAGAAGAGGCCACTGAAGGAGAGAACAACTGCTTGTTACACCCTGT

GTGCCAGCATGGAATGGAGGACCCGGAGAGAGAAGTGTTAANGTGGAGATTTAA

CAGCAGACTAGCATTTGAACACAAGGCCCGAATACTGCATCCGGAGTACTACAA

AGACTGCTGACACCGAGTTTNCTACAAGGGACTTTCCGCTGGGGACTTTCCAGGG

AGGCGTAACCGGGGCGGGACTGGGGAGTGGCTAACCCTCAGATGCTGCATATAA

GCAGCTGCTTTTTGCCTGTACTGGGTCTCTCTGGTTAGACCAGATTTGAGCCTGAG

AGCTCTCTGGCTAGCTAGGGAACCCACTGCTTAAGCCTCAATAAAGCTTGCCTTG

AGTGCTTCAAGTAGTGTGTGCCCGTCTGTTGTGTGACTCTGGTAACTAGAGATCC

CTCAGACCCCTTTAGTCAGAGTGGAAAATCTCTAGCAGTGGCGCCCGAACAGGG

ACCTGAAAGCGAAAGTAGAACCAGAGGAGCTCTCTCGACGCAGGACTCGGCTTG

CTGAAGCGCGCACGGCAAGAGGCGAGGGGCAGCGACTGGTGAGTACGCTAAAA

ANTTTTGACTAGCGGAGGCTAGAAGGAGAGAGATGGGTGCGAGAGCGTCAGTAT

TAAGCGGGGGAAAATTAGATGAATGGGAAAAAATTCGGTTACGGCCAGGGGGA

AAGAAAAAATATAGACTAAAACATATAGTATGGGCAAGCAGGGAGCTAGAACG

ATTTGCACTTAATCCTGGCCTTTTAGAAACATCAGAAGGCTGTAAACAAATAATA

GGACAGCTACAACCAGCTATTCAGACAGGATCAGAGGAACTTAAATCATTATAT

AATACAGTAGCAACCCTCTATTGTGTACATGAAAGGATAAAGGTAACAGACACC

AAGGAAGCTTTAGACAAGATAGAGGAAGAACAAACCAAAAGTAAGAAAAAAGC

ACAGCAAGCAACAGCTGACACAAGAAACAGCAGCCAGGTCAGCCAAAATTATCC
```

-continued

```
TATAGTGCAAAACCTACAGGGGCAAATGGTACACCAGGCCATATCACCTAGAAC

TTTGAACGCATGGGTAAAAGTAATAGAGGAGAAGGCTTTCAGCCCAGAAGTAAT

ACCCATGTTTTCAGCATTATCAGAAGGAGCCACCCCACAAGATTTAAACACCATG

CTAAACACAGTGGGGGGACATCAAGCAGCCATGCAAATGTTAAAAGAGACCATC

AATGAGGAAGCTGCAGAATGGATAGGCTACATCCAGTGCATGCAGGGCCTATT

GCACCAGGCCAAATGAGAGAACCAAGGGGAAGTGATATAGCAGGAACTACTAG

TACCCTTCAGGAACAAATAGGATGGATGACAAGCAATCCACCTATCCCAGTAGG

AGAAATCTATAAAAGATGGATAATCCTAGGATTAAATAAAATAGTAAGAATGTA

TAGCCCTGTCAGCATTTTGGACATAAGACAAGGACCAAAGGAACCCTTTAGAGA

CTATGTAGATCGGTTCTATAAAACTCTAAGAGCCGAGCAAGCTTCACAGGATGTA

AAAAATTGGATGACTGAAACCTTGTTGGTCCAAAATGCAAACCCAGATTGTAAA

ACTATCTTAAAAGCATTGGGACCAGCGGCTACATTAGAAGAAATGATGACAGCA

TGTCAGGGAGTGGGGGGACCCAGTCATAAAGCAAGAGTTTTGGCTGAGGCAATG

AGCCAAGCAACAAATGCAAATGCTGCTATAATGATGCAGAGAGGCAATTTTAAG

GGCCCAAAGAAAATCATTAAGTGTTTCAACTGTGGCAAAGAAGGGCACATAGCA

AAAAATTGCAGGGCTCCTAGGAAAAAGGGCTGTTGGAAATGTGGAAGGGAAGG

ACACCAAATGAAAGATTGCACTGAAAGACAGGCTAATTTTTTAGGGAAAATTTG

GCCTTCCCACAAGGGAAGGCCAGGGAACTTCCTTCAGAGCAGACCAGAGCCAAC

AGCCCCACCAGCAGAGAGCTTCGGGTTTGGGGAGGAGATAACACCCTCTCAGAA

ACAGGAGCAGAAAGACAAGGAACTGTATCCTTTAGCTTCCCTCAAATCACTCTTT

GGCAACGACCCCTTGTCACAGTAAAGATAGGGGACAGCTAAAGGAAGCTCTAT

TAGATACAGGAGCAGATGATACAGTATTAGAAGAAATAAATTTGCCAGGAAAAT

GGAAACCAAAAATGATAGGGGAATTGGAGGCTTTATCAAAGTAAGACAGTATG

ATCAAATACTCGTAGAAATCTGTGGACATAAAGCTATAGGTACAGTATTAGTAG

GACCTACACCTGTCAACATAATTGGAAGAAATTTGTTGACTCAGATTGGTTGCAC

TTTAAATTTTCCAATTAGTCCTATTGAAACTGTACCAGTAAAATTAAAGCCAGGG

ATGGATGGCCCAAAAGTTAAACAATGGCCATTGACAGAAGAAAAAATAAAAGC

ACTAACAGAAATTTGTACAGAAATGGAAAAGGAAGGAAAAATTTCAAGAATTGG

GCCTGAAAATCCATACAATACTCCAATATTTGCCATAAAGAAAAAAGACAGTAC

TAAGTGGAGAAAATTAGTAGATTTCAGAGAACTTAATAAGAGAACTCAAGACTT

CTGGGAAGTTCAACTAGGAATACCACATCCTGCAGGGCTAAAAAAGAAAAAATC

AGTAACAGTACTGGATGTGGGTGATGCATATTTTTCAGTTCCCTTAGATGAAGAC

TTTAGAAAATATACTGCATTCACCATACCTAGTATAAACAATGAGACACCAGGA

ATTAGATATCAGTACAATGTGCTTCCACAAGGATGGAAAGGATCACCGGCAATA

TTCCAAAGTAGCATGACAAAAATCTTAGAACCTTTTAGAAAACAAAATCCAGAA

ATGGTTATCTATCAATACATGGATGATTTGTATGTAGGATCTGACTTAGAAATAG

GGCAGCATAGAATAAAAATAGAGGAATTAAGGGAACACCTATTGAAGTGGGGAT

TTACCACACCAGACAAAAAGCATCAGAAAGAACCTCCATTTCTTTGGATGGGTTA

TGAACTCCATCCTGATAAATGGACAGTACAGCCTATAAAACTGCCAGAAAAAGA

AAGCTGGACTGTCAATGATATACAGAAGTTAGTGGGAAAATTAAATTGGGCAAG

CCAGATTTATCCAGGAATTAAAGTAAGACAATTATGCAAATGCCTTAGGGGAGC
```

-continued

```
CAAAGCACTGACAGAAGTAGTACCACTGACAGAAGAAGCAGAATTAGAACTGGC

AGAAAACAGGGAAATTCTAAAAGAACCAGTACATGGAGTGTATTATGACCCATC

AAAAGACTTAATAGCAGAAATACAGAAACAAGGGCAAGACCAATGGACATATC

AAATTTATCAAGAACAATATAAAAATCTGAAAACAGGAAAGTATGCAAAAATGA

GGGGTACCCACACTAATGATGTAAAACAATTAACAGAGGCAGTGCAAAAAATAG

CCCAAGAATGTATAGTGATATGGGGAAAGACTCCTAAATTTAGACTACCCATAC

AAAAGGAAACATGGGAAACATGGTGGACAGAGTATTGGCAGGCCACCTGGATTC

CTGAGTGGGAGTTTGTCAATACCCCTCCTTTAGTTAAATTATGGTACCAGTTAGA

GAAGGAACCCATAGTAGGAGCAGAAACTTTCTATGTAGATGGGGCAGCTAATAG

AGAGACTAAATTAGGAAAAGCAGGATATGTTACTGACAGAGGAAGACAGAAAG

TTGTCTCTCTAACTGACACAACAAATCAGAAGACTGAATTACAAGCCATTAATCT

AGCTTTGCAGGATTCGGGATTAGAAGTAAACATAGTAACAGACTCACAATATGC

ATTAGGAATCATTCAAGCACAACCAGATAAGAGTGAATCAGAGTTAGTCAGTCA

AATAATAGAGCAGTTAATAAAAAAGGAAAAGGTCTACCTATCATGGGTACCAGC

ACACAAGGGGATTGGAGGAAATGAACAAGTAGATAAATTAGTCAGTAATGGAAT

CAGAAAAATACTATTCTTGGATGGAATAGATAAGGCTCAAGAAGAACATGAGAA

ATACCACAACAATTGGAGAGCAATGGCTAGTGATTTTAACCTGCCACCTGTGGTA

GCAAAAGAAATAGTAGCTAGCTGTGATAAATGTCAGCTAAAAGGAGAAGCCTTG

CATGGACAAGTAGACTGTAGTCCAGGAATATGGCAATTAGATTGTACACATTTAG

AAGGAAAAGTTATCCTGGTAGCAGTCCATGTAGCCAGTGGCTATATAGAAGCAG

AAGTTATTCCAGCAGAAACAGGGCAGGAAACAGCCTACTTTCTCTTAAAATTAGC

AGGAAGATGGCCAGTAAAAGTAGTACATACAGACAATGGCAGCAATTTCACCAG

CGCTGCAGTTAAGGCCGCCTGTTGGTGGGCAGGCATCAAGCAGGAATTTGGAAT

TCCCTACAATCCCCAAAGTCAAGGAGTAGTAGAATCTATGAATAAAGAATTAAA

GAAAATTATAGGACAGGTAAGAGATCAAGCTGAACATCTTAAGACAGCAGTACA

AATGGCAGTATTCATCCACAATTTTAAAAGAAAAGGGGGGATTGGGGGGTACAG

TGCAGGGGAAAGAATAATAGACATAATAGCAACAGACATACAAACTAAAGAATT

ACAAAAACAAATCATAAAAATTCAAAATTTTCGGGTTTATTACAGGGACAGCAG

AGATCCAATTTGGAAAGGACCAGCAAAGCTTCTCTGGAAAGGTGAAGGGGCAGT

AGTAATACAAGACAATAGTGAAATAAAGGTAGTACCAAGAAGAAAAGTAAAGA

TCATTAGGGATTATGGAAAACAGATGGCAGGTGATGATTGTGTGGCAAGTAGAC

AGGATGAGGATTAGAACATGGAAGAGTTTAGTAAAACATCATATGTATGTTTCA

AAGAAAGCTCAAGGATGGTTGTATAGACATCACTATGACTGCCCACACCCAAAA

ATAAGTTCAGAAGTACACATCCCACTAGGAGAAGCTAGACTGGTAGTAAAAACA

TATTGGGGTCTGCATACAGGAGAAAGAGAATGGCATCTGGGTCAGGGAGTCTCC

ATAGAATGGAGGAAAAGGAGATATAGCACACAAGTAGACCCTGGCCTGGCAGA

CCAACTAATTCATATATATTATTTTGATTGTTTTGCAGAATCTGCTATAAGAAAAG

CCATATTAGGACATATAGTTACTCCTAGGTGTAATTATCAAGCAGGACATAACAA

GGTAGGATCTTTACAATATTTGGCACTAACAGCATTAATAACACCAAAAAAGAT

AAAACCACCTTTGCCTAGTGTTAGGAAGCTGACAGAAGACAGATGGAACAAGCC
```

```
CCAGAGGACCAAGGGCCACAGAGGGAGCCATACAATGAATGGACATTAGAGCTT

TTAGAGGAGCTTAAGAGTGAAGCTGTTAGACACTTTCCTAGGATATGGCTTCATG

GCCTAGGACAACATATCTATGAAACTTATGGGGATACCTGGACAGGAGTTGAAG

CTATAATAAGAATCCTTCAACAACTACTGTTTATCCATTTCAGAATTGGGTGTCA

ACATAGCAGAATAGGCATTACTCGACAGAGAAGAACAAGAAATGGATCCAGTAG

ATCCTAACCTAGAGCCCTGGAACCATCCAGGAAGTCAGCCTAGGACTCCTTGTAA

CAAGTGTTATTGTAAAAAGTGTTGCTATCATTGCCAANTTTGCTTCATAACGAAA

GGCTTAGGCATCTCCTATGGCAGGAAGAAGCGGAGACAGCGACGAAGACCTCCT

CAAGGCGGTCAGGCTCATCAAGATCCTATACCAAAGCAGTAAGTAGTACATGTA

ATGCAATCTTTAGTGATATTAGCAATAGTAGCATTAGTAGTAGCGCTAATAATAG

CAATAGTTGTGTGGACTATAGTATTCATAGAGTGTAGAAGATTAAAAAGGCAAA

GAAAAATAGACTGGTTAATTGATAGAATAAGAGAAAGAGCAGAAGATAGTGGC

AATGAGAGTGAGGGAGATAGAGAGGAATTATCAGCACTTGTGGAGATGGGGCAC

CATGCTCCTTGGGATGTTGATGACATGTAGTGTTGCAGGAAAGTTGTGGGTCACA

GTTTATTATGGGGTACCTGTGTGGAAAGAAGCAACCACTACTCTATTTTGTGCAT

CAGATGCTAAATCATATAAAACAGAGGCACATAATATCTGGGCTACACATGCCT

GTGTACCAACAGACCCCAACCCACAAGAAATAAAACTAGAAAATGTCACAGAAA

ACTTTAACATGTGGAAAAATAACATGGTGGAGCAGATGCATGAGGATATAATCA

GTTTATGGGATCAAAGCCTAAAACCATGTGTAAAATTAACCCCACTCTGTGTCAC

TTTAAACTGCACTGATTGGAAGAATAANAATACCACTANTATAACACNAATGAG

GANATAGGAATGAAAAACTGCTCTTTCAATATAACCACAGAAGTAAGAGATAAG

AAGAAGCAAGTACATGCACTTTTTTATAAACTTGATGTGGTACAAATAGATAATA

TAATACTAATAATACCAGCTATAGATTAATAAATTGTAATACCTCAGCCATTACA

CAGGCGTGTCCAAAGGTAACCTTTGAGCCAATTCCCATACATTATTGTGCCCCAG

CTGGATTTGCAATTCTAAAATGTAATGATAAGAAGTTCAATGGGACGGGTCCATG

CAAAAATGTCAGCACAGTACAGTGTACACATGGGATTAAGCCAGTAGTGTCAAC

TCAACTGTTGTTGAATGGCAGTCTAGCAGAAGAAGAGATAATAATTAGATCTGA

AAATCTCACAAATAATGCTAAAATCATAATAGTACAGCTTAATGAGTCTGTAACA

ATTAATTGCACAAGGCCCTACAACAATACAAGACAAAGTATACATATAGGACCA

GGGCAAGCACTCTATACAACAAAAATAATAGGAGATATAAGACAAGCACATTGT

AATATTAGTAGAGCAGAATGGAATAAAACTTTACAACAGGTAGCTAAAAAATTA

GGAGACCTTCTTAACAAGACAACAATAATTTTTAAACCATCCTCGGGAGGGGAC

CCAGAAATTACAACACACAGCTTTAATTGTGGAGGGGAATTTTTCTACTGCAATA

CATCAGGACTGTTTAATAGTACATGGAATAATAATANTAANAATAGTAATGNG

AAAAAAAATGATACAATCACACTCCCATGCAGAATAAAACAAATTATAAACATG

TGGCAGGGAGTAGGAAAAGCAATGTATGCCCCTCCCATTGAAGGACTAATCAAA

TGTTCATCAAATATTACAGGACTATTGTTGACAAGAGATGGTGGTAATAATAATA

GTCAGAATGAGACCTTCAGACCTGGAGGAGGAGATATGAGAGACAATTGGAGAA

GTGAATTATACAAATATAAAGTAGTAAGAATTGAACCACTAGGTCTAGCACCCA

CCAAGGCAAAGAGAAGAGTGGTGGAAAGAGAAAAAAGAGCAATAGGACTAGGA

GCTATGTTCCTTGGGTTCTTGGGAGCAGCAGGAAGCACGATGGGCGCAGCGTCA
```

-continued

```
CTGACGCTGACGGTACAGGCCAGACAGTTATTGTCTGGTATAGTGCAACAGCAA

AACAATTTGCTGAGGGCTATAGAGGCGCAACAGCATCTGTTGCAACTCACAGTCT

GGGGCATTAAACAGCTCCAGGCAAGAGTCCTGGCTGTGGAAAGATACCTAAAGG

ATCAACAGCTCCTAGGAATTTGGGGTTGCTCTGGAAAACACATTTGCACCACTAA

TGTGCCCTGGAACTCTAGCTGGAGTAATAAATCTCTAGATGAGATTTGGGATAAC

ATGACCTGGATGGAGTGGGAAAGAGAAATTGACAATTACACAGGTTTAATATAC

AGCTTAATTGAAGAATCGCAAACCCAGCAAGAAAAGAATGAACAAGAACTATTG

CAATTGGACAAATGGGCAAGTTTGTGGAATTGGTTTAGCATAACAAAATGGCTGT

GGTATATAAAAATATTCATAATGATAGTAGGAGGCTTGATAGGTTTAAGAATAGT

TTTTGCTGTGCTTTCTTTAGTAAATAGAGTTAGGCAGGGATATTCACCTCTGTCGT

TTCAGACCCTCCTCCCAGCCCCGAGGGGACCCGACAGGCCCGAAGGAATAGAAG

AAGAAGGTGGAGAGCAAGGCAGAGGCAGATCCATTCGATTGGTGAACGGATTCT

CAGCACTTATCTGGGACGATCTGAGGAACCTGTGCCTCTTCAGCTACCACCGCTT

GAGAGACTTAATCTTAATTGCAACGAGGATTGTGGAACTTCTGGGACGCAGGGG

GTGGGAAGCCATCAAATATCTGTGGAATCTCCTGCAGTATTGGATTCAGGAACTA

AAGAATAGTGCTATTAGCTTGCTTAATACCACAGCAATAGCAGTAGCTGAGGGG

ACAGATAGGGTTATAGAAATAGTACAAAGAGCTGTTAGAGCTATTCTTAACATA

CCCAGACGAATAAGACAGGGCTTGGAAAGGGCTTTACTATAAAATGGGTGGCAA

ATGGTCAAAAAGTAGTATAGTTGGATGGCCTGCTATAAGGGAAAGAATAAGAAG

AACTGATCCAGCAGCAGAAGGGGTGGGAGCAGTATCTCGGGACCTGGAAAAACA

TGGGGCAATCACAAGTAGCAATACAGCACANACTAATCCTGACTGTGCCTGGCT

AGAAGCACAAGAAGAGGACGAGGAAGTGGGTTTTCCAGTCAGACCTCAGGTACC

ATTAAGACCAATGACTTACAAGGGAGCTGTAGATCTGAGCCACTTTTTAAAAGA

AAAGGGGGGACTGGAAGGGTTAATTTGGTCCCAGAAAAGACAAGAGATCCTTGA

TCTTTGGGTCTACCACACACAAGGCTACTTCCCTGATTGGCAAAACTACACACCA

GGGCCAGGGATTAGATATCCACTGACCTTTGGATGGTGCTTCGAGCTAGTACCAG

TTGATCCAAAGGAGGTAGAAGAGGACACTGAAGGAGAGAACAACTGCTTGTTAC

ACCCTATGTGCCAGCATGGAATGGAGGACCCGGAGAGAGAAGTGTTAATGTGGA

GATTTAACAGCAGACTAGCATTTGAACACAAGGCCCGAATGAAGCATCCGGAGT

TCTACAAAGACTGCTGACACCGAGTTTTCTACAAGGGACTTTCCGCTGGGGACTT

TCCAGGGAGGCGTAACAGGGGCGGGACTGGGAGTGGCTAACCCTCAGATGCTGC

ATATAAGCAGCTGCTTTTTGCCTGTACTGGGTCTCTCTTGTTAGACCAGATTTGAG

CCTGAGAGCTCTCTGGCTAGCTAGGGAACCCACTGCT
```

SEQ F1_Majority

SEQ ID NO: 8

```
CAGTGGCGCCCGAACAGGGACGNGAAAGCGAAAGTAGAACCAGAGAAGATCTC

TCGACGCAGGACTCGGCTTGCTGAAGTGCACACGGCAAGAGGCGAGAGCGGCGA

CTGGTGAGTACGCCAAATTTTGACTAGCGGAGGCTAGAAGGAGAGAGATGGGTG

CGAGAGCGTCAGTATTAAGCGGGGGAAAANTAGATGCATGGGAAAAAATTCGGT

TAAGGCCGGGGGGAAAGAAAAAATATAGAATGAANCATCTAGTATGGGCAAGC

AGGGAGCTAGAACGATTTGCAATTGATCCTGGCCTTCTAGAAACATCAGAAGGC
```

-continued

```
TGTCAAAAAATAATAGGACAGTTACAACCATCCCTTCAGACAGGATCAGAAGAG
CTTAGATCATTATATAATACAGTAGCAGTCCTCTATTTTGTACATCAAANGATAG
AGGTAAANGACACCAAGGAAGCTTTAGACAAGCTAGAGGAAGAACAAAACAAA
AGTCAGCAAAAGACACAGCAAGCGGCAGCTGACAAAGGGGTCAGTCAAAATTA
CCCTATAGTACAGAATCTTCAGGGACAAATGGTACATCAGTCTATATCACCTAGA
ACTTTAAATGCATGGGTAAAGGTGATAGAAGAGAAGGCTTTTAGCCCAGAAGTA
ATACCCATGTTTTCAGCATTATCAGAAGGGGCCACTCCACAAGATTTAAACACCA
TGNTAAATACAGTGGGGGGACATCAAGCAGCCATGCAAATGTTAAAAGACACCA
TCAATGAGGAAGCTGCAGAATGGGACAGATTACATCCAGNGCANGCAGGACCTA
TCCCACCAGGCCAGATNAGGGAACCTAGGGGAAGTGATATAGCTGGAACTACTA
GTACCCTTCAGGAACAAATACAATGGATGACAAGCAACCCACCTGTCCCAGTGG
GAGANATCTATAAAAGATGGATCATCCTAGGATTAAATAAAATAGTAAGAATGT
ATAGCCCTGTCAGCATTTTGGACATAAGACAAGGGCCAAANGAACCCTTTAGAG
ACTATGTAGACAGGTTCTTTAAAACCCTAAGAGCTGAGCAAGCTACACAGGAAG
TAAAGGGTTGGATGACAGACACCTTGTTGGTCCAAAATGCGAACCCAGATTGTA
AGACCATTTTAAAAGCATTGGGACCAGGGGCTACACTAGAAGAAATGATGACAG
CATGTCAGGGAGTGGGAGGACCTGGCCATAAGGCAAGAGTTTTGGCTGAGGCAA
TGAGCCAAGCAACAAATGCANCTATAATGATGCAGAAAAGTAANTTTAAGGGCC
AAAGAAGAATTGTTAAATGTTTTAATTGTGGCAAAGAAGGACACATAGCCAAAA
ATTGCAGGGCCCCTAGAAAAAAGGGCTGTTGGAAATGTGGAAGAGAAGGACACC
AAATGAAAGACTGCACTGAAAGACAGGCTAATTTTTTAGGGAAAATTTGGCCTTC
CAACAAGGGGAGGCCCGGAAATTTCCTTCAGAACAGGCCAGAGCCAACAGCCCC
GCCAGCAGAGAGCTTCGGGTTCAGAGAGGAGATAACCCCCTCTCCGAAGCAGGA
GCAGAAAGANGAGGGACTGTACCCTCCCTTAGCTTCCCTCAAATCACTCTTTGGC
AACGACCCCTAGTCACAATAAAAGTAGGGGGACAGCTAAAGGAAGCTCTATTAG
ATACAGGAGCAGATGATACAGTATTAGAAGACATAAATTTGCCAGGAAAATGGA
AACCAAAAATGATAGGGGGAATTGGAGGTTTTATCAAAGTAAAACAGTATGATA
ACATACTCATAGAAATTTGTGGACACAAGGCTATAGGTACAGTGTTAGTAGGAC
CTACGCCTGTCAACATAATTGGAAGAAATATGTTGACTCAGATTGGTTGTACTTT
AAATTTTCCAATTAGTCCTATTGAAACTGTACCAGTAAAATTGAAGCCAGGAATG
GATGGCCCAAAGGTTAAACAATGGCCATTGACAGAAGAAAAAATAAAAGCATTA
ACAGAAATATGTACAGAAATGGAAAAAGAAGGAAAAATTTCAAAAATTGGGCCT
GAAAATCCATACAATACTCCAGTATTTGCCATAAAGAAAAAAGACAGTACTAAA
TGGAGGAAATTAGTAGATTTCAGAGAACTTAATAAAAGAACTCAAGATTTTTGG
GAGGTTCAATTAGGAATACCACATCCTGCAGGGTTAAAAAAGAAAAAGTCAGTA
ACAGTACTGGATGTGGGGGATGCATATTTTTCAGTTCCCTTAGATAAGGATTTCA
GGAAGTACACTGCATTCACCATACCTAGTGTCAACAATGAGACACCAGGAATTA
GGTACCAGTACAATGTGCTTCCACAAGGATGGAAAGGATCACCAGCAATATTCC
AATGTAGCATGACAAAAATCTTAGANCCCTTTAGAACAAAAAATCCAGACATAG
TTATCTACCAATACATGGATGATTTGTATGTAGGGTCTGACTTAGAAATAGGGCA
GCATAGAACAAAAATAGAGGAGTTAAGAGAACATCTACTGAAATGGGGATTTAC
```

-continued

```
TACACCAGACAAAAAACATCANAAAGAACCCCCATTCCTTTGGATGGGGTATGA
ACTCCATCCTGATAAATGGACAGTGCAGCCTATACAATTGCCAGACAAGGACAG
CTGGACTGTCAATGATATACAGAAGTTAGTAGGAAAACTAAATTGGGCAAGTCA
GATTTATCCAGGGATTAAAGTAAAGCAATTATGTAAACTCCTTAGGGGAGCCAA
GGCACTAACAGACATAGTGCCACTGACTNCAGAAGCAGAGTTAGAATTGGCAGA
GAATAGGGAGATTCTAAAAGAACCAGTACATGGGGTATATTATGACCCNTCAAA
AGACTTAATAGCAGAAATACAGAAACAAGGGCAAGGGCAATGGACATATCAAA
TTTATCAAGAGCCATTTAAAAATCTAAAAACAGGAAAGTATGCAAAAATGAGGT
CTGCCCACACTAATGATGTAAAACAATTAACAGAAGCAGTGCAAAAGATAGCTC
TAGAAAGCATAGTAATATGGGGAAAGACTCCTAAGTTTAAACTACCCATACTAA
AAGAGACATGGGATACATGGTGGACAGAGTATTGGCAAGCCACCTGGATTCCTG
AATGGGAGTTTGTCAATACCCCCCCTCTAGTAAAACTATGGTATCAGTTAGAAAC
AGAGCCCATAGCAGGAGCAGAAACCTTCTATGTAGATGGGGCATCTAATAGAGA
GACCAAAAAGGAAAAGCAGGATATGTTACTGACAGAGGAANACAAAAGGCTG
TCTCCCTAACTGAGACCACAAATCAGAAGGCTGAGTTACAAGCAATTCATTTAGC
TTTACAGGATTCAGGATCAGAAGTGAACATAGTAACAGACTCACAGTATGCATT
AGGAATCATTCAAGCACAACCAGATAAGAGTGAATCAGAGTTAGTCAATCAAAT
AATAGAGCAATTAATACAAAAGGAAAAGGTCTACCTGTCATGGGTACCAGCACA
CAAAGGGATTGGAGGAAATGAACAAGTAGATAAATTAGTCAGTGCTGGAATCAG
NAAAATACTGTTTTTAGATGGGATAGATAAGGCACAAGAGGAACATGAAAAATA
TCACAACAATTGGAGAGCAATGGCTAGTGATTTTAATCTGCCACCTGTAGTAGCA
AAAGAAATAGTAGCTAGCTGTGATAAGTGTCAGCTAAAAGGGGAAGCCATGCAT
GGACAAGTAGANTGTAGTCCAGGGATATGGCAATTAGATTGTACACATTTAGAA
GGAAAANTTATCCTGGTAGCAGTCCATGTAGCTAGTGGGTACNTAGAAGCAGAA
GTTATCCCAGCAGAAACAGGACANGAAACAGCCTACTTCATACTAAAGTTAGCA
GGAAGATGGCCAGTAAAAANAATACATACAGACAATGGCANCAATTTCACCAGT
GCCGCGGTTAAGGCAGCCTGTTGGTGGGCAGGTATCCAGCAGGAATTTGGAATT
CCCTACAACCCCCAAAGTCAAGGAGTAGTAGAATCTATGAATAAAGAGCTAAAG
AAGATCATAGGACAGGTAAGAGATCAAGCTGAACATCTTAAGACAGCAGTACAA
ATGGCAGTATTCATCCACAATTTTAAAAGAAAAGGGGGGATTGGGGGNTACAGT
GCAGGGGAAAGAATAATAGACATAATATCAACAGACATACAAACTANAGAATTA
CAAAAACAAATTATAAAAATTCAAAATTTCCGGGTTTATTACAGGGACAGCAGA
GACCCAGTTTGGAAAGGACCAGCAAAGCTACTCTGGAAAGGTGAAGGGGCAGTA
GTCATACAAGACAATAGTGAAATAAAGGTAGTACCAAGAAGAAAAGCAAAGAT
CATTAGGGATTATGGAAAACAGATGGCAGGTGATGATTGTGTGGCAGGTAGACA
GGATGAGGATTAACACATGGAAAGTTTAGTAAAATACCATATGCATGTTTCAA
AGAAAGCCAAAAGATGGTNTTATAGACATCACTTTGAAAGCAGGCATCCAANAN
TAAGTTCAGAAGTACACATCCCACTAGAGGAAGCTAAATTAGTAATAACAACAT
ANTGGGGCTGCATACAGGAGAAAGAGATTGGCATCTGGGTCAGGGAGTCTCCA
TAGAATGGAGGCAGGGGAGGTATAGGACACAAATAGACCCTGGCCTGGCAGACC
```

-continued

```
AACTGATCCATATATATTATTTTGATTGTTTTCAGAATCTGCCATAAGGAAAGCC
ATATTAGGACATANAATTAGCCCTAGGTGTAACTATCAAGCAGGACATAACAAG
GTAGGATCNCTACAATATTTGGCACTAACAGCATTAATAGCTCCAAAGAAGACA
AAGCCGCCTTTGCCTAGTGTCAAGAAACTAGTAGAAGACAGATGGAACAAGCCC
CAGGAGACCAGGGGCCACAGAGGGAGCCATACAATGAATGGACACTAGAGCTTT
TAGAGGAGCTTAAGAATGAAGCTGTTAGACATTTTCCTAGGCCATGGCTNCATGG
CTTAGGACAACATATCTATAACACCTATGGGGATACTTGGGAGGGAGTTGAAGC
TATAATAAGGATATTGCAACAACTACTGTTTATCCATTTCAGAATTGGGTGCCAT
CATAGCAGAATAGGCATTANTCGACAGAGAAGAGTAAGAAATGGAGCTAGTAG
ATCCTAACTTAGATCCCTGGAACCATCCAGGAAGCCAGCCTACAACTCCTTGTAC
CAAATGNTATTGTAAACGNTGTTGCTTTCATTGNNANTGGTGCTTTACAACGAAG
GGCTTAGGCATCTCCTATGGCAGGAAGAAGCGGAGACAGCGACACAGAACTCCT
CANAGCAGTCAGATACATCAAGATCNTGTACCAAAGCAGTAAGTATTGNNNNTA
GTATATGTAATGTCANATTTGTTAGCAATAAGNATAGCAGCATTAATAGTAGCAC
TAATAATAGCAATAGTTGTGTGGACTATAGTATATATAGAATATAAGAAACTGNT
AAGGCAAAGAAAAATAAATAGGTTATATNAAAGAATAAGAGAAAGAGCAGAAG
ACAGTGGCAATGAGAGTGAGGGGGATGCAGAGGAATTGGCAGCACTTGGGGAA
ATGGGGCCTTTTATTCCTGGGGATATTAATAATCTGTAATGCTGCAGAAAACTTG
TGGGTCACAGTCTATTATGGGGTACCTGTGTGGAAAGAAGCAACCACTACTCTAT
TCTGTGCATCAGATGCTAAATCATATGAAANAGAGGTACATAATGTCTGGGCTAC
ACATGCCTGTGTACCCACAGANCCCAATCCACAAGAAGTAGTTCTGGAAAATGT
AACAGAAAATTTTGATATGTGGAAAAATAACATGGTAGAACAAATGCATACAGA
TATAATCAGTTTATGGGATCAAAGCCTAAAGCCATGTGTNAAGTTAACCCCACTC
TGTGTTACTTTAAATTGTACTAATGCCACTACNANNAGTACCACTACTNNNAANG
ACANCACCCTGAAGGAAGAACCAGGGGCAATACAAAACTGTTCTTTCAATATGA
CCACAGAAGTAAGAGATAAGNAGCNGAAAGTACATGCACTTTTTTATANACTTG
ATATAGTACCAATCAGCAATNNAANANNAGTAGAGAATANAGGCTAATAAATTG
TAATACCTCAACCATTACACAGGCTTGTCCAAAGGTATCTTGGGATCCAATTCCC
ATACATTATTGTGCTCCAGCTGGTTATGCGATTCTAAAGTGTAATGATAAAANGT
TCAATGGGACAGGGCCATGCAAGAATGTCAGCACAGTACAATGTACACATGGAA
TTAAACCAGTGGTATCAACTCAATTGTTGTTAAATGGCAGCCTAGCAGAAGAAG
ATATAATAATCAGATCTCAAAATATCTCAGATAATGCAAAAACCATAATAGTAC
ACCTTAATGAATCTGTACAGATTAATTGTACAAGACCCAACAACAATACAAGAA
AAAGTATACATTTAGGACCAGGACNAGCATTTTATGCAACAGGAGAAATAATAG
GAGACATNAGAAAGGCACATTGTAACNTTAGTGGAACACAATGGAATAAAACTT
TAGAACAGGTAAAGGCAAAGTTAAAGTCTCATTTNCCTAATACAACAATAAAAT
TTAACTCATCCTCAGGAGGGGACCTAGAAATTACAATGCATAGTTTTAATTGTAG
AGGAGAATTTTTCTACTGCAATACATCAGGACTGTTTAATGACACAGGANTACAA
TGGCACTATCACTCTCCCATGTCGAATAAAACAAATTGTAAACATGTGGCAGGAA
GTAGGACGAGCAATGTATGCCGCTCCCATTGCAGGAAACATTACCTGTAACTCAA
ATATTACAGGTCTACTATTGACAAGAGATGGTGGTNANAATAATANTAAGACTG
```

-continued

```
AGACCTTCAGACCTGGGGGAGGAAATATGAAAGACAATTGGAGAAGTGAANTAT
ATAANTATAAAGTAGTAGAAATTGAACCACTAGGAGTAGCACCCACCANGGCAA
AAAGACAAGTGGTGAAGAGAGAAANAAGAGCAGTGGGAATAGGAGCTTTGTTC
CTTGGGTTCTTGNGCGCAGCAGGAAGCACTATGGGCGCGGCGTCAATAACGCTG
ACGGTACAGGCCAGACAATTATTGTCTGGAATAGTGCAACAGCAGANCAATCTG
CTGAGGGCTATTGAAGCGCAACAGCATCTGTTGCAGCTCACAGTCTGGGCATTA
AACAGCTCCAGGCAAGAGTCCTGGCTGTGGAAAGATACCTAAAGGATCAACAGC
TCCTAGGGCTTTGGGGCTGCTCTGGAAAACTCATCTGCACCACTAATGTGCCCTG
GAACTCTAGTTGGAGTAATAAATCTCAGGAGGAGATTTGGNAGAACATGACCTG
GATGGAGTGGGAAAAAGAGATTAGCAATTACTCAAACNAAATATACAGGTTAAT
TGAAGAATCNCAGAACCAGCAGGAAAAGAATGAACAAGAATTATTGGCATTGGA
CAAATGGGCAAGTCTGTGGAATTGGTTTGACATATCAAACTGGCTGTGGTATATA
AAAATATTCATAATGATAGTAGGAGGCTTGATAGGCTTAAGAATAGTTTTTGCTG
TGCTTTCTATAGTAAATAGAGTTAGGAAGGGATACTCACCTTTGTCATTACAGAC
CCNTATCCCAAGCCCGAGGGAACCCGACAGGCCCGAAGGAATCGAAGAAGGAG
GTGGAGAGCAAGGCAAAGACAGATCCGTGCGATTAGTGAACGGATTCTTAGCTC
TTGTCTGGGACGACCTGAGGAACCTGTGCCTCTTCAGCTACCGCCACTTGAGAGA
CTTCATATTAATTGCAGCGAGGATTGTGGACAGGGGCTGAGGAGGGGTGGGA
AGCCCTCAAATATCTGGGGAATCTCACNCAGTATTGGNGTCAGGAACTAAAGAA
TAGTGCTATTAGCTTGNTTAATACCACAGCAATAGTAGTAGCTGAGGGNACAGAT
AGANTTATAGAAGCTTTGCAAAGAGCTGGTAGAGCTNTTCTCAACATACCTAGA
AGAATAAGACAGGGCTTAGAAAGGGCTTTGCTATAAAATGGGTGGCAAGTGGTC
AAAAAGTAGTATAGTTGGATGGCCTGCTATAAGGGAAAGAATGAGACGAACCNN
NNNNNCNCCTCCAGCAGCAGAAGGGGTGGGAGCAGTGTCTCAAGACTTAGAAAG
ACGGGGGGCAATTACAAGCAGCAATACTAGAGCTANTAATCCTGACTTGGCCTG
GCTGGAAGCACAAGAGGANGAGGAAGTAGGCTTTCCAGTCAGACCTCAGGTACC
TTTAAGACCAATGACTTATAAGGCAGCTNTAGATCTCAGNCACTTTTTAAAAGAA
AAGGGGGGACTGGAAGGGTTAATTTACTCCAAGAAAAGACAAGAGATCCTTGAT
CTGTGGGTNTACCACACACAAGGCTNCTTCCCTGATTGGCAGAACTACACACCAG
GGCCAGGGNTCAGATATCCACTGACCTTTGGGTGGTGCTTCAAGCTAGTACCAGT
TGACCCAGAGGAGGTAGAAAAGGCCAATGAAGGAGAGAACAACTGCTTGCTAC
ACCCCATGAGCCAACATGGAATGGANGATGAAGACAGAGAAGTACTGANNTGG
AAGTTTGACAGCNGCCTGGCACTGAGACACATAGCCAGAGAGANACATCCGGAG
TTCTACCAAGACTGAGACTGCTGACACAGAGATTGCTGACACAGAAGAATCTAA
AGGGACTTTCCACTGGGGACTTTCCAGAGGGCGGGCCAGAGGGCGGGACTGGGG
AGTGGCTCACCCTCAGATGCTGCATATAAGCAGCCGCTTTTCGCCTGTACTGGGT
CTCTCTAGTTAGACCAGATTTGAGCCCGGGAGCTCTCTGGCTAGCTAGGGAACCC
ACTGCTTAANNNNNNNNNNNNNNNNNNNNNNNNNN
```

-continued

SEQ F2_Majority
SEQ ID NO: 9

ATGGGTGCGAGAGCGTCAGTATTAAGCGGGGGAAAATTAGATGNATGGGAAAA

AATTCGGTTAAGGCCGGGGGGAAGAAAAAATATAGGCTNAAACATATAGTATG

GGCAAGCAGGGAGCTAGAACGATTTGCACTTAATCCTGGCCTTTTAGAGACAAC

AGAAGGCTGTAANNAAATAATAGGACAACTACAANCATCCCTTCAGACAGGATC

AGAAGAGCTTAAATCATTATNNAACACANTAGTAGTNCTCTATTATGTACATCAA

ANGATAGAANTAAGAGACACCAAGGAAGCTTTAGATAAGCTACAGGAAGAACA

AGACAAAANTCAGCAAAAAACACAACNAGCAGCGGCTGACAAAGGGGTCAGTC

AAAATTACCCTATAGTACAGAATCTTCAGGGGCAAATGGTACACCAGGCTCTATC

ACCTAGAACTTTAAATGCATGGGTAAAAGTAATAGAAGAGAAGGCTTTCAGCCC

AGAAGTAATACCCATGTTTTCAGCATTATCAGAAGGGGCCACCCCACAAGATTTA

AACACCATGCTAAACACAGTGGGGGGACATCAAGCAGCCATGCAAATGTTAAAA

GATACCATCAATGAGGAAGCTGCAGAATGGGACAGGTTACATCCAGTGCANGCA

GGACCTATCCCACCAGGTCAGATNAGAGAACCTAGGGGAAGTGATATAGCAGGA

ACTACTAGTACCCTTCAGGAACAAATAGCATGGATGACAAGCAACCCACCTGTC

CCAGTAGGAGAAATCTATAAAAGATGGATAATCCTAGGATTAAATAAAATAGTA

AGAATGTATAGCCCTGTCAGCATTTTGGACATAAAACAAGGGCCAAAAGAACCC

TTTAGAGACTATGTAGACAGGTTCTTTAAAACTCTAAGAGCTGAGCAAGCTACAC

AGGAAGTAAAAGGCTGGATGACAGANACCTTGTTGGTCCAAAATGCGAACCCAG

ATTGTAAGACCATTTTAAAAGCATTNGGACCAGGGGCTACACTAGAAGAAATGA

TGACAGCATGTCAGGGAGTGGGAGGACCTGGCCATAAAGCAAGAATTTTGGCTG

AGGCAATGAGCNAAGNAACAGNTACAGCCATAATGATGCAGAAAAGCAACTTTA

AGGGCCAAANAAGAATTGTTAAGTGTTTCAACTGTGGCAAAGAAGGACATATAG

CTANAAATTGCAGGGCCCCTAGAAAAAGGGGCTGTTGGAAATGTGGAAAGGAAG

GACACCAAATGAAAGACTGCACTGANAGACAGGCTAATTTTTTAGGGAAAATTT

GGCCTTCCAACAAGGGGAGGCCTGGAAATTTTCTTCAGAACAGACCAGAGCCAA

CAGCCCCGCCAGCAGAGAGCTTCGGGTTCGGAGANGAGATAACTCCCTCCCCGA

AGCAGGAGCAGAAAGACAAGGAACNGNATCCTCCCTTGANTTCCCTCAAATCAC

TCTTTGGCANCGACCCNTAGTCACAATAAAAGTAGNGGGGCAACTAAGGGAGGC

TCTATTAGATACAGGGGCAGATGATACAGTATTAGAAGATATAAATTTGNCAGG

AAAATGGAAACCAANAATGATAGGGGAATTGGAGGTTTTATCAAAGTAAGACA

GTATGATCAANTACCCATAGAAATTTGTGGACAAAAGGCTATAGGTACAGTATT

AGTAGGNCCTACGCCTGTCAACATAATTGGAAGAAATATGTTGACTCAGATTGGT

TGCACTTTAAATTTTCCAATTAGTCCTATTGAAACTGTACCAGTAAAATTAAAGC

CAGGAATGGATGGCCCAAAGGTTAAACAATGGCCATTGACAGAAGAAAAAATA

AAAGCANTAACAGAAATCTGTACAGAGATGGAAAAAGAAGGAAAAATTTCAAA

AATTGGGCCAGAAAATCCATACAATACTCCAGTATTTGCCATAAAGAAAAAGGA

CAGTACTAAATGGAGAAAATTAGTAGATTTCAGAGANCTTAATAAAAGAACTCA

AGATTTTTGGGAGGTTCAATTAGGAATACCACACCCTGCAGGGTTAAAAAAGAA

AAAATCAGTAACAGTACTGGATGTGGGGGATGCATATTTTTCAGTTCCCTTAGAT

-continued

```
AAGGAGTTCAGGAAGTACACTGCNTTCACCATACCTAGTATCAACAATGAGACA
CCAGGAATTAGATATCAGTACAATGTGCTTCCACAGGGATGGAAAGGGTCACCA
GCAATATTCCAAAGTAGCATGACAAAAATCTTAGAGCCCTTTAGAGCAAAAAT
CCAGAAATAGTTATCTACCAATACATGGATGATTTGTATGTAGGGTCTGACTTAG
AAATAGGGCAGCATAGGNCAAAAATAGAGGAGTTAAGAGAACATCTATTGAGAT
GGGGATTTACTACACCAGATAAAAAACATCAGAANGAACCCCCATTTCTTTGGAT
GGGGTATGAACTCCATCCTGACAAATGGACAGTACAGGCTATACAATTGCCAGA
CAAGAGCAGCTGGACTGTCAATGATATACAGAAGTTAGTGGGAAAACTAAATTG
GGCAAGTCAGATTTATCCAGGGATTAGAGTAAAGCACTTATGTAAACTCCTTAGG
GGAGCCAAAGCACTAACAGANGTAGTGCCACTNACTGCAGAAGCAGAGTTAGAA
CTGGCAGAGAACAGGGAAATTCTAAAAGAACCAGTACATGGGTATATTATGAC
CCATCAAAAGATTTAATAGCAGAAATACAGAAACAAGGGCANGACAATGGAC
ATATCAAATTTATCAAGANCCACATAAAAATCTGAAAACAGGAAAGTATGCAAN
AAGGANGTCTGCCCACACTAATGATGTAAAACAATTAACAGAAGTAGTNCAAAA
AATAGCCACAGAAGGCATAGTAATATGGGGAAANGTTCCTAAATTTAGACTACC
CATACAAAANGAAACATGGGAAANATGGTGGACAGAGTATTGGCANGCCACCTG
GATTCCTGAATGGGAGTTTGTCAATACCCCTCCTCTAGTAAAATTATGGTACCAN
TTAGAAACAGANCCCATAATAGGAGCAGAAACTTTCTATGTAGATGGGGCAGCT
AATAGAGAGACTAAANTAGGAAAAGCAGGATATGTTACTGACAGAGGAAGACA
AAANGTTGTCNCCCTAACTGAGACAACAAATCAGAAGACTGAATTACAAGCAAT
TCATTTAGCTTTGCAGGACTCAGGATCAGAAGTAAACATAGTAACAGACTCACA
GTATGCATTAGGAATCATTCAAGCACACCCAGATAAGAGTGAATCAGAGTTAGT
CAACCAAATAATAGAGCAATTAATACAAAAGGAAANGGTCTACCTGTCATGGGT
ACCAGCACATAAAGGGATTGGAGGAAATGAACAAGTAGATAAATTAGTCAGTAC
TGGAATCAGGAAAGTACTGTTTTTGGATGGGATAGATAAGGCTCAAGAAGAACA
TGAAAAATATCACANCAATTGGAGAGCAATGGCTAGTGATTTTAATCTGCCACCT
GTAGTAGCAAAAGAAATAGTAGCCAGCTGTGATAAATGTCAGCTAAAAGGGGAA
GCCATGCATGGACAAGTAGACTGCAGTCCAGGGATATGGCAATTAGATTGTACA
CATTTAGAAGGAAAAATTATCCTGGTAGCAGTCCATGTAGCTAGTGGCTATATAG
AAGCAGAAGTTATNCCAGCAGAAACNGGACAGGAAACAGCCTACTTCATACTAA
AGTTAGCAGGAAGATGGCCAGTAAAAATAATACATACAGACAATGGCAGCAATT
TCACCAGTACTGTGGTTAAGGCAGCCTGTTGGTGGGCAGGTATCCAGCAGGAATT
TGGAATTCCCTACAATCCCCAAAGTCAAGGAGTAGTAGAATCTATGAATAAAGA
ATTAAAGAAAATNATAGGACANGTAAGAGATCAAGCTGAACATCTTAAGACAGC
AGTGCAAATGGCAGTATTCATTCACAATTTTAAAAGAAAAGGGGGGATTGGGGG
GTACAGTGCAGGGGAAAGAATAATAGACATAATAGCAACAGACATACAAACTA
AAGAATTACAAAAACAAATTNCAAAAATTCAAAATTTTCGGGTTTATTTCAGGGA
CAGCAGAGACCCANTTTGGAAAGGACCAGCAAAGCTACTCTGGAAAGGTGAAGG
GGCAGTAGTCATACAAGACAATAATGAAATAAAAGTAGTACCAAGAAGAAAAG
CAAANATCATTAGGGATTATGGAAAACAGATGGCAGGTGATGATTGTGTGGCAG
GTAGACAGGATGAGGATTAGAACATGGAACAGNTTAGTAAAACACCATATGTAT
```

```
GTTTCAAGGAGAGCTAAAGGATGGTTTTATAGACATCACTATGAAAGCAGGCAT

CCAAGAGTAAGTTCAGAAGTACACATCCCACTAGAGGATGATTCTAAATTAGTA

ATANTAACCTATTGGGGTCTACATACAGGAGAAAGAGATTGGCATTTGGGTCAA

GGAGTCTCCATAGAATGGAGGCAGAAAAGGTATAGGACACAAGTAGACCCTGGC

TTGGCAGACCAACTAATTCATCTGNATTATTTTGATTGTTTTTCAGAATCTGCCAT

AAGGAAAGCCATATTAGGACANAGAGTTAGTCCTAGGTGTAANTATCAAGCAGG

ACATAACAAGGTAGGATCCCTACAATATTTGGCACTAACAGCATTAATAACCCCA

AANAAGATAAAGCCGCCTTTGCCTAGTGTCAGGAAACTAGTAGAGGATAGATGG

AACAACCCCCAGAAGACCANGGGCCACAGAGGGAGCCATACAATGAATGGACA

CTAGAGCTTTTAGAGGAGCTTAAGCATGAAGCTGTTAGACATTTNCCTAGGGAGT

GGCTCCATGGCTTAGGACAGCATATCTATAACACCTATGGGGATACTTGGGAGG

GAGTTGAAGCTATAATAAGGANACTGCAACAACTACTATTTATCCATTTCAGAAT

TGGGTGCCATCATAGCAGAATAGGCATTATTCGACAAAGAAGANTAAGAAATGG

AANTGGTAGATCCTAAACTAGATCCCTGGAACCATCCAGGAAGTCAGCCTGAGA

CTCCTTGTAATAAATGNTATTGTAAAAAGTGTTGCTTTCATTGCCAANTGTGCTTT

ACAAGGAAGGGCTTAGGCATCTCCTATGGCAGGAAGAAGCGGAGACAGCGACG

AAGANCTNCTCAAAGCAGTNAGNTACATCAAGATCCTGTANCAAAGCAGTAAGT

AGTATATGTAATGTCATCTTTGCTAANAGTAGTAATAGCAGCATNTATAGTAGCN

CTAATAATAGCAATAATTGTGTGGACTATAGTATATATAGAATATAAGAAACTGT

TAAGGCAAAAAGAATAAATAGGTTATATGAAAGAATAAGAGAAAGAGCAGAA

GACAGTGGCAATGAGAGTGAGGGAGATGCAGAGGAATTGGCAGCACTTGGGA

AGTGGGCCTTTTATTCCTGGGGATATTAATAATCTGTAATGCTGCAGATAACTT

GTGGGTCACAGTCTATTATGGAGTACCTGTGTGGAAAGAAGCAACCACTACTCTA

TTTTGTGCATCAGATGCTAAAGCATATGAAAGAGAGGTACATAATGTCTGGGCTA

CATATGCCTGTGTACCTACAGACCCCAACCCACAAGAATTNGTTCTGGGAAATGT

AACAGAAAATTTTAACATGTGGAAAAATAACATGGTAGACCAGATGCATGAAGA

TATAATCAGTTTATGGGATCAAAGCCTAAANCCATGTGTAAAGNTAACCCCACTC

TGTGTTACNTTAAANTGTACTGATGTTAATATTANCNTCACTAATAACAATACCN

CTGATANCATCACCCTGGAAGANCAAGGGGAAATAAAAAACTGTTCTTTCAATA

TNACCACAGAGATAAAAGATAAGAAGAAAAAAGAATATGCANTTTTTTATANAC

TTGATGTAGTACCAATNAATAATAGTACTACTANATATAGGCTAATAAGTTGTAA

TACCTCAACCGTTACACAGGCTTGTCCAAAGGTGTCCTTTGATCCAATTCCTATAC

ATTATTGTGCTCCTGCTGGTTNTGCGATTCTAAAGTGTAATGATAAAAGGTTCAA

TGGGACAGGGTTATGCAGGAATGTCAGCACAGTACAATGTACACATGGAATTAA

ACCAGTGGTATCAACTCAACTACTGTTAAATGGCAGCCTAGCAGAAGAANATAT

AATAATTAGATCTGAAAATATCNCAGATAATNCAAAAACCATAATAGTACAGTT

TAATANATCTGTAAAAATTAANTGTACAAGACCCAACAACAATACAAGAANAAG

TATACGTATAGGACCAGGACNAGNATTNTATGCAACAGGTGAGATAATAGGAGA

TATAAGAAAGGCANATTGTANCATTAATGGAACACTGTGGAATGAAACTTTAAA

AANGGTAGCTNCAGAGNTCAAAAACCACTTTAATANANCANTANCATTTGAGCC
```

-continued

```
ATCATCAGGAGGGGANCTAGAANTTACAACACATAGTTTTAATTGTAGAGGAGA

NTTTTTCTACTGCAACACAACAGCNCTGTTTAATGAAACAAANNNTGNCTAATNC

AACNAAGANNANAAATGNCACTATCACTCTTCCATGTAGAATAANACAAATTGT

AAACATGTGGCAAAGAGTAGGACGAGCAATGTATGCCCCTCCCATTGCAGGAAA

AATTCAGTGTAACTCAAATATCACAGGTCTACTATTGACAAGAGATGGTGGGAA

NNANNNNAANNAGANAGANANCCTCAGACCTNNAGGGGGAGATATGAGAGACA

ATTGGAGAAGTGAACTATATAAATATAAGGTAGTAAAAATTGAACCACTAGGAG

TAGCACCCACCAAGGCAAAAAGACAAGTGGTGCAGAGAGAAAAAAGAGCAGTG

GGAATNGGAGCTGTGNTCCTTGGGTTCTTGGGAGCAGCAGGAAGCACTATGGGC

GCGGCGTCAATAACGCTGACGGTACAGGCCAGACAATTATTGTCTGGTATAGTGC

AACAGCAAANCAATTTGCTGAAGGCTATAGAAGCGCAACAGCATCTGTTGCAGC

TCACAGTCTGGGGCATTAAACAGCTCCAGGCGAGAATCCTGGCTGTGGAAAGAT

ACCTAAAGGACCAACAGCTCCTAGGGATTTGGGGNTGCTCTGGAAAACTCATCT

GCACCACTAATGTGCCCTGGAATTCTAGTTGGAGTAATAAATCTCAGGATGAAAT

TTGGGNAAACATGACCTGGATGCAGTGGGAAAAAGAGATNGNNAATTACACAG

ACACAATATACAGATTAATNGAANATGCNCAAAACCAGCAGGAAAAGAATGAA

CAGGACTTATTGGCATTGGACAANTGGGACANTCTGTGGAGTTGGTTTNCTATAA

CAAACTGGTTGTGGTACATAAAAATATTCATAATGATAGTAGGAGGCTTGATAG

GATTAAGAATAGTTTTTGCTGTGCTTTCTNTAATAAATAGNGTTAGGCAGGGATA

CTCACCTTTGTCATTACAGACCCTTATCCCAANCCCGAGGGGACCCGANAGGCCC

GGAGGAATCGAAGAAGAAGGTGGAGAGCAAGACAAAGACAGATCCNTNAGATT

AGTGAGCGGATTCTTAGCACTTGCCTGGGACGACCTACGGAGCCTGTGCCTCTTC

AGCTACCGCCACTTGAGAGACTTCATATTAATTGCAGCGAGGACTGTGGACAAG

GGACTGAAANGGGGGTGGGAAGTCCTCAAATATCTGTGGAATCTCGCGCAGTAT

TGGGGTCGGGAACTAAAGAATAGTGCTATTAGTCTGNTTNATACCACAGCAATA

GNNGTAGCTGAAGGGACAGATAGAATCATAGAANTTNTGCAAAGAGCTGGTAGA

GCTNTTCTCCACATACCTAGAAGAATAAGACAGGGTGNTGAAAGGGCTTTGCTAT

AAAATGGGTGGCAAGTGGTCAAAAAGTAGTATAGTTGGATGGCCTANTNTAAGG

GAAAGAATNAGANNNNNNNGCAGCAGAAGGGGTGGGANNAGTGTCTCAAGACTT

AGATAAACATGGGGCAATTACAAGCAGCAATACTNGGGCTACTAATNCTGACTT

GGCCTGGCTNGAAGCGCAAGAGGATNNNGAAGTAGGTTTTCCAGTCAGACCTCA

GGTACCTTTAAGACCAATGACTTATAAGGNAGCTGTCGATCTCAGTCACTTTTTA

AAAGAAAAGGGGGGACTGGAAGGGTTAATTTACTCCANGAAAAGACAAGAAAT

CCTTGATCTGTGGGTCTACCACACACAAGGCTACTTCCCTGATTGGCAGAACTAC

ACACCAGGGCCAGGGACCAGATATCCACTGACCTTTGGATGGTGCTTCAAGCTA

GTACCAGTTGATCCAGAGGAGGTAGAAAAGGCCAATGAAGGAGAGAACAACTG

TTTGTTACACCCTATGAGCCTACATGGAATGGAGGATGAAGACAGGGAAGTGTT

AAAGTGGAAGTTTGACAGCNGCCTAGCACTGAGACACATAGCCAGAGAGAGACA

TCCGGAGTACTACAAAGAC
```

SEQ G_Majority
SEQ ID NO: 10
ACTTGACCTATGGGCTATAATACCAAAGGATTCTTCCCAGATTGGCAGAACTACA

CACCAGGGCCAGGGACTAGATTCCCACTGACCCTTGGGTGGTGCTTCAAACTGGT

ACCAATGGATCCATCAGAGGTAGAGGAAGCCAATAAAGGAGAGAACAACAGTC

TATTACACCCCATCTGCCAGCATGGAATGGAGGACGAAGACAGAGAAGTGCTGG

TGTGGAAATTTGACAGTAGCCTAGCACGGAGACACATAGCCCGAGAGCTGCATC

CGGAGTACTACAAAGACTGCTGACACAGAAGTTGCTGACAAGGGGACTTTCCGC

CTGGGACTTTCCAGGGGAGGCGCGGCCTGGGAGGGGCTGGGGAGTGGCTAACCC

TCAGAAGCTGCATATAAGCAGCCGCTTCTCGCCTGTACTGGGTCTCTCTTGTTAG

ACCAGATTTGAGCCTGGGAGCTCTCTGGCTAGCAGGGGAACCCACTGCTTAGAG

CCTCAATAAAGCTTGCCTTGAGTGCTTCAAGTAGTGTGTGCCCGTCTGTTGTGTG

ACTCTGGTAACTAGAGATCCCTCAGACCACTCTAGATAGTGTAAAAATCTCTAGC

AGTGGCGCCCGAACAGGGACTTGAAAGCGAAAGTTAACAGGGACTCGAAAGCG

AAAGTTCCAGAGAAGTTCTCTCGACGCAGGACTCGGCTTGCTGAGGTGCACACA

GCAAGAGGCGAGAGCGGCGACTGGTGAGTACGCCANAATTTTTGACTAGCGGAG

GCTAGAAGGAGAGATGGGTGCGAGAGCGTCAGTATTAAGCGGGGGAAAATT

AGATGCTTGGGAAAAAATTCGGTTGAGGCCAGGGGGAAAGAAAAAATATAGAN

TGAAACATTTAGTATGGGCAAGCAGGGAGCTGGAGAGATTTGCACTTAACCCTG

ACCTTTTAGAAACAGCAGAAGGTTGTCAGCAAATAATGGGACAGTTGCAACCAG

CTCTCCAGACAGGAACAGAGGAGATTAGATCATTATTTAATACAGTAGCAACCCT

CTATTGTGTACATCAAAAGATAGAGGTAAAAGACACCAAAGAAGCTCTAGAGGA

AGTGGAAAAGATACAAAAGAAAAGTCAGCAAAAAATACAGCAGGCAGCAATGG

ATGAAGGAAACAGCAGCCAAGTCAGCCAAAATTATCCTATAGTGCAGAATGCAC

AAGGGCAAATGGTACACCAGGCCATATCACCTAGAACTTTAAATGCATGGGTAA

AAGTAGTAGAAGAAAAGGCCTTCAGTCCAGAAGTAATACCCATGTTTTCAGCATT

ATCAGAAGGAGCCACCCCACAAGATTTAAATACCATGCTAAACACAGTGGGGGG

GCATCAAGCAGCTATGCAAATGCTAAAGGATACTATCAATGAGGAAGCTGCAGA

GTGGGACAGGATACATCCACANCAGGCAGGGCCTATTCCACCAGGCCAGATAAG

AGAACCAAGGGGAAGTGATATAGCAGGAACTACTAGTACCCTGCAGGAACAAAT

AAGATGGATGACCAGCAACCCACCTATCCCAGTGGGAGAAATTTATAAAAGATG

GATAATCCTGGGATTAAATAAAATAGTAAGAATGTATAGCCCTGTCAGCATTTTG

GACATAAGACAAGGGCCAAAAGAACCCTTTAGAGATTATGTAGATAGGTTCTTT

AAAACTTTGAGAGCTGAGCAAGCTACACAGGAAGTAAAAGGCTGGATGACAGAC

ACCTTGTTGGTCCAAAATGCGAACCCAGATTGTAAGACCATCTTAAGAGCATTAG

GACCAGGAGCTACACTAGAAGAAATGATGACAGCATGTCAGGGAGTGGGAGGA

CCCAGCCATAAAGCAAGAGTTTTAGCTGAGGCAATGAGCCAGGCATCAGGTGCA

GCAGCAGCCATAATGATGCAGAAAAGCAATTTTAAGGGCCCAAGAAGAACTATT

AAGTGTTTCAACTGTGGCAAGGAAGGACATCTAGCCAGAAATTGCAGGGCCCCT

AGGAAAAAGGGCTGTTGGAAATGTGGAAAGGAGGGACATCAAATGAAAGACTG

CACAGAGAGACAGGCTAATTTTTTAGGGAAAATTTGGCCTTCCAACAAGGGGAG

```
-continued
GCCAGGGAATTTTCTCCAGAACAGGCCAGAGCCAACAGCCCCACCCGCAGAGAG

CTTCGGGTTCGGAGAGGAGATAGCCCCCTCCCCGAAGCAGGAGCNGAAGGAAAA

GGAGCTATATCCCTTAGCCTCCCTCAAATCACTCTTTGGCAGCGACCCCTAGTCA

CAGTAAAAATAGGGGGACAGCTAATAGAAGCCCTATTAGACACAGGAGCAGATG

ATACAGTATTAGAAGAAATAAATTTACCAGGAAAATGGAAACCAAAAATGATAG

GGGGAATTGGAGGTTTTATCAAAGTAAGACAGTATGATCAAATACTTATAGAAA

TTAGTGGAAAAAAGGCTATAGGGACAGTATTAGTAGGACCTACACCTATCAACA

TAATTGGGAGAAATATGTTGACTCAGATTGGTTGTACTTTAAATTTTCCAATTAGT

CCTATTGAAACTGTACCAGTAAAATTAAAGCCAGGAATGGATGGNCCAAGGGTT

AAACAATGGCCATTGACAGAAGAGAAAATAAAAGCATTAACAGAAATTTGTAAA

GAAATGGAAAAGGAAGGAAAAATTTCAAAAATTGGGCCTGAAAATCCATACAAC

ACTCCAATATTTGCCATAAAGAAAAAAGACAGTACTAAATGGAGAAAATTGGTA

GATTTCAGAGAGCTCAATAAAAGAACTCAAGACTTCTGGGAGGTCCAATTAGGA

ATACCTCATCCCGCGGGGTTAAAAAAGAAAAAATCAGTAACAGTACTAGATGTG

GGGGATGCATACTTTTCAGTTCCCTTAGATGAAAACTTTAGAAAGTATACTGCAT

TCACTATACCTAGTACAAATAATGAGACACCAGGGATTAGATATCAGTACAATGT

GCTTCCACAGGGATGGAAAGGATCACCAGCAATATTTCAGAGTAGCATGACAAA

AATCTTAGAGCCCTTTAGAACAAAAAATCCAGAAATAGTGATCTACCAATACAT

GGATGATTTATATGTAGGATCTGACTTAGAAATAGGGCAGCATAGAGCAAAAAT

AGAGGAGTTAAGAGAACATCTATTGAGATGGGGATTTACCACACCAGATAAAAA

ACATCAGAAAGAACCTCCATTCCTTTGGATGGGATATGAGCTCCATCCTGACAAA

TGGACGGTACAACCTATACAGCTGCCAGACAAGGAAAGCTGGACTGTCAATGAT

ATACAAAAGTTAGTGGGAAAACTAAATTGGGCAAGTCAGATTTATCCAGGGATT

AAAGTAAAGCAACTATGTAAACTCCTTAGGGGGGCCAAAGCACTAACAGACATA

GTACCACTGACTGCAGAAGCAGAAATGGAATTGGCAGAGAACAGGGANATTCTA

AAAGAACCTGTACATGGAGTCTATTATGACCCATCAAAAGAATTAATAGCAGAA

GTACAGAAACAAGGGCTAGACCAATGGACATATCAAATTTATCAAGAGCCATAC

AAAAATCTGAAAACAGGAAAATATGCAAAAAGGGGGTCTGCCCACACTAATGAT

GTAAAACAATTAACAGAAGTAGTGCAAAAAATAGCCACAGAGAGCATAGTAATA

TGGGGAAAGACTCCTAAATTTAAACTACCTATACGAAAGAAACATGGGAAGTA

TGGTGGACAGANTATTGGCAGGCCACCTGGATTCCTGAGTGGGAGTTTGTCAATA

CCCCTCCTCTAGTAAAATTATGGTATCGGTTAGAAACAGAACCCATACCAGGAGC

AGAAACTTACTATGTAGATGGGGCAGCTAATAGGGAGACAAAATTAGGAAAGGC

AGGATATGTTACTGACAAAGGAAAACAAAAAATTATTACCCTAACTGAAACAAC

AAACCAAAAGGCTGAATTACANGCAATTCANCTAGCTTTGCAGGACTCANGATC

AGAAGTAAACATAGTAACAGACTCACAGTATGCATTAGGAATCATTCAAGCACA

ACCAGATAGGAGTGAATCAGAATTAGTCAATCAAATAATAGAACAGCTAATAAA

AAAGGAAAAGGTCTACCTGTCATGGGTACCAGCACACAAAGGGATTGGAGGAAA

TGAACAAGTAGATAAATTAGTCAGTAGTGGAATCAGGAAAGTATTATTTTTAGAT

GGCATAGATAAAGCCCAAGAAGACCATGAAAGATATCACAGCAATTGGAGAGC

AATGGCTAGTGATTTTAATCTGCCACCTATAGTAGCAAAAGAAATAGTGGCCAGC
```

-continued

```
TGTGATAAATGTCAGCTAAAAGGGGAAGCCATGCATGGACAAGTAGACTGTAGT

CCAGGAATATGGCAATTAGATTGTACACATTTAGAAGGAAAAATTATCCTGGTA

GCAGTNCATGTAGCCAGTGGCTATATAGAAGCAGAAGTTATCCCAGCAGAAACA

GGACAGGAAACAGCATACTTTATATTAAAATTAGCAGGAAGGTGGCCAGTAAAA

GTAATACATACAGACAATGGCAGCAATTTCACCAGTGCTGCAGTAAAGGCAGCA

TGTTGGTGGGCAAATATCACACAGGAATTTGGAATTCCCTACAATCCCCAAAGCC

AAGGAGTAGTGGAATCTATGAATAAGGAATTAAAGAAAATCATCGGGCAGGTCA

GGGATCAAGCTGAACATCTTAAGACAGCAGTACAGATGGCAGTATTCATTCACA

ATTTTAAAAGAAAAGGGGGGATTGGGGGGTACAGTGCAGGGGAAAGAATAATA

GACATAATAGCATCAGATATACAAACTAAAGAACTACAAAAACAAATTACAAAA

ATTCAAAATTTTCGGGTTTATTACAGGGACAGCAGAGACCCAATTTGGAAAGGA

CCAGCAAAGCTACTCTGGAAAGGTGAAGGGGCAGTAGTAATACAAGACAATAAC

GAAATAAAGGTAGTACCAAGAAGAAAAGCAAAGATCATTAGGGATTATGGAAA

ACAGATGGCAGGTGATGATTGTGTGGCAGGTAGACAGGATGAGGATTAGAACAT

GGAACAGTTTAGTAAAACATCATATGTATGTCTCAAAGAAAGCTAAAGGCTGGT

TTTATAGACATCACTATGAAAGCAGGCATCCAAAAGTAAGTTCAGAAGTACACA

TCC CACTAGGAGATGCTACACTAGTAGTAAGAACATATTGGGGTCTGCATACAG

GAGAAAAAGANTGGCAATTGGGTCATGGGGTCTCCATAGAATGGAGGCAGAGA

AGATATAGNACACAAATAGATCCTGACCTAGCAGACCANCTGATTCATCTGCATT

ATTTTGACTGTTTTTCAGAATCTGCCATAAGGAAAGCCATATTAGGAAAAATAGT

TAGTCCTAGGTGTGAATATCAAGCAGGACATAATAAGGTAGGATCTCTACAATAT

TTGGCATTGAAAGCATTAGTAACACCAACAAGGACAAGGCCACCTTTGCCTAGT

GTTAGGAAATTAACAGAAGATAGATGGAACAAGCCCCAGAAGACCAGGGGCCA

CAGAGAGAACCCTACAATGAATGGGCATTAGAACTGTTAGAAGAGCTTAAAAAT

GAAGCTGTTAGACATTTTCCTAGGCCCTGGCTCCATGGCTTAGGACAGTATATCT

ATAACACTTATGGGGATACTTGGGAAGGAGTTGAAGCCATAATAAGAATACTAC

AACAACTACTGTTTATCCATTTCAGAATTGGGTGCCAACATAGCAGAATAGGCAT

TACTCCACAGAGAAGAGTAAGGGATGGACCCGGTAGATCCTAACCTAGAGCCCT

GGAATCATCCGGGGAGTCAGCCTAAAACTCCCTGTAACAACTGCTATTGTAAAA

NGTGTTGCTGGCATTGCCAAGTTTGCTTTCTGAACAAAGGCTTAGGCATCTCCTA

TGGCAGGAAGAAGCGGAAGCACCGACGAGGAACTCCTCAGAGCAGTAAGGATC

ATCAAAATCCTGTACCAAAGCAGTAAGTAGTAATAATTAGTATATGTAATGCAAC

CATTAGAAATATCTGCAATAGTAGGACTAATAGTAGCATTCATAGCAGCCATAAT

TGTGTGGACTATAGTATTTATAGAATATAGGGAAATAAGAAAACAGAAAAAAAT

AGAAAAGTTACTTGATAGAATAAGAGAAAGAGCAGAAGACAGTGGAAATGAGA

GTGANGGGGATACAGAGGAATTGGCAACACTTATGGAAATGGGGACTTTGATC

CTTGGGTTGGTGATAATTTGTAGTGCCTCAAATAACTTGTGGGTCACAGTCTATT

ATGGGGTACCTGTGTGGAAGATGCAAATACCACTCTATTTTGTGCATCTGATGC

TAAAGCATATAGTACTGAAAGNCATAATGTCTGGGCTACACATGCCTGTGTACCC

ACAGACCCCAACCCACAAGAAATACCTATGGAAAATGTAACAGAAAATTTTAAC
```

```
ATGTGGAAAAATAACATGGTAGAACAGATGCATGAGGATATAATCAGTTTATGG

GATGAAAGCCTAAAGCCATGTGTAAAGCTAACCCCTCTCTGTGTTACTTTAAACT

GTACTAATGTAACCAACAATAGNANTNNTNAACAATAACANTATNGNNGACAAA

GAAGAAATAAAAAACTGCTCTTTCAATATAACCACAGAAATAAGAGATAAGAAG

AAGCAAGAATACGCGCTTTTCTATAGACTTGATGTAGTACCAATTAATGATAATN

TNNAGTAATNNNANTAATTATAGGCTAATAAATTGTAATGTCTCAACCATTAAAC

AGGCTTGTCCAAAGGTAACTTTTGACCCAATTCCCATACATTATTGTGCTCCAGCT

GGTTTTGCGATTTTAAAGTGTAGGGATAAGGAGTTCAATGGAACAGGACCATGT

AAAAATGTCAGTACAGTACAATGTACACATGGAATTAAGCCAGTGGTATCAACT

CAACTACTGCTGAATGGCAGTTTAGCAGAAGAAGAAATAATAATTAGATCTGAA

AATATCACAGACAATACCAAAGTCATAATAGTGCAGCTTAATGAAACTATAGAA

ATTAATTGTATCAGACCCAACAACAATACAAGAAAAAGTATAANANTCGGACCA

GGACAAGCGTTCTATGCAACAGGTGACATAATAGGAGACATAAGACAAGCACAT

TGTAATGTTAGTAGAACAAAATGGAATAAGATGNTAAAGAATGTCACNGCANAA

CTAAANAAAATCTTTAATAACAAGAACATAACCTTTAACTCATCTGCAGGAGGG

GACCTAGAAATTACAACACATAGTTTCAATTGTAGAGGAGAATTTTTCTATTGTA

ATACATCAGGACTGTTTAATAATAGTNTGNNNGTAGNNNNANTAATAGTAATAA

TGAGACTATCACACTCCCATGTAAAATAAAACAAATTGTGAGAATGTGGCAGAG

AGTGGGACAAGCAATGTATGCCCCTCCCATCGCAGGAAACATTACATGTAAATC

AAACATTACAGGACTAATATTAACAAGAGATGGTGGNAATAATAATACAAGTGC

GACTGAGATCTTCAGACCTGGAGGAGGAGATATGAAGGACAATTGGAGAAGTGA

ATTATATAAGTATAAAACAGTAAAAATCAAATCACTAGGAGTAGCACCCACCAG

GGCAAGGAGAAGAGTGGTGGAGAGAGAAAAAAGAGCAGTTGGACTGGGAGCTG

TCTTCCTTGGGTTCTTAGGAGCAGCAGGAAGCACTATGGGCGCGGCGTCAATAAC

GCTGACGGTACAGGTCAGACAATTATTGTCTGGCATAGTGCAACAGCAAAGCAA

TTTGCTGAGGGCTATAGAGGCGCAGCAGCATCTGTTGCAACTCACAGTCTGGGC

ATTAAACAGCTCCAGGCAAGAGTCCTGGCTGTGGAAAGATACCTAAAGGATCAA

CAGCTCCTAGGGATTTGGGGCTGCTCTGGAAAACTCATCTGCACCACTAATGTGC

CCTGGAACGCTAGTTGGAGTAATAAATCTTATAATGAAATTTGGGATAACATGAC

TTGGATAGAATGGGAAGGGAAATTAACAATTACACACAACAAATATACAGCCT

AATTGAAGAATCGCAGAACCAGCAGGAAAAGAATGAACAAGACTTATTGGCATT

GGACAAGTGGGCAAGTTTGTGGAATTGGTTTGACATATCAAANTGGCTATGGTAT

ATAAAAATATTTATAATGATAGTAGGAGGTTTAATAGGTTTAAGAATAGTTTTTG

CTGTGCTTTCTATAGTAAATAGAGTTAGGCAGGGATACTCACCTTTGTCATTCCA

GACCCTTACCCACCACCAGAGGGAACCCGACAGGCCCGGAAGAATCGAAGAAG

AAGGTGGAGAGCAAGACAAAGACAGATCCATTCGATTAGTGAGCGGATTCTTAG

CGCTTGCCTGGGACGACCTGCGGAGCCTGTGCCTCTTCAGCTACCACCGCTTGAG

AGACTTCNTCTTGATTGCAGCGAGGACAGTGGAACTTCTGGGACGCAGCAGNCT

CAAGGGACTGAGACTGGGGTGGGAAGGCCTCAAATATTTGTGGAATCTTCTGTTG

TATTGGGGTCGGGAACTAAAGAATAGTGCTATTAATTTGCTTGATACAATAGCAA

TAGCAGTAGCTAACTGGACAGATAGGGTTATAGAAGTAGCACAAAGAGCTGGTA
```

-continued

```
GAGCTATTCTCAACATACCTACAAGAATAAGACAAGGCTTAGAAAGAGCTTTGC

TATAAAATGGGAGGCAAGTGGTCAAAAAGTAGCATAGTTGGATGGCCTGAGGTA

AGGGAAAGAATAAGACAAACCCCTNCAGCAGCAGAAGGAGTAGGAGCAGTATC

TCAAGATTTAGCTAGGCATGGAGCAATCACAAGCAGCAATACAGCAGCCAATAA

TCCTGATTGTGCCTGGCTGGAAGCACAAGANGAGGANTCAGAGGTAGGCTTTCC

AGTCAGACCACAGGTACCTNTGAGACCAATGACTTATAAGGCTGCTTTTGATCTC

AGCTTCTTTTTAAAAGAAAAGGGGGGACTGGATGGGCTAATTTACTCCAAGAAA

AGACAAGACATCCTTGACCTGTGGGTCTATAATACACAAGGATTCTTCCCAGATT

GGCAGAACTACACACCAGGGCCAGGGACTAGATTCCCACTGACCTTTGGGTGGT

GCTTCAAACTAGTACCAATGGATCCAGCAGAGGTAGAGGAAGCCANTAAAGGAG

AGAACAACAGTCTATTACACCCCATCTGCCAGCATGGAATGGAGGANGAAGACA

GAGAAGTGCTGNTATGGAGATTTGACAGTAGCCTAGCACGGAGACACATAGCCC

GAGAGCTGCATCCGGAGTNCTACAAAGACTGCTGACACAGAAGTTGCTGACAAA

GGGACTTTCCGCCTGGGACTTTCCGGGGAGGCGCGGCCTGGGAGGGGCTGGGGA

GTGGCTAACCCTCAGAAGCTGCATATAAGCAGCCGCTTCTCGCCTGTACNGGGTC

TCTCTTGTTGACCAGATTTGAGCCTGGGAGCTCTCTGGNTNGCAGGNGAACCACT

GCTTANGCCTCAATAAAGCTTGCCNNGNN
```

SEQ NC_001802.1

SEQ ID NO: 11

```
GGTCTCTCTGGTTAGACCAGATCTGAGCCTGGGAGCTCTCTGGCTAACTAGGGAA

CCCACTGCTTAAGCCTCAATAAAGCTTGCCTTGAGTGCTTCAAGTAGTGTGTGCC

CGTCTGTTGTGTGACTCTGGTAACTAGAGATCCCTCAGACCCTTTTAGTCAGTGTG

GAAAATCTCTAGCAGTGGCGCCCGAACAGGGACCTGAAAGCGAAAGGGAAACC

AGAGGAGCTCTCTCGACGCAGGACTCGGCTTGCTGAAGCGCGCACGGCAAGAGG

CGAGGGGCGGCGACTGGTGAGTACGCCAAAAATTTTGACTAGCGGAGGCTAGAA

GGAGAGAGATGGGTGCGAGAGCGTCAGTATTAAGCGGGGGAGAATTAGATCGAT

GGGAAAAAATTCGGTTAAGGCCAGGGGGAAAGAAAAAATATAAATTAAAACAT

ATAGTATGGGCAAGCAGGGAGCTAGAACGATTCGCAGTTAATCCTGGCCTGTTA

GAAACATCAGAAGGCTGTAGACAAATACTGGGACAGCTACAACCATCCCTTCAG

ACAGGATCAGAAGAACTTAGATCATTATATAATACAGTAGCAACCCTCTATTGTG

TGCATCAAAGGATAGAGATAAAAGACACCAAGGAAGCTTTAGACAAGATAGAG

GAAGAGCAAAACAAAAGTAAGAAAAAAGCACAGCAAGCAGCAGCTGACACAGG

ACACAGCAATCAGGTCAGCCAAAATTACCCTATAGTGCAGAACATCCAGGGGCA

AATGGTACATCAGGCCATATCACCTAGAACTTTAAATGCATGGGTAAAAGTAGT

AGAAGAGAAGGCTTTCAGCCCAGAAGTGATACCCATGTTTTCAGCATTATCAGA

AGGAGCCACCCCACAAGATTTAAACACCATGCTAAACACAGTGGGGGGACATCA

AGCAGCCATGCAAATGTTAAAAGAGACCATCAATGAGGAAGCTGCAGAATGGGA

TAGAGTGCATCCAGTGCATGCAGGGCCTATTGCACCAGGCCAGATGAGAGAACC

AAGGGGAAGTGACATAGCAGGAACTACTAGTACCCTTCAGGAACAAATAGGATG

GATGACAAATAATCCACCTATCCCAGTAGGAGAAATTTATAAAAGATGGATAAT

CCTGGGATTAAATAAAATAGTAAGAATGTATAGCCCTACCAGCATTCTGGACATA
```

-continued

```
AGACAAGGACCAAAGGAACCCTTTAGAGACTATGTAGACCGGTTCTATAAAACT

CTAAGAGCCGAGCAAGCTTCACAGGAGGTAAAAAATTGGATGACAGAAACCTTG

TTGGTCCAAAATGCGAACCCAGATTGTAAGACTATTTTAAAAGCATTGGGACCAG

CGGCTACACTAGAAGAAATGATGACAGCATGTCAGGGAGTAGGAGGACCCGGCC

ATAAGGCAAGAGTTTTGGCTGAAGCAATGAGCCAAGTAACAAATTCAGCTACCA

TAATGATGCAGAGAGGCAATTTTAGGAACCAAAGAAAGATTGTTAAGTGTTTCA

ATTGTGGCAAAGAAGGGCACACAGCCAGAAATTGCAGGGCCCCTAGGAAAAAG

GGCTGTTGGAAATGTGGAAAGGAAGGACACCAAATGAAAGATTGTACTGAGAGA

CAGGCTAATTTTTTAGGGAAGATCTGGCCTTCCTACAAGGGAAGGCCAGGGAATT

TTCTTCAGAGCAGACCAGAGCCAACAGCCCCACCAGAAGAGAGCTTCAGGTCTG

GGGTAGAGACAACAACTCCCCCTCAGAAGCAGGAGCCGATAGACAAGGAACTGT

ATCCTTTAACTTCCCTCAGGTCACTCTTTGGCAACGACCCCTCGTCACAATAAAG

ATAGGGGGGCAACTAAAGGAAGCTCTATTAGATACAGGAGCAGATGATACAGTA

TTAGAAGAAATGAGTTTGCCAGGAAGATGGAAACCAAAAATGATAGGGGGAATT

GGAGGTTTTATCAAAGTAAGACAGTATGATCAGATACTCATAGAAATCTGTGGA

CATAAAGCTATAGGTACAGTATTAGTAGGACCTACACCTGTCAACATAATTGGAA

GAAATCTGTTGACTCAGATTGGTTGCACTTTAAATTTTCCCATTAGCCCTATTGAG

ACTGTACCAGTAAAATTAAAGCCAGGAATGGATGGCCCAAAAGTTAAACAATGG

CCATTGACAGAAGAAAAAATAAAAGCATTAGTAGAAATTTGTACAGAGATGGAA

AAGGAAGGGAAAATTTCAAAAATTGGGCCTGAAAATCCATACAATACTCCAGTA

TTTGCCATAAAGAAAAAAGACAGTACTAAATGGAGAAAATTAGTAGATTTCAGA

GAACTTAATAAGAGAACTCAAGACTTCTGGGAAGTTCAATTAGGAATACCACAT

CCCGCAGGGTTAAAAAAGAAAAAATCAGTAACAGTACTGGATGTGGGTGATGCA

TATTTTTCAGTTCCCTTAGATGAAGACTTCAGGAAGTATACTGCATTTACCATACC

TAGTATAAACAATGAGACACCAGGGATTAGATATCAGTACAATGTGCTTCCACA

GGGATGGAAAGGATCACCAGCAATATTCCAAAGTAGCATGACAAAAATCTTAGA

GCCTTTTAGAAAACAAAATCCAGACATAGTTATCTATCAATACATGGATGATTTG

TATGTAGGATCTGACTTAGAAATAGGGCAGCATAGAACAAAAATAGAGGAGCTG

AGACAACATCTGTTGAGGTGGGGACTTACCACACCAGACAAAAAACATCAGAAA

GAACCTCCATTCCTTTGGATGGGTTATGAACTCCATCCTGATAAATGGACAGTAC

AGCCTATAGTGCTGCCAGAAAAAGACAGCTGGACTGTCAATGACATACAGAAGT

TAGTGGGAAATTGAATTGGGCAAGTCAGATTTACCCAGGGATTAAAGTAAGGC

AATTATGTAAACTCCTTAGAGGAACCAAAGCACTAACAGAAGTAATACCACTAA

CAGAAGAAGCAGAGCTAGAACTGGCAGAAAACAGAGAGATTCTAAAAGAACCA

GTACATGGAGTGTATTATGACCCATCAAAAGACTTAATAGCAGAAATACAGAAG

CAGGGGCAAGGCCAATGGACATATCAAATTTATCAAGAGCCATTTAAAAATCTG

AAAACAGGAAAATATGCAAGAATGAGGGGTGCCCACACTAATGATGTAAAACA

ATTAACAGAGGCAGTGCAAAAAATAACCACAGAAAGCATAGTAATATGGGGAA

AGACTCCTAAATTTAAACTGCCCATACAAAAGGAAACATGGGAAACATGGTGGA

CAGAGTATTGGCAAGCCACCTGGATTCCTGAGTGGGAGTTTGTTAATACCCCTCC

CTTAGTGAAATTATGGTACCAGTTAGAGAAAGAACCCATAGTAGGAGCAGAAAC
```

-continued

```
CTTCTATGTAGATGGGGCAGCTAACAGGGAGACTAAATTAGGAAAAGCAGGATA

TGTTACTAATAGAGGAAGACAAAAAGTTGTCACCCTAACTGACACAACAAATCA

GAAGACTGAGTTACAAGCAATTTATCTAGCTTTGCAGGATTCGGGATTAGAAGTA

AACATAGTAACAGACTCACAATATGCATTAGGAATCATTCAAGCACAACCAGAT

CAAAGTGAATCAGAGTTAGTCAATCAAATAATAGAGCAGTTAATAAAAAAGGAA

AAGGTCTATCTGGCATGGGTACCAGCACACAAAGGAATTGGAGGAAATGAACAA

GTAGATAAATTAGTCAGTGCTGGAATCAGGAAAGTACTATTTTTAGATGGAATAG

ATAAGGCCCAAGATGAACATGAGAAATATCACAGTAATTGGAGAGCAATGGCTA

GTGATTTTAACCTGCCACCTGTAGTAGCAAAAGAAATAGTAGCCAGCTGTGATAA

ATGTCAGCTAAAAGGAGAAGCCATGCATGGACAAGTAGACTGTAGTCCAGGAAT

ATGGCAACTAGATTGTACACATTTAGAAGGAAAAGTTATCCTGGTAGCAGTTCAT

GTAGCCAGTGGATATATAGAAGCAGAAGTTATTCCAGCAGAAACAGGGCAGGAA

ACAGCATATTTTCTTTTAAAATTAGCAGGAAGATGGCCAGTAAAAACAATACATA

CTGACAATGGCAGCAATTTCACCGGTGCTACGGTTAGGGCCGCCTGTTGGTGGGC

GGGAATCAAGCAGGAATTTGGAATTCCCTACAATCCCCAAAGTCAAGGAGTAGT

AGAATCTATGAATAAAGAATTAAAGAAAATTATAGGACAGGTAAGAGATCAGGC

TGAACATCTTAAGACAGCAGTACAAATGGCAGTATTCATCCACAATTTTAAAGA

AAAGGGGGGATTGGGGGGTACAGTGCAGGGGAAAGAATAGTAGACATAATAGC

AACAGACATACAAACTAAAGAATTACAAAAACAAATTACAAAAATTCAAAATTT

TCGGGTTTATTACAGGGACAGCAGAAATCCACTTTGGAAAGGACCAGCAAAGCT

CCTCTGGAAAGGTGAAGGGGCAGTAGTAATACAAGATAATAGTGACATAAAAGT

AGTGCCAAGAAGAAAAGCAAAGATCATTAGGGATTATGGAAAACAGATGGCAG

GTGATGATTGTGTGGCAAGTAGACAGGATGAGGATTAGAACATGGAAAAGTTTA

GTAAAACACCATATGTATGTTTCAGGGAAAGCTAGGGGATGGTTTTATAGACATC

ACTATGAAAGCCCTCATCCAAGAATAAGTTCAGAAGTACACATCCCACTAGGGG

ATGCTAGATTGGTAATAACAACATATTGGGGTCTGCATACAGGAGAAAGAGACT

GGCATTTGGGTCAGGGAGTCTCCATAGAATGGAGGAAAAAGAGATATAGCACAC

AAGTAGACCCTGAACTAGCAGACCAACTAATTCATCTGTATTACTTTGACTGTTT

TTCAGACTCTGCTATAAGAAAGGCCTTATTAGGACACATAGTTAGCCCTAGGTGT

GAATATCAAGCAGGACATAACAAGGTAGGATCTCTACAATACTTGGCACTAGCA

GCATTAATAACACCAAAAAAGATAAAGCCACCTTTGCCTAGTGTTACGAAACTG

ACAGAGGATAGATGGAACAAGCCCCAGAAGACCAAGGGCCACAGAGGGAGCCA

CACAATGAATGGACACTAGAGCTTTTAGAGGAGCTTAAGAATGAAGCTGTTAGA

CATTTTCCTAGGATTTGGCTCCATGGCTTAGGGCAACATATCTATGAAACTTATG

GGGATACTTGGGCAGGAGTGGAAGCCATAATAAGAATTCTGCAACAACTGCTGT

TTATCCATTTTCAGAATTGGGTGTCGACATAGCAGAATAGGCGTTACTCGACAGA

GGAGAGCAAGAAATGGAGCCAGTAGATCCTAGACTAGAGCCCTGGAAGCATCCA

GGAAGTCAGCCTAAAACTGCTTGTACCAATTGCTATTGTAAAAAGTGTTGCTTTC

ATTGCCAAGTTTGTTTCATAACAAAAGCCTTAGGCATCTCCTATGGCAGGAAGAA

GCGGAGACAGCGACGAAGAGCTCATCAGAACAGTCAGACTCATCAAGCTTCTCT
```

-continued

```
ATCAAAGCAGTAAGTAGTACATGTAATGCAACCTATACCAATAGTAGCAATAGT

AGCATTAGTAGTAGCAATAATAATAGCAATAGTTGTGTGGTCCATAGTAATCATA

GAATATAGGAAAATATTAAGACAAAGAAAAATAGACAGGTTAATTGATAGACTA

ATAGAAAGAGCAGAAGACAGTGGCAATGAGAGTGAAGGAGAAATATCAGCACT

TGTGGAGATGGGGGTGGAGATGGGGCACCATGCTCCTTGGGATGTTGATGATCT

GTAGTGCTACAGAAAAATTGTGGGTCACAGTCTATTATGGGGTACCTGTGTGGAA

GGAAGCAACCACCACTCTATTTTGTGCATCAGATGCTAAAGCATATGATACAGAG

GTACATAATGTTTGGGCCACACATGCCTGTGTACCCACAGACCCCAACCCACAAG

AAGTAGTATTGGTAAATGTGACAGAAAATTTTAACATGTGGAAAAATGACATGG

TAGAACAGATGCATGAGGATATAATCAGTTTATGGGATCAAAGCCTAAAGCCAT

GTGTAAAATTAACCCCACTCTGTGTTAGTTTAAAGTGCACTGATTTGAAGAATGA

TACTAATACCAATAGTAGTAGCGGGAGAATGATAATGGAGAAAGGAGAGATAA

AAAACTGCTCTTTCAATATCAGCACAAGCATAAGAGGTAAGGTGCAGAAAGAAT

ATGCATTTTTTATAAACTTGATATAATACCAATAGATAATGATACTACCAGCTA

TAAGTTGACAAGTTGTAACACCTCAGTCATTACACAGGCCTGTCCAAAGGTATCC

TTTGAGCCAATTCCCATACATTATTGTGCCCCGGCTGGTTTTGCGATTCTAAAATG

TAATAATAAGACGTTCAATGGAACAGGACCATGTACAAATGTCAGCACAGTACA

ATGTACACATGGAATTAGGCCAGTAGTATCAACTCAACTGCTGTTAAATGGCAGT

CTAGCAGAAGAAGAGGTAGTAATTAGATCTGTCAATTTCACGGACAATGCTAAA

ACCATAATAGTACAGCTGAACACATCTGTAGAAATTAATTGTACAAGACCCAAC

AACAATACAAGAAAAAGAATCCGTATCCAGAGAGGACCAGGGAGAGCATTTGTT

ACAATAGGAAAAATAGGAAATATGAGACAAGCACATTGTAACATTAGTAGAGCA

AAATGGAATAACACTTTAAAACAGATAGCTAGCAAATTAAGAGAACAATTTGGA

AATAATAAAACAATAATCTTTAAGCAATCCTCAGGAGGGGACCCAGAAATTGTA

ACGCACAGTTTTAATTGTGGAGGGGAATTTTTCTACTGTAATTCAACACAACTGT

TTAATAGTACTTGGTTTAATAGTACTTGGAGTACTGAAGGGTCAAATAACACTGA

AGGAAGTGACACAATCACCCTCCCATGCAGAATAAAACAAATTATAAACATGTG

GCAGAAAGTAGGAAAAGCAATGTATGCCCCTCCCATCAGTGGACAAATTAGATG

TTCATCAAATATTACAGGGCTGCTATTAACAAGAGATGGTGGTAATAGCAACAAT

GAGTCCGAGATCTTCAGACCTGGAGGAGGAGATATGAGGGACAATTGGAGAAGT

GAATTATATAAATATAAAGTAGTAAAAATTGAACCATTAGGAGTAGCACCCACC

AAGGCAAAGAGAAGAGTGGTGCAGAGAGAAAAAAGAGCAGTGGGAATAGGAGC

TTTGTTCCTTGGGTTCTTGGGAGCAGCAGGAAGCACTATGGGCGCAGCCTCAATG

ACGCTGACGGTACAGGCCAGACAATTATTGTCTGGTATAGTGCAGCAGCAGAAC

AATTTGCTGAGGGCTATTGAGGCGCAACAGCATCTGTTGCAACTCACAGTCTGGG

GCATCAAGCAGCTCCAGGCAAGAATCCTGGCTGTGGAAAGATACCTAAAGGATC

AACAGCTCCTGGGGATTTGGGGTTGCTCTGGAAAACTCATTTGCACCACTGCTGT

GCCTTGGAATGCTAGTTGGAGTAATAAATCTCTGGAACAGATTTGGAATCACACG

ACCTGGATGGAGTGGGACAGAGAAATTAACAATTACACAAGCTTAATACACTCC

TTAATTGAAGAATCGCAAAACCAGCAAGAAAAGAATGAACAAGAATTATTGGAA

TTAGATAAATGGGCAAGTTTGTGGAATTGGTTTAACATAACAAATTGGCTGTGGT
```

-continued

```
ATATAAAATTATTCATAATGATAGTAGGAGGCTTGGTAGGTTTAAGAATAGTTTT
TGCTGTACTTTCTATAGTGAATAGAGTTAGGCAGGGATATTCACCATTATCGTTTC
AGACCCACCTCCCAACCCCGAGGGGACCCGACAGGCCCGAAGGAATAGAAGAA
GAAGGTGGAGAGAGAGACAGAGACAGATCCATTCGATTAGTGAACGGATCCTTG
GCACTTATCTGGGACGATCTGCGGAGCCTGTGCCTCTTCAGCTACCACCGCTTGA
GAGACTTACTCTTGATTGTAACGAGGATTGTGGAACTTCTGGGACGCAGGGGGTG
GGAAGCCCTCAAATATTGGTGGAATCTCCTACAGTATTGGAGTCAGGAACTAAA
GAATAGTGCTGTTAGCTTGCTCAATGCCACAGCCATAGCAGTAGCTGAGGGGAC
AGATAGGGTTATAGAAGTAGTACAAGGAGCTTGTAGAGCTATTCGCCACATACC
TAGAAGAATAAGACAGGGCTTGGAAAGGATTTTGCTATAAGATGGGTGGCAAGT
GGTCAAAAGTAGTGTGATTGGATGGCCTACTGTAAGGGAAAGAATGAGACGAG
CTGAGCCAGCAGCAGATAGGGTGGGAGCAGCATCTCGAGACCTGGAAAAACATG
GAGCAATCACAAGTAGCAATACAGCAGCTACCAATGCTGCTTGTGCCTGGCTAG
AAGCACAAGAGGAGGAGGAGGTGGGTTTTCCAGTCACACCTCAGGTACCTTTAA
GACCAATGACTTACAAGGCAGCTGTAGATCTTAGCCACTTTTTAAAAGAAAAGG
GGGGACTGGAAGGGCTAATTCACTCCCAAAGAAGACAAGATATCCTTGATCTGT
GGATCTACCACACACAAGGCTACTTCCCTGATTAGCAGAACTACACACCAGGGC
CAGGGGTCAGATATCCACTGACCTTTGGATGGTGCTACAAGCTAGTACCAGTTGA
GCCAGATAAGATAGAAGAGGCCAATAAAGGAGAGAACACCAGCTTGTTACACCC
TGTGAGCCTGCATGGGATGGATGACCCGGAGAGAGAAGTGTTAGAGTGGAGGTT
TGACAGCCGCCTAGCATTTCATCACGTGGCCCGAGAGCTGCATCCGGAGTACTTC
AAGAACTGCTGACATCGAGCTTGCTACAAGGGACTTTCCGCTGGGGACTTTCCAG
GGAGGCGTGGCCTGGGCGGACTGGGGAGTGGCGAGCCCTCAGATCCTGCATAT
AAGCAGCTGCTTTTTGCCTGTACTGGGTCTCTCTGGTTAGACCAGATCTGAGCCT
GGGAGCTCTCTGGCTAACTAGGGAACCCACTGCTTAAGCCTCAATAAAGCTTGCC
TTGAGTGCTTC
```

V. Sequences Shown in Figures

| Sequence | ID |
|---|---|
| CCTGCCATTTGTTTTCCAT | SEQ ID NO: 132 |
| TCACCTGCCATCTGTTTT | SEQ ID NO: 133 |
| CCTGCCATCTGTTTTCCA | SEQ ID NO: 134 |
| TCACCTGCCATCTGTTTG | SEQ ID NO: 135 |
| ATTCCCTACAATCCCCAAAG | SEQ ID NO: 136 |
| TACAATCCCCAAAGTCAAGGAGTAGT | SEQ ID NO: 137 |
| TACAATCCCCAAAGCCAAGGAGTAGT | SEQ ID NO: 138 |
| TACAATCCCCAAAGTCAGGGAGTAGT | SEQ ID NO: 139 |
| ACAGCAGTACAAATGGCAGTATTCAT | SEQ ID NO: 140 |
| ACAGCAGTACAGATGGCAGTATACAT | SEQ ID NO: 141 |
| ACAGCAGTACAGATGGCAGTGTTCAT | SEQ ID NO: 142 |
| ATTCCCTACAATCCCCAAAG | SEQ ID NO: 143 |
| ATTCCCTRCAATCCTCAAAG | SEQ ID NO: 144 |
| ATTCCCTACAATCCTCAAAG | SEQ ID NO: 145 |
| TACAATCCCCAAAGTCAAGGAGTAGT | SEQ ID NO: 146 |
| TRCAATCCTCAAAGTCAAGGAGTAGT | SEQ ID NO: 147 |
| TACAATCCCCAAAGTCRAGGGGTAGT | SEQ ID NO: 148 |
| TACAATCCTCAAAGTCATGGAGTAGT | SEQ ID NO: 149 |
| CACAATTTTAAAAGAAAAGGGG | SEQ ID NO: 150 |
| CASAATTWTAAAAGAAAAGGGG | SEQ ID NO: 151 |
| ACAGMAGTAYAAATSRCAGTAYTYAT | SEQ ID NO: 152 |

Other Embodiments

While a number of embodiments of this invention are described herein, the present disclosure and examples may be altered to provide other methods and compositions of this invention. Therefore, it will be appreciated that the scope of this invention is to be defined by the appended claims in addition to the specific embodiments that have been represented by way of example. All references cited herein are hereby incorporated by reference.

The invention claimed is:

1. A composition comprising a pair of oligonucleotide primers and at least one probe,
wherein the pair of oligonucleotide primers comprises a forward oligonucleotide primer and a reverse oligonucleotide primer that upon hybridization to an HIV nucleic acid molecule, flank an amplicon sequence;
wherein the forward oligonucleotide primer comprises a nucleic acid sequence according to one of SEQ ID NOs: 23 and 35-39 and the reverse oligonucleotide primer comprises a nucleic acid sequence complementary to a nucleic acid sequence according to one of SEQ ID NOs: 40 and 52-55; and
wherein the at least one probe comprises a labeled oligonucleotide probe comprising a fluorescent moiety.

2. A composition that is an amplification reaction mixture, the composition comprising:
an HIV nucleic acid molecule;
a pair of oligonucleotide primers comprising a forward oligonucleotide primer and a reverse oligonucleotide primer that, upon hybridization to the HIV nucleic acid molecule, flank an amplicon sequence, wherein the forward oligonucleotide primer comprises a nucleic acid sequence according to one of SEQ ID NOs: 23 and 35-39 and the reverse oligonucleotide primer comprises a nucleic acid sequence complementary to a nucleic acid sequence according to one of SEQ ID NOs: 40 and 52-55;
at least one probe, wherein the at least one probe comprises a labeled oligonucleotide probe comprising a fluorescent moiety; and
an amplicon molecule having a sequence derived from a portion of the HIV nucleic acid molecule sequence, and the sequence of the forward oligonucleotide primer or the sequence of the reverse oligonucleotide primer.

3. The composition of claim 1 or 2, wherein the at least one probe comprises at least 15 consecutive nucleotides of a nucleic acid sequence having at least 80% sequence identity with one of SEQ ID NOs: 56-84.

4. A kit comprising:
a pair of oligonucleotide primers comprising a forward oligonucleotide primer and a reverse oligonucleotide primer that, upon hybridization to an HIV nucleic acid molecule, flank an amplicon sequence, wherein the forward oligonucleotide primer comprises a nucleic acid sequence according to one of SEQ ID NOs: 23 and 35-39 and the reverse oligonucleotide primer comprises a nucleic acid sequence complementary to a nucleic acid sequence according to one of SEQ ID NOs: 40 and 52-55; and
at least one probe, wherein the at least one probe comprises a labeled oligonucleotide probe comprising a fluorescent moiety.

5. The composition of claim 1, wherein the forward oligonucleotide primer comprises no more than two mismatched nucleotides, in that no more than two nucleotides differ from the sequence of a corresponding portion of the HIV nucleic acid molecule.

6. The composition of claim 1, wherein the reverse oligonucleotide primer comprises no more than two mismatched nucleotides, in that no more than two nucleotides differ from the sequence of a corresponding portion of the HIV nucleic acid molecule.

7. The composition of claim 1, wherein the composition comprises a first probe and a second probe, the first probe comprising at least 15 consecutive nucleotides of a nucleic acid sequence having at least 80% sequence identity with one of SEQ ID NOs: 56-67 and the second probe comprising at least 15 consecutive nucleotides of a nucleic acid sequence having at least 80% sequence identity with one of SEQ ID NOs: 68-79.

8. The composition of claim 7, wherein the first probe comprises at least 15 consecutive nucleotides of a nucleic acid sequence having at least 80% sequence identity with SEQ ID NO: 56 and the second probe comprises at least 15 consecutive nucleotides of a nucleic acid sequence having at least 80% sequence identity with SEQ ID NO: 68.

9. The composition of claim 8, wherein the first probe comprises the sequence of SEQ ID NO: 56 and the second probe comprises the sequence of SEQ ID NO: 68.

10. The composition of claim 7, wherein:
a) the first probe comprises at least 15 consecutive nucleotides of a nucleic acid sequence having at least 80% sequence identity with SEQ ID NO: 57 and the second probe comprises at least 15 consecutive nucleotides of a nucleic acid sequence having at least 80% sequence identity with SEQ ID NO: 69;
b) the first probe comprises at least 15 consecutive nucleotides of a nucleic acid sequence having at least 80% sequence identity with SEQ ID NO: 58 and the second probe comprises at least 15 consecutive nucleotides of a nucleic acid sequence having at least 80% sequence identity with SEQ ID NO: 70;
c) the first probe comprises at least 15 consecutive nucleotides of a nucleic acid sequence having at least 80% sequence identity with SEQ ID NO: 59 and the second probe comprises at least 15 consecutive nucleotides of a nucleic acid sequence having at least 80% sequence identity with SEQ ID NO: 71;
d) the first probe comprises at least 15 consecutive nucleotides of a nucleic acid sequence having at least 80% sequence identity with SEQ ID NO: 60 and the second probe comprises at least 15 consecutive nucleotides of a nucleic acid sequence having at least 80% sequence identity with SEQ ID NO: 72;

e) the first probe comprises at least 15 consecutive nucleotides of a nucleic acid sequence having at least 80% sequence identity with SEQ ID NO: 61 and the second probe comprises at least 15 consecutive nucleotides of a nucleic acid sequence having at least 80% sequence identity with SEQ ID NO: 73;

f) the first probe comprises at least 15 consecutive nucleotides of a nucleic acid sequence having at least 80% sequence identity with SEQ ID NO: 62 and the second probe comprises at least 15 consecutive nucleotides of a nucleic acid sequence having at least 80% sequence identity with SEQ ID NO: 74;

g) the first probe comprises at least 15 consecutive nucleotides of a nucleic acid sequence having at least 80% sequence identity with SEQ ID NO: 63 and the second probe comprises at least 15 consecutive nucleotides of a nucleic acid sequence having at least 80% sequence identity with SEQ ID NO: 75;

h) the first probe comprises at least 15 consecutive nucleotides of a nucleic acid sequence having at least 80% sequence identity with SEQ ID NO: 64 and the second probe comprises at least 15 consecutive nucleotides of a nucleic acid sequence having at least 80% sequence identity with SEQ ID NO: 76;

i) the first probe comprises at least 15 consecutive nucleotides of a nucleic acid sequence having at least 80% sequence identity with SEQ ID NO: 65 and the second probe comprises at least 15 consecutive nucleotides of a nucleic acid sequence having at least 80% sequence identity with SEQ ID NO: 77;

j) the first probe comprises at least 15 consecutive nucleotides of a nucleic acid sequence having at least 80% sequence identity with SEQ ID NO: 66 and the second probe comprises at least 15 consecutive nucleotides of a nucleic acid sequence having at least 80% sequence identity with SEQ ID NO: 78; or k) the first probe comprises at least 15 consecutive nucleotides of a nucleic acid sequence having at least 80% sequence identity with SEQ ID NO: 67 and the second probe comprises at least 15 consecutive nucleotides of a nucleic acid sequence having at least 80% sequence identity with SEQ ID NO: 79.

11. The composition of claim 3, wherein the at least one probe comprises at least 15 consecutive nucleotides of a nucleic acid sequence having at least 80% sequence identity with one of SEQ ID NOs: 107-128.

12. The composition of claim 11, wherein the composition comprises a first probe and a second probe, the first probe comprising at least 15 consecutive nucleotides of a nucleic acid sequence having at least 80% sequence identity with one of SEQ ID NOs: 107-117 and the second probe comprising at least 15 consecutive nucleotides of a nucleic acid sequence having at least 80% sequence identity with one of SEQ ID NOs: 118-128.

13. The composition of claim 12, wherein:

a) the first probe comprises at least 15 consecutive nucleotides of a nucleic acid sequence having at least 80% sequence identity with SEQ ID NO: 107 and the second probe comprises at least 15 consecutive nucleotides of a nucleic acid sequence having at least 80% sequence identity with SEQ ID NO: 118;

b) the first probe comprises at least 15 consecutive nucleotides of a nucleic acid sequence having at least 80% sequence identity with SEQ ID NO: 108 and the second probe comprises at least 15 consecutive nucleotides of a nucleic acid sequence having at least 80% sequence identity with SEQ ID NO: 119;

c) the first probe comprises at least 15 consecutive nucleotides of a nucleic acid sequence having at least 80% sequence identity with SEQ ID NO: 109 and the second probe comprises at least 15 consecutive nucleotides of a nucleic acid sequence having at least 80% sequence identity with SEQ ID NO: 120;

d) the first probe comprises at least 15 consecutive nucleotides of a nucleic acid sequence having at least 80% sequence identity with SEQ ID NO: 110 and the second probe comprises at least 15 consecutive nucleotides of a nucleic acid sequence having at least 80% sequence identity with SEQ ID NO: 121;

e) the first probe comprises at least 15 consecutive nucleotides of a nucleic acid sequence having at least 80% sequence identity with SEQ ID NO: 111 and the second probe comprises at least 15 consecutive nucleotides of a nucleic acid sequence having at least 80% sequence identity with SEQ ID NO: 122;

f) the first probe comprises at least 15 consecutive nucleotides of a nucleic acid sequence having at least 80% sequence identity with SEQ ID NO: 112 and the second probe comprises at least 15 consecutive nucleotides of a nucleic acid sequence having at least 80% sequence identity with SEQ ID NO: 123;

g) the first probe comprises at least 15 consecutive nucleotides of a nucleic acid sequence having at least 80% sequence identity with SEQ ID NO: 113 and the second probe comprises at least 15 consecutive nucleotides of a nucleic acid sequence having at least 80% sequence identity with SEQ ID NO: 124;

h) the first probe comprises at least 15 consecutive nucleotides of a nucleic acid sequence having at least 80% sequence identity with SEQ ID NO: 114 and the second probe comprises at least 15 consecutive nucleotides of a nucleic acid sequence having at least 80% sequence identity with SEQ ID NO: 125;

i) the first probe comprises at least 15 consecutive nucleotides of a nucleic acid sequence having at least 80% sequence identity with SEQ ID NO: 115 and the second probe comprises at least 15 consecutive nucleotides of a nucleic acid sequence having at least 80% sequence identity with SEQ ID NO: 126;

j) the first probe comprises at least 15 consecutive nucleotides of a nucleic acid sequence having at least 80% sequence identity with SEQ ID NO: 116 and the second probe comprises at least 15 consecutive nucleotides of a nucleic acid sequence having at least 80% sequence identity with SEQ ID NO: 127; or k) the first probe comprises at least 15 consecutive nucleotides of a nucleic acid sequence having at least 80% sequence identity with SEQ ID NO: 117 and the second probe comprises at least 15 consecutive nucleotides of a nucleic acid sequence having at least 80% sequence identity with SEQ ID NO: 128.

14. The composition of claim 7, wherein one or both of the first probe and the second probe comprises, includes no more than two mismatched nucleotides, in that no more than two nucleotides differ from the sequence of a corresponding portion of the HIV nucleic acid molecule.

15. A composition comprising:

a pair of oligonucleotide primers comprising a forward oligonucleotide primer and a reverse oligonucleotide primer that, upon hybridization to the HIV nucleic acid molecule, flank an amplicon sequence, wherein the forward oligonucleotide primer comprises a nucleic acid sequence according to one of SEQ ID NOs: 23 and 35-39 and the reverse oligonucleotide primer comprises a nucleic acid sequence complementary to a nucleic acid sequence according to one of SEQ ID NOs: 40 and 52-55;

at least one probe, wherein the at least one probe comprises a labeled oligonucleotide probe comprising a fluorescent moiety; and a buffer.

16. The composition of claim 15, wherein the at least one probe comprises at least 15 consecutive nucleotides of a nucleic acid sequence having at least 80% sequence identity with one of SEQ ID NOs: 56-84.

17. The composition of claim 15, wherein the composition comprises a first probe and a second probe, the first probe comprising at least 15 consecutive nucleotides of a nucleic acid sequence having at least 80% sequence identity with one of SEQ ID NOs: 56-67 and the second probe comprising at least 15 consecutive nucleotides of a nucleic acid sequence having at least 80% sequence identity with one of SEQ ID NOs: 68-79.

18. The composition of claim 17, wherein the first probe comprises at least 15 consecutive nucleotides of a nucleic acid sequence having at least 80% sequence identity with SEQ ID NO: 56 and the second probe comprises at least 15 consecutive nucleotides of a nucleic acid sequence having at least 80% sequence identity with SEQ ID NO: 68.

19. The composition of claim 18, wherein the the first probe comprises the sequence of SEQ ID NO: 56 and the second probe comprises the sequence of SEQ ID NO: 68.

20. The composition of claim 17, wherein:
a) the first probe comprises at least 15 consecutive nucleotides of a nucleic acid sequence having at least 80% sequence identity with SEQ ID NO: 57 and the second probe comprises at least 15 consecutive nucleotides of a nucleic acid sequence having at least 80% sequence identity with SEQ ID NO: 69;
b) the first probe comprises at least 15 consecutive nucleotides of a nucleic acid sequence having at least 80% sequence identity with SEQ ID NO: 58 and the second probe comprises at least 15 consecutive nucleotides of a nucleic acid sequence having at least 80% sequence identity with SEQ ID NO: 70;
c) the first probe comprises at least 15 consecutive nucleotides of a nucleic acid sequence having at least 80% sequence identity with SEQ ID NO: 59 and the second probe comprises at least 15 consecutive nucleotides of a nucleic acid sequence having at least 80% sequence identity with SEQ ID NO: 71;
d) the first probe comprises at least 15 consecutive nucleotides of a nucleic acid sequence having at least 80% sequence identity with SEQ ID NO: 60 and the second probe comprises at least 15 consecutive nucleotides of a nucleic acid sequence having at least 80% sequence identity with SEQ ID NO: 72;
e) the first probe comprises at least 15 consecutive nucleotides of a nucleic acid sequence having at least 80% sequence identity with SEQ ID NO: 61 and the second probe comprises at least 15 consecutive nucleotides of a nucleic acid sequence having at least 80% sequence identity with SEQ ID NO: 73;
f) the first probe comprises at least 15 consecutive nucleotides of a nucleic acid sequence having at least 80% sequence identity with SEQ ID NO: 62 and the second probe comprises at least 15 consecutive nucleotides of a nucleic acid sequence having at least 80% sequence identity with SEQ ID NO: 74;
g) the first probe comprises at least 15 consecutive nucleotides of a nucleic acid sequence having at least 80% sequence identity with SEQ ID NO: 63 and the second probe comprises at least 15 consecutive nucleotides of a nucleic acid sequence having at least 80% sequence identity with SEQ ID NO: 75;
h) the first probe comprises at least 15 consecutive nucleotides of a nucleic acid sequence having at least 80% sequence identity with SEQ ID NO: 64 and the second probe comprises at least 15 consecutive nucleotides of a nucleic acid sequence having at least 80% sequence identity with SEQ ID NO: 76;
i) the first probe comprises at least 15 consecutive nucleotides of a nucleic acid sequence having at least 80% sequence identity with SEQ ID NO: 65 and the second probe comprises at least 15 consecutive nucleotides of a nucleic acid sequence having at least 80% sequence identity with SEQ ID NO: 77;
j) the first probe comprises at least 15 consecutive nucleotides of a nucleic acid sequence having at least 80% sequence identity with SEQ ID NO: 66 and the second probe comprises at least 15 consecutive nucleotides of a nucleic acid sequence having at least 80% sequence identity with SEQ ID NO: 78; or
k) the first probe comprises at least 15 consecutive nucleotides of a nucleic acid sequence having at least 80% sequence identity with SEQ ID NO: 67 and the second probe comprises at least 15 consecutive nucleotides of a nucleic acid sequence having at least 80% sequence identity with SEQ ID NO: 79.

21. The composition of claim 16, wherein the at least one probe comprises at least 15 consecutive nucleotides of a nucleic acid sequence having at least 80% sequence identity with one of SEQ ID NOs: 107-128.

22. The composition of claim 21, wherein the first probe comprises at least 15 consecutive nucleotides of a nucleic acid sequence having at least 80% sequence identity with one of SEQ ID NOs: 107-117 and a second probe comprises at least 15 consecutive nucleotides of a nucleic acid sequence having at least 80% sequence identity with one of SEQ ID NOs: 118-128.

23. The composition of claim 22, wherein:
a) the first probe comprises at least 15 consecutive nucleotides of a nucleic acid sequence having at least 80% sequence identity with SEQ ID NO: 107 and the second probe comprises at least 15 consecutive nucleotides of a nucleic acid sequence having at least 80% sequence identity with SEQ ID NO: 118;
b) the first probe comprises at least 15 consecutive nucleotides of a nucleic acid sequence having at least 80% sequence identity with SEQ ID NO: 108 and the second probe comprises at least 15 consecutive nucleotides of a nucleic acid sequence having at least 80% sequence identity with SEQ ID NO: 119;
c) the first probe comprises at least 15 consecutive nucleotides of a nucleic acid sequence having at least 80% sequence identity with SEQ ID NO: 109 and the second probe comprises at least 15 consecutive nucleotides of a nucleic acid sequence having at least 80% sequence identity with SEQ ID NO: 120;
d) the first probe comprises at least 15 consecutive nucleotides of a nucleic acid sequence having at least 80% sequence identity with SEQ ID NO: 110 and the second probe comprises at least 15 consecutive nucleotides of a nucleic acid sequence having at least 80% sequence identity with SEQ ID NO: 121;
e) the first probe comprises at least 15 consecutive nucleotides of a nucleic acid sequence having at least 80% sequence identity with SEQ ID NO: 111 and the second probe comprises at least 15 consecutive nucleotides of a nucleic acid sequence having at least 80% sequence identity with SEQ ID NO: 122;

f) the first probe comprises at least 15 consecutive nucleotides of a nucleic acid sequence having at least 80% sequence identity with SEQ ID NO: 112 and the second probe comprises at least 15 consecutive nucleotides of a nucleic acid sequence having at least 80% sequence identity with SEQ ID NO: 123;

g) the first probe comprises at least 15 consecutive nucleotides of a nucleic acid sequence having at least 80% sequence identity with SEQ ID NO: 113 and the second probe comprises at least 15 consecutive nucleotides of a nucleic acid sequence having at least 80% sequence identity with SEQ ID NO: 124;

h) the first probe comprises at least 15 consecutive nucleotides of a nucleic acid sequence having at least 80% sequence identity with SEQ ID NO: 114 and the second probe comprises at least 15 consecutive nucleotides of a nucleic acid sequence having at least 80% sequence identity with SEQ ID NO: 125;

i) the first probe comprises at least 15 consecutive nucleotides of a nucleic acid sequence having at least 80% sequence identity with SEQ ID NO: 115 and the second probe comprises at least 15 consecutive nucleotides of a nucleic acid sequence having at least 80% sequence identity with SEQ ID NO: 126;

j) the first probe comprises at least 15 consecutive nucleotides of a nucleic acid sequence having at least 80% sequence identity with SEQ ID NO: 116 and the second probe comprises at least 15 consecutive nucleotides of a nucleic acid sequence having at least 80% sequence identity with SEQ ID NO: 127; or k) the first probe comprises at least 15 consecutive nucleotides of a nucleic acid sequence having at least 80% sequence identity with SEQ ID NO: 117 and the second probe comprises at least 15 consecutive nucleotides of a nucleic acid sequence having at least 80% sequence identity with SEQ ID NO: 128.

24. The composition of claim 17, wherein one or both of the first probe and the second probe comprises no more than two mismatched nucleotides, in that no more than two nucleotides differ from the sequence of a corresponding portion of the HIV nucleic acid molecule.

25. The composition of claim 1, 2, or 15, wherein the at least one probe comprises a quenching moiety capable of quenching the signal of the fluorescent moiety.

26. The kit of claim 4, wherein the at least one probe comprises a quenching moiety capable of quenching the signal of the fluorescent moiety.

27. The kit of claim 4, wherein the at least one probe comprises at least 15 consecutive nucleotides of a nucleic acid sequence having at least 80% sequence identity with one of SEQ ID NOs: 56-84.

28. The kit of claim 4, wherein the kit further comprises a positive control sample which comprises an HIV nucleic acid molecule that produces an amplicon molecule when subjected to one or more amplification cycles in the presence of the forward and reverse oligonucleotide primers.

* * * * *

SEQUENCE LISTING

```
<160> NUMBER OF SEQ ID NOS: 152

<210> SEQ ID NO 1
<211> LENGTH: 9684
<212> TYPE: DNA
<213> ORGANISM: Human immunodeficiency virus
<220> FEATURE:
<221> NAME/KEY: modified_base
<222> LOCATION: (2218)..(2218)
<223> OTHER INFORMATION: a, c, t, g, unknown or other
<220> FEATURE:
<221> NAME/KEY: modified_base
<222> LOCATION: (6064)..(6064)
<223> OTHER INFORMATION: a, c, t, g, unknown or other
<220> FEATURE:
<221> NAME/KEY: modified_base
<222> LOCATION: (6796)..(6796)
<223> OTHER INFORMATION: a, c, t, g, unknown or other
<220> FEATURE:
<221> NAME/KEY: modified_base
<222> LOCATION: (7402)..(7402)
<223> OTHER INFORMATION: a, c, t, g, unknown or other
<220> FEATURE:
<221> NAME/KEY: modified_base
<222> LOCATION: (7423)..(7423)
<223> OTHER INFORMATION: a, c, t, g, unknown or other
<220> FEATURE:
<221> NAME/KEY: modified_base
<222> LOCATION: (7426)..(7426)
<223> OTHER INFORMATION: a, c, t, g, unknown or other
<220> FEATURE:
<221> NAME/KEY: modified_base
<222> LOCATION: (7432)..(7433)
<223> OTHER INFORMATION: a, c, t, g, unknown or other
<220> FEATURE:
<221> NAME/KEY: modified_base
<222> LOCATION: (7436)..(7436)
<223> OTHER INFORMATION: a, c, t, g, unknown or other
<220> FEATURE:
<221> NAME/KEY: modified_base
<222> LOCATION: (7543)..(7543)
<223> OTHER INFORMATION: a, c, t, g, unknown or other

<400> SEQUENCE: 1
tggatgggct aatttactcc aagaaaagac aagagatcct tgacttatgg gtctataata      60
cacaaggctt cttccctgat tggcaaaact acacaccagg gccagggatc agatacccac     120
tgtgttttgg atggtgcttc aagctagtac cagttgaccc aagagaagta gaggaggaca     180
acaaaggaga aaacaactgc ctgttacacc ccatgagcca gcatggaata gatgacgaag     240
aaagagaagt gctgatgtgg aagtttgaca gtgccctagc acgaaaacac atagcccgag     300
aactgcatcc agagtactat aaagactgct gacaaagaag tttctaacca ggacttccgc     360
tggggacttt ccaggggagg tgtggccggg gcggagttgg ggagtggcta accctcagat     420
gctgcataaa agcagccgct tttcgcttgt actgggtctc tcttgttaga ccaggtcgag     480
cccgggagct ctctggctag caagggaacc cactgcttaa agcctcaata agcttgcct      540 tgagtgctta aagtggtgtg tgcccgtctg tgttaggact ctggtaacta gagatccctc     600
agaccactct agactgagta aaaatctcta gcagtggcgc ccgaacaggg acttgaaagc     660
gaaagttaat agggactcga agcgaaagt tccagagaag ttctctcgac gcaggactcg     720
gcttgctgag gtgcacacag caagaggcga gagcggcgac tggtgagtac gccaaatttt     780
gactagcgga ggctagaagg agagagatgg gtgcgagagc gtcagtatta agtgggggaa     840
aattagatgc atgggaaaaa attcggttac ggccaggggg aaagaaaaaa tataggatga     900
```

|  |  |
|---|---|
| aacatttagt atgggcaagc agagagttag aaagattcgc acttaaccct ggccttttag | 960 |
| aaacagcaga aggatgtcaa caaataatag aacagttaca gtcaactctc aagacaggat | 1020 |
| cagaagaact taaatcatta tttaatacag tagcaaccct ctggtgcgta caccaaagga | 1080 |
| tagaggtaaa agacaccaag gaagctttag ataaaataga ggaagtacaa aataagagcc | 1140 |
| agcaaaagac acagcaggca gcagctggca caggaagcag cagcaaagtc agccaaaatt | 1200 |
| accctatagt gcaaaatgca caagggcaaa tggtacatca gcctttatca cctagaactt | 1260 |
| tgaatgcatg ggtgaaagta gtagaagaaa agggttttaa cccagaagta atacccatgt | 1320 |
| tctcagcatt atcagaggga gccacccac aagatttaaa tatgatgcta aatatagtgg | 1380 |
| ggggacacca ggcagcaatg caaatgttaa aagaaaccat caatgaggaa gctgcagaat | 1440 |
| gggatagggt acacccagta catgcagggc ctattccacc aggccagatg agggaaccaa | 1500 |
| ggggaagtga catagcagga actactagta cccttcaaga acaaatagga tggatgacaa | 1560 |
| acaatccacc tatcccagtg ggagacatct ataaaaggtg gataatcctg ggattaaata | 1620 |
| aaatagtaag aatgtatagc cctgttagca ttttggacat aagacaaggg ccaaaagaac | 1680 |
| ccttcagaga ctatgtagat aggttctata aaactctcag agcggaacaa gctacacagg | 1740 |
| aggtaaaaaa ctggatgaca gaaaccttgc tagtccaaaa tgcgaatcca gactgtaagt | 1800 |
| ccattttaaa agcattagga acaggagcta cattagaaga aatgatgaca gcatgccagg | 1860 |
| gagtgggagg acctagccat aaagcaaggg ttttggctga ggcaatgagc caagcacaac | 1920 |
| atgcaaatat aatgatgcag agaggcaatt ttaagggcca gaaaagaatt aagtgcttca | 1980 |
| actgtgcaa agaaggacac ctagccgaaa attgcagggc ccctagaaaa aagggttgtt | 2040 |
| ggaaatgtgg gaaggaagga catcaaatga aagactgcac tgagagacag gctaattttt | 2100 |
| tagggaaaat ttggccttcc aacaagggaa ggccggggaa ttttcctcag agcagaccag | 2160 |
| agccaacagc cccaccagca gaaaactggg ggatggggga agagataacc tccttacnga | 2220 |
| agcaggagca gaaagacaag gaacatcctc ctcctttagt ttccctcaaa tcactctttg | 2280 |
| gcaacgaccc cttgtcacag taaaaatagg aggacagctg aaagaagctc tattagatac | 2340 |
| aggagcagat gatacagtat tagaagatat aaatttgcca ggaaaatgga aaccaaaaat | 2400 |
| gatagggga attggaggtt ttatcaaggt aaggcaatat gatcagatac ttatagaaat | 2460 |
| ttgtggaaaa aaggctatag gtacagtatt agtaggacct acacctgtca acataattgg | 2520 |
| acgaaatatg ttgactcaga ttggttgtac tttaaatttc ccaattagtc ctattgacac | 2580 |
| tgtaccagta acattaaagc caggaatgga tggaccaaag gttaaacagt ggccattgac | 2640 |
| agaagaaaaa ataaaagcat taacagaaat ttgtaaagag atggaagagg aaggaaaaat | 2700 |
| ctcaaaaatt gggcctgaaa atccatacaa tactccagta tttgctataa agaaaaagga | 2760 |
| cagcaccaaa tggaggaaat tagtagattt cagagagctc aataaaagaa ctcaggactt | 2820 |
| ttgggaagtt caattaggaa taccgcatcc agcaggttta aaaagaaaa atcagtaac | 2880 |
| agtactagat gtgggagatg catatttttc agttccttta gatgaaagct ttagaaagta | 2940 |
| tactgcattc accataccta gtataaacaa tgagacacca ggaatcagat atcagtacaa | 3000 |
| tgtgctgcca cagggatgga aaggatcacc ggcaatattc cagagtagca tgacaaaaat | 3060 |
| cttagagccc tttagaataa aaaatccaga aatggttatc tatcaataca tggatgactt | 3120 |
| gtatgtagga tctgatttag aaatagggca gcacagaaca aaaatagagg agctaagagc | 3180 |
| tcatctattg agctggggat ttactacacc agacaaaaag catcagaagg aacctccatt | 3240 |
| cctttggatg ggatatgaac tccatcctga cagatggaca gtccagccta tagaactgcc | 3300 |

```
agaaaaagac agctggactg tcaatgatat acagaaatta gtgggaaaac taaattgggc    3360
aagtcaaatt tatgcaggga ttaaggtaaa gcaactgtgt aaactcctca ggggagctaa    3420
agcactaaca gacatagtac cactgactga agaagcagaa ttagagttgg cagagaacag    3480
ggagattcta aaaacccctg tgcatggagt atattatgac ccatcaaaag acttagtagc    3540
agaagtacag aaacaagggc aggaccaatg gacatatcaa atttatcaag agccatttaa    3600
aaatctaaaa acaggaaaat atgccagaaa aaggtctgct cacactaatg atgtaagaca    3660
attaacagaa gtggtgcaaa aaatagccac agaaagcata gtaatatggg gaaagacccc    3720
taaatttaga ctacccatac aaagagaaac atgggaaaca tggtggatgg agtattggca    3780
ggctacctgg attcctgaat gggagtttgt taatacccct cctctagtaa aattatggta    3840
ccaattagaa aaagaccccc atagtaggagc agagactttc tatgtagatg gggcagctag    3900
tagggagact aagctaggaa aagcagggta tgtcactgac agaggaagac aaaaggtagt    3960
ttccctaact gagacaacaa atcaaaagac tgaattacat gcgatccatt tagccttgca    4020
ggattcagga tcagaagtaa atatagtaac agactcacaa tatgcattag gaatcattca    4080
ggcacaacca gacaggagtg aatcagaagt agtcaaccaa ataatagagg agctaataaa    4140
aaaggaaaaa gtctacctgt catgggtacc agcacacaag gggattggag gaaatgaaca    4200
agtagataaa ttagtcagtt caggaatcag gaaggtgcta tttttagatg ggatagataa    4260
ggctcaagaa gaacatgaaa gatatcacag caattggaga acaatggcta gtgattttaa    4320
tttgccacct atagtagcaa aggaaatagt agccaactgt gataaatgtc aactaaaagg    4380
ggaagctatg catggacaag tagactgtag tccagggata tggcaattag attgcacaca    4440
tctagaagga aaagtcatcc tggtagcagt ccacgtggcc agtggatata tagaagcaga    4500
agttatccca gcagaaacag gacaggagac agcatacttt ctgctaaaat tagcaggaag    4560
atggccagta aaagtaatac acacagacaa cggtagcaat ttcaccagcg ctgcagttaa    4620
agcagcctgt tggtgggcca atgtccgaca ggaatttggg atcccctaca atccccaaag    4680
tcaaggagta gtagaatcta tgaataagga attaaagaaa atcatagggc aggtaagaga    4740
gcaagctgaa caccttaaga cagcagtaca atggcagta ttcattcaca attttaaaag    4800
aaaagggggg attggggggt acagtgcagg ggaaagaata atagacataa tagcaacaga    4860
catacaaact aaagaattac aaaaacaaat tacaaaaatt caaaattttc gggtttatta    4920
cagggacagc agagacccaa tttggaaagg accagcaaaa ctactctgga aaggtgaagg    4980
ggcagtagta atacaagaca atagtgatat aaaagtagta ccaagaagaa aagcaaagat    5040
cattagggat tatggaaaac agatggcagg tgatgattgt gtggcaggta gacaggatga    5100
ggattagaac atggaacagt ttagtaaaac atcatatgta tatctcaaag aaagctaaaa    5160
agtggtttta tagacatcat tatgaaagcc agcatccaaa ggtaagttca gaagtacata    5220
tcccactagg agaggctaga ttagtaataa gaacatattg gggtctgcag acaggagaaa    5280
aggactggca attgggtcat ggagtctcca tagaatggag gcagagaaaa tatagcacac    5340
aaatagatcc tgacctagca gaccaactga ttcatctaca atattttgac tgtttttcag    5400
actctgccat aaggaaagcc atattaggac aagtagttag acgtaggtgt gaatatccat    5460
caggacataa caaggtagga tccctacaat atttggcact gaaagcatta acaacaccaa    5520
aaaggataag gccacctctg cctagtgtta agaaattaac agaagataga tggaacaagc    5580
cccagaagat caggggccac agagagaacc ctacaatgaa tggacattag aactgttaga    5640
```

```
ggagcttaaa aatgaagctg ttagacattt tcctaggccc tggctccatg gcttaggaca    5700
gtacatctat aacaattatg gggatacttg ggaaggggtt gaagctataa taagaatttt    5760
gcaacaacta ctgtttgttc atttcagaat tgggtgtcaa catagcagaa taggcattat    5820
accagggaga agaggcagga atggagccgg tagatcctaa cctagagccc tggaatcatc    5880
cgggaagtca gcctacaact gcttgtagca agtgttactg taaaatatgt tgctggcatt    5940
gccaactatg ctttctgaaa aaggcttag gcatctccta tggcaggaag aagcggaagc     6000
accgacgagg aactcctcag agcagtaagg atcatcaaaa tcctatacca gagcagtaag    6060
taanaagtat atgtaatgtc acctttggaa attagtgcaa tagtaggact gatagtagcg    6120
ctaatcttag caatagtagt gtggactata gtagctatag aatttaagaa aatactaagg    6180
caaagaaaaa tagacaggtt agttaagaga ataagagaaa gagcagaaga cagtggaaat    6240
gagagtgaag gagacacaga tgaattggcc aaacttgtgg aaatggggga ctttgatcct    6300
tgggttggtg ataatttgta gtgcctcaga caacttgtgg gttacagttt attatggggt    6360
tcctgtgtgg agagatgcag ataccaccct attttgtgca tcagatgcca aagcacatga    6420
gacagaagtg cacaatgtct gggccacaca tgcctgtgta cccacagacc ccaacccaca    6480
agaaatacac ctggaaaatg taacagaaaa ttttaacatg tggaaaaata acatggtaga    6540
gcagatgcag gaggatgtaa tcagtttatg ggatcaaagt ctaaagccat gtgtaaagtt    6600
aactcctctc tgcgttactt taaattgtac caatgctaat ttgaccaatg tcaataacac    6660
aaccaatgtc tctaacataa taggaaatat aacagatgaa gtaagaaact gttcttttaa    6720
tatgaccaca gaactaagag ataagaagca gaaggtccat gcactttttt ataagcttga    6780
tatagtacaa attganaata aaatagtagt gagtataggt taataaattg taatacttca    6840
gtcattaagc aggcttgtcc aaagatatcc tttgatccaa ttcctataca ttattgtact    6900
ccagctggtt atgcgatttt aaagtgtaat gataagaatt tcaatgggac agggccatgt    6960
aaaaatgtca gctcagtaca atgcacacat ggaattaagc cagtggtatc aactcaattg    7020
ctgttaaatg gcagtctagc agaagaagag ataataatca gatctgaaaa tctcacaaac    7080
aatgccaaaa ccataatagt gcaccttaat aaatctgtag aaatcaattg taccagaccc    7140
tccaacaata caagaacaag tataactata ggaccaggac aagtattcta tagaacagga    7200
gacataatag gagatataag aaaagcatat tgtgagatta atggaacaaa atggaatgaa    7260
gttttaaaac aggtaactga aaaattaaaa gagcacttta ataataagac aataatcttt    7320
caaccaccct caggaggaga tctagaaatt acaatgcatc attttaattg tagagggga    7380 tttttctatt gcaatacaac anaactgttt aataatactt gcntangaaa tnnaancagg    7440
aggggtgtaa tggcactatc acacttccat gcaagataaa gcaaattata acatgtggc    7500 agggagcagg acaagcaatg tatgctcctc ccatcagtgg aanaattaat tgtgtatcaa    7560 atattcagg aatactattg acaagagatg gtggtgctaa taacgaat aacgagacct     7620 tcagacctgg aggaggaaat ataaaggaca attggagaag tgaattatat aaatataaag    7680
tagtacaaat tgaaccacta ggaatagcac ccaccagggc aaagagaaga gtggtggaga    7740
gagaaaaaag agcagtggga ataggagcta tgatctttgg gttcttagga gcagcaggaa    7800
gcactatggg cgcggcgtca ataacgctga cggtacaggc cagacaatta ttgtctggta    7860
tagtgcaaca gcaaagcaat ttgctgaggg ctatagaggc gcagcagcat ctgttgcaac    7920
tcacagtctg gggcattaaa cagctccagg caagagtcct ggctgtggaa agataccta    7980 aggatcaaaa gttcctagga ctttgggct gctctggaaa aatcatctgc accactgctg    8040
```

-continued

```
tgccctggaa ctccacttgg agtaataaat cttttgaaga gatttggaac aacatgacat    8100
ggatagaatg ggagagagaa attagcaatt acacaaacca aatatatgag atacttacag    8160
aatcgcagaa ccagcaggac aggaatgaaa aggatttgtt agaattggat aaatgggcaa    8220
gtctgtggaa ttggtttgac ataacaaatt ggctgtggta tataaaaata tttataatga    8280
tagtaggagg tttaataggt ttaagaataa ttttgctgt gctttctata gtaaatagag     8340
ttaggcaggg atactcacct ttgtctttcc agacccctac ccatcatcag agggaacccg    8400
acagacccga agaatcgaa gaaggaggtg gcgagcaagg cagagacaga tccgtgcgat     8460
tagtgagcgg attcttagca cttgcctggg acgatctacg gagcctgtgc ctcttcagct    8520
accaccgctt gagagacttc atcttgattg cagcgaggac tgtggaactt ctgggacaca    8580
gcagtctcaa gggactgaga cggggtgggg aaggcctcaa atatctgggg aatcttctgt    8640
tatattgggg ccaggaacta aaaattagtg ctatttcttt gcttgatgct acagcaatag    8700
cagtagcggg gtggacagat agggttatag aagtagcaca aggagcttgg agagccattc    8760
tccacatacc tagaagaatc agacagggct tagaaagggc tttgctataa catgggaggc    8820
aagtggtcaa aaagtagcat agtgggatgg cctcaggtca gggaaagaat aaagcaaact    8880
cctccagcag cagaaggagt aggagcagta tctcaagatc tagataaaca tggagcagta    8940
acaagtagta atatgaataa tgctgattgt gtctggctga gcacaagag ggaagaggag      9000
gtaggctttc cagtcaggcc gcaggtacct ctaagaccaa tgacttataa gggagctttt    9060
gatcttagct tctttttaaa agaaaagggg ggactggatg ggctaattta ctccaagaaa    9120
agacaagaga tccttgactt atgggtctat aatacacaag gcttcttccc tgattggcaa    9180
aactacacac cagggccagg gatcagatac ccactgtgtt ttggatggtg cttcaagcta    9240
gtaccagttg acccaagaga agtagaggag gacaacaaag gagaaaacaa ctgcctgtta    9300
caccccatga gccagcatgg aatagaggac gaagaaagag aagtgctgat gtggaagttt    9360
gacagtgccc tagcacgaaa acacatagcc cgagaactgc atccagagta ctataaagac    9420
tgctgacaaa gaagtttcta actaggactt ccgctgggga cttccaggg gaggtgtggc     9480
cggggcggag ttggggagtg gctaaccctc agatgctgca taaaagcagc cgcttttcgc    9540
ttgtactggg tctctcttgt tagaccaggt cgagcccggg agctctctgg ctagcaaggg    9600
aacccactgc ttaaagcctc aataaagctt gccttgagtg cttaaagtgg tgtgtgcccg    9660
tctgtgttag gactctggta acta                                           9684
```

<210> SEQ ID NO 2
<211> LENGTH: 9186
<212> TYPE: DNA
<213> ORGANISM: Human immunodeficiency virus
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (6)..(9)
<223> OTHER INFORMATION: a, c, t, g, unknown or other
<220> FEATURE:
<221> NAME/KEY: modified_base
<222> LOCATION: (57)..(57)
<223> OTHER INFORMATION: a, c, t, g, unknown or other
<220> FEATURE:
<221> NAME/KEY: modified_base
<222> LOCATION: (101)..(101)
<223> OTHER INFORMATION: a, c, t, g, unknown or other
<220> FEATURE:

-continued

```
<221> NAME/KEY: modified_base
<222> LOCATION: (108)..(109)
<223> OTHER INFORMATION: a, c, t, g, unknown or other
<220> FEATURE:
<221> NAME/KEY: modified_base
<222> LOCATION: (113)..(113)
<223> OTHER INFORMATION: a, c, t, g, unknown or other
<220> FEATURE:
<221> NAME/KEY: modified_base
<222> LOCATION: (115)..(115)
<223> OTHER INFORMATION: a, c, t, g, unknown or other
<220> FEATURE:
<221> NAME/KEY: modified_base
<222> LOCATION: (153)..(153)
<223> OTHER INFORMATION: a, c, t, g, unknown or other
<220> FEATURE:
<221> NAME/KEY: modified_base
<222> LOCATION: (163)..(163)
<223> OTHER INFORMATION: a, c, t, g, unknown or other
<220> FEATURE:
<221> NAME/KEY: modified_base
<222> LOCATION: (174)..(174)
<223> OTHER INFORMATION: a, c, t, g, unknown or other
<220> FEATURE:
<221> NAME/KEY: modified_base
<222> LOCATION: (187)..(187)
<223> OTHER INFORMATION: a, c, t, g, unknown or other
<220> FEATURE:
<221> NAME/KEY: modified_base
<222> LOCATION: (198)..(198)
<223> OTHER INFORMATION: a, c, t, g, unknown or other
<220> FEATURE:
<221> NAME/KEY: modified_base
<222> LOCATION: (200)..(200)
<223> OTHER INFORMATION: a, c, t, g, unknown or other
<220> FEATURE:
<221> NAME/KEY: modified_base
<222> LOCATION: (209)..(209)
<223> OTHER INFORMATION: a, c, t, g, unknown or other
<220> FEATURE:
<221> NAME/KEY: modified_base
<222> LOCATION: (218)..(218)
<223> OTHER INFORMATION: a, c, t, g, unknown or other
<220> FEATURE:
<221> NAME/KEY: modified_base
<222> LOCATION: (242)..(242)
<223> OTHER INFORMATION: a, c, t, g, unknown or other
<220> FEATURE:
<221> NAME/KEY: modified_base
<222> LOCATION: (262)..(263)
<223> OTHER INFORMATION: a, c, t, g, unknown or other
<220> FEATURE:
<221> NAME/KEY: modified_base
<222> LOCATION: (273)..(274)
<223> OTHER INFORMATION: a, c, t, g, unknown or other
<220> FEATURE:
<221> NAME/KEY: modified_base
<222> LOCATION: (282)..(282)
<223> OTHER INFORMATION: a, c, t, g, unknown or other
<220> FEATURE:
<221> NAME/KEY: modified_base
<222> LOCATION: (284)..(284)
<223> OTHER INFORMATION: a, c, t, g, unknown or other
<220> FEATURE:
<221> NAME/KEY: modified_base
<222> LOCATION: (286)..(286)
<223> OTHER INFORMATION: a, c, t, g, unknown or other
<220> FEATURE:
<221> NAME/KEY: modified_base
<222> LOCATION: (293)..(293)
<223> OTHER INFORMATION: a, c, t, g, unknown or other
<220> FEATURE:
<221> NAME/KEY: modified_base
<222> LOCATION: (304)..(305)
<223> OTHER INFORMATION: a, c, t, g, unknown or other
<220> FEATURE:
<221> NAME/KEY: modified_base
<222> LOCATION: (315)..(317)
<223> OTHER INFORMATION: a, c, t, g, unknown or other
```

-continued

```
<220> FEATURE:
<221> NAME/KEY: modified_base
<222> LOCATION: (340)..(340)
<223> OTHER INFORMATION: a, c, t, g, unknown or other
<220> FEATURE:
<221> NAME/KEY: modified_base
<222> LOCATION: (350)..(350)
<223> OTHER INFORMATION: a, c, t, g, unknown or other
<220> FEATURE:
<221> NAME/KEY: modified_base
<222> LOCATION: (376)..(376)
<223> OTHER INFORMATION: a, c, t, g, unknown or other
<220> FEATURE:
<221> NAME/KEY: modified_base
<222> LOCATION: (383)..(383)
<223> OTHER INFORMATION: a, c, t, g, unknown or other
<220> FEATURE:
<221> NAME/KEY: modified_base
<222> LOCATION: (386)..(389)
<223> OTHER INFORMATION: a, c, t, g, unknown or other
<220> FEATURE:
<221> NAME/KEY: modified_base
<222> LOCATION: (420)..(420)
<223> OTHER INFORMATION: a, c, t, g, unknown or other
<220> FEATURE:
<221> NAME/KEY: modified_base
<222> LOCATION: (505)..(505)
<223> OTHER INFORMATION: a, c, t, g, unknown or other
<220> FEATURE:
<221> NAME/KEY: modified_base
<222> LOCATION: (658)..(658)
<223> OTHER INFORMATION: a, c, t, g, unknown or other
<220> FEATURE:
<221> NAME/KEY: modified_base
<222> LOCATION: (661)..(661)
<223> OTHER INFORMATION: a, c, t, g, unknown or other
<220> FEATURE:
<221> NAME/KEY: modified_base
<222> LOCATION: (3511)..(3511)
<223> OTHER INFORMATION: a, c, t, g, unknown or other
<220> FEATURE:
<221> NAME/KEY: modified_base
<222> LOCATION: (5935)..(5935)
<223> OTHER INFORMATION: a, c, t, g, unknown or other
<220> FEATURE:
<221> NAME/KEY: modified_base
<222> LOCATION: (6625)..(6625)
<223> OTHER INFORMATION: a, c, t, g, unknown or other
<220> FEATURE:
<221> NAME/KEY: modified_base
<222> LOCATION: (6654)..(6654)
<223> OTHER INFORMATION: a, c, t, g, unknown or other
<220> FEATURE:
<221> NAME/KEY: modified_base
<222> LOCATION: (7407)..(7407)
<223> OTHER INFORMATION: a, c, t, g, unknown or other
<220> FEATURE:
<221> NAME/KEY: modified_base
<222> LOCATION: (7414)..(7414)
<223> OTHER INFORMATION: a, c, t, g, unknown or other
<220> FEATURE:
<221> NAME/KEY: modified_base
<222> LOCATION: (8540)..(8540)
<223> OTHER INFORMATION: a, c, t, g, unknown or other
<220> FEATURE:
<221> NAME/KEY: modified_base
<222> LOCATION: (8771)..(8771)
<223> OTHER INFORMATION: a, c, t, g, unknown or other
<220> FEATURE:
<221> NAME/KEY: modified_base
<222> LOCATION: (8773)..(8773)
<223> OTHER INFORMATION: a, c, t, g, unknown or other

<400> SEQUENCE: 2
tggntnnnnt aatttactcc aagaaaagac aagagatcct tgatctgtgg gtctatnaca    60
cacaaggatt cttcccagat tggcagaact acacaccagg nccagggnnt agntncccac   120
```

```
tgacctttgg gtggtgcttc aaactagtac cantggatcc agnagagata gagnaagcca      180
atgaagnaga gaacaacngn ttattacanc ccatctgnca gcatggaatg gaggacgaag      240
anagagaagt gctggtctgg anntttgaca gtnncctggc antnanacac atngctcgag      300
aganncatcc ggagnnntac aaagactgct gacacagaan ttgctgacan gggactttcc      360
gctggggact ttccgnggga ggngtnnnnt gggaggagtt ggggagtggc tagccctcan      420
atgctgcata taagcagctg cttctcgcct gtactgggtc tctcttgcta gaccagatct      480
gagcctggga gctctctggc tagcnggga acccactgct taagcctcaa taaagcttgc      540
cttgagtgct tcaagtagtg tgtgcccgtc tgttgtgtga ctctggtaac tagagatccc      600
tcagaccact ctagactgtg taaaaatctc tagcagtggc gcccgaacag ggacttgnag      660
ntaataggga ctcgaaagcg aaagttccag agaagatctc tcgacgcagg gactcggctt      720
gctgaggtgc acacagcaag aggcgagagc ggcgactggt gagtacgcca aattttgact      780
agcggaggct agaaggagag atgggtgcg gagagcgtca gtattaagtg ggggaaaatt      840
agatgcatgg gagaaaattc ggttaaggcc aggggggaaag aaaaaatata gactaaaaca      900
tctagtatgg gcaagcaggg agctggaaag attcgcactt aaccctggcc ttttagaaac      960
agcagaagga tgtcaacaaa taatggaaca gttacaatca actctcaaga caggatcaga      1020
agaacttaaa tcattattta atacaatagc aacccctttgg tgcgtacatc aaaggataga      1080
cataaaagac accaaggaag ccttagataa aatagaggaa atacaaaata gagcaagca      1140 aaagacacag caggcagcag ctgccacagg aagcagcagc caaaattacc ctatagtgca      1200
aaatgcacaa gggcaaatga cacatcagac catgtcacct aggactttga atgcatgggt      1260
gaaggtaata gaagaaaagg cttttcagccc agaagtaata cccatgtttt cagcattatc      1320
agagggagcc accccacaag atttaaatat gatgctaaac atagtggggg acaccaggc       1380 agcaatgcag atgttaaaag ataccatcaa tgaggaagct gcagaatggg acagggtaca      1440
tccagtacat gcagggccta ttccaccagg ccagatgagg gaaccaaggg gaagtgacat      1500
agcaggaact actagtaccc ttcaagaaca aataggatgg atgacaagca atccacctat      1560
cccagtggga gaaatctata aaagatggat aatcctggga ttaaataaaa tagtaagaat      1620
gtatagccct gtcagcattt tggacataag acaagggcca aaagaaccct ttagagatta      1680
tgtagatagg ttcttaaaa ctttgagagc tgaacaagct acgcaggagg taaaaaactg      1740
gatgacagaa accttgctgg tccaaaatgc gaatccagac tgtaagtcca ttttaagagc      1800
attaggacca ggggctacat tagaagaaat gatgacagca tgtcagggag tgggaggacc      1860
tggccataaa gcaagggttt tggctgaggc aatgagtcaa gtacaacagg ccaacataat      1920
gatgcagaga ggcaatttta ggggccagag aacaataaag tgtttcaact gtggcaaaga      1980
aggacaccta gccagaaatt gcaaggcccc taggaaaagg ggctgttgga aatgtgggaa      2040
ggaaggacac caaatgaaag actgtactga gagacaggct aattttttag ggaaaatttg      2100
gccttccagc aaggggaggc caggaaattt tcctcagagc agaccggaac caacagcccc      2160
accagcagag agctttggga tggggaaga gataacctcc tctccgaagc aggaaccgag      2220
ggacaaggga ctatatcctc ctttaacttc cctcaaatca ctctttggca acgacccta      2280 gtcacagtaa gaatagggg acagctaata gaagccctat tagacacagg agcagatgat      2340
acagtattag aagaaataaa tttaccagga aaatggaaac caaaatgat aggggaatt       2400 ggaggtttta tcaaagtaag acagtatgat cagatactta tagaaatttg tggaaaaaag      2460
gccataggta cagtattagt aggacctaca cctgtcaaca taattggacg aaatatgttg      2520
```

-continued

```
actcagattg gttgtacttt aaattttcca attagtccta ttgaaactgt gccagtaaaa    2580
ttaaagccag gaatggatgg cccaaaggtt aaacaatggc cattgacaga agaaaaaata    2640
aaagcattaa cagaaatttg tacagagatg gaaaggaag gaaaaatttc aaaaattggg     2700
cctgaaaatc catacaatac tccagtattt gccataaaga aaaagataag tactaaatgg    2760
agaaaattag tagatttcag agaactcaat aagagaactc aagacttctg ggaggtccaa    2820
ttaggaatac ctcatcccgc gggattaaaa agaaaaaat cagtaacagt actagatgtg     2880
ggggatgcat atttttcagt tcccttagat aaagacttta gaaagtatac tgcattcact    2940
atacctagtg taaataatga gacaccaggg attagatatc agtacaatgt gcttccacag    3000
ggatggaaag gatcaccagc aatatttcag gcaagcatga caaaaatctt agagcccttt    3060
agaacaaaaa atccagagat agtgatctac caatatatgg atgatttata tgtaggatct    3120
gacttagaga tagggcagca tagagcaaaa atagaggagt tgagagaaca tctactgaga    3180
tggggattta ccacaccaga caaaaaacat cagaaagaac ctccatttct ttggatggga    3240
tatgaactcc atcctgacaa atggacagtc cagcctatac agctgccaga aaaagacagc    3300
tggactgtca atgatataca gaaattagtg ggaaaactaa attgggcaag tcagatttat    3360
gcaggaatta aagtaaagca actgtgtaaa ctcctcaggg gagccaaagc actaacagat    3420
atagtaacac tgactgagga agcagaatta gaattggcag agaacaggga aattctaaaa    3480
gaacctgtac atggagtata ttatgaccca ncaaaagact tagtagcaga aatacagaaa    3540
caagggcaag accaatggac atatcaaatt tatcaagagc catttaaaaa tctaaaaaca    3600
ggaaaatatg caaaaaagag gtctgcccac actaatgatg taaaacaatt aacagaggta    3660
gtgcaaaaag tggctacaga aagcatagta atatggggaa agaccctaa atttagacta    3720 cccatacaaa gagaaacatg gaagcatgg tggatggagt attggcaggc tacctggatt    3780
cctgaatggg agtttgtcaa tacccctcct ctagtaaaat tatggtacca gttagagaaa    3840
gaccccatag taggagcaga aactttctat gtagatgggg cagctaatag ggagactaag    3900
ctaggaaaag cagggtatgt cactgacaga ggaagacaaa aggttgtttc cctaactgag    3960
acaacaaatc aaaagactga attacatgca attcatctag ccttgcagga ttcaggatca    4020
gaagtaaata tagtaacaga ctcacagtat gcattaggaa tcattcaggc acaaccagac    4080
aggagtgaat cagagttagt caatcaaata atagagaagc taatagaaaa ggacaaagtc    4140
tacctgtcat gggtaccagc acacaaaggg attggaggaa atgaacaagt agataaatta    4200
gtcagtaatg gaatcaggaa agtactattt ttagatggca tagataaagc ccaagaagag    4260
catgaaagat atcacagcaa ttggagagca atggctagtg attttaatct gccacctata    4320
gtagcaaaag aaatagtggc cagctgtgat aaatgtcagc taaaagggga agccatgcat    4380
ggacaagtag actgtagtcc aggaatatgg caattagatt gtacacattt agaaggaaaa    4440
attatcctgg tagcagtcca tgtagccagt ggctatatag aagcagaagt tatcccagca    4500
gaaacaggac aggagacagc atactttata ttaaaattag caggaagatg gccagtgaaa    4560
gtaatacaca cagacaatgg cagcaatttc accagtgctg cagtaaaggc agcatgttgg    4620
tgggcaaatg tcacacaaga atttggaatt ccctacaatc cccaaagcca aggagtagtg    4680
gaatctatga ataaagaatt aaagaaaatt atagggcagg tcagggatca agctgaacac    4740
cttaagacag cagtacagat ggcagtattc attcacaatt ttaaaagaaa aggggggatt    4800
ggggggtaca gtgcagggga aagaataata gacataatag catcagatat acaaactaaa    4860
```

```
gaactacaaa aacaaattac aaaaattcaa aattttcggg tttattacag ggacagcaga    4920
gaccccattt ggaaaggacc agcaaaacta ctctggaaag gtgaagggc agtagtaata     4980 caggacaata gtgatataaa ggtagtacca agaagaaaag caaaaatcat taaggattat   5040
ggaaaacaga tggcaggtga tgattgtgtg gcaggtagac aggatgagga ttagaacatg   5100
gaacagttta gtaaaacatc atatgtatat ctctaagaaa gctaagaatt ggttttatag   5160
acatcactat gaaagtaggc atccaaaagt aagttcagaa gtacacatcc cactagggga   5220
tgctagatta gtagtaagaa catattgggg tctgcataca ggagaaagag actggcactt   5280
gggtcatggg gtctccatag aatggaagca gagaagatat agcacacaaa tagatcctga   5340
cctagcagac caactgattc acctgcatta ttttgactgt ttttcagaat ctgccataag   5400
gaaagccata ttaggacaag tagttagacc taggtgtgaa tatcaagcag gacataataa   5460
ggtaggatcg ctacaatatt tggcactgaa agcattagta acaccaacaa ggacaaagcc   5520
acctttgcct agtgttaaga agttagcaga agacagatgg aacaagcccc agaagaccag   5580
gggccacaga gggagccgtt caatgaatgg acactagaac tgttagaaga gcttaaacat   5640
gaagctgtta gacattttcc taggccatgg ctccatggat taggacaaca tatctatgaa   5700
acatatgggg atacttggga aggggttgaa gctataataa gaattttgca acaactactg   5760
tttgttcatt tcagaattgg gtgtcaacat agcagaatag gcattattcg agggagaaga   5820
ggcaggaatg gagccggtag atcctagcct agagccctgg aaccacccgg gaagtcagcc   5880
tacaactgct tgtagcaatt gttactgtaa aaaatgctgc tggcattgcc aattntgctt   5940
tctgaacaag gcttaggca tctcctatgg caggaagaag cggagacgcc gacgaggaac    6000
tcctcagagc cgtcaggatc atcaaaatcc tgtaccaaag cagtgagtag taataattag   6060
tatatgtgat gcaatcttta gaaatagctg caatagtagg actagtagta gcattcatag   6120
cagccatagt tgtgtggacc atagtattta tagaatatag gaaaataagg aaacagaaga   6180
aaatagacag gttacttgat agaataagag aaagagcaga agatagtggc aatgagagtg   6240
atggggatac agaggaatta tccactctta tggagatggg gtatgatgat attttggata   6300
atgataattt gtaatgctga aaatttgtgg gtcacggtct actatggggt acctgtgtgg   6360
agagacgcag agaccaccct attttgtgca tcagatgcta aagcatatga tacagaagca   6420
cataatgtct gggctacaca tgcctgtgta cccacagacc ctaacccaca agaaatacat   6480
ttggaaaatg taacagaaaa gtttaacatg tggaaaaata acatggtaga gcagatgcat   6540
gaagatataa ttagtctatg ggaccaaagc ctaaagccat gtgtaaagtt aacccctctc   6600
tgcgttactt tagattgtca taacntcaac agcaacaaca gcaacaatat ctantgacat   6660
gaaaggggaa ataaaaaact gctctttcaa tatgaccaca gaactaagag ataagaaaca   6720
gaaagtgtat gcacttttt atagacttga tgtagtacaa attaatgaaa ataataatag   6780
tcagtatagg ttaataaatt gtaataccctc agccattaca caggcttgtc caaaggtatc   6840
ctttgagcca attcccatac attattgtgc cccagctggt tttgcaattc taaagtgtaa   6900
tgataagaag ttcaatggaa cagggccatg caagaatgtc agcacagtac aatgcacaca   6960
tggaatcaag ccagtagtat caactcaact gctgttaaat ggcagtctag cagaagaaga   7020
ggtagtgatt agatctgaaa atatcacaaa caatgccaaa accataatag tacagttgga   7080
taagcctgta aaaattaatt gtaccagacc tagcaacaat acaagaaaaa gtgtacgtat   7140
aggaccagga caaacattct atgcaacagg tgacataata ggggatataa gacaagcaca   7200
ttgtaatgtc agtagaacag aatggaataa aactttacaa caggtagcta cacaattaag   7260
```

```
gaagtacttt aagaatacaa caataatctt tgctaactcc tcaggagggg atttagaaat    7320
tacaacacat agttttaatt gtggaggaga attttctat tgcaatacat cagaactgtt     7380
taatagcact tggaataata atactancaa cacnaacaac acaaaggcaa atgacactat    7440
aactctccaa tgcagaataa agcaaattgt aaatatgtgg cagagagtag acaagcaat    7500 gtatgcccct cccatccaag gagtaataag gtgtgaatca acattacag gactactatt    7560 aacaagagat ggagggaata ataatagtac aaatgagaca ttcaggcctg gaggaggaga   7620
tatgagggac aattggagaa gtgaattata taagtataaa gtagtaaaaa ttgaaccact   7680
aggtgtagca cccacccatg caaaagaag agtggtggag agagaaaaaa gagcagttgg    7740
actgggagct gtcttccttg ggttcttagg agcagcagga agcactatgg gcgcggcgtc   7800
aataacgctg acggtacagg ccagacaatt attgtctggt atagtgcaac agcagagcaa   7860
tttgctgagg gctatagagg ctcaacaaca tctgttgaaa ctcacggtct ggggcattaa   7920
acagctccag gcaagagtcc tggctctgga aagataccta aaggatcaac agctcctagg   7980
aatttggggc tgctctggaa aactcatctg caccactact gtgccctgga actctagttg    8040
gagtaataaa acttataatg acatatggga taacatgacc tggctgcaat gggataaaga    8100
aattagcaat tacacagaca taatatataa tctaattgaa gaatcgcaga accagcagga    8160
aaagaatgaa caagacttat tggcattgga caagtgggca agtctgtgga attggtttga    8220
cataacaaat tggctatggt atataaaaat atttataatg atagtaggag gtttgatagg    8280
tttaagaata gtttttgctg tgcttactat aataaataga gttaggcagg gatactcacc    8340
tttgtcattc cagacccta cccaccacca gagggaaccc gacaggcccg aaagaatcga     8400
agaaggaggt ggcgagcaag acagagacag atccgtgcga ttagtgagcg gattcttagc    8460
acttgcctgg gacgatctgc ggagcctgtg cctcttcagc taccaccgat tgagagactt    8520
tgtcttgatt gcagcgaggn ctgtggaact tctgggacac agcagtctca agggactgag    8580
actggggtgg gaagccctca aatatctggg gaatcttcta tcatactggg gtcaggaact    8640
aaagaatagt gctattaatt tgcttgatac aatagcaata gcagtagcta actggacaga    8700
tagagttata gaaataggac aaagagctgg tagagctatt cttaacatac ctagaagaat    8760
cagacagggc ntngaaaggg cttttgctata acatgggtgg caagtggtca aaaagcagca   8820
tagtgggatg gcctcaggtt agggaaagaa taagacaaac ccctccagca gcaacaggag    8880
taggagcagc atctcaagat ttagatagac atggagcaat cacaagcagt aatacagcag    8940
ctactaatgc tgattgtgcc tggctggaag cacaagagga agaggaggta ggctttccag    9000
tcaggccgca ggtacctttg agaccaatga cttataaggc agctgtcgat ctcagccact    9060 tttaaaaga aaggggggga ctggatgggt taatttactc caagaaaaga caagagatcc     9120
ttgatctgtg ggtctatcac acacaaggat tcttcccaga ttggcagaac tacacaccag    9180
ggccag                                                              9186
```

<210> SEQ ID NO 3
<211> LENGTH: 9595
<212> TYPE: DNA
<213> ORGANISM: Human immunodeficiency virus
<220> FEATURE:
<221> NAME/KEY: modified_base
<222> LOCATION: (399)..(399)
<223> OTHER INFORMATION: a, c, t, g, unknown or other
<220> FEATURE:
<221> NAME/KEY: modified_base
<222> LOCATION: (550)..(550)

```
<223> OTHER INFORMATION: a, c, t, g, unknown or other
<220> FEATURE:
<221> NAME/KEY: modified_base
<222> LOCATION: (575)..(575)
<223> OTHER INFORMATION: a, c, t, g, unknown or other
<220> FEATURE:
<221> NAME/KEY: modified_base
<222> LOCATION: (615)..(615)
<223> OTHER INFORMATION: a, c, t, g, unknown or other
<220> FEATURE:
<221> NAME/KEY: modified_base
<222> LOCATION: (6633)..(6633)
<223> OTHER INFORMATION: a, c, t, g, unknown or other
<220> FEATURE:
<221> NAME/KEY: modified_base
<222> LOCATION: (6767)..(6767)
<223> OTHER INFORMATION: a, c, t, g, unknown or other
<220> FEATURE:
<221> NAME/KEY: modified_base
<222> LOCATION: (7401)..(7401)
<223> OTHER INFORMATION: a, c, t, g, unknown or other
<220> FEATURE:
<221> NAME/KEY: modified_base
<222> LOCATION: (7406)..(7406)
<223> OTHER INFORMATION: a, c, t, g, unknown or other
<220> FEATURE:
<221> NAME/KEY: modified_base
<222> LOCATION: (7411)..(7411)
<223> OTHER INFORMATION: a, c, t, g, unknown or other
<220> FEATURE:
<221> NAME/KEY: modified_base
<222> LOCATION: (8665)..(8665)
<223> OTHER INFORMATION: a, c, t, g, unknown or other

<400> SEQUENCE: 3
tggatgggtt aatttactcc aggaaaagac aagaaatcct tgatctgtgg gtctacaaca      60
cacaaggcta cttccctgat tggcagaatt acacaccagg gccagggatc agattcccac     120
taacatttgg atggtgcttc aagctagtac cagttgatcc agatgaagta gaaaaggcta     180
ctgagggaga gaacaacagc ctattacacc ctataagcca acatggaatg gatgatgaag     240
aaagagaaac attaatgtgg aagtttgaca gccgcctggc acttacacac agagcccgag     300
agctgcatcc ggagttctac aaagactgct gacacagaag ttgctgacag ggactttccg     360
ctggggactt tccaggggag gtgtggtttg ggcggagtng gggagtggct aaccctcaga     420
tgctgcatat aagcagctgc ttttcgcctg tactgggtct ctcttgttag accagatcga     480
gcctgggagc tctctggcta gctagggaac ccactgctta agcctcaata agcttgcct      540 tgagtgcttn aagtagtgtg tgcccgtctg ttgtntgact ctggtaacta gagatccctc     600
agaccactct agacngtgta aaatctcta gcagtggcgc ccgaacaggg actcgaaagc     660
gaaagttcca gagaagttct ctcgacgcag gactcggctt gctgaggtgc acacagcaag     720
aggcgagagc ggcgactggt gagtacgcca ttttttgact agcggaggct agaaggagag     780
agatgggtgc gagagcgtca gtattaagtg ggggaaaatt agatgcatgg gagaaaattc     840
ggttaaggcc agggggaaag aaaaaatata gactgaaaca tctagtatgg gcaagcaggg     900
agctggaaag atttgcactt aaccctagcc ttttagaaac agcagaagga tgtcaacaaa     960
taatggaaca gttacaacca gctctcaaga caggaacaga agaacttaga tcattattta    1020
atacagtagc aaccctctat tgtgtacatc aacggataga tgtaaaagac accaaggaag    1080
ctctagataa aatagaggaa atacaaaata agagcaagca aaagacacaa caggcagcag    1140
ctgacacagg aaacagcagc aaggtcagcc aaaattaccc tatagtgcaa aatgcacaag    1200
ggcaaatgat acaccagtcc ttgtcaccta ggactttgaa tgcatgggta aaagtaatag    1260
aagaaaaggc tttcagccca gaagtaatac ccatgttctc agcattatca gaggagccac    1320
```

```
ccccacaaga tttaaatatg atgctgaaca tagtgggggg acaccaggca gctatgcaaa   1380
tgttaaaaga taccatcaat gaggaagctg cagaatggga caggttacat ccagtacatg   1440
cagggcctat tccaccaggc cagatgagag aaccaagggg aagtgacata gcaggaacta   1500
ctagtacccc tcaagaacaa ataggatgga tgacaggcaa cccacctatc ccagtgggag   1560
acatctataa aagatggata atcctgggat taaataaaat agtaagaatg tatagccctg   1620
ttagcatttt ggatataaaa caagggccaa agaacccctt cagagattat gtagataggt   1680
tctttaaaac tctcagagct gagcaagcta cacaggaggt aaaaggttgg atgacagaaa   1740
cattactggt ccaaaatgca aatccagatt gtaagtccat tttaagagca ttaggagcag   1800
gggctacatt agaagaaatg atgacagcat gccagggagt gggaggaccc ggccataaag   1860
caagggtttt ggctgaggca atgagtcaag tacaacatac aaacataatg atgcagagag   1920
gcaattttag gggccagaaa aggattaagt gtttcaactg tggcaaagaa ggacacctag   1980
ccagaaattg cagggcccct aggaaaaagg gctgttggaa atgtgggaag agggacacc    2040 aaatgaaaga ctgcactgaa agacaggcta attttttagg gaaaatttgg ccttccagca   2100
aggggaggcc aggaaatttt cctcagagca gaccggagcc aacagcccca ccagcagaga   2160
tctttgggat gggggaagag atagcctccc ctccgaagca ggagcagaaa gacagggaac   2220 aggcccacc tttagtttcc ctcaaatcac tctttggcaa cgaccccttg tcacagtaag    2280
aataggggga cagctaaaag aagctctatt agatacagga gcagatgata cagtattaga   2340
agacataaat ttgccaggaa aatggaaacc aaaaatgata gggggaattg gaggtttcat   2400
caaggtaaaa cagtatgatc agatacttat agaaatttgt ggaaaaaagg ctataggtac   2460
agtattagta ggacctacac ctgtcaacat aattggaaga aatatgttga cccagattgg   2520
ttgtacttta aatttcccaa ttagtcctat tgagactgta ccagtaaaat taaagccagg   2580
aatggatggc ccaaaggtta acaatggcc attgacagaa gaaaaaataa agcattaac    2640 agaaatttgt acagagatgg aaaaggaagg aaaaatttca aaaattgggc ctgaaaatcc   2700
atacaatact ccaatatttg ctataaagaa aaaagatagc actaaatgga ggaaattagt   2760
agatttcaga gagctcaata aaagaactca agacttttgg gaagttcaat taggaatacc   2820
gcatccagcg ggcctaaaaa agaaaaaatc agtaacagta ctagatgtgg gggacgcata   2880
tttttcagtt cctttagatg aaagctttag aaagtatact gcattcacca tacctagtac   2940
aaacaatgag acaccaggaa tcaggtatca gtacaatgtg cttccacagg gatggaaagg   3000
atcaccggca atattccaga gtagcatgac aaaaatctta gagcccttta gatcaaaaaa   3060
tccagaaata attatctatc aatacatgga tgacttgtat gtaggatctg atttagaaat   3120
agggcagcat agaacaaaaa tagaagagtt aagagctcat ctattgagct ggggatttac   3180
tacaccagac aaaaagcatc agaaagaacc tccatttctt tggatgggat atgaactcca   3240
tcctgacaag tggacagtcc agcctataga gctgccagaa aaagaaagct ggactgtcaa   3300
tgatatacag aaattagtgg gaaaactaaa ttgggcaagt caaatttatg cagggattaa   3360
agtaaagcaa ttgtgtaaac tcctcagggg agccaaagca ctaacagata tagtaacatt   3420
gactgaggaa gcagaattag aattggcaga gaacaggag attctaaaag accctgtgca   3480
tggagtatat tatgacccat caaaagactt aatagcagaa atacagaaac aagggcaaga   3540
ccaatggaca tatcaaattt atcaagagcc atttaaaaat ctaaaaacag gaaaatatgc   3600
aagaaaaagg tctgctcaca ctaatgatgt aaaacaatta gcagaagtgg tgcaaaaggt   3660
```

```
ggtcatggaa agcatagtaa tatggggaaa gactcctaaa tttaaactac ccatacaaaa    3720
agaaacatgg gaaacatggt ggatggacta ttggcaggct acctggattc ctgaatggga    3780
gtttgtcaat accccctcctc tagtaaaatt atggtaccag ttagagaaag accccatagt   3840
aggagcagag actttctatg tagatggggc agccaatagg gagactaagc taggaaaagc    3900
agggtatgtc actgacagag gaagacaaaa ggttgtttcc ctaactgaga caacaaatca    3960
aaagactgaa ctacatgcaa tccatctagc cttgcaggat tcaggatcag aagtaaacat    4020
agtaacagac tcacagtatg cattaggaat cattcaggca caaccagaca ggagtgaatc    4080
agagttagtc aatcaaataa tagagaagct aataggaaag gacaaagtct acctgtcatg    4140
ggtaccagca cacaaaggaa ttggaggaaa tgaacaagta gataaattag tcagttctgg    4200
aatcaggaag gtgctatttt tagatgggat agataaagct caagaagaac atgaaagata    4260
tcacagcaat tggagagcaa tggctagtga ttttaatctg ccacctatag tagcaaagga    4320
aatagtagcc agctgtgata atgtcagct aaaggggaa gccatgcatg gacaagtaga    4380
ctgcagtcca gggatatggc aattagattg cacacatcta gaaggaaaag taattctggt    4440
agcagtccat gtagccagtg gctatataga agcagaagtt atcccagcag aaacaggaca    4500
ggagacagca tactttctac taaaattagc aggaagatgg ccagtaaaag tagtacacac    4560
agacaatggc agcaatttca ccagcgctgc atttaaagca gcctgttggt gggcaaatat    4620
ccaacaggaa tttgggattc cctacaatcc ccaaagtcaa ggagtagtgg aatctatgaa    4680
taaggaatta agaaaatca tagggcaggt aagagagcaa gctgaacacc ttaaaacagc    4740
agtacaaatg gcagtattca ttcacaattt taaaagaaaa ggggggattg ggggtacag    4800
tgcagggga agaataatag acataatagc aacagacata caaactaaag aattacaaaa    4860
acaaattaca aaaattcaaa attttcgggt ttattacagg gacagcagag atccaatttg    4920
gaaaggacca gcaaaactac tctggaaagg tgaaggggca gtagtaatac aggacaatag    4980
tgatataaag gtagtaccaa gaagaaaagc aaagatcatt agggattatg gaaaacagat    5040
ggcaggtgat gattgtgtgg caggtagaca ggatgaggat tagaacatgg aacagtttag    5100
taaaacatca tatgtatgtc tcaaagaaag ctaaagattg gttttataga catcactatg    5160
aaagcaggca tccaaaagta agttcagaag tacacatccc actaggggat gctagattag    5220
tagtaagaac atattggggt ctgcatacag gagaaaaaga ctggcacttg ggtcatgggg    5280
tctccataga atggaggcta aaaagatata gcacacaaat agatcctgac ctggcagacc    5340
aactaattca tctgcattat tttgactgtt tttcagactc tgccataagg aaagccatat    5400
taggacaagt agttagccct aggtgtgaat atcaaacagg acataacaag gtaggatctc    5460
tacaatattt agcactgaaa gcattagtaa caccaacaaa gacaaagcca cctttgccta    5520
gtgttaggaa attaacagag gatagatgga acaagcccca gaagaccagg gccccagag    5580
ggagccatac aatgaatgga tgttagaact gttagaagat cttaagcatg aagctgttag    5640
acatttttcct aggccatggc ttcatggatt aggacaacat atctataaca cctatgggga    5700
tacttgggaa ggagttgaag ctataataag aattttgcaa caactactgt ttgttcattt    5760
cagaattggg tgccaacata gcagaatagg cattattcga gggagaagag tcagggatgg    5820
atccggtaga tcctaaccta gagccctgga accatccggg aagtcagcct acaactcctt    5880
gtagcaagtg ttactgtaaa aagtgttgct atcattgcca gtttgctttt ctgaacaaag    5940
gcttaggcat ctcctatggc aggaagaagc ggagacagcg acgaggaact cctcaaagca    6000
gtaaggatca tcaaaatcct ataccaaagc agtaagtatt agtaattagt atatgtaatg    6060
```

```
cctcctttgg aaatctgtgc aatagtagga ctgatagtag cgctaatcct agcaatagtt    6120
gtgtggacta tagtaggtat agaatataag aaattgctaa agcaaagaaa aatagacagg    6180
ttaattgaga gaataagaga aagagcagaa gacagtggca atgagagtga tggggataca    6240
gaggaattgt caacacttat tgagatgggg aactatgatc ttggggatga taataatctg    6300
tagtgctgca gaaaacttgt gggttactgt ctactatggg gtacctgtgt ggaaagatgc    6360
agagaccacc ttattttgtg catcagatgc taaagcatat gagacagaag tgcataatgt    6420
ctgggctaca catgcctgtg tacccacaga ccccaaccca caagaaatac atttggaaaa    6480
tgtgacagaa gagtttaaca tgtggaaaaa taacatggta gagcagatgc atacagatat    6540
aatcagtcta tgggaccaaa gcctaaagcc atgtgtaaag ttaaccccctc tctgcgttac    6600 tttaaattgt agcaatgtca acatcaacaa cancaacaca atatcaccaa taacatgaaa    6660
gaagaaataa aaaactgctc tttcaatatg accacagaac taagggataa gaaacagaaa    6720
gtatattcac ttttttatag acttgatgta gtacaaatta atgaaantaa tagtaatagt    6780
agtgagtata gattaataaa ttgtaatacc tcagccatta cacaggcttg tccaaaggta    6840
tcctttgagc caattcccat acattattgt gccccagctg gttttgcgat cctaaagtgt    6900
aaggataagg agttcaatgg aacagggcca tgcaagaatg tcagcacagt acaatgcaca    6960
catggaatca agccagtagt atcaactcaa ctgctgttaa atggcagtct agcagaagaa    7020
gaggtaataa ttagatctga aaatatcaca aacaatgcca aaaccataat agtacaactt    7080
accaagcctg taaaaattaa ttgtaccaga cctaacaaca atacaagaaa aagtatacgt    7140
ataggaccag gacaagcatt ctatgcaaca ggtgacataa taggggatat aagacaagca    7200
cattgtaatg tcagtagatc agaatggaat aaaactttac aaaaggtagc taaacaatta    7260
agaaaatact ttaagaacaa aacaataatc tttactaact cctcaggagg ggatctagaa    7320
attacaacac atagttttaa ttgtggagga gaattttct attgtaatac atcaggcctg    7380
tttaatagca cttggaataa naacantaac nagacaaata gcacggagtc aaatgacact    7440
ataactctcc catgcagaat aaagcaaatt ataaatatgt ggcagagagc aggacaagca    7500
atgtatgccc ctcccatcca aggagtaata aggtgtgaat caaacattac aggactacta    7560
ttaacaagag atggtgggaa taataacagt acaaatgaaa ccttcagacc tggaggagga    7620
gatatgaggg acaattggag aagtgaatta tataagtata agtagtaaa aattgaacca    7680 ctaggagtag cacccaccag ggcaaagaga agagtggtgg agagagaaaa aagagcagtt    7740
ggaataggag ctgtcttcct tgggttctta ggagcagcag gaagcactat gggcgcggcg    7800
tcaataacgc tgacggtaca ggccagacaa ttattgtctg gcatagtgca acagcaaagc    7860
aatttgctga gggctataga ggctcaacag catctgttga aactcacggt ctggggcatt    7920
aaacagctcc aggcaagagt cctggctgtg gaaagatacc taaaggatca acagctccta    7980
ggaatttggg gctgctctgg aaaactcatc tgcaccacta atgtgccctg gaactctagt    8040
tggagtaata aatctcagaa tgagatatgg gataacatga cctggctgca atgggataaa    8100
gaaattagca attacacaca cataatatat aatctaattg aagaatcgca gaaccagcag    8160
gaaaagaatg aacaagactt attggcattg gacaagtggg caaatctgtg gaattggttt    8220
gacatatcaa actggctgtg gtatataaaa atatttataa tgatagtagg aggcttaata    8280
ggattaagaa tagttttttgc tgtgctttct ataataaaata gagttaggca gggatactca    8340
cctttgtcgt ttcagaccca taccccaaac ccaaggggtc tcgacaggcc cggaagaatc    8400
```

-continued

```
gaagaagaag gtggagagca aggcagagac agatcgattc gattagtgag cggattctta    8460
gcacttgcct gggacgatct gcggagcctg tgcctcttca gctaccaccg cttgagagac    8520
ttcatcttga ttgcagcgag gactgtggaa cttctgggac acagcagtct caaggggttg    8580
agactggggt gggaaggcct caagtatctg tggaatctcc tgttatattg ggtcgggaa    8640 ctaaaaatta gtgctattaa tttgnttgat accatagcaa tagcagtagc tggctggaca    8700 gataggggtta tagaaatagg acaaagaatt ggtagagcta ttctccacat acctagaaga    8760
atcagacagg gcttagaaag ggctttgcta taacatgggt ggcaagtggt caaaaagtag    8820
catagtggga tggcctgagg ttagggaaag aataagacga actcctccag cagcaacagg    8880
agtaggagca gtatctcaag atttagataa acatggagca gtcacaagca gtaatataaa    8940
tcaccctagt tgcgcctggc tggaagcgca agaggaagag gaggtaggct ttccagtcag    9000
gccacaagta cctctaagac caatgactta caagggagct ctggatctca gccactttt    9060 aaaagaaaag gggggactgg atgggttaat ttactccagg aaaagacaag aaatccttga    9120
tctgtgggtc taccacacac aaggctactt ccctgattgg cagaattaca caccagggcc    9180
agggatcaga tacccactaa catttggatg gtgcttcaag ctagtaccag ttgatccaga    9240
tgaagtagag aaggctactg agggagagaa caacagccta ttacaccta tatgccaaca    9300 tggaatggat gatgaggaga gagaagtatt aatgtggaag tttgacagcc gcctggcact    9360
aaaacacaga gcccaagagc tgcatccgga gttctacaaa gactgctgac acagaagttg    9420
ctgacaggga ctttccgctg ggactttcc aggggaggtg tggtttgggc ggagttgggg    9480
agtggctaac cctcagatgc tgcatataag cagctgcttt tcgcctgtac tgggtctctc    9540
ttgttagacc agatcgagcc tgggagctct ctggctagcg agggaaccca ctgct        9595
```

<210> SEQ ID NO 4
<211> LENGTH: 8980
<212> TYPE: DNA
<213> ORGANISM: Human immunodeficiency virus
<220> FEATURE:
<221> NAME/KEY: modified_base
<222> LOCATION: (26)..(30)
<223> OTHER INFORMATION: a, c, t, g, unknown or other
<220> FEATURE:
<221> NAME/KEY: modified_base
<222> LOCATION: (34)..(34)
<223> OTHER INFORMATION: a, c, t, g, unknown or other
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: modified_base
<222> LOCATION: (43)..(43)
<223> OTHER INFORMATION: a, c, t, g, unknown or other
<220> FEATURE:
<221> NAME/KEY: modified_base
<222> LOCATION: (48)..(48)
<223> OTHER INFORMATION: a, c, t, g, unknown or other
<220> FEATURE:
<221> NAME/KEY: modified_base
<222> LOCATION: (50)..(50)
<223> OTHER INFORMATION: a, c, t, g, unknown or other
<220> FEATURE:
<221> NAME/KEY: modified_base
<222> LOCATION: (66)..(66)
<223> OTHER INFORMATION: a, c, t, g, unknown or other
<220> FEATURE:
<221> NAME/KEY: modified_base
<222> LOCATION: (104)..(105)
<223> OTHER INFORMATION: a, c, t, g, unknown or other
<220> FEATURE:
<221> NAME/KEY: modified_base

```
<222> LOCATION: (109)..(109)
<223> OTHER INFORMATION: a, c, t, g, unknown or other
<220> FEATURE:
<221> NAME/KEY: modified_base
<222> LOCATION: (112)..(112)
<223> OTHER INFORMATION: a, c, t, g, unknown or other
<220> FEATURE:
<221> NAME/KEY: modified_base
<222> LOCATION: (130)..(130)
<223> OTHER INFORMATION: a, c, t, g, unknown or other
<220> FEATURE:
<221> NAME/KEY: modified_base
<222> LOCATION: (144)..(144)
<223> OTHER INFORMATION: a, c, t, g, unknown or other
<220> FEATURE:
<221> NAME/KEY: modified_base
<222> LOCATION: (181)..(181)
<223> OTHER INFORMATION: a, c, t, g, unknown or other
<220> FEATURE:
<221> NAME/KEY: modified_base
<222> LOCATION: (186)..(186)
<223> OTHER INFORMATION: a, c, t, g, unknown or other
<220> FEATURE:
<221> NAME/KEY: modified_base
<222> LOCATION: (192)..(192)
<223> OTHER INFORMATION: a, c, t, g, unknown or other
<220> FEATURE:
<221> NAME/KEY: modified_base
<222> LOCATION: (204)..(204)
<223> OTHER INFORMATION: a, c, t, g, unknown or other
<220> FEATURE:
<221> NAME/KEY: modified_base
<222> LOCATION: (264)..(264)
<223> OTHER INFORMATION: a, c, t, g, unknown or other
<220> FEATURE:
<221> NAME/KEY: modified_base
<222> LOCATION: (288)..(288)
<223> OTHER INFORMATION: a, c, t, g, unknown or other
<220> FEATURE:
<221> NAME/KEY: modified_base
<222> LOCATION: (300)..(300)
<223> OTHER INFORMATION: a, c, t, g, unknown or other
<220> FEATURE:
<221> NAME/KEY: modified_base
<222> LOCATION: (306)..(307)
<223> OTHER INFORMATION: a, c, t, g, unknown or other
<220> FEATURE:
<221> NAME/KEY: modified_base
<222> LOCATION: (322)..(323)
<223> OTHER INFORMATION: a, c, t, g, unknown or other
<220> FEATURE:
<221> NAME/KEY: modified_base
<222> LOCATION: (325)..(327)
<223> OTHER INFORMATION: a, c, t, g, unknown or other
<220> FEATURE:
<221> NAME/KEY: modified_base
<222> LOCATION: (338)..(338)
<223> OTHER INFORMATION: a, c, t, g, unknown or other
<220> FEATURE:
<221> NAME/KEY: modified_base
<222> LOCATION: (343)..(343)
<223> OTHER INFORMATION: a, c, t, g, unknown or other
<220> FEATURE:
<221> NAME/KEY: modified_base
<222> LOCATION: (345)..(346)
<223> OTHER INFORMATION: a, c, t, g, unknown or other
<220> FEATURE:
<221> NAME/KEY: modified_base
<222> LOCATION: (351)..(351)
<223> OTHER INFORMATION: a, c, t, g, unknown or other
<220> FEATURE:
<221> NAME/KEY: modified_base
<222> LOCATION: (367)..(367)
<223> OTHER INFORMATION: a, c, t, g, unknown or other
<220> FEATURE:
<221> NAME/KEY: modified_base
<222> LOCATION: (369)..(369)
<223> OTHER INFORMATION: a, c, t, g, unknown or other
<220> FEATURE:
```

```
<221> NAME/KEY: modified_base
<222> LOCATION: (389)..(389)
<223> OTHER INFORMATION: a, c, t, g, unknown or other
<220> FEATURE:
<221> NAME/KEY: modified_base
<222> LOCATION: (406)..(406)
<223> OTHER INFORMATION: a, c, t, g, unknown or other
<220> FEATURE:
<221> NAME/KEY: modified_base
<222> LOCATION: (410)..(410)
<223> OTHER INFORMATION: a, c, t, g, unknown or other
<220> FEATURE:
<221> NAME/KEY: modified_base
<222> LOCATION: (422)..(423)
<223> OTHER INFORMATION: a, c, t, g, unknown or other
<220> FEATURE:
<221> NAME/KEY: modified_base
<222> LOCATION: (426)..(426)
<223> OTHER INFORMATION: a, c, t, g, unknown or other
<220> FEATURE:
<221> NAME/KEY: modified_base
<222> LOCATION: (434)..(434)
<223> OTHER INFORMATION: a, c, t, g, unknown or other
<220> FEATURE:
<221> NAME/KEY: modified_base
<222> LOCATION: (436)..(436)
<223> OTHER INFORMATION: a, c, t, g, unknown or other
<220> FEATURE:
<221> NAME/KEY: modified_base
<222> LOCATION: (441)..(441)
<223> OTHER INFORMATION: a, c, t, g, unknown or other
<220> FEATURE:
<221> NAME/KEY: modified_base
<222> LOCATION: (492)..(498)
<223> OTHER INFORMATION: a, c, t, g, unknown or other
<220> FEATURE:
<221> NAME/KEY: modified_base
<222> LOCATION: (504)..(504)
<223> OTHER INFORMATION: a, c, t, g, unknown or other
<220> FEATURE:
<221> NAME/KEY: modified_base
<222> LOCATION: (513)..(513)
<223> OTHER INFORMATION: a, c, t, g, unknown or other
<220> FEATURE:
<221> NAME/KEY: modified_base
<222> LOCATION: (531)..(531)
<223> OTHER INFORMATION: a, c, t, g, unknown or other
<220> FEATURE:
<221> NAME/KEY: modified_base
<222> LOCATION: (533)..(533)
<223> OTHER INFORMATION: a, c, t, g, unknown or other
<220> FEATURE:
<221> NAME/KEY: modified_base
<222> LOCATION: (541)..(563)
<223> OTHER INFORMATION: a, c, t, g, unknown or other
<220> FEATURE:
<221> NAME/KEY: modified_base
<222> LOCATION: (619)..(619)
<223> OTHER INFORMATION: a, c, t, g, unknown or other
<220> FEATURE:
<221> NAME/KEY: modified_base
<222> LOCATION: (823)..(823)
<223> OTHER INFORMATION: a, c, t, g, unknown or other
<220> FEATURE:
<221> NAME/KEY: modified_base
<222> LOCATION: (1301)..(1301)
<223> OTHER INFORMATION: a, c, t, g, unknown or other
<220> FEATURE:
<221> NAME/KEY: modified_base
<222> LOCATION: (1303)..(1303)
<223> OTHER INFORMATION: a, c, t, g, unknown or other
<220> FEATURE:
<221> NAME/KEY: modified_base
<222> LOCATION: (1564)..(1564)
<223> OTHER INFORMATION: a, c, t, g, unknown or other
<220> FEATURE:
<221> NAME/KEY: modified_base
<222> LOCATION: (1569)..(1570)
<223> OTHER INFORMATION: a, c, t, g, unknown or other
```

-continued

```
<220> FEATURE:
<221> NAME/KEY: modified_base
<222> LOCATION: (1596)..(1596)
<223> OTHER INFORMATION: a, c, t, g, unknown or other
<220> FEATURE:
<221> NAME/KEY: modified_base
<222> LOCATION: (1608)..(1611)
<223> OTHER INFORMATION: a, c, t, g, unknown or other
<220> FEATURE:
<221> NAME/KEY: modified_base
<222> LOCATION: (1613)..(1613)
<223> OTHER INFORMATION: a, c, t, g, unknown or other
<220> FEATURE:
<221> NAME/KEY: modified_base
<222> LOCATION: (3416)..(3416)
<223> OTHER INFORMATION: a, c, t, g, unknown or other
<220> FEATURE:
<221> NAME/KEY: modified_base
<222> LOCATION: (3425)..(3425)
<223> OTHER INFORMATION: a, c, t, g, unknown or other
<220> FEATURE:
<221> NAME/KEY: modified_base
<222> LOCATION: (3458)..(3458)
<223> OTHER INFORMATION: a, c, t, g, unknown or other
<220> FEATURE:
<221> NAME/KEY: modified_base
<222> LOCATION: (3584)..(3584)
<223> OTHER INFORMATION: a, c, t, g, unknown or other
<220> FEATURE:
<221> NAME/KEY: modified_base
<222> LOCATION: (3615)..(3615)
<223> OTHER INFORMATION: a, c, t, g, unknown or other
<220> FEATURE:
<221> NAME/KEY: modified_base
<222> LOCATION: (3668)..(3668)
<223> OTHER INFORMATION: a, c, t, g, unknown or other
<220> FEATURE:
<221> NAME/KEY: modified_base
<222> LOCATION: (3884)..(3884)
<223> OTHER INFORMATION: a, c, t, g, unknown or other
<220> FEATURE:
<221> NAME/KEY: modified_base
<222> LOCATION: (3893)..(3893)
<223> OTHER INFORMATION: a, c, t, g, unknown or other
<220> FEATURE:
<221> NAME/KEY: modified_base
<222> LOCATION: (3927)..(3927)
<223> OTHER INFORMATION: a, c, t, g, unknown or other
<220> FEATURE:
<221> NAME/KEY: modified_base
<222> LOCATION: (4028)..(4028)
<223> OTHER INFORMATION: a, c, t, g, unknown or other
<220> FEATURE:
<221> NAME/KEY: modified_base
<222> LOCATION: (4163)..(4163)
<223> OTHER INFORMATION: a, c, t, g, unknown or other
<220> FEATURE:
<221> NAME/KEY: modified_base
<222> LOCATION: (4343)..(4343)
<223> OTHER INFORMATION: a, c, t, g, unknown or other
<220> FEATURE:
<221> NAME/KEY: modified_base
<222> LOCATION: (4519)..(4519)
<223> OTHER INFORMATION: a, c, t, g, unknown or other
<220> FEATURE:
<221> NAME/KEY: modified_base
<222> LOCATION: (4526)..(4526)
<223> OTHER INFORMATION: a, c, t, g, unknown or other
<220> FEATURE:
<221> NAME/KEY: modified_base
<222> LOCATION: (4539)..(4539)
<223> OTHER INFORMATION: a, c, t, g, unknown or other
<220> FEATURE:
<221> NAME/KEY: modified_base
<222> LOCATION: (4857)..(4857)
<223> OTHER INFORMATION: a, c, t, g, unknown or other
<220> FEATURE:
<221> NAME/KEY: modified_base
<222> LOCATION: (4894)..(4894)
```

```
<223> OTHER INFORMATION: a, c, t, g, unknown or other
<220> FEATURE:
<221> NAME/KEY: modified_base
<222> LOCATION: (4903)..(4903)
<223> OTHER INFORMATION: a, c, t, g, unknown or other
<220> FEATURE:
<221> NAME/KEY: modified_base
<222> LOCATION: (4978)..(4978)
<223> OTHER INFORMATION: a, c, t, g, unknown or other
<220> FEATURE:
<221> NAME/KEY: modified_base
<222> LOCATION: (4989)..(4989)
<223> OTHER INFORMATION: a, c, t, g, unknown or other
<220> FEATURE:
<221> NAME/KEY: modified_base
<222> LOCATION: (5136)..(5136)
<223> OTHER INFORMATION: a, c, t, g, unknown or other
<220> FEATURE:
<221> NAME/KEY: modified_base
<222> LOCATION: (5186)..(5186)
<223> OTHER INFORMATION: a, c, t, g, unknown or other
<220> FEATURE:
<221> NAME/KEY: modified_base
<222> LOCATION: (5239)..(5239)
<223> OTHER INFORMATION: a, c, t, g, unknown or other
<220> FEATURE:
<221> NAME/KEY: modified_base
<222> LOCATION: (5265)..(5265)
<223> OTHER INFORMATION: a, c, t, g, unknown or other
<220> FEATURE:
<221> NAME/KEY: modified_base
<222> LOCATION: (5285)..(5285)
<223> OTHER INFORMATION: a, c, t, g, unknown or other
<220> FEATURE:
<221> NAME/KEY: modified_base
<222> LOCATION: (5292)..(5292)
<223> OTHER INFORMATION: a, c, t, g, unknown or other
<220> FEATURE:
<221> NAME/KEY: modified_base
<222> LOCATION: (5322)..(5323)
<223> OTHER INFORMATION: a, c, t, g, unknown or other
<220> FEATURE:
<221> NAME/KEY: modified_base
<222> LOCATION: (5392)..(5392)
<223> OTHER INFORMATION: a, c, t, g, unknown or other
<220> FEATURE:
<221> NAME/KEY: modified_base
<222> LOCATION: (5397)..(5397)
<223> OTHER INFORMATION: a, c, t, g, unknown or other
<220> FEATURE:
<221> NAME/KEY: modified_base
<222> LOCATION: (5402)..(5402)
<223> OTHER INFORMATION: a, c, t, g, unknown or other
<220> FEATURE:
<221> NAME/KEY: modified_base
<222> LOCATION: (5422)..(5422)
<223> OTHER INFORMATION: a, c, t, g, unknown or other
<220> FEATURE:
<221> NAME/KEY: modified_base
<222> LOCATION: (5480)..(5480)
<223> OTHER INFORMATION: a, c, t, g, unknown or other
<220> FEATURE:
<221> NAME/KEY: modified_base
<222> LOCATION: (5495)..(5495)
<223> OTHER INFORMATION: a, c, t, g, unknown or other
<220> FEATURE:
<221> NAME/KEY: modified_base
<222> LOCATION: (5554)..(5554)
<223> OTHER INFORMATION: a, c, t, g, unknown or other
<220> FEATURE:
<221> NAME/KEY: modified_base
<222> LOCATION: (5590)..(5590)
<223> OTHER INFORMATION: a, c, t, g, unknown or other
<220> FEATURE:
<221> NAME/KEY: modified_base
<222> LOCATION: (5650)..(5650)
<223> OTHER INFORMATION: a, c, t, g, unknown or other
<220> FEATURE:
<221> NAME/KEY: modified_base
```

```
<222> LOCATION: (5654)..(5654)
<223> OTHER INFORMATION: a, c, t, g, unknown or other
<220> FEATURE:
<221> NAME/KEY: modified_base
<222> LOCATION: (5664)..(5664)
<223> OTHER INFORMATION: a, c, t, g, unknown or other
<220> FEATURE:
<221> NAME/KEY: modified_base
<222> LOCATION: (5684)..(5684)
<223> OTHER INFORMATION: a, c, t, g, unknown or other
<220> FEATURE:
<221> NAME/KEY: modified_base
<222> LOCATION: (5691)..(5691)
<223> OTHER INFORMATION: a, c, t, g, unknown or other
<220> FEATURE:
<221> NAME/KEY: modified_base
<222> LOCATION: (5809)..(5809)
<223> OTHER INFORMATION: a, c, t, g, unknown or other
<220> FEATURE:
<221> NAME/KEY: modified_base
<222> LOCATION: (6025)..(6025)
<223> OTHER INFORMATION: a, c, t, g, unknown or other
<220> FEATURE:
<221> NAME/KEY: modified_base
<222> LOCATION: (6028)..(6028)
<223> OTHER INFORMATION: a, c, t, g, unknown or other
<220> FEATURE:
<221> NAME/KEY: modified_base
<222> LOCATION: (6036)..(6049)
<223> OTHER INFORMATION: a, c, t, g, unknown or other
<220> FEATURE:
<221> NAME/KEY: modified_base
<222> LOCATION: (6161)..(6162)
<223> OTHER INFORMATION: a, c, t, g, unknown or other
<220> FEATURE:
<221> NAME/KEY: modified_base
<222> LOCATION: (6167)..(6168)
<223> OTHER INFORMATION: a, c, t, g, unknown or other
<220> FEATURE:
<221> NAME/KEY: modified_base
<222> LOCATION: (6185)..(6185)
<223> OTHER INFORMATION: a, c, t, g, unknown or other
<220> FEATURE:
<221> NAME/KEY: modified_base
<222> LOCATION: (6371)..(6371)
<223> OTHER INFORMATION: a, c, t, g, unknown or other
<220> FEATURE:
<221> NAME/KEY: modified_base
<222> LOCATION: (6619)..(6619)
<223> OTHER INFORMATION: a, c, t, g, unknown or other
<220> FEATURE:
<221> NAME/KEY: modified_base
<222> LOCATION: (6793)..(6794)
<223> OTHER INFORMATION: a, c, t, g, unknown or other
<220> FEATURE:
<221> NAME/KEY: modified_base
<222> LOCATION: (6799)..(6800)
<223> OTHER INFORMATION: a, c, t, g, unknown or other
<220> FEATURE:
<221> NAME/KEY: modified_base
<222> LOCATION: (6808)..(6809)
<223> OTHER INFORMATION: a, c, t, g, unknown or other
<220> FEATURE:
<221> NAME/KEY: modified_base
<222> LOCATION: (6812)..(6813)
<223> OTHER INFORMATION: a, c, t, g, unknown or other
<220> FEATURE:
<221> NAME/KEY: modified_base
<222> LOCATION: (6819)..(6820)
<223> OTHER INFORMATION: a, c, t, g, unknown or other
<220> FEATURE:
<221> NAME/KEY: modified_base
<222> LOCATION: (6838)..(6838)
<223> OTHER INFORMATION: a, c, t, g, unknown or other
<220> FEATURE:
<221> NAME/KEY: modified_base
<222> LOCATION: (6845)..(6845)
<223> OTHER INFORMATION: a, c, t, g, unknown or other
<220> FEATURE:
```

```
<221> NAME/KEY: modified_base
<222> LOCATION: (6980)..(6980)
<223> OTHER INFORMATION: a, c, t, g, unknown or other
<220> FEATURE:
<221> NAME/KEY: modified_base
<222> LOCATION: (6986)..(6986)
<223> OTHER INFORMATION: a, c, t, g, unknown or other
<220> FEATURE:
<221> NAME/KEY: modified_base
<222> LOCATION: (6988)..(6988)
<223> OTHER INFORMATION: a, c, t, g, unknown or other
<220> FEATURE:
<221> NAME/KEY: modified_base
<222> LOCATION: (7140)..(7140)
<223> OTHER INFORMATION: a, c, t, g, unknown or other
<220> FEATURE:
<221> NAME/KEY: modified_base
<222> LOCATION: (7528)..(7528)
<223> OTHER INFORMATION: a, c, t, g, unknown or other
<220> FEATURE:
<221> NAME/KEY: modified_base
<222> LOCATION: (7856)..(7856)
<223> OTHER INFORMATION: a, c, t, g, unknown or other
<220> FEATURE:
<221> NAME/KEY: modified_base
<222> LOCATION: (8001)..(8001)
<223> OTHER INFORMATION: a, c, t, g, unknown or other
<220> FEATURE:
<221> NAME/KEY: modified_base
<222> LOCATION: (8019)..(8019)
<223> OTHER INFORMATION: a, c, t, g, unknown or other
<220> FEATURE:
<221> NAME/KEY: modified_base
<222> LOCATION: (8057)..(8057)
<223> OTHER INFORMATION: a, c, t, g, unknown or other
<220> FEATURE:
<221> NAME/KEY: modified_base
<222> LOCATION: (8214)..(8214)
<223> OTHER INFORMATION: a, c, t, g, unknown or other
<220> FEATURE:
<221> NAME/KEY: modified_base
<222> LOCATION: (8569)..(8980)
<223> OTHER INFORMATION: a, c, t, g, unknown or other

<400> SEQUENCE: 4
ttgaaaagcg aaagtaacag ggactnnnnn gaangcgana gtnccagngn agttctctcg      60
acgcangact cggcttgctg aggtgcacac ggcaagaggc gagnngcgnc gnctggtgag     120
tacgcctaan atttttgact agcngaggct agaaggagag agatgggtgc gagagcgtca     180
ntattnagcg gnggaaaatt agangcttgg gagaaaattc ggttaaggcc aggggaaag      240 aaaaaatata gactgaaaca tttngtatgg gcaagcaggg agctgganaa attctcaatn     300
aacccnngcc ttttagaaac annannngga tgtagacnaa tantnnggca nttacaacca     360
gctctcnana caggaacaga agaacttana tcattatata atacantagn agtcctctac     420
tnngtncatc aaangntaga ngtaaaagac accaaggaag ctctagataa aatagaggaa     480
gaacaaaaca annnnnnnca gaanacacag cangcagcag ctgacacagg nancagcagc     540
nnnnnnnnnn nnnnnnnnnn nnncagtcaa aattacccta tagtgcaaaa tgcacaaggg     600
caaatggtac accaggccnt atcacctagg actttgaatg catgggtcaa agtagtagaa     660
gaaaaggctt tcagcccaga agtaataccc atgtttacag cattatcaga aggagccacc     720
ccacaagact aaatactat gctaaacaca gtgggggac atcaagcagc tatgcaaatg      780
ttaaaagata ccatcaatga ggaagctgca gaatgggaca ggntacatcc agtacatgca     840
gggcctattc caccaggcca gatgagagaa ccaaggggaa gtgacatagc aggaactact     900
agtacccttc aggaacaaat aggatggatg accagcaacc cacctatccc agtgggagaa     960
atctataaaa gatggataat cctgggatta aataaaatag taagaatgta tagccctgtc    1020
```

```
agcattttgg acataagaca agggccaaaa gaacccttta gagactatgt agataggttc    1080
tttaaaactc tcagagctga gcaagctaca caggaggtaa aaaactggat gacagacacc    1140
ttgctggtcc aaaatgcgaa cccagattgt aaatccatct tgagagcatt aggaccaggg    1200
gctacattag aagaaatgat gacagcatgt cagggagtgg gaggacccgg ccataaagca    1260
agggttttgg ctgaagcaat gagccaagta caaaatacaa ntncaaacat aatgatgcag    1320
agaggcaatt ttaggggtca aaaaagaatt aagtgtttca actgtggcaa ggaaggacac    1380
ctagccagaa attgcagggc ccctaggaaa aagggctgct ggaaatgtgg gaaggaagga    1440
catcaaatga aagactgcac tgagagacag gctaattttt tagggaaaat ttggccttcc    1500
aacaaaggga ggccaggaaa ttttcctcag agcagaacag agccaacagc cccaccagca    1560
gagnacttnn gaatggggga agagataacc tcctcnctga agcaggannn nancagggaa    1620
ccgtacactc ctgcaatttc cctcaaatca ctctttggca acgacctctt gtcacagtaa    1680
aaatagaagg acagctaaga gaagctctat tagatacagg agcagatgat acagtgttag    1740
aagacataaa tttgccagga aaatggaaac caaaaatgat agggggaatt ggaggtttta    1800
tcaaagtaag acaatatgat cagatagcta tagaaatttg tggaaaaagg gccataggta    1860
cagtattagt aggacctaca cctgtcaaca taattggaag aaatatgttg gttcagcttg    1920
gttgtacttt aaattttcca attagtccta ttgaaactgt accagtaaaa ttaaagccag    1980
gaatggatgg tccaaaggtt aaacaatggc cattgacaga agaaaaaata aaagcattaa    2040
cagaaatttg taaagaaatg gaaaaggaag gaaaaatttc aaaaattggg cctgaaaatc    2100
catacaacac tccagtgttt gctataaaga aaaagacag cactaaatgg agaaaattag    2160
tagatttcag agaactcaat aagagaactc aagacttctg gaagttcag ttaggaatac    2220 cacatccagc aggattaaaa aagaaaaaat cagtaacagt actagatgtg ggggacgcat    2280
atttttccgt tcccttacat gaagacttca gaaaatatac tgcattcacc atacctagta    2340
taaacaatga gacaccagga attaggtatc agtacaatgt acttccacag ggatggaaag    2400
gatcaccagc aatattccag agtagcatga caaaaatctt agagccctt agatcaaaaa    2460 atccagagat ggtcatctac caatacatgg atgacttgta tgtaggatct gatttagaaa    2520
taggtcagca tagagcaaaa atagaggaat taagggctca tttattaaga tggggattta    2580
ctacaccaga caaaaaacat cagaaagaac ctccatttct ttggatggga tatgagcttc    2640
atcctgacaa atggacagtc cagcctataa agctgccaga aaaagacagc tggactgtca    2700
atgatataca gaaattagta ggaaagttaa attgggcaag tcagatttat gcagggatta    2760
aagtaaagca actgtgtaaa ctccttagag gaaccaaagc actaacagac atagtaacac    2820
tgactaaaga agcagaatta gaattggaag agaacaggga gattctaaaa acccctgtac    2880
atggggtata ctatgaccca tcaaaagact aatagcaga atacagaaa caagggcaag    2940 accaatggac atatcaaatt tatcaagaac catttaaaaa tctaaaaaca gggaaatatg    3000
caaaaaggaa gtccacccac actaatgatg taaaacaatt aacagaagca gtacaaaaaa    3060 tagcccataga aagcatagta atatggggaa agactcctaa atttagatta cccatacaaa    3120
aagaaacatg ggagacatgg tggacggagt attggcaggc tacctggatt cctgagtggg    3180
agtttgtcaa taccccctcct ctagtaaaac tatggtacca gttagaaaca gaacccatag    3240
caggagcaga aactttctat gtagatgggg cagctaatag agagactaaa ctaggaaagg    3300
cagggtatgt cactgacaga ggaagacaaa aaattgtctc cctgacggag acaacaaatc    3360
```

```
aaaagactga attacatgca atctatttgg ctttacagga ttcaggatta gaagtnaaca    3420
tagtnacaga ttcacagtat gcattaggaa tcattcangc acaaccagat aggagtgaat    3480
cagagttagt caatcaaata atagaaaagt taatagaaaa ggaaagggtc tacctgtcat    3540
gggtaccagc acacaaaggg attggaggaa atgaacaggg aganaaatta gtcagttctg    3600
gaatcaggaa agtgntattt ttagatggga tagataaggc tcaagaagaa catgaaagat    3660
atcacagnaa ttggagagca atggctcatg actttaatct gccacctata gtagcaaaag    3720
aaatagtagc tagctgtgat aaatgtcagc taaaagggga agccatgcat ggacaagtag    3780
actgtagtcc aggaatatgg caactagatt gcacacatct agaaggaaaa gttatcctgg    3840
tagcagtcca tgtagccagt ggctatatag aagcagaagt catnccagca ganacaggac    3900
aggaaacagc atactttata ttaaaantag caggaagatg gccagtaaaa gtaatacata    3960
cagacaatgg gcccaatttc accagtgcaa cagttaaggc agcctgttgg tgggcaggtg    4020
tccaacanga atttgggatt ccctacaatc cccaaagtca aggagtagtg gaatctatga    4080
ataaagaatt aaagaaaatc atagggcagg taagagatca agctgaacac cttaagacag    4140
cagtacaaat ggcagtattc atncacaatt ttaaaagaaa agggggggatt ggggggataca    4200 gtgcagggga aagaataata gacataatag caacagatat acaaactaaa gaattacaaa    4260
aacaaattat aaaaattcaa aattttcggg tttattacag ggacagcaga gatccaattt    4320
ggaaaggacc agcaaaactc ctntggaaag gtgaaggggc agtagtaata caagacaata    4380
gtgatataaa ggtagtacca agaagaaaag caaagatcat tagggattat ggaaaacaga    4440
tggcaggtga tgattgtgtg gcaggtagac aggatgagga ttagaacatg gaacagttta    4500
gtaaaacatc atatgtatnt ttcaangaaa gctaaagant ggttctatag acatcactat    4560
gaaagcagac atccaagagt aagttcagaa gtacacatcc cgctagggga ggctagatta    4620
atagtaagaa catattgggg tctgcaccca ggagaaaaag actggcactt gggtcatggg    4680
gtctccatag aatggaggca gaaaaggtat agtacacaaa tagaccctga tctggcagac    4740
catctaatcc atctgtatta ttttgactgt ttttcagaat ctgccataag gaaagccata    4800
ttaggagaaa tagttagtcc taggtgtgaa tatcaagcag gacataacaa ggtaggntct    4860
ctgcaatatt tggcattgaa agcattagta gctncaacaa ggncaaagcc acctttgcct    4920
agtgttagga aattagtaga ggatagatgg aacaagcccc agaagaccag ggccacnga    4980 gggagccana caatgaatgg gtgttagaac tgttagagga gctcaagcag gaagctgtta    5040
gacatttccc taggcagtgg ctacatggcc taggacaaca tatctataat acctatgggg    5100
atacttggga aggagttgaa gctataataa gaactntgca acaactactg tttgtccatt    5160
tcagaattgg gtgccaacat agcagnatag gcattattcg aagaagaaga gtaagggatg    5220
gagccagtag accctaaant agagccctgg aaccatccgg gaagncagcc taaaactgct    5280
tgtancaagt gntattgtaa aaagtgttgc tatcattgcc anntgtgctt tctaaacaaa    5340
ggcttaggca tctcctatgg caggaagaag cggagacccc gacgaggacc tnctcanagc    5400
antaaggatc atcaaaatcc tntaccaaag cagtaagtag tagtaattaa tatatgtaat    5460 gttacccttta gcaatattgn caatagtagg actgntagta gcattaatct agcaatagt    5520 tgtatggact atagtatttta tagaatatag gaanattaag aagcaaagga aaatagactg    5580
gttaatcaan agaataagtg aaagagcaga agacagtggc aatgagagtg atggggacac    5640
agaggaattn tcancacttg tggngatggg gaatcttgat tttngggatg ntaataatgt    5700
gtaaagctac agatttgtgg gtcacagtat actatggagt acctgtgtgg aaagatgcag    5760
```

```
ataccaccct attttgtgca tcagatgcta aagcatatga tacagaagng cataatgtct    5820
gggccacaca tgcctgtgta cccacagacc ccaacccaca agaagtaaac ctggaaaatg    5880
taacagaaga ttttaacatg tggaaaaata acatggtaga gcagatgcat gaagatataa    5940
tcagtctatg ggatcaaagc ctaaagccat gtgtaaaatt aacccctctc tgcgtcactt    6000
taaattgtag caatgccaac accantanca ccaatnnnnn nnnnnnnnna gcactgaaga    6060
aataaaaaac tgctcttaca atattaccac agaactaaga gataaaacac agaaagtcta    6120
ttcactgttt tataaacttg atgtagtaca acttaatgaa nnaatannac aagtagtaat    6180
actcngtata gactaataaa ttgtaatacc tcagccatca cacaagcttg tccaaaggta    6240
tcctttgagc caattcctat acattattgt gccccagctg gttttgcgat tctaaagtgt    6300
aaggatccga gattcaatgg aacagggtca tgcaataatg ttagctcagt acaatgtaca    6360
catggaatta ngccagtagc atcaactcaa ctgctgttga atggcagtct agcagaagga    6420
gaggtaatga ttagatctga aaatattaca acaatgcca aaaacataat agtacagttt    6480
aataaacctg taccaattac ttgtatcaga cccaacaaca atacaagaaa aagtatacgc    6540
tttggaccag acaagccctt ctatacaaat gacataatag gggatataag acaagcacat    6600
tgtaatatca acaaaacana atggaatgcc actttacaaa aggtagctga acaattaaga    6660
gaacacttcc ctaataaaac aataatcttt actaactcct caggagggga cctagaaatt    6720
acaacacata gttttaattg tggaggagaa ttttttctatt gcaatacaac aggcctgttt    6780
aatagcacat ggnngatann ggcaccannc annagaatnn cacggagaca atggaanta    6840 taacnctccc atgcagaata aaacaaatta taaacatgtg gcagagagta ggacgagcaa    6900
tgtatgcccc tcccattgca ggagtaataa agtgtacatc aaacattaca ggaataatat    6960
tgacaagaga tggtgggaan aacagnanta atgagacctt cagacctgga ggaggagata    7020
tgagggacaa ttggagaagt gaattatata agtataaagt agtaaaaatt gaaccactag    7080
gagtagcacc caccagggca aagagaagag tggtggagag agaaaaaaga gcagttggan    7140
tgggagctgt tttccttggg ttcttgggag cagcaggaag cactatgggc gcggcgtcaa    7200
taacgctgac ggtacaggcc agacaattat tgtctggcat agtgcaacag caaagcaatt    7260
tgctgaaggc tatagaggct caacagcatc tgttgaaact cacagtctgg ggcattaaac    7320
agctccaggc aagagtcctg gctctggaaa gatacctaca ggatcaacag ctcctgggaa    7380
tttggggctg ctctggaaaa ctcatctgcg ccactactgt gccctggaac tctagttgga    7440
gtaataagac tcaggaggag atttggaaca acatgacctg gttgcaatgg gataaagaaa    7500
ttagcaatta cacaaacata atatatangc tacttgaaga atcgcagaac cagcaggaaa    7560
agaatgaaca agacttattg gcattagaca aatgggcaaa tttgtggaat tggtttaaca    7620
taacaaactg gctgtggtat ataagaatat ttataatgat agtaggaggc ttgataggat    7680
taagaatagt tattgctata atttctgtag taaatagagt taggcaggga tactcaccct    7740
tgtcatttca gatccctacc ccaaacccag agggtctcga caggcccgga agaatcgaag    7800
aaggaggtgg agagcaaggc agagacagat cgattcgatt agtgagcgga ttcttngcac    7860
ttgcctggga cgacctacgg agcctgtgcc tcttcagcta ccaccgcttg agagattgca    7920
tcttgattgc agcgaggact gtggaacttc tgggacacag cagtctcaag ggactgagac    7980
tggggtggga aggcctcaaa natctgtgga atcttctgnt atattgggt cgggaattga    8040 agaatagtgc tattagntta cttgatacca tagcagtagc agtagctgag tggacagata    8100
```

```
gggttataga aataggacaa agagcttgca gagctattct caacatacct agaagaatca    8160
gacagggctt cgaaagggct ttactataaa atgggggggca agtggtcaaa aagnaccata    8220
gtgggatggc ctgctattag ggagagaatg agaagaactc ctccagcagc agaaggaaca    8280
agaccaactc ctccagcagc agaaggagta ggagcagtgt ctcaagattt agctacacat    8340
ggagcagtca caagcagtaa tacagcagct aataatcctg attgcgcctg ggtggaagcg    8400
caagaagagg aggaagtagg cttcccagtc aggccacagg tacctttaag gccaatgacc    8460
ttcaagggag cttttgatct cagccacttt ttaaaagaaa aggggggact ggatgggtta    8520
atttactccc agaaaagaca agacatcctt gatctgtggg tctacaacnn nnnnnnnnn     8580 nnnnnnnnnn nnnnnnnnnn nnnnnnnnnn nnnnnnnnnn nnnnnnnnnn nnnnnnnnnn    8640
nnnnnnnnnn nnnnnnnnnn nnnnnnnnnn nnnnnnnnnn nnnnnnnnnn nnnnnnnnnn    8700
nnnnnnnnnn nnnnnnnnnn nnnnnnnnnn nnnnnnnnnn nnnnnnnnnn nnnnnnnnnn    8760
nnnnnnnnnn nnnnnnnnnn nnnnnnnnnn nnnnnnnnnn nnnnnnnnnn nnnnnnnnnn    8820
nnnnnnnnnn nnnnnnnnnn nnnnnnnnnn nnnnnnnnnn nnnnnnnnnn nnnnnnnnnn    8880
nnnnnnnnnn nnnnnnnnnn nnnnnnnnnn nnnnnnnnnn nnnnnnnnnn nnnnnnnnnn    8940
nnnnnnnnnn nnnnnnnnnn nnnnnnnnnn nnnnnnnnnn                         8980

<210> SEQ ID NO 5
<211> LENGTH: 9621
<212> TYPE: DNA
<213> ORGANISM: Human immunodeficiency virus
<220> FEATURE:
<221> NAME/KEY: modified_base
<222> LOCATION: (221)..(221)
<223> OTHER INFORMATION: a, c, t, g, unknown or other
<220> FEATURE:
<221> NAME/KEY: modified_base
<222> LOCATION: (263)..(263)
<223> OTHER INFORMATION: a, c, t, g, unknown or other
<220> FEATURE:
<221> NAME/KEY: modified_base
<222> LOCATION: (325)..(325)
<223> OTHER INFORMATION: a, c, t, g, unknown or other
<220> FEATURE:
<221> NAME/KEY: modified_base
<222> LOCATION: (502)..(502)
<223> OTHER INFORMATION: a, c, t, g, unknown or other
<220> FEATURE:
<221> NAME/KEY: modified_base
<222> LOCATION: (5374)..(5374)
<223> OTHER INFORMATION: a, c, t, g, unknown or other
<220> FEATURE:
<221> NAME/KEY: modified_base
<222> LOCATION: (6642)..(6642)
<223> OTHER INFORMATION: a, c, t, g, unknown or other
<220> FEATURE:
<221> NAME/KEY: modified_base
<222> LOCATION: (7411)..(7411)
<223> OTHER INFORMATION: a, c, t, g, unknown or other
<220> FEATURE:
<221> NAME/KEY: modified_base
<222> LOCATION: (7414)..(7414)
<223> OTHER INFORMATION: a, c, t, g, unknown or other
<220> FEATURE:
<221> NAME/KEY: modified_base
<222> LOCATION: (7587)..(7587)
<223> OTHER INFORMATION: a, c, t, g, unknown or other
<220> FEATURE:
<221> NAME/KEY: modified_base
<222> LOCATION: (8744)..(8744)
<223> OTHER INFORMATION: a, c, t, g, unknown or other
<220> FEATURE:
<221> NAME/KEY: modified_base
<222> LOCATION: (9572)..(9572)
<223> OTHER INFORMATION: a, c, t, g, unknown or other
```

<400> SEQUENCE: 5

```
ctggaagggc taatttactc ccaaaaaaga caagatatcc ttgatctgtg ggtctaccac    60
acacaaggct acttccctga ttggcagaac tacacaccag ggccagggat cagatatcca   120
ctgacctttg gatggtgctt caagctagta ccagttgagc cagagaaggt agaagaggcc   180
aatgaaggag agaacaacag cttgttacac cctatgagcc ngcatgggat ggatgacccg   240
gagaaagaag tgttagtgtg gangtttgac agccgcctag catttcatca catggcccga   300
gagctgcatc cggagtacta caagnactgc tgacatcgag cttttctacaa gggacttttcc   360
gctgggact ttccagggag gcgtggcctg ggcgggactg gggagtggcg agccctcaga   420
tgctgcatat aagcagctgc tttttgcctg tactgggtct ctctggttag accagatctg   480
agcctgggag ctctctggct anctagggaa cccactgctt aagcctcaat aaagcttgcc   540
ttgagtgctt caagtagtgt gtgcccgtct gttgtgtgac tctggtaact agagatccct   600
cagacccttt tagtcagtgt ggaaaatctc tagcagtggc gcccgaacag ggacttgaaa   660
gcgaaagtga accagagga gctctctcga cgcaggactc ggcttgctga gcgcgcacg    720
gcaagaggcg aggggcggcg actggtgagt acgccaaaaa ttttgactag cggaggctag   780
aaggagagag atgggtgcga gagcgtcagt attaagcggg ggagaattag atagatggga   840
aaaaattcgg ttaaggccag ggggaaagaa aaaatataaa ttaaaacata tagtatgggc   900
aagcagggag ctagaacgat tcgcagttaa tcctggcctg ttagaaacat cagaaggctg   960
tagacaaata ctgggacagc tacaaccatc ccttcagaca ggatcagaag aacttagatc  1020
attatataat acagtagcaa ccctctattg tgtgcatcaa aggatagagg taaaagacac  1080
caaggaagct ttagagaaga tagaggaaga gcaaaacaaa agtaagaaaa agcacagca   1140
agcagcagct gacacaggaa acagcagcca ggtcagccaa aattaccctata tagtgcagaa   1200
cctccagggg caaatggtac atcaggccat atcacctaga actttaaatg catgggtaaa   1260
agtagtagaa gagaaggctt tcagcccaga agtaatacc atgttttcag cattatcaga   1320
aggagccacc ccacaagatt taaacaccat gctaaacaca gtggggggac atcaagcagc   1380
catgcaaatg ttaaaagaga ccatcaatga ggaagctgca gaatgggata gattgcatcc   1440
agtgcatgca gggcctattg caccaggcca gatgagagaa ccaaggggaa gtgacatagc   1500
aggaactact agtacccttc aggaacaaat aggatggatg acaaataatc cacctatccc   1560
agtaggagaa atctataaaa gatggataat cctgggatta aataaaatag taagaatgta   1620
tagccctacc agcattctgg acataagaca aggaccaaag gaacccttta gagactatgt   1680
agaccggttc tataaaactc taagagccga gcaagcttca caggaggtaa aaaattggat   1740
gacagaaacc ttgttggtcc aaaatgcgaa cccagattgt aagactattt taaaagcatt   1800
gggaccagca gctacactag aagaaatgat gacagcatgt cagggagtgg gaggacccgg   1860
ccataaagca agagttttgg ctgaagcaat gagccaagta acaaattcag ctaccataat   1920
gatgcagaga ggcaatttta ggaaccaaag aaagactgtt aagtgtttca attgtggcaa   1980
agaagggcac atagccaaaa attgcagggc ccctaggaaa aagggctgtt ggaaatgtgg   2040
aaaggaagga caccaaatga aagattgtac tgagagacag gctaattttt tagggaagat   2100
ctggccttcc cacaagggaa ggccagggaa ttttcttcag agcagaccag agccaacagc   2160
cccaccagaa gagagcttca ggtttgggga agacaacaa actccctctc agaagcagga   2220
gccgatagac aaggaactgt atcctttagc ttccctcaga tcactctttg gcaacgaccc   2280
```

```
ctcgtcacaa taaagatagg ggggcaacta aaggaagctc tattagatac aggagcagat    2340
gatacagtat tagaagaaat gaatttgcca ggaagatgga aaccaaaaat gataggggga    2400
attggaggtt ttatcaaagt aagacagtat gatcagatac tcatagaaat ctgtggacat    2460
aaagctatag gtacagtatt agtaggacct acacctgtca acataattgg aagaaatctg    2520
ttgactcaga ttggttgcac tttaaatttt cccattagtc ctattgaaac tgtaccagta    2580
aaattaaagc caggaatgga tggcccaaaa gttaaacaat ggccattgac agaagaaaaa    2640
ataaaagcat tagtagaaat ttgtacagaa atggaaaagg aagggaaaat ttcaaaaatt    2700
gggcctgaaa atccatacaa tactccagta tttgccataa agaaaaaaga cagtactaaa    2760
tggagaaaat tagtagattt cagagaactt aataagagaa ctcaagactt ctgggaagtt    2820
caattaggaa taccacatcc cgcagggtta aaaagaaaaa atcagtaac agtactggat     2880
```

```
gtagaatcta tgaataaaga attaaagaaa attataggac aggtaagaga tcaggctgaa    4740
catcttaaga cagcagtaca aatggcagta ttcatccaca attttaaaag aaaagggggg    4800 attgggggt acagtgcagg ggaaagaata gtagacataa tagcaacaga catacaaact    4860
aaagaattac aaaaacaaat tacaaaaatt caaaattttc gggtttatta cagggacagc    4920
agagatccac tttggaaagg accagcaaag cttctctgga aaggtgaagg ggcagtagta    4980
atacaagata atagtgacat aaaagtagtg ccaagaagaa aagcaaagat cattagggat    5040
tatggaaaac agatggcagg tgatgattgt gtggcaagta gacaggatga ggattagaac    5100
atggaaaagt ttagtaaaac accatatgta tatttcaagg aaagctaagg gatggtttta    5160
tagacatcac tatgaaagca ctcatccaag aataagttca gaagtacaca tcccactagg    5220
ggatgctaaa ttggtaataa caacatattg gggtctgcat acaggagaaa gagactggca    5280
tttgggtcag ggagtctcca tagaatggag gaaaaagaga tatagcacac aagtagaccc    5340
tgacctagca gaccaactaa ttcatctgta ttantttgat tgttttttcag aatctgctat    5400 aagaaatgcc atattaggac atatagttag tcctaggtgt gaatatcaag caggacataa    5460
caaggtagga tctctacagt acttggcact agcagcatta ataacaccaa aaaagataaa    5520
gccacctttg cctagtgtta cgaaactgac agaggataga tggaacaagc cccagaagac    5580
caagggccac agagggagcc atacaatgaa tggacactag agcttttaga ggagcttaag    5640
agtgaagctg ttagacattt tcctaggata tggctccatg gcttaggaca acatatctat    5700
gaaacttatg gggatacttg ggcaggagtg gaagccataa taagaattct gcaacaactg    5760
ctgtttattc atttcagaat tgggtgtcaa catagcagaa taggcattac tcgacagagg    5820
agagcaagaa atggagccag tagatcctag actagagccc tggaagcatc caggaagtca    5880
gcctaagact gcttgtacca attgctattg taaaaagtgt tgctttcatt gccaagtttg    5940
tttcataaca aaaggcttag gcatctccta tggcaggaag aagcggagac agcgacgaag    6000
agctcctcaa gacagtcaga ctcatcaagt ttctctatca aagcagtaag tagtacatgt    6060
aatgcaatct ttacaaatat tagcaatagt agcattagta gtagcagcaa taatagcaat    6120
agttgtgtgg accatagtat tcatagaata taggaaaata ttaagacaaa gaaaaataga    6180
caggttaatt gatagaataa gagaaagagc agaagacagt ggcaatgaga gtgaagggga    6240
tcaggaagaa ttatcagcac ttgtggagat ggggcaccat gctccttggg atgttgatga    6300
tctgtagtgc tgcagaaaaa ttgtgggtca cagtctatta tggggtacct gtgtggaaag    6360
aagcaaccac cactctattt tgtgcatcag atgctaaagc atatgataca gaggtacata    6420
atgtttgggc cacacatgcc tgtgtaccca cagaccccaa cccacaagaa gtagtattgg    6480
aaaatgtgac agaaaatttt aacatgtgga aaataacat ggtagaacag atgcatgagg    6540
atataatcag tttatgggat caaagcctaa agccatgtgt aaaattaacc ccactctgtg    6600
ttactttaaa ttgcactgat ttgaagaata ctactaatac tntatactac tagtagtagt    6660
ggggaaaaga tggagaaagg agaaataaaa aactgctctt tcaatatcac cacaagcata    6720
agagataagg tgcagaaaga atatgcactt ttttataaac ttgatgtagt accaatagat    6780
aataataata ctagctatag gttgataagt tgtaacacct cagtcattac acaggcctgt    6840
ccaaaggtat cctttgagcc aattcccata cattattgtg ccccggctgg ttttgcgatt    6900
ctaaagtgta atgataagaa gttcaatgga acaggaccat gtacaaatgt cagcacagta    6960
caatgtacac atggaattag gccagtagta tcaactcaac tgctgttaaa tggcagtcta    7020
```

```
gcagaagaag aggtagtaat tagatctgac aatttcacgg acaatgctaa aaccataata    7080
gtacagctga atgaatctgt agaaattaat tgtacaagac ccaacaacaa tacaagaaaa    7140
agtatacata taggaccagg gagagcattt tatacaacag gagaaataat aggagatata    7200
agacaagcac attgtaacat tagtagagca aaatggaata cactttaaa acagatagtt     7260 aaaaaattaa gagaacaatt tgggaataaa acaatagtct ttaatcaatc ctcaggaggg    7320
gacccagaaa ttgtaatgca cagttttaat tgtggagggg aattttttcta ctgtaataca   7380 acacaactgt ttaatagtac ttggataata ntantaatag tactaataat actgaaggaa    7440
atgaaactat cacactccca tgcagaataa aacaaattat aaacatgtgg caggaagtag    7500
gaaaagcaat gtatgcccct cccatcagag acaaattag atgttcatca aatattacag     7560
ggctgctatt aacaagagat ggtggtnaat aacaacaacg agaccgagat cttcagacct    7620
ggaggaggag atatgaggga caattggaga agtgaattat ataaatataa agtagtaaaa    7680
attgaaccat taggagtagc acccaccaag gcaaagagaa gagtggtgca gagagaaaaa    7740
agagcagtgg gaataggagc tatgttcctt gggttcttgg gagcagcagg aagcactatg    7800
ggcgcagcgt caatgacgct gacggtacag gccagacaat tattgtctgg tatagtgcaa    7860
cagcagaaca atttgctgag ggctattgag gcgcaacagc atctgttgca actcacagtc     7920
tggggcatca agcagctcca ggcaagagtc ctggctgtgg aaagataccct aaaggatcaa    7980 cagctcctgg ggatttgggg ttgctctgga aaactcattt gcaccactgc tgtgccttgg     8040
aatgctagtt ggagtaataa atctctggat gagatttgga ataacatgac ctggatggag    8100
tgggaaagag aaaattgaca attacacaagc ttaatataca ccttaattga agaatcgcag    8160
aaccaacaag aaaagaatga acaagaatta ttggaattgg ataaatgggc aagtttgtgg    8220
aattggtttg acataacaaa ctggctgtgg tatataaaaa tattcataat gatagtagga    8280
ggcttggtag gtttaagaat agttttttgct gtactttcta tagtgaatag agttaggcag    8340
ggatactcac cattatcgtt tcagacccgc ctcccagccc cgaggggacc cgacaggccc    8400
gaaggaatcg aagaagaagg tggagagaga gacagagaca gatccggtcg attagtgaat    8460
ggattcttag cacttatctg ggacgacctg cggagcctgt gcctcttcag ctaccaccgc    8520
ttgagagact tactcttgat tgtaacgagg attgtggaac ttctgggacg caggggggtgg    8580 gaagccctca atattggtg gaatctcctg cagtattgga gtcaggaact aaagaatagt     8640
gctgttagct tgctcaatgc cacagctata gcagtagctg aggggacaga tagggttata    8700
gaagtagtac aaagagctta tagagctatt ctccacatac ctanaagaat aagacagggc    8760
ttggaaaggg ctttgctata agatgggtgg caagtggtca aaacgtagtg tgggtggatg    8820
gcctactgta agggaaagaa tgagacgagc tgagccagca gcagatgggg tgggagcagt    8880
atctcgagac ctggaaaaac atggagcaat cacaagtagc aatacagcag ctactaatgc    8940
tgattgtgcc tggctagaag cacaagagga ggaggaggtg ggttttccag tcagacctca    9000 ggtacctta agaccaatga cttacaaggc agctgtagat cttagccact ttttaaaaga     9060 aaaggggggga ctggaagggc taatttactc ccaaaaaaga caagatatcc ttgatctgtg    9120
ggtctaccac acacaaggct acttccctga ttggcagaac tacacaccag gccagggat     9180 cagatatcca ctgacctttg gatggtgctt caagctagta ccagttgagc cagagaaggt    9240
agaagaggcc aatgaaggag agaacaacag cttgttacac cctatgagcc tgcatgggat    9300
ggatgacccg gagaaagaag tgttagtgtg aagtttgac agccgcctag catttcatca    9360
catggcccga gagctgcatc cggagtacta caagaactgc tgacatcgag ctttctacaa    9420
```

```
gggactttcc gctggggact ttccagggag gcgtggcctg ggcgggactg gggagtggcg    9480
agccctcaga tgctgcatat aagcagctgc tttttgcctg tactgggtct ctctggttag    9540
accagatctg agcctgggag ctctctggct anctagggaa cccactgctt aagcctcaat    9600
aaagcttgcc ttgagtgctt a                                              9621
```

<210> SEQ ID NO 6
<211> LENGTH: 9611
<212> TYPE: DNA
<213> ORGANISM: Human immunodeficiency virus
<220> FEATURE:
<221> NAME/KEY: modified_base
<222> LOCATION: (274)..(274)
<223> OTHER INFORMATION: a, c, t, g, unknown or other
<220> FEATURE:
<221> NAME/KEY: modified_base
<222> LOCATION: (947)..(947)
<223> OTHER INFORMATION: a, c, t, g, unknown or other
<220> FEATURE:
<221> NAME/KEY: modified_base
<222> LOCATION: (5201)..(5201)
<223> OTHER INFORMATION: a, c, t, g, unknown or other
<220> FEATURE:
<221> NAME/KEY: modified_base
<222> LOCATION: (7384)..(7384)
<223> OTHER INFORMATION: a, c, t, g, unknown or other
<220> FEATURE:
<221> NAME/KEY: modified_base
<222> LOCATION: (8424)..(8424)
<223> OTHER INFORMATION: a, c, t, g, unknown or other

<400> SEQUENCE: 6

```
tggaagggtt aatttactcc aagaaaaggc aagagatcct tgatttgtgg gtctatcaca      60
cacaaggcta cttccctgat tggcaaaact acacaccggg accagggtc agatatccac      120 tgacctttgg atggtgcttc aagctagtgc cagttgaccc aagggaagta aagaggcca      180 acgaaggaga agacaactgt ttgctacacc ctatgagcca gcatggaatg gaggatgaag      240
acagagaagt attaaaatgg aagtttgaca gtcngctagc acgcagacac atggcccgcg      300
agctacatcc ggagtattac aaagactgct gacacagaag gactttccg ctgggacttt      360 ccactggggc gttccaggag gtgtggtctg ggcgggactg gggagtggtc aaccctcaga      420
tgctgcatat aagcagctgc ttttcgcctg tactgggtct ctctaggtag accagatctg      480
agcctgggag ctctctggct atctagggaa cccactgctt aagcctcaat aaagcttgcc      540
ttgagtgctc taagtagtgt gtgcccgtct gttgtgtgac tctggtaact agagatccct      600 cagaccctt tggtagtgt ggaaaatctc tagcagtggc gcccgaacag ggacttgaaa      660
gcgaaagtaa gaccagagga gatctctcga cgcaggactc ggcttgctga agtgcactcg      720
gcaagaggcg agagcggcgg ctggtgagta cgccaaattt tatttgacta gcggaggcta      780
gaaggagaga gatgggtgcg agagcgtcaa tattaagagg gggaaaatta gataaatggg      840
aaaaaattag gttaaggcca ggggggaaaga acactatat gctaaaacac ctagtatggg      900
caagcaggga gctggaaaga tttgcactta accctggcct tttaganaca tcagaaggct      960
gtaaacaaat aataaaacag ctacaaccag ctcttcagac aggaacagag gaacttagat     1020
cattatacaa cacagtagca actctctatt gtgtacatga aagatagag gtacgagaca     1080 ccaaggaagc cttagacaag atagaggaag aacaaaacaa aagtcagcaa aaaacacagc     1140
aggcaaaagc ggctgacgga aaggtcagtc aaaattatcc tatagtgcag aatctccaag     1200
ggcaaatggt acaccaggcc atatcaccta gaactttgaa tgcatgggta aaagtaatag     1260
```

```
aggagaaggc ttttagccca gaggtaatac ccatgtttac agcattatca gaaggagcca    1320
ccccacaaga tttaaacacc atgttaaata cagtgggggg acatcaagca gccatgcaaa    1380
tgttaaaaga taccatcaat gaggaggctg cagaatggga tagattacat ccagtacatg    1440
cagggcctat tgcaccaggc caaatgagag aaccaagggg aagtgacata gcaggaacta    1500
ctagtacccT tcaggaacaa atagcatgga tgacaagtaa cccacctatt ccagtgggag    1560
acatctataa aagatggata attctggggt taaataaaat agtaagaatg tatagccctg    1620
tcagcatttt ggacataaaa caagggccaa aggaacccTt tagagactat gtagaccggt    1680
tctttaaaac tttaagagct gaacaagcta cacaagatgt aaaaaattgg atgacagaca    1740
ccttgttggt ccaaaatgcg aacccagatt gtaagaccat tttaagagca ttaggaccag    1800
gggctacatt agaagaaatg atgacagcat gtcagggagt ggggaggacct ggccacaaag    1860 caagagtgtt ggctgaggca atgagccaag caaacaatac aaacataatg atgcagagaa    1920
gcaattttaa aggccctaaa agaattgtta aatgtttcaa ctgtggcaag gaagggcaca    1980
tagccagaaa ttgcagggcc cctaggaaaa aaggctgttg gaaatgtgga aaggaaggac    2040
accaaatgaa agactgtact gagaggcagg ctaattttTt agggaaaatt tggccttccc    2100 acaagggag gccagggaat ttccttcaga acagaccaga gccaacagcc ccaccagcag    2160
agagcttcag gttcgaggag acaaccccCg ctccgaagca ggagccgaaa gacagggaac    2220
ccttaacttc cctcaaatca ctctttggca gcgaccccTt gtctcaataa agtaggggg    2280 ccagataaag gaggctctct tagacacagg agcagatgat acagtattag aagaaataaa    2340
tttgccagga aaatggaaac caaaaatgat aggaggaatt ggaggtttta tcaaagtaag    2400
acagtatgat caaatactta tagaaatttg tggaaaaaag gctataggta cagtattagt    2460
aggacctaca cctgtcaaca taattggaag aaatatgttg actcagcttg gatgcacact    2520
aaatttccca attagtccca ttgaaactgt accagtaaaa ttaaagccag gaatggatgg    2580
cccaaaggtt aaacaatggc cattgacaga agagaaaata aaagcattaa cagcaatttg    2640
tgaagaaatg gagaaggaag gaaaaattac aaaaattggg cctgaaaatc catataacac    2700
tccagtattt gccataaaaa agaaggacag tactaagtgg agaaaattag tagatttcag    2760
ggaactcaat aaaagaactc aagacttttg ggaagttcaa ttaggaatac cacacccagc    2820
agggttaaaa aagaaaaaat cagtgacagt actggatgtg ggggatgcat attttTcagt    2880
tcctTtagat gaaggcttca ggaaatatac tgcattcacc ataccTagta taaacaatga    2940
aacaccaggg attagatatc aatataatgt gcttccacag ggatggaaag gatcaccagc    3000
aatattccag agtagcatga caaaaatctT agagcccttt agagcacaaa atccagaaat    3060
agtcatctat caatatatgg atgacttgta tgtaggatct gacttagaaa tagggcaaca    3120
tagagcaaaa atagaggagt taagagaaca tctattaaag tggggattta ccacaccaga    3180
caagaaacat cagaaagaac ccccatttct ttggatgggg tatgaactcc atcctgacaa    3240
atggacagta cagcctatac agctgccaga aaaggatagc tggactgtca atgatataca    3300
gaagttagtg ggaaaattaa actgggcaag tcagatttac ccagggatta agtaaggca    3360 actttgtaaa ctccttaggg gggccaaagc actaacagac atagtaccac taactgaaga    3420
agcagaatta gaattggcag agaacaggga aattctaaaa gaaccagtac atggagtata    3480
ttatgaccca tcaaaagact tgatagctga aatacagaaa caggggcatg accaatggac    3540
atatcaaatt taccaagaac cattcaaaaa tctgaaaaca gggaagtatg caaaaatgag    3600
gactgcccac actaatgatg taaaacagtt aacagaggca gtgcaaaaaa tagccatgga    3660
```

```
aagcatagta atatggggaa agactcctaa atttagacta cccatccaaa aagaaacatg   3720
ggagacatgg tggacagact attggcaagc cacctggatt cctgagtggg agtttgttaa   3780
tacccctccc ctagtaaaat tatggtacca gctggagaaa gaacccatag caggagcaga   3840
aactttctat gtagatggag cagctaatag ggaaactaaa ataggaaaag cagggtatgt   3900
tactgacaga ggaaggcaga aaattgtttc tctaactgaa acaacaaatc agaagactga   3960
attacaagca attcagctag ctttgcaaga ttcaggatca gaagtaaaca tagtaacaga   4020
ctcacagtat gcattaggaa tcattcaagc acaaccagat aagagtgaat cagagttagt   4080
caaccaaata atagaacaat taataaaaaa ggaaaagggtc tacctgtcat gggtaccagc   4140
acataaagga attggaggaa atgaacaagt agataaatta gtaagtagtg gaatcaggaa   4200
agtgctgttt ctagatggaa tagataaggc tcaagaagag catgaaaagt atcacagcaa   4260
ttggagagca atggctagtg agtttaatct gccacccata gtagcaaaag aaatagtagc   4320
tagctgtgat aaatgtcagc taaaagggga agccatacat ggacaagtag actgtagtcc   4380
agggatatgg caattagatt gtacacattt agaaggaaaa atcatcctgg tagcagtcca   4440
tgtagccagt ggctacatag aagcagaggt tatcccagca gaaacaggac aagaaacagc   4500
atactatata ctaaaattag caggaagatg gccagtcaaa gtaatacata cagacaatgg   4560
cagtaatttc accagtgctg cagttaaggc agcctgttgg tgggcaggta tccaacagga   4620
atttggaatt ccctacaatc cccaaagtca gggagtagta gaatccatga ataaagaatt   4680
aaagaaaatc atagggcagg taagagatca agctgagcac cttaagacag cagtacaaat   4740
ggcagtattc attcacaatt ttaaaagaaa aggggggatt ggggggtaca gtgcagggga   4800
aagaataata gacataatag caacagacat acaaactaaa gaattacaaa acaaaattat   4860
aaaaattcaa aattttcggg tttattacag agacagcaga gaccctattt ggaaaggacc   4920
agccaaacta ctctggaaag gtgaaggggc agtagtaata caagataata gtgacataaa   4980
ggtagtacca aggaggaaag caaaaatcat taaggactat ggaaaacaga tggcaggtgc   5040
tgattgtgtg gcaggtagac aggatgaaga ttagaacatg gaatagttta gtaaagcacc   5100
atatgtatat ttcaaggaga gctaatggat ggttttacag acatcattat gaaagcagac   5160
atccaaaagt aagttcagaa gtacacatcc cattagggga ngctagatta gtaataaaaa   5220
catattgggg tttgcaaaca ggagaaagag attggcattt gggtcatgga gtctccatag   5280
aatggagatt gagaagatat agcacacaag tagaccctgg cctggcagac cagctaattc   5340
atatgcatta ttttgattgt tttgcagact ctgccataag aaaagccata ttaggacaca   5400
tagttattcc taggtgtgac tatcaagcag gacataataa ggtaggatct ctacaatact   5460
tggcactgac agcattgata aaaccaaaaa agataaagcc acctctgcct agtgttagga   5520
aattagtaga ggatagatgg aacaagcccc agaagaccag gggccgcaga gggaaccata   5580
caatgaatgg acactagagc ttctagagga actcaagcag gaagctgtca gacactttcc   5640
tagaccatgg ctccatagct taggacaata tatctatgaa acctatgggg atacttggac   5700
aggagttgaa gctataataa gaatactgca acaactactg tttattcatt tcagaattgg   5760
gtgccagcat agcagaatag gcattttgcg acagagaaga gcaagaaatg gagccagtag   5820
atcctaacct agagccctgg aaccatccag gaagtcagcc taaaactgct tgtaataagt   5880
gctattgtaa acactgtagc tatcattgtc tagtttgctt tcagacaaaa ggcttaggca   5940
tttcctatgg caggaagaag cggagacagc gacgaagcgc tcctccaagc agtgaggatc   6000
```

```
atcaaaatcc tatatcaaag cagtaagtat atgtaatgtt agatttacta gcaagagtag    6060
attatagatt aggagtagga gcattgatag tagcactaat catagcaata gttgtgtgga    6120
ccatagtata tatagaatat aggaaattgt taagacaaag aaaatagac tggttaatta     6180 aaagaattag ggaaagagca gaagacagtg gcaatgagag tgaggggat actgaggaat    6240 tgtcaacaat ggtggatatg gggcatctta ggcttttgga tgttaatgat ttgtaatgtg    6300
gtggggaact tgtgggtcac agtctattat ggggtacctg tgtggaaaga agcaaaaact    6360
actctattct gtgcatcaga tgctaaagca tatgagaaag aagtgcataa tgtctgggct    6420
acacatgcct gtgtacccac agaccccaac ccacaagaaa tagttttgga aaatgtaaca    6480
gaaaatttta acatgtggaa aaatgacatg gtggatcaga tgcatgagga tataatcagt    6540
ttatgggatc aaagcctaaa gccatgtgta aagttgaccc cactctgtgt cactttaaac    6600
tgtacaaatg ttaatattac taataataat aaacaataat aacatgaatg aagaaataaa    6660
aaattgctct ttcaatataa ccacagaaat aagagataag aaacagaaag tgtatgcact    6720
tttttataga cttgatatag taccacttaa tgagaataac aattctagtg agtatagatt    6780
aataaattgt aatacctcaa ccataacaca agcctgtcca aaggtctctt ttgacccaat    6840
tcctatacat tattgtgctc cagctggtta tgcgattcta aagtgtaata ataagacatt    6900
caatgggaca ggaccatgca ataatgtcag cacagtacaa tgtacacatg gaattaagcc    6960
agtggtatca actcaactac tgttaaatgg tagcctagca gaagaagaga taataattag    7020
atctgaaaat ctgacaaaca atgtcaaaac aataatagta catcttaatg aatctgtaga    7080
aattgtgtgt acaagaccca acaataatac aagaaaagt ataaggatag gaccaggaca     7140
aacattctat gcaacaggag acataatagg agacataaga caagcacatt gtaacattag    7200
tgaagataaa tggaataaaa ctttacaaaa ggtaagtaaa aaattaaaag aacacttccc    7260
taataaaaca ataaaatttg aaccatcctc aggaggggac ctagaaatta caacacatag    7320
ctttaattgt agaggagaat ttttctattg caatacatca aaactgtttta atagtacata    7380 caanaataat actaataata atacaaattc aaccatcaca ctcccatgca gaataaaaca    7440
aattataaac atgtggcagg aggtaggacg agcaatgtat gcccctccca ttgcaggaaa    7500
cataacatgt aaatcaaata tcacaggact actattgaca cgtgatggag gaaaaaaaa     7560 taataacaca gagatattca gacctggagg aggagatatg agggacaatt ggagaagtga    7620
attatataaa tataaagtgg tagaaattaa gccattggga gtagcaccca ctgaggcaaa    7680
aaggagagtg gtggagagag aaaaaagagc agtgggaata ggagctgtgt tccttgggtt    7740
cttgggagca gcaggaagca ctatgggcgc ggcgtcaata acgctgacgg tacaggccag    7800
acaattgttg tctggtatag tgcaacagca aagcaatttg ctgagggcta tagaggcgca    7860
acagcatatg ttgcaactca cggtctgggg cattaagcag ctccagacaa gagtcctggc    7920
tatagaaaga tacctaaagg atcaacagct cctagggatt tggggctgct ctggaaaact    7980
catctgcacc actgctgtgc cttggaactc cagttggagt aataaatctc aagaagatat    8040
ttgggataac atgacctgga tgcagtggga tagagaaatt agtaattaca cagacacaat    8100
atacaggttg cttgaagact cgcaaaacca gcaggaaaaa aatgaaaaag atttattagc    8160
attggacagt tggaaaaatc tgtggaattg gtttgacata acaaattggc tgtggtatat    8220
aaaaatattc ataatgatag taggaggctt gataggttta agaataattt ttgctgtgct    8280
ctctatagtg aatagagtta ggcagggata ctcacctttg tcgtttcaga cccttacccc    8340
aaacccgagg ggacccgaca ggctcggaag aatcgaagaa gaaggtggag agcaagacag    8400
```

```
agacagatcc attcgattag tgancggatt cttagcactt gcctgggacg atctgcggag    8460
cctgtgcctc ttcagctacc accgattgag agacttcata ttggtggcag cgagagcagt    8520
ggaacttctg ggacgcagca gtctcagggg actacagagg gggtgggaag cccttaagta    8580
tctgggaagt cttgtgcagt attggggtct ggagctaaaa aagagtgcta ttagtctgct    8640
tgataccata gcaatagcag tagctgaagg aacagatagg attatagaat taatacaaag    8700
aatttgtaga gctatccgca acatacctag aagaataaga cagggctttg aagcagcttt    8760
gctataaaat gggggggcaag tggtcaaaaa gcagtatagt tggatggcct gctgtaagag    8820
aaagaataag aagaactgag ccagcagcag agggagtagg agcagcgtct caagacttag    8880
ataaacatgg agcacttaca agcagcaaca cagccaccaa taatgctgat tgtgcctggc    8940
tggaagcaca agaggaggaa gaagaagtag gctttccagt cagacctcag gtgccttta    9000 gaccaatgac ttataaggga gcattcgatc tcagcttctt tttaaaagaa aagggggggac    9060 tggaagggtt aatttactct aagaaaaggc aagagatcct tgatttgtgg gtctatcaca    9120
cacaaggcta cttccctgat tggcaaaact acacaccggg accagggggtc agatatccac    9180 tgacctttgg atggtgcttc aagctagtgc cagttgaccc aagggaagta gaagaggcca    9240
acgaaggaga aaacaactgt ttgctacacc ctatgagcca gcatggaatg gaggatgaag    9300
acagagaagt attaaagtgg aagtttgaca gtagcctagc acgcagacac atggcccgcg    9360
agctacatcc ggagtattac aaagactgct gacacagaag ggactttccg ctgggacttt    9420
ccactggggc gttccaggag gtgtggtctg ggcgggactg ggagtggtca accctcagat    9480
gctgcatata agcagctgct tttcgcctgt actgggtctc tctaggtaga ccagatctga    9540
gcctgggagc tctctggcta tctagggaac ccactgctta agcctcaata aagcttgcct    9600
tgagtgctct a                                                         9611

<210> SEQ ID NO 7
<211> LENGTH: 9581
<212> TYPE: DNA
<213> ORGANISM: Human immunodeficiency virus
<220> FEATURE:
<221> NAME/KEY: modified_base
<222> LOCATION: (24)..(25)
<223> OTHER INFORMATION: a, c, t, g, unknown or other
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: modified_base
<222> LOCATION: (260)..(260)
<223> OTHER INFORMATION: a, c, t, g, unknown or other
<220> FEATURE:
<221> NAME/KEY: modified_base
<222> LOCATION: (347)..(347)
<223> OTHER INFORMATION: a, c, t, g, unknown or other
<220> FEATURE:
<221> NAME/KEY: modified_base
<222> LOCATION: (764)..(764)
<223> OTHER INFORMATION: a, c, t, g, unknown or other
<220> FEATURE:
<221> NAME/KEY: modified_base
<222> LOCATION: (5940)..(5940)
<223> OTHER INFORMATION: a, c, t, g, unknown or other
<220> FEATURE:
<221> NAME/KEY: modified_base
<222> LOCATION: (6636)..(6636)
<223> OTHER INFORMATION: a, c, t, g, unknown or other
<220> FEATURE:
<221> NAME/KEY: modified_base
<222> LOCATION: (6647)..(6647)
```

```
<223> OTHER INFORMATION: a, c, t, g, unknown or other
<220> FEATURE:
<221> NAME/KEY: modified_base
<222> LOCATION: (6656)..(6656)
<223> OTHER INFORMATION: a, c, t, g, unknown or other
<220> FEATURE:
<221> NAME/KEY: modified_base
<222> LOCATION: (6665)..(6665)
<223> OTHER INFORMATION: a, c, t, g, unknown or other
<220> FEATURE:
<221> NAME/KEY: modified_base
<222> LOCATION: (7408)..(7408)
<223> OTHER INFORMATION: a, c, t, g, unknown or other
<220> FEATURE:
<221> NAME/KEY: modified_base
<222> LOCATION: (7412)..(7412)
<223> OTHER INFORMATION: a, c, t, g, unknown or other
<220> FEATURE:
<221> NAME/KEY: modified_base
<222> LOCATION: (7423)..(7423)
<223> OTHER INFORMATION: a, c, t, g, unknown or other
<220> FEATURE:
<221> NAME/KEY: modified_base
<222> LOCATION: (8922)..(8922)
<223> OTHER INFORMATION: a, c, t, g, unknown or other

<400> SEQUENCE: 7
attatggaag ggctaatttg gtcnnaaaga agacaagana tccttgatct ttgggtctac      60
cacacacaag gcttcttccc tgattggcaa aactacacac cagggccagg gattagatat     120
ccactgacct ttggatggtg cttcgagcta gtaccagttg atccagagga ggtagaagag     180
gccactgaag gagagaacaa ctgcttgtta caccctgtgt gccagcatgg aatggaggac     240
ccggagagag aagtgttaan gtggagattt aacagcagac tagcatttga acacaaggcc     300
cgaatactgc atccggagta ctacaaagac tgctgacacc gagtttncta caagggactt     360
tccgctgggg actttccagg gaggcgtaac cggggcggga ctggggagtg gctaaccctc     420
agatgctgca tataagcagc tgcttttttgc ctgtactggg tctctctggt tagaccagat     480
ttgagcctga gagctctctg gctagctagg gaacccactg cttaagcctc aataaagctt     540
gccttgagtg cttcaagtag tgtgtgcccg tctgttgtgt gactctggta actagagatc     600
cctcagaccc ctttagtcag agtggaaaat ctctagcagt ggcgcccgaa cagggacctg     660
aaagcgaaag tagaaccaga ggagctctct cgacgcagga ctcggcttgc tgaagcgcgc     720
acggcaagag gcgaggggca gcgactggtg agtacgctaa aaantttga ctagcggagg     780 ctagaaggag agagatgggt gcgagagcgt cagtattaag cggggggaaaa ttagatgaat     840 gggaaaaaat tcggttacgg ccagggggaa agaaaaaata tagactaaaa catatagtat     900
gggcaagcag ggagctagaa cgatttgcac ttaatcctgg cctttttagaa acatcagaag     960 gctgtaaaca ataatagga cagctacaac cagctattca gacaggatca gaggaactta    1020
aatcattata taatacagta gcaaccctct attgtgtaca tgaaaggata aaggtaacag    1080
acaccaagga agctttagac aagatagagg aagaacaaac caaaagtaag aaaaaagcac    1140
agcaagcaac agctgacaca agaaacagca gccaggtcag ccaaaattat cctatagtgc    1200
aaaacctaca ggggcaaatg gtacaccagg ccatatcacc tagaactttg aacgcatggg    1260
taaaagtaat agaggagaag gctttcagcc cagaagtaat acccatgttt tcagcattat    1320
cagaaggagc caccccacaa gatttaaaca ccatgctaaa cacagtgggg ggacatcaag    1380
cagccatgca aatgttaaaa gagaccatca atgaggaagc tgcagaatgg gataggctac    1440
atccagtgca tgcagggcct attgcaccag gccaaatgag agaaccaagg ggaagtgata    1500
tagcaggaac tactagtacc cttcaggaac aaataggatg gatgacaagc aatccaccta    1560
```

```
tcccagtagg agaaatctat aaaagatgga taatcctagg attaaataaa atagtaagaa   1620
tgtatagccc tgtcagcatt ttggacataa gacaaggacc aaaggaaccc tttagagact   1680
atgtagatcg gttctataaa actctaagag ccgagcaagc ttcacaggat gtaaaaaatt   1740
ggatgactga aaccttgttg gtccaaaatg caaacccaga ttgtaaaact atcttaaaag   1800
cattgggacc agcggctaca ttagaagaaa tgatgacagc atgtcaggga gtgggggggac  1860
ccagtcataa agcaagagtt ttggctgagg caatgagcca agcaacaaat gcaaatgctg   1920
ctataatgat gcagagaggc aattttaagg gcccaaagaa aatcattaag tgtttcaact   1980
gtggcaaaga agggcacata gcaaaaaatt gcagggctcc taggaaaaag gctgttggaa  2040
aatgtggaag ggaaggacac caaatgaaag attgcactga agacaggct aatttttag    2100
ggaaaatttg gccttcccac aagggaaggc cagggaactt ccttcagagc agaccagagc   2160
caacagcccc accagcagag agcttcgggt ttggggagga gataacaccc tctcagaaac   2220
aggagcagaa agacaaggaa ctgtatcctt tagcttccct caaatcactc tttggcaacg   2280
acccettgte acagtaaaga taggggggaca gctaaaggaa gctctattag atacaggage  2340
agatgataca gtattagaag aaataaattt gccaggaaaa tggaaaccaa aaatgatagg   2400
gggaattgga ggctttatca aagtaagaca gtatgatcaa atactcgtag aaatctgtgg   2460
acataaagct ataggtacag tattagtagg acctacacct gtcaacataa ttggaagaaa   2520
tttgttgact cagattggtt gcactttaaa ttttccaatt agtcctattg aaactgtacc   2580
agtaaaatta aagccaggga tggatggccc aaaagttaaa caatggccat tgacagaaga   2640
aaaaataaaa gcactaacag aaatttgtac agaaatggaa aaggaaggaa aaatttcaag   2700
aattgggcct gaaaatccat acaatactcc aatatttgcc ataaagaaaa aagacagtac   2760
taagtggaga aaattagtag atttcagaga acttaataag agaactcaag acttctggga   2820
agttcaacta ggaataccac atcctgcagg gctaaaaaag aaaaaatcag taacagtact   2880
ggatgtgggt gatgcatatt tttcagttcc cttagatgaa gactttagaa aatatactgc   2940
attcaccata cctagtataa acaatgagac accaggaatt agatatcagt acaatgtgct   3000
tccacaagga tggaaaggat caccggcaat attccaaagt agcatgacaa aaatcttaga   3060
acctttataga aaacaaaatc cagaaatggt tatctatcaa tacatggatg atttgtatgt   3120
aggatctgac ttagaaatag ggcagcatag aataaaaata gaggaattaa gggaacacct   3180
attgaagtgg ggatttacca caccagacaa aaagcatcag aaagaacctc catttctttg   3240
gatgggttat gaactccatc ctgataaatg gacagtacag cctataaaac tgccagaaaa   3300
agaaagctgg actgtcaatg atatacagaa gttagtggga aaattaaatt gggcaagcca   3360
gatttatcca ggaattaaag taagacaatt atgcaaatgc cttaggggag ccaaagcact   3420
gacagaagta gtaccactga cagaagaagc agaattagaa ctggcagaaa cagggaaat    3480
tctaaaagaa ccagtacatg gagtgtatta tgacccatca aaagacttaa tagcagaaat   3540
acagaaacaa gggcaagacc aatggacata tcaaatttat caagaacaat ataaaaatct   3600
gaaaacagga aagtatgcaa aaatgagggg tacccacact aatgatgtaa aacaattaac   3660
agaggcagtg caaaaaatag cccaagaatg tatagtgata tggggaaaga ctcctaaatt   3720
tagactaccc atacaaaagg aaacatggga acatggtgg acagagtatt ggcaggccac    3780
ctggattcct gagtgggagt ttgtcaatac ccctcccttta gttaaattat ggtaccagtt   3840
agagaaggaa cccatagtag gagcagaaac tttctatgta gatggggcag ctaatagaga   3900
```

```
gactaaaatta ggaaaagcag gatatgttac tgacagagga agacagaaag ttgtctctct   3960
aactgacaca acaaatcaga agactgaatt acaagccatt aatctagctt tgcaggattc   4020
gggattagaa gtaaacatag taacagactc acaatatgca ttaggaatca ttcaagcaca   4080
accagataag agtgaatcag agttagtcag tcaaataata gagcagttaa taaaaaagga   4140
aaaggtctac ctatcatggg taccagcaca aagggggatt ggaggaaatg aacaagtaga   4200
taaattagtc agtaatggaa tcagaaaaat actattcttg gatggaatag ataaggctca   4260
agaagaacat gagaaatacc acaacaattg gagagcaatg gctagtgatt ttaacctgcc   4320
acctgtggta gcaaaagaaa tagtagctag ctgtgataaa tgtcagctaa aggagaagc   4380 cttgcatgga caagtagact gtagtccagg aatatggcaa ttagattgta cacatttaga   4440
aggaaaagtt atcctggtag cagtccatgt agccagtggc tatatagaag cagaagttat   4500
tccagcagaa acagggcagg aaacagccta ctttctctta aaattagcag gaagatggcc   4560
agtaaaagta gtacatacag acaatggcag caatttcacc agcgctgcag ttaaggccgc   4620
ctgttggtgg gcaggcatca agcaggaatt tggaattccc tacaatcccc aaagtcaagg   4680
agtagtagaa tctatgaata aagaattaaa gaaaattata ggacaggtaa gagatcaagc   4740
tgaacatctt aagacagcag tacaaatggc agtattcatc cacaattttaa aaagaaaagg   4800 ggggattggg ggtacagtg caggggaaag aataatagac ataatagcaa cagacataca   4860
aactaaagaa ttacaaaaac aaatcataaa aattcaaaat tttcgggttt attacaggga   4920
cagcagagat ccaatttgga aaggaccagc aaagcttctc tggaaaggtg aaggggcagt   4980
agtaatacaa gacaatagtg aaataaaggt agtaccaaga agaaaagtaa agatcattag   5040
ggattatgga aaacagatgg caggtgatga ttgtgtggca agtagacagg atgaggatta   5100
gaacatggaa gagtttagta aaacatcata tgtatgtttc aaagaaagct caaggatggt   5160
tgtatagaca tcactatgac tgcccacacc caaaaataag ttcagaagta cacatcccac   5220
taggagaagc tagactggta gtaaaaacat attggggtct gcatacagga gaaagagaat   5280
ggcatctggg tcagggagtc tccatagaat ggaggaaaag gagatatagc acacaagtag   5340
accctggcct ggcagaccaa ctaattcata tatattattt tgattgtttt gcagaatctg   5400
ctataagaaa agccatatta ggacatatag ttactcctag gtgtaattat caagcaggac   5460
ataacaaggt aggatcttta caatatttgg cactaacagc attaataaca ccaaaaaaga   5520
taaaaccacc tttgcctagt gttaggaagc tgacagaaga cagatggaac aagccccaga   5580
ggaccaaggg ccacagaggg agccatacaa tgaatggaca ttagagcttt tagaggagct   5640
taagagtgaa gctgttagac actttcctag gatatggctt catggcctag gacaacatat   5700
ctatgaaact tatggggata cctggacagg agttgaagct ataataagaa tccttcaaca   5760
actactgttt atccatttca gaattgggtg tcaacatagc agaataggca ttactcgaca   5820
gagaagaaca agaaatggat ccagtagatc ctaacctaga gccctggaac catccaggaa   5880
gtcagcctag gactccttgt aacaagtgtt attgtaaaaa gtgttgctat cattgccaan   5940
tttgcttcat aacgaaaggc ttaggcatct cctatggcag gaagaagcgg agacagcgac   6000
gaagacctcc tcaaggcggt caggctcatc aagatcctat accaaagcag taagtagtac   6060
atgtaatgca atctttagtg atattagcaa tagtagcatt agtagtagcg ctaataatag   6120
caatagttgt gtggactata gtattcatag agtgtagaag attaaaaagg caaagaaaaa   6180
tagactggtt aattgataga ataagagaaa gagcagaaga tagtggcaat gagagtgagg   6240
gagatagaga ggaattatca gcacttgtgg agatggggca ccatgctcct tgggatgttg   6300
```

```
atgacatgta gtgttgcagg aaagttgtgg gtcacagttt attatggggt acctgtgtgg    6360
aaagaagcaa ccactactct attttgtgca tcagatgcta aatcatataa aacagaggca    6420
cataatatct gggctacaca tgcctgtgta ccaacagacc ccaacccaca agaaataaaa    6480
ctagaaaatg tcacagaaaa ctttaacatg tggaaaaata acatggtgga gcagatgcat    6540
gaggatataa tcagtttatg ggatcaaagc ctaaaaccat gtgtaaaatt aaccccactc    6600
tgtgtcactt taaactgcac tgattggaag aataanaata ccactantat aacacnaatg    6660
agganatagg aatgaaaaac tgctctttca atataaccac agaagtaaga gataagaaga    6720
agcaagtaca tgcactttt tataaacttg atgtggtaca aatagataat ataatactaa    6780
taataccagc tatagattaa taaattgtaa tacctcagcc attacacagg cgtgtccaaa    6840 ggtaacctt gagccaattc ccatacatta ttgtgcccca gctggatttg caattctaaa    6900
atgtaatgat aagaagttca atgggacggg tccatgcaaa aatgtcagca cagtacagtg    6960
tacacatggg attaagccag tagtgtcaac tcaactgttg ttgaatggca gtctagcaga    7020
agaagagata ataattagat ctgaaaatct cacaaataat gctaaaatca taatagtaca    7080
gcttaatgag tctgtaacaa ttaattgcac aaggccctac aacaatacaa gacaaagtat    7140
acatatagga ccagggcaag cactctatac aacaaaaata ataggagata taagacaagc    7200
acattgtaat attagtagag cagaatggaa taaaacttta caacaggtag ctaaaaaatt    7260
aggagacctt cttaacaaga caacaataat tttaaaacca tcctcgggag ggacccaga    7320 aattacaaca cacagctttta attgtggagg ggaatttttc tactgcaata catcaggact    7380
gtttaatagt acatggaaat aataatanta anaatagtaa tgngaaaaaa aatgatacaa    7440
tcacactccc atgcagaata aaacaaatta taaacatgtg gcaggagta ggaaaagcaa    7500 tgtatgcccc tcccattgaa ggactaatca aatgttcatc aaatattaca ggactattgt    7560
tgacaagaga tggtggtaat aataatagtc agaatgagac cttcagacct ggaggaggag    7620
atatgagaga caattggaga agtgaattat acaaatataa agtagtaaga attgaaccac    7680
taggtctagc acccaccaag gcaaagagaa gagtggtgga aagagaaaaa agagcaatag    7740
gactaggagc tatgttcctt gggttcttgg agcagcagg aagcacgatg ggcgcagcgt    7800
cactgacgct gacggtacag gccagacagt tattgtctgg tatagtgcaa cagcaaaaca    7860
atttgctgag ggctatagag cgcaacagc atctgttgca actcacagtc tggggcatta    7920
aacagctcca ggcaagagtc ctggctgtgg aaagatacct aaaggatcaa cagctcctag    7980
gaatttgggg ttgctctgga aaacacattt gcaccactaa tgtgccctgg aactctagct    8040
ggagtaataa atctctagat gagatttggg ataacatgac ctggatggag tgggaaagag    8100
aaattgacaa ttcacaggt ttaatataca gcttaattga agaatcgcaa acccagcaag    8160
aaaagaatga acaagaacta ttgcaattgg acaaatgggc aagtttgtgg aattggttta    8220
gcataacaaa atggctgtgg tatataaaaa tattcataat gatagtagga ggcttgatag    8280
gtttaagaat agttttgct gtgctttctt tagtaaatag agttaggcag ggatattcac    8340
ctctgtcgtt tcagaccctc ctcccagccc cgagggacc cgacaggccc gaaggaatag    8400
aagaagaagg tggagagcaa ggcagaggca gatccattcg attggtgaac ggattctcag    8460
cacttatctg gacgatctg aggaacctgt gcctcttcag ctaccaccgc ttgagagact    8520
taatcttaat tgcaacgagg attgtggaac ttctgggacg cagggggtgg gaagccatca    8580
aatatctgtg gaatctcctg cagtattgga ttcaggaact aaagaatagt gctattagct    8640
```

-continued

```
tgcttaatac cacagcaata gcagtagctg aggggacaga tagggttata gaaatagtac    8700
aaagagctgt tagagctatt cttaacatac ccagacgaat aagacagggc ttggaaaggg    8760
ctttactata aaatgggtgg caaatggtca aaaagtagta tagttggatg gcctgctata    8820
agggaaagaa taagaagaac tgatccagca gcagaagggg tgggagcagt atctcgggac    8880
ctggaaaaac atggggcaat cacaagtagc aatacagcac anactaatcc tgactgtgcc    8940
tggctagaag cacaagaaga ggacgaggaa gtgggttttc cagtcagacc tcaggtacca    9000
ttaagaccaa tgacttacaa gggagctgta gatctgagcc acttttaaa agaaaagggg     9060 ggactggaag ggttaatttg gtcccagaaa agacaagaga tccttgatct ttgggtctac    9120
cacacacaag gctacttccc tgattggcaa aactacacac cagggccagg gattagatat    9180
ccactgacct ttggatggtg cttcgagcta gtaccagttg atccaaagga ggtagaagag    9240
gacactgaag gagagaacaa ctgcttgtta caccctatgt gccagcatgg aatggaggac    9300
ccggagagag aagtgttaat gtggagattt aacagcagac tagcatttga acacaaggcc    9360
cgaatgaagc atccggagtt ctacaaagac tgctgacacc gagttttcta caagggactt    9420
tccgctgggg actttccagg gaggcgtaac aggggcggga ctgggagtgg ctaaccctca    9480
gatgctgcat ataagcagct gctttttgcc tgtactgggt ctctcttgtt agaccagatt    9540
tgagcctgag agctctctgg ctagctaggg aacccactgc t                        9581
```

<210> SEQ ID NO 8
<211> LENGTH: 8976
<212> TYPE: DNA
<213> ORGANISM: Human immunodeficiency virus
<220> FEATURE:
<221> NAME/KEY: modified_base
<222> LOCATION: (23)..(23)
<223> OTHER INFORMATION: a, c, t, g, unknown or other
<220> FEATURE:
<221> NAME/KEY: modified_base
<222> LOCATION: (191)..(191)
<223> OTHER INFORMATION: a, c, t, g, unknown or other
<220> FEATURE:
<221> NAME/KEY: modified_base
<222> LOCATION: (250)..(250)
<223> OTHER INFORMATION: a, c, t, g, unknown or other
<220> FEATURE:
<221> NAME/KEY: modified_base
<222> LOCATION: (426)..(426)
<223> OTHER INFORMATION: a, c, t, g, unknown or other
<220> FEATURE:
<221> NAME/KEY: modified_base
<222> LOCATION: (439)..(439)
<223> OTHER INFORMATION: a, c, t, g, unknown or other
<220> FEATURE:
<221> NAME/KEY: modified_base
<222> LOCATION: (704)..(704)
<223> OTHER INFORMATION: a, c, t, g, unknown or other
<220> FEATURE:
<221> NAME/KEY: modified_base
<222> LOCATION: (795)..(795)
<223> OTHER INFORMATION: a, c, t, g, unknown or other
<220> FEATURE:
<221> NAME/KEY: modified_base
<222> LOCATION: (799)..(799)
<223> OTHER INFORMATION: a, c, t, g, unknown or other
<220> FEATURE:
<221> NAME/KEY: modified_base
<222> LOCATION: (826)..(826)
<223> OTHER INFORMATION: a, c, t, g, unknown or other
<220> FEATURE:
<221> NAME/KEY: modified_base
<222> LOCATION: (922)..(922)
<223> OTHER INFORMATION: a, c, t, g, unknown or other
<220> FEATURE:
<221> NAME/KEY: modified_base -continued

```
<222> LOCATION: (1012)..(1012)
<223> OTHER INFORMATION: a, c, t, g, unknown or other
<220> FEATURE:
<221> NAME/KEY: modified_base
<222> LOCATION: (1262)..(1262)
<223> OTHER INFORMATION: a, c, t, g, unknown or other
<220> FEATURE:
<221> NAME/KEY: modified_base
<222> LOCATION: (1285)..(1285)
<223> OTHER INFORMATION: a, c, t, g, unknown or other
<220> FEATURE:
<221> NAME/KEY: modified_base
<222> LOCATION: (1576)..(1576)
<223> OTHER INFORMATION: a, c, t, g, unknown or other
<220> FEATURE:
<221> NAME/KEY: modified_base
<222> LOCATION: (2406)..(2406)
<223> OTHER INFORMATION: a, c, t, g, unknown or other
<220> FEATURE:
<221> NAME/KEY: modified_base
<222> LOCATION: (2565)..(2565)
<223> OTHER INFORMATION: a, c, t, g, unknown or other
<220> FEATURE:
<221> NAME/KEY: modified_base
<222> LOCATION: (2788)..(2788)
<223> OTHER INFORMATION: a, c, t, g, unknown or other
<220> FEATURE:
<221> NAME/KEY: modified_base
<222> LOCATION: (2862)..(2862)
<223> OTHER INFORMATION: a, c, t, g, unknown or other
<220> FEATURE:
<221> NAME/KEY: modified_base
<222> LOCATION: (3287)..(3287)
<223> OTHER INFORMATION: a, c, t, g, unknown or other
<220> FEATURE:
<221> NAME/KEY: modified_base
<222> LOCATION: (3570)..(3570)
<223> OTHER INFORMATION: a, c, t, g, unknown or other
<220> FEATURE:
<221> NAME/KEY: modified_base
<222> LOCATION: (3744)..(3744)
<223> OTHER INFORMATION: a, c, t, g, unknown or other
<220> FEATURE:
<221> NAME/KEY: modified_base
<222> LOCATION: (3793)..(3793)
<223> OTHER INFORMATION: a, c, t, g, unknown or other
<220> FEATURE:
<221> NAME/KEY: modified_base
<222> LOCATION: (3829)..(3829)
<223> OTHER INFORMATION: a, c, t, g, unknown or other
<220> FEATURE:
<221> NAME/KEY: modified_base
<222> LOCATION: (3864)..(3864)
<223> OTHER INFORMATION: a, c, t, g, unknown or other
<220> FEATURE:
<221> NAME/KEY: modified_base
<222> LOCATION: (3914)..(3914)
<223> OTHER INFORMATION: a, c, t, g, unknown or other
<220> FEATURE:
<221> NAME/KEY: modified_base
<222> LOCATION: (3935)..(3935)
<223> OTHER INFORMATION: a, c, t, g, unknown or other
<220> FEATURE:
<221> NAME/KEY: modified_base
<222> LOCATION: (4158)..(4158)
<223> OTHER INFORMATION: a, c, t, g, unknown or other
<220> FEATURE:
<221> NAME/KEY: modified_base
<222> LOCATION: (4211)..(4211)
<223> OTHER INFORMATION: a, c, t, g, unknown or other
<220> FEATURE:
<221> NAME/KEY: modified_base
<222> LOCATION: (4506)..(4506)
<223> OTHER INFORMATION: a, c, t, g, unknown or other
<220> FEATURE:
<221> NAME/KEY: modified_base
<222> LOCATION: (4539)..(4539)
<223> OTHER INFORMATION: a, c, t, g, unknown or other
<220> FEATURE:
```

```
<221> NAME/KEY: modified_base
<222> LOCATION: (4541)..(4541)
<223> OTHER INFORMATION: a, c, t, g, unknown or other
<220> FEATURE:
<221> NAME/KEY: modified_base
<222> LOCATION: (4597)..(4597)
<223> OTHER INFORMATION: a, c, t, g, unknown or other
<220> FEATURE:
<221> NAME/KEY: modified_base
<222> LOCATION: (4773)..(4773)
<223> OTHER INFORMATION: a, c, t, g, unknown or other
<220> FEATURE:
<221> NAME/KEY: modified_base
<222> LOCATION: (4822)..(4822)
<223> OTHER INFORMATION: a, c, t, g, unknown or other
<220> FEATURE:
<221> NAME/KEY: modified_base
<222> LOCATION: (5025)..(5025)
<223> OTHER INFORMATION: a, c, t, g, unknown or other
<220> FEATURE:
<221> NAME/KEY: modified_base
<222> LOCATION: (5159)..(5159)
<223> OTHER INFORMATION: a, c, t, g, unknown or other
<220> FEATURE:
<221> NAME/KEY: modified_base
<222> LOCATION: (5254)..(5254)
<223> OTHER INFORMATION: a, c, t, g, unknown or other
<220> FEATURE:
<221> NAME/KEY: modified_base
<222> LOCATION: (5266)..(5266)
<223> OTHER INFORMATION: a, c, t, g, unknown or other
<220> FEATURE:
<221> NAME/KEY: modified_base
<222> LOCATION: (5281)..(5282)
<223> OTHER INFORMATION: a, c, t, g, unknown or other
<220> FEATURE:
<221> NAME/KEY: modified_base
<222> LOCATION: (5284)..(5284)
<223> OTHER INFORMATION: a, c, t, g, unknown or other
<220> FEATURE:
<221> NAME/KEY: modified_base
<222> LOCATION: (5359)..(5359)
<223> OTHER INFORMATION: a, c, t, g, unknown or other
<220> FEATURE:
<221> NAME/KEY: modified_base
<222> LOCATION: (5382)..(5382)
<223> OTHER INFORMATION: a, c, t, g, unknown or other
<220> FEATURE:
<221> NAME/KEY: modified_base
<222> LOCATION: (5405)..(5408)
<223> OTHER INFORMATION: a, c, t, g, unknown or other
<220> FEATURE:
<221> NAME/KEY: modified_base
<222> LOCATION: (5426)..(5426)
<223> OTHER INFORMATION: a, c, t, g, unknown or other
<220> FEATURE:
<221> NAME/KEY: modified_base
<222> LOCATION: (5443)..(5443)
<223> OTHER INFORMATION: a, c, t, g, unknown or other
<220> FEATURE:
<221> NAME/KEY: modified_base
<222> LOCATION: (5519)..(5519)
<223> OTHER INFORMATION: a, c, t, g, unknown or other
<220> FEATURE:
<221> NAME/KEY: modified_base
<222> LOCATION: (5549)..(5549)
<223> OTHER INFORMATION: a, c, t, g, unknown or other
<220> FEATURE:
<221> NAME/KEY: modified_base
<222> LOCATION: (5767)..(5767)
<223> OTHER INFORMATION: a, c, t, g, unknown or other
<220> FEATURE:
<221> NAME/KEY: modified_base
<222> LOCATION: (5813)..(5813)
<223> OTHER INFORMATION: a, c, t, g, unknown or other
<220> FEATURE:
<221> NAME/KEY: modified_base
<222> LOCATION: (5939)..(5939)
<223> OTHER INFORMATION: a, c, t, g, unknown or other
```

-continued

```
<220> FEATURE:
<221> NAME/KEY: modified_base
<222> LOCATION: (5987)..(5987)
<223> OTHER INFORMATION: a, c, t, g, unknown or other
<220> FEATURE:
<221> NAME/KEY: modified_base
<222> LOCATION: (5989)..(5990)
<223> OTHER INFORMATION: a, c, t, g, unknown or other
<220> FEATURE:
<221> NAME/KEY: modified_base
<222> LOCATION: (6003)..(6005)
<223> OTHER INFORMATION: a, c, t, g, unknown or other
<220> FEATURE:
<221> NAME/KEY: modified_base
<222> LOCATION: (6008)..(6008)
<223> OTHER INFORMATION: a, c, t, g, unknown or other
<220> FEATURE:
<221> NAME/KEY: modified_base
<222> LOCATION: (6013)..(6013)
<223> OTHER INFORMATION: a, c, t, g, unknown or other
<220> FEATURE:
<221> NAME/KEY: modified_base
<222> LOCATION: (6084)..(6084)
<223> OTHER INFORMATION: a, c, t, g, unknown or other
<220> FEATURE:
<221> NAME/KEY: modified_base
<222> LOCATION: (6088)..(6088)
<223> OTHER INFORMATION: a, c, t, g, unknown or other
<220> FEATURE:
<221> NAME/KEY: modified_base
<222> LOCATION: (6112)..(6112)
<223> OTHER INFORMATION: a, c, t, g, unknown or other
<220> FEATURE:
<221> NAME/KEY: modified_base
<222> LOCATION: (6138)..(6139)
<223> OTHER INFORMATION: a, c, t, g, unknown or other
<220> FEATURE:
<221> NAME/KEY: modified_base
<222> LOCATION: (6142)..(6142)
<223> OTHER INFORMATION: a, c, t, g, unknown or other
<220> FEATURE:
<221> NAME/KEY: modified_base
<222> LOCATION: (6144)..(6145)
<223> OTHER INFORMATION: a, c, t, g, unknown or other
<220> FEATURE:
<221> NAME/KEY: modified_base
<222> LOCATION: (6157)..(6157)
<223> OTHER INFORMATION: a, c, t, g, unknown or other
<220> FEATURE:
<221> NAME/KEY: modified_base
<222> LOCATION: (6279)..(6279)
<223> OTHER INFORMATION: a, c, t, g, unknown or other
<220> FEATURE:
<221> NAME/KEY: modified_base
<222> LOCATION: (6522)..(6522)
<223> OTHER INFORMATION: a, c, t, g, unknown or other
<220> FEATURE:
<221> NAME/KEY: modified_base
<222> LOCATION: (6559)..(6559)
<223> OTHER INFORMATION: a, c, t, g, unknown or other
<220> FEATURE:
<221> NAME/KEY: modified_base
<222> LOCATION: (6578)..(6578)
<223> OTHER INFORMATION: a, c, t, g, unknown or other
<220> FEATURE:
<221> NAME/KEY: modified_base
<222> LOCATION: (6640)..(6640)
<223> OTHER INFORMATION: a, c, t, g, unknown or other
<220> FEATURE:
<221> NAME/KEY: modified_base
<222> LOCATION: (6764)..(6764)
<223> OTHER INFORMATION: a, c, t, g, unknown or other
<220> FEATURE:
<221> NAME/KEY: modified_base
<222> LOCATION: (6915)..(6915)
<223> OTHER INFORMATION: a, c, t, g, unknown or other
<220> FEATURE:
<221> NAME/KEY: modified_base
<222> LOCATION: (6917)..(6917)
```

```
<223> OTHER INFORMATION: a, c, t, g, unknown or other
<220> FEATURE:
<221> NAME/KEY: modified_base
<222> LOCATION: (6925)..(6925)
<223> OTHER INFORMATION: a, c, t, g, unknown or other
<220> FEATURE:
<221> NAME/KEY: modified_base
<222> LOCATION: (6984)..(6984)
<223> OTHER INFORMATION: a, c, t, g, unknown or other
<220> FEATURE:
<221> NAME/KEY: modified_base
<222> LOCATION: (6992)..(6992)
<223> OTHER INFORMATION: a, c, t, g, unknown or other
<220> FEATURE:
<221> NAME/KEY: modified_base
<222> LOCATION: (7036)..(7036)
<223> OTHER INFORMATION: a, c, t, g, unknown or other
<220> FEATURE:
<221> NAME/KEY: modified_base
<222> LOCATION: (7066)..(7066)
<223> OTHER INFORMATION: a, c, t, g, unknown or other
<220> FEATURE:
<221> NAME/KEY: modified_base
<222> LOCATION: (7107)..(7107)
<223> OTHER INFORMATION: a, c, t, g, unknown or other
<220> FEATURE:
<221> NAME/KEY: modified_base
<222> LOCATION: (7195)..(7195)
<223> OTHER INFORMATION: a, c, t, g, unknown or other
<220> FEATURE:
<221> NAME/KEY: modified_base
<222> LOCATION: (7407)..(7407)
<223> OTHER INFORMATION: a, c, t, g, unknown or other
<220> FEATURE:
<221> NAME/KEY: modified_base
<222> LOCATION: (7458)..(7458)
<223> OTHER INFORMATION: a, c, t, g, unknown or other
<220> FEATURE:
<221> NAME/KEY: modified_base
<222> LOCATION: (7484)..(7484)
<223> OTHER INFORMATION: a, c, t, g, unknown or other
<220> FEATURE:
<221> NAME/KEY: modified_base
<222> LOCATION: (7696)..(7696)
<223> OTHER INFORMATION: a, c, t, g, unknown or other
<220> FEATURE:
<221> NAME/KEY: modified_base
<222> LOCATION: (7937)..(7937)
<223> OTHER INFORMATION: a, c, t, g, unknown or other
<220> FEATURE:
<221> NAME/KEY: modified_base
<222> LOCATION: (7947)..(7947)
<223> OTHER INFORMATION: a, c, t, g, unknown or other
<220> FEATURE:
<221> NAME/KEY: modified_base
<222> LOCATION: (7980)..(7980)
<223> OTHER INFORMATION: a, c, t, g, unknown or other
<220> FEATURE:
<221> NAME/KEY: modified_base
<222> LOCATION: (8012)..(8012)
<223> OTHER INFORMATION: a, c, t, g, unknown or other
<220> FEATURE:
<221> NAME/KEY: modified_base
<222> LOCATION: (8022)..(8022)
<223> OTHER INFORMATION: a, c, t, g, unknown or other
<220> FEATURE:
<221> NAME/KEY: modified_base
<222> LOCATION: (8055)..(8055)
<223> OTHER INFORMATION: a, c, t, g, unknown or other
<220> FEATURE:
<221> NAME/KEY: modified_base
<222> LOCATION: (8179)..(8185)
<223> OTHER INFORMATION: a, c, t, g, unknown or other
<220> FEATURE:
<221> NAME/KEY: modified_base
<222> LOCATION: (8187)..(8187)
<223> OTHER INFORMATION: a, c, t, g, unknown or other
<220> FEATURE:
<221> NAME/KEY: modified_base
```

```
<222> LOCATION: (8270)..(8270)
<223> OTHER INFORMATION: a, c, t, g, unknown or other
<220> FEATURE:
<221> NAME/KEY: modified_base
<222> LOCATION: (8307)..(8307)
<223> OTHER INFORMATION: a, c, t, g, unknown or other
<220> FEATURE:
<221> NAME/KEY: modified_base
<222> LOCATION: (8371)..(8371)
<223> OTHER INFORMATION: a, c, t, g, unknown or other
<220> FEATURE:
<221> NAME/KEY: modified_base
<222> LOCATION: (8382)..(8382)
<223> OTHER INFORMATION: a, c, t, g, unknown or other
<220> FEATURE:
<221> NAME/KEY: modified_base
<222> LOCATION: (8460)..(8460)
<223> OTHER INFORMATION: a, c, t, g, unknown or other
<220> FEATURE:
<221> NAME/KEY: modified_base
<222> LOCATION: (8477)..(8477)
<223> OTHER INFORMATION: a, c, t, g, unknown or other
<220> FEATURE:
<221> NAME/KEY: modified_base
<222> LOCATION: (8515)..(8515)
<223> OTHER INFORMATION: a, c, t, g, unknown or other
<220> FEATURE:
<221> NAME/KEY: modified_base
<222> LOCATION: (8640)..(8640)
<223> OTHER INFORMATION: a, c, t, g, unknown or other
<220> FEATURE:
<221> NAME/KEY: modified_base
<222> LOCATION: (8663)..(8664)
<223> OTHER INFORMATION: a, c, t, g, unknown or other
<220> FEATURE:
<221> NAME/KEY: modified_base
<222> LOCATION: (8680)..(8680)
<223> OTHER INFORMATION: a, c, t, g, unknown or other
<220> FEATURE:
<221> NAME/KEY: modified_base
<222> LOCATION: (8711)..(8711)
<223> OTHER INFORMATION: a, c, t, g, unknown or other
<220> FEATURE:
<221> NAME/KEY: modified_base
<222> LOCATION: (8949)..(8976)
<223> OTHER INFORMATION: a, c, t, g, unknown or other

<400> SEQUENCE: 8
cagtggcgcc cgaacaggga cgngaaagcg aaagtagaac cagagaagat ctctcgacgc      60
aggactcggc ttgctgaagt gcacacggca agaggcgaga gcggcgactg gtgagtacgc     120
caaattttga ctagcggagg ctagaaggag agagatgggt gcgagagcgt cagtattaag     180
cgggggaaaa ntagatgcat gggaaaaaat tcggttaagg ccgggggaa agaaaaaata     240 tagaatgaan catctagtat gggcaagcag ggagctagaa cgatttgcaa ttgatcctgg     300
ccttctagaa acatcagaag gctgtcaaaa ataatagga cagttacaac catcccttca     360
gacaggatca gaagagctta gatcattata taatacagta gcagtcctct attttgtaca     420
tcaaangata gaggtaaang acaccaagga agctttagac aagctagagg aagaacaaaa     480
caaaagtcag caaaagacac agcaagcgga agctgacaaa ggggtcagtc aaaattaccc     540
tatagtacag aatcttcagg gacaaatggt acatcagtct atatcaccta gaactttaaa     600
tgcatgggta aggtgatag aagagaaggc ttttagccca gaagtaatac ccatgttttc     660
agcattatca gaaggggcca ctccacaaga tttaaacacc atgntaaata cagtgggggg     720
acatcaagca gccatgcaaa tgttaaaaga caccatcaat gaggaagctg cagaatggga     780
cagattacat ccagngcang caggacctat cccaccaggc cagatnaggg aacctagggg     840
aagtgatata gctggaacta ctagtaccct tcaggaacaa atacaatgga tgacaagcaa     900
```

```
cccacctgtc ccagtgggag anatctataa aagatggatc atcctaggat taaataaaat    960
agtaagaatg tatagccctg tcagcatttt ggacataaga caagggccaa angaacccett   1020
tagagactat gtagacaggt tctttaaaac cctaagagct gagcaagcta cacaggaagt    1080
aaagggttgg atgacagaca ccttgttggt ccaaaatgcg aacccagatt gtaagaccat    1140
tttaaaagca ttgggaccag gggctacact agaagaaatg atgacagcat gtcagggagt    1200
gggaggacct ggccataagg caagagtttt ggctgaggca atgagccaag caacaaatgc    1260
anctataatg atgcagaaaa gtaantttaa gggccaaaga agaattgtta aatgttttaa    1320
ttgtggcaaa gaaggacaca tagccaaaaa ttgcagggcc cctagaaaaa agggctgttg    1380
gaaatgtgga agagaaggac accaaatgaa agactgcact gaaagacagg ctaattttt    1440
agggaaaatt tggccttcca acaagggag gcccggaaat ttccttcaga acaggccaga    1500
gccaacagcc ccgccagcag agagcttcgg gttcagagag gagataaccc cctctccgaa    1560
gcaggagcag aaagangagg gactgtaccc tcccttagct tccctcaaat cactctttgg    1620
caacgacccc tagtcacaat aaaagtaggg ggacagctaa aggaagctct attagataca    1680
ggagcagatg atacagtatt agaagacata aatttgccag gaaatggaa accaaaaatg    1740
ataggggggaa ttggaggttt tatcaaagta aaacagtatg ataacatact catagaaatt    1800
tgtggacaca aggctatagg tacagtgtta gtaggaccta cgcctgtcaa cataattgga    1860
agaaatatgt tgactcagat tggttgtact ttaaattttc caattagtcc tattgaaact    1920
gtaccagtaa aattgaagcc aggaatggat ggcccaaagg ttaaacaatg gccattgaca    1980
gaagaaaaaa taaaagcatt aacagaaata tgtacagaaa tggaaaaaga aggaaaaatt    2040
tcaaaaattg ggcctgaaaa tccatacaat actccagtat ttgccataaa gaaaaaagac    2100
agtactaaat ggagaaaatt agtagatttc agagaactta ataaaagaac tcaagatttt    2160
tgggaggttc aattaggaat accacatcct gcagggttaa aaagaaaaa gtcagtaaca    2220
gtactggatg tgggggatgc atattttca gttccccttag ataaggattt caggaagtac    2280
actgcattca ccatacctag tgtcaacaat gagacaccag gaattaggta ccagtacaat    2340
gtgcttccac aaggatggaa aggatcacca gcaatattcc aatgtagcat gacaaaaatc    2400
ttagancccct ttagaacaaa aaatccagac atagttatct accaatacat ggatgatttg    2460
tatgtagggt ctgacttaga aatagggcag catagaacaa aaatagagga gttaagagaa    2520
catctactga aatgggggatt tactacacca gacaaaaaac atcanaaaga accccccattc    2580
ctttggatgg ggtatgaact ccatcctgat aaatggacag tgcagcctat acaattgcca    2640
gacaaggaca gctggactgt caatgatata cagaagttag taggaaaact aaaattgggca    2700
agtcagattt atccagggat taaagtaaag caattatgta aactccttag gggagccaag    2760
gcactaacag acatagtgcc actgactnca gaagcagagt tagaattggc agagaatagg    2820
gagattctaa aagaaccagt acatggggta tattatgacc cntcaaaaga cttaatagca    2880
gaaatacaga aacaagggca agggcaatgg acatatcaaa tttatcaaga gccatttaaa    2940
aatctaaaaa caggaaagta tgcaaaaatg aggtctgccc acactaatga tgtaaaacaa    3000
ttaacagaag cagtgcaaaa gatagctcta gaaagcatag taatatgggg aaagactcct    3060
aagtttaaac tacccatact aaaagagaca tgggatacat ggtggacaga gtattggcaa    3120
gccacctgga ttcctgaatg ggagtttgtc aatacccccc ctctagtaaa actatgggtat    3180
cagttagaaa cagagcccat agcaggagca gaaaaccttct atgtagatgg ggcatctaat    3240
agagagacca aaaaaggaaa agcaggatat gttactgaca gaggaanaca aaaggctgtc    3300
```

```
tccctaactg agaccacaaa tcagaaggct gagttacaag caattcattt agctttacag    3360
gattcaggat cagaagtgaa catagtaaca gactcacagt atgcattagg aatcattcaa    3420
gcacaaccag ataagagtga atcagagtta gtcaatcaaa taatagagca attaatacaa    3480
aaggaaaagg tctacctgtc atgggtacca gcacacaaag ggattggagg aaatgaacaa    3540
gtagataaat tagtcagtgc tggaatcagn aaaatactgt ttttagatgg gatagataag    3600
gcacaagagg aacatgaaaa atatcacaac aattggagag caatggctag tgattttaat    3660
ctgccacctg tagtagcaaa agaaatagta gctagctgtg ataagtgtca gctaaaaggg    3720
gaagccatgc atggacaagt agantgtagt ccagggatat ggcaattaga ttgtacacat    3780
ttagaaggaa aanttatcct ggtagcagtc catgtagcta gtgggtacnt agaagcagaa    3840
gttatcccag cagaaacagg acangaaaca gcctacttca tactaaagtt agcaggaaga    3900
tggccagtaa aaanaataca tacagacaat ggcancaatt tcaccagtgc cgcggttaag    3960
gcagcctgtt ggtgggcagg tatccagcag gaatttggaa ttccctacaa cccccaaagt    4020
caaggagtag tagaatctat gaataaagag ctaaagaaga tcataggaca ggtaagagat    4080
caagctgaac atcttaagac agcagtacaa atggcagtat tcatccacaa ttttaaaaga    4140 aaaggggggga ttgggggnta cagtgcaggg gaaagaataa tagacataat atcaacagac    4200
atacaaacta nagaattaca aaaacaaatt ataaaaattc aaaatttccg ggtttattac    4260
agggacagca gagacccagt ttggaaagga ccagcaaagc tactctggaa aggtgaaggg    4320
gcagtagtca tacaagacaa tagtgaaata aaggtagtac caagaagaaa agcaaagatc    4380
attagggatt atggaaaaca gatggcaggt gatgattgtg tggcaggtag acaggatgag    4440
gattaacaca tggaaaagtt tagtaaaata ccatatgcat gtttcaaaga aagccaaaag    4500
atggtnttat agacatcact ttgaaagcag gcatccaana ntaagttcag aagtacacat    4560
cccactagag gaagctaaat tagtaataac aacatantgg gggctgcata caggagaaag    4620
agattggcat ctgggtcagg gagtctccat agaatggagg caggggaggt ataggacaca    4680
aatagaccct ggcctggcag accaactgat ccatatatat tattttgatt gttttttcaga    4740 atctgccata aggaaagcca tattaggaca tanaattagc cctaggtgta actatcaagc    4800
aggacataac aaggtaggat cnctacaata tttggcacta acagcattaa tagctccaaa    4860
gaagacaaag ccgcctttgc ctagtgtcaa gaaactagta gaagacagat ggaacaagcc    4920
ccaggagacc aggggccaca gagggagcca tacaatgaat ggacactaga gcttttagag    4980
gagcttaaga atgaagctgt tagacatttt cctaggccat ggctncatgg cttaggacaa    5040
catatctata acacctatgg ggatacttgg gagggagttg aagctataat aaggatattg    5100
caacaactac tgtttatcca tttcagaatt gggtgccatc atagcagaat aggcattant    5160
cgacagagaa gagtaagaaa tggagctagt agatcctaac ttagatccct ggaaccatcc    5220
aggaagccag cctacaactc cttgtaccaa atgntattgt aaacgntgtt gctttcattg    5280
nnantggtgc tttacaacga agggcttagg catctcctat ggcaggaaga agcggagaca    5340
gcgacacaga actcctcana gcagtcagat acatcaagat cntgtaccaa agcagtaagt    5400
attgnnnnta gtatatgtaa tgtcanattt gttagcaata agnatagcag cattaatagt    5460
agcactaata atagcaatag ttgtgtggac tatagtatat atagaatata agaaactgnt    5520
aaggcaaaga aaaataaata ggttatatna aagaataaga gaaagagcag aagacagtgg    5580
caatgagagt gagggggatg cagaggaatt ggcagcactt ggggaaatgg ggccttttat    5640
```

```
tcctggggat attaataatc tgtaatgctg cagaaaactt gtgggtcaca gtctattatg    5700
gggtacctgt gtggaaagaa gcaaccacta ctctattctg tgcatcagat gctaaatcat    5760
atgaaanaga ggtacataat gtctgggcta cacatgcctg tgtacccaca gancccaatc    5820
cacaagaagt agttctggaa aatgtaacag aaaattttga tatgtggaaa ataacatgg     5880 tagaacaaat gcatacagat ataatcagtt tatgggatca aagcctaaag ccatgtgtna    5940
agttaacccc actctgtgtt actttaaatt gtactaatgc cactacnann agtaccacta    6000
ctnnnaanga cancaccctg aaggaagaac caggggcaat acaaaactgt tctttcaata    6060
tgaccacaga agtaagagat aagnagcnga agtacatgc acttttttat anacttgata    6120
tagtaccaat cagcaatnna anannagtag agaatanagg ctaataaatt gtaataccte    6180 aaccattaca caggcttgtc caaggtatc ttgggatcca attcccatac attattgtgc     6240
tccagctggt tatgcgattc taaagtgtaa tgataaaang ttcaatggga cagggccatg    6300
caagaatgtc agcacagtac aatgtacaca tggaattaaa ccagtggtat caactcaatt    6360
gttgttaaat ggcagcctag cagaagaaga tataataatc agatctcaaa atatctcaga    6420
taatgcaaaa accataatag tacaccttaa tgaatctgta cagattaatt gtacaagacc    6480
caacaacaat acaagaaaaa gtatacattt aggaccagga cnagcatttt atgcaacagg    6540
agaaataata ggagacatna gaaaggcaca ttgtaacntt agtggaacac aatggaataa    6600
aactttagaa caggtaaagg caaagttaaa gtctcatttn cctaatacaa caataaaatt    6660
taactcatcc tcaggagggg acctagaaat tacaatgcat agttttaatt gtagaggaga    6720 attttttctac tgcaatacat caggactgtt taatgacaca ggantacaat ggcactatca    6780
ctctcccatg tcgaataaaa caaattgtaa acatgtggca ggaagtagga cgagcaatgt    6840
atgccgctcc cattgcagga aacattacct gtaactcaaa tattacaggt ctactattga    6900
caagagatgg tggtnanaat aatantaaga ctgagacctt cagacctggg ggaggaaata    6960
tgaaagacaa ttggagaagt gaantatata antataaagt agtagaaatt gaaccactag    7020
gagtagcacc caccanggca aaaagacaag tggtgaagag agaaanaaga gcagtgggaa    7080
taggagcttt gttccttggg ttcttgngcg cagcaggaag cactatgggc gcggcgtcaa    7140
taacgctgac ggtacaggcc agacaattat tgtctggaat agtgcaacag cagancaatc    7200
tgctgagggc tattgaagcg caacagcatc tgttgcagct cacagtctgg ggcattaaac    7260
agctccaggc aagagtcctg gctgtggaaa gatacctaaa ggatcaacag ctcctagggc    7320 tttgggctg ctctggaaaa ctcatctgca ccactaatgt gccctggaac tctagttgga     7380
gtaataaatc tcaggaggag atttggnaga acatgacctg gatggagtgg gaaaaagaga    7440
ttagcaatta ctcaaacnaa atatacaggt taattgaaga atcncagaac cagcaggaaa    7500
agaatgaaca agaattattg gcattggaca atgggcaag tctgtggaat ggtttgaca     7560 tatcaaactg gctgtggtat ataaaaatat tcataatgat agtaggaggc ttgataggct    7620
taagaatagt ttttgctgtg ctttctatag taaatagagt taggaaggga tactcaccett    7680 tgtcattaca gacccntatc ccaagcccga gggaacccga caggcccgaa ggaatcgaag    7740
aaggaggtgg agagcaaggc aaagacagat ccgtgcgatt agtgaacgga ttcttagctc    7800
ttgtctggga cgacctgagg aacctgtgcc tcttcagcta ccgccacttg agagacttca    7860
tattaattgc agcgaggatt gtggacaggg ggctgaggag ggggtgggaa gccctcaaat    7920
atctggggaa tctcacncag tattggngtc aggaactaaa gaatagtgct attagcttgn    7980
ttaataccac agcaatagta gtagctgagg gnacagatag anttatagaa gctttgcaaa    8040
```

```
gagctggtag agctnttctc aacataccta gaagaataag acagggctta gaaagggctt    8100
tgctataaaa tgggtggcaa gtggtcaaaa agtagtatag ttggatggcc tgctataagg    8160
gaaagaatga gacgaaccnn nnnnncncct ccagcagcag aaggggtggg agcagtgtct    8220
caagacttag aaagacgggg ggcaattaca agcagcaata ctagagctan taatcctgac    8280
ttggcctggc tggaagcaca agaggangag gaagtaggct ttccagtcag acctcaggta    8340
cctttaagac caatgactta taaggcagct ntagatctca gncacttttt aaagaaaag    8400 gggggactgg aagggttaat ttactccaag aaaagacaag agatccttga tctgtgggtn    8460
taccacacac aaggctnctt ccctgattgg cagaactaca caccagggcc agggntcaga    8520
tatccactga cctttgggtg gtgcttcaag ctagtaccag ttgacccaga ggaggtagaa    8580
aaggccaatg aaggagagaa caactgcttg ctacacccca tgagccaaca tggaatggan    8640
gatgaagaca gagaagtact ganntggaag tttgacagcn gcctggcact gagacacata    8700
gccagagaga nacatccgga gttctaccaa gactgagact gctgacacag agattgctga    8760
cacagaagaa tctaaaggga cttttccactg ggactttcc agagggcggg ccagagggcg    8820
ggactgggga gtggctcacc ctcagatgct gcatataagc agccgctttt cgcctgtact    8880
gggtctctct agttagacca gatttgagcc cgggagctct ctggctagct agggaaccca    8940
ctgcttaann nnnnnnnnnn nnnnnnnnnn nnnnn                               8976
```

<210> SEQ ID NO 9
<211> LENGTH: 8574
<212> TYPE: DNA
<213> ORGANISM: Human immunodeficiency virus
<220> FEATURE:
<221> NAME/KEY: modified_base
<222> LOCATION: (44)..(44)
<223> OTHER INFORMATION: a, c, t, g, unknown or other
<220> FEATURE:
<221> NAME/KEY: modified_base
<222> LOCATION: (93)..(93)
<223> OTHER INFORMATION: a, c, t, g, unknown or other
<220> FEATURE:
<221> NAME/KEY: modified_base
<222> LOCATION: (174)..(175)
<223> OTHER INFORMATION: a, c, t, g, unknown or other
<220> FEATURE:
<221> NAME/KEY: modified_base
<222> LOCATION: (196)..(196)
<223> OTHER INFORMATION: a, c, t, g, unknown or other
<220> FEATURE:
<221> NAME/KEY: modified_base
<222> LOCATION: (236)..(237)
<223> OTHER INFORMATION: a, c, t, g, unknown or other
<220> FEATURE:
<221> NAME/KEY: modified_base
<222> LOCATION: (244)..(244)
<223> OTHER INFORMATION: a, c, t, g, unknown or other
<220> FEATURE:
<221> NAME/KEY: modified_base
<222> LOCATION: (252)..(252)
<223> OTHER INFORMATION: a, c, t, g, unknown or other
<220> FEATURE:
<221> NAME/KEY: modified_base
<222> LOCATION: (272)..(272)
<223> OTHER INFORMATION: a, c, t, g, unknown or other
<220> FEATURE:
<221> NAME/KEY: modified_base
<222> LOCATION: (280)..(280)
<223> OTHER INFORMATION: a, c, t, g, unknown or other
<220> FEATURE:
<221> NAME/KEY: modified_base
<222> LOCATION: (332)..(332)
<223> OTHER INFORMATION: a, c, t, g, unknown or other
<220> FEATURE:

```
<221> NAME/KEY: modified_base
<222> LOCATION: (350)..(350)
<223> OTHER INFORMATION: a, c, t, g, unknown or other
<220> FEATURE:
<221> NAME/KEY: modified_base
<222> LOCATION: (645)..(645)
<223> OTHER INFORMATION: a, c, t, g, unknown or other
<220> FEATURE:
<221> NAME/KEY: modified_base
<222> LOCATION: (672)..(672)
<223> OTHER INFORMATION: a, c, t, g, unknown or other
<220> FEATURE:
<221> NAME/KEY: modified_base
<222> LOCATION: (945)..(945)
<223> OTHER INFORMATION: a, c, t, g, unknown or other
<220> FEATURE:
<221> NAME/KEY: modified_base
<222> LOCATION: (999)..(999)
<223> OTHER INFORMATION: a, c, t, g, unknown or other
<220> FEATURE:
<221> NAME/KEY: modified_base
<222> LOCATION: (1093)..(1093)
<223> OTHER INFORMATION: a, c, t, g, unknown or other
<220> FEATURE:
<221> NAME/KEY: modified_base
<222> LOCATION: (1097)..(1097)
<223> OTHER INFORMATION: a, c, t, g, unknown or other
<220> FEATURE:
<221> NAME/KEY: modified_base
<222> LOCATION: (1103)..(1103)
<223> OTHER INFORMATION: a, c, t, g, unknown or other
<220> FEATURE:
<221> NAME/KEY: modified_base
<222> LOCATION: (1145)..(1145)
<223> OTHER INFORMATION: a, c, t, g, unknown or other
<220> FEATURE:
<221> NAME/KEY: modified_base
<222> LOCATION: (1193)..(1193)
<223> OTHER INFORMATION: a, c, t, g, unknown or other
<220> FEATURE:
<221> NAME/KEY: modified_base
<222> LOCATION: (1269)..(1269)
<223> OTHER INFORMATION: a, c, t, g, unknown or other
<220> FEATURE:
<221> NAME/KEY: modified_base
<222> LOCATION: (1386)..(1386)
<223> OTHER INFORMATION: a, c, t, g, unknown or other
<220> FEATURE:
<221> NAME/KEY: modified_base
<222> LOCATION: (1430)..(1430)
<223> OTHER INFORMATION: a, c, t, g, unknown or other
<220> FEATURE:
<221> NAME/KEY: modified_base
<222> LOCATION: (1432)..(1432)
<223> OTHER INFORMATION: a, c, t, g, unknown or other
<220> FEATURE:
<221> NAME/KEY: modified_base
<222> LOCATION: (1445)..(1445)
<223> OTHER INFORMATION: a, c, t, g, unknown or other
<220> FEATURE:
<221> NAME/KEY: modified_base
<222> LOCATION: (1469)..(1469)
<223> OTHER INFORMATION: a, c, t, g, unknown or other
<220> FEATURE:
<221> NAME/KEY: modified_base
<222> LOCATION: (1476)..(1476)
<223> OTHER INFORMATION: a, c, t, g, unknown or other
<220> FEATURE:
<221> NAME/KEY: modified_base
<222> LOCATION: (1495)..(1495)
<223> OTHER INFORMATION: a, c, t, g, unknown or other
<220> FEATURE:
<221> NAME/KEY: modified_base
<222> LOCATION: (1563)..(1563)
<223> OTHER INFORMATION: a, c, t, g, unknown or other
<220> FEATURE:
<221> NAME/KEY: modified_base
<222> LOCATION: (1582)..(1582)
<223> OTHER INFORMATION: a, c, t, g, unknown or other
```

```
-continued

<220> FEATURE:
<221> NAME/KEY: modified_base
<222> LOCATION: (1632)..(1632)
<223> OTHER INFORMATION: a, c, t, g, unknown or other
<220> FEATURE:
<221> NAME/KEY: modified_base
<222> LOCATION: (1682)..(1682)
<223> OTHER INFORMATION: a, c, t, g, unknown or other
<220> FEATURE:
<221> NAME/KEY: modified_base
<222> LOCATION: (1845)..(1845)
<223> OTHER INFORMATION: a, c, t, g, unknown or other
<220> FEATURE:
<221> NAME/KEY: modified_base
<222> LOCATION: (1982)..(1982)
<223> OTHER INFORMATION: a, c, t, g, unknown or other
<220> FEATURE:
<221> NAME/KEY: modified_base
<222> LOCATION: (2132)..(2132)
<223> OTHER INFORMATION: a, c, t, g, unknown or other
<220> FEATURE:
<221> NAME/KEY: modified_base
<222> LOCATION: (2343)..(2343)
<223> OTHER INFORMATION: a, c, t, g, unknown or other
<220> FEATURE:
<221> NAME/KEY: modified_base
<222> LOCATION: (2414)..(2414)
<223> OTHER INFORMATION: a, c, t, g, unknown or other
<220> FEATURE:
<221> NAME/KEY: modified_base
<222> LOCATION: (2618)..(2618)
<223> OTHER INFORMATION: a, c, t, g, unknown or other
<220> FEATURE:
<221> NAME/KEY: modified_base
<222> LOCATION: (2630)..(2630)
<223> OTHER INFORMATION: a, c, t, g, unknown or other
<220> FEATURE:
<221> NAME/KEY: modified_base
<222> LOCATION: (2747)..(2747)
<223> OTHER INFORMATION: a, c, t, g, unknown or other
<220> FEATURE:
<221> NAME/KEY: modified_base
<222> LOCATION: (2750)..(2750)
<223> OTHER INFORMATION: a, c, t, g, unknown or other
<220> FEATURE:
<221> NAME/KEY: modified_base
<222> LOCATION: (2777)..(2777)
<223> OTHER INFORMATION: a, c, t, g, unknown or other
<220> FEATURE:
<221> NAME/KEY: modified_base
<222> LOCATION: (2812)..(2812)
<223> OTHER INFORMATION: a, c, t, g, unknown or other
<220> FEATURE:
<221> NAME/KEY: modified_base
<222> LOCATION: (2818)..(2818)
<223> OTHER INFORMATION: a, c, t, g, unknown or other
<220> FEATURE:
<221> NAME/KEY: modified_base
<222> LOCATION: (2861)..(2861)
<223> OTHER INFORMATION: a, c, t, g, unknown or other
<220> FEATURE:
<221> NAME/KEY: modified_base
<222> LOCATION: (2900)..(2900)
<223> OTHER INFORMATION: a, c, t, g, unknown or other
<220> FEATURE:
<221> NAME/KEY: modified_base
<222> LOCATION: (2930)..(2930)
<223> OTHER INFORMATION: a, c, t, g, unknown or other
<220> FEATURE:
<221> NAME/KEY: modified_base
<222> LOCATION: (2944)..(2944)
<223> OTHER INFORMATION: a, c, t, g, unknown or other
<220> FEATURE:
<221> NAME/KEY: modified_base
<222> LOCATION: (2966)..(2966)
<223> OTHER INFORMATION: a, c, t, g, unknown or other
<220> FEATURE:
<221> NAME/KEY: modified_base
<222> LOCATION: (3029)..(3029)
```

```
<223> OTHER INFORMATION: a, c, t, g, unknown or other
<220> FEATURE:
<221> NAME/KEY: modified_base
<222> LOCATION: (3041)..(3041)
<223> OTHER INFORMATION: a, c, t, g, unknown or other
<220> FEATURE:
<221> NAME/KEY: modified_base
<222> LOCATION: (3099)..(3099)
<223> OTHER INFORMATION: a, c, t, g, unknown or other
<220> FEATURE:
<221> NAME/KEY: modified_base
<222> LOCATION: (3140)..(3140)
<223> OTHER INFORMATION: a, c, t, g, unknown or other
<220> FEATURE:
<221> NAME/KEY: modified_base
<222> LOCATION: (3147)..(3147)
<223> OTHER INFORMATION: a, c, t, g, unknown or other
<220> FEATURE:
<221> NAME/KEY: modified_base
<222> LOCATION: (3334)..(3334)
<223> OTHER INFORMATION: a, c, t, g, unknown or other
<220> FEATURE:
<221> NAME/KEY: modified_base
<222> LOCATION: (3475)..(3475)
<223> OTHER INFORMATION: a, c, t, g, unknown or other
<220> FEATURE:
<221> NAME/KEY: modified_base
<222> LOCATION: (3692)..(3692)
<223> OTHER INFORMATION: a, c, t, g, unknown or other
<220> FEATURE:
<221> NAME/KEY: modified_base
<222> LOCATION: (3704)..(3704)
<223> OTHER INFORMATION: a, c, t, g, unknown or other
<220> FEATURE:
<221> NAME/KEY: modified_base
<222> LOCATION: (3908)..(3908)
<223> OTHER INFORMATION: a, c, t, g, unknown or other
<220> FEATURE:
<221> NAME/KEY: modified_base
<222> LOCATION: (3917)..(3917)
<223> OTHER INFORMATION: a, c, t, g, unknown or other
<220> FEATURE:
<221> NAME/KEY: modified_base
<222> LOCATION: (4077)..(4077)
<223> OTHER INFORMATION: a, c, t, g, unknown or other
<220> FEATURE:
<221> NAME/KEY: modified_base
<222> LOCATION: (4125)..(4125)
<223> OTHER INFORMATION: a, c, t, g, unknown or other
<220> FEATURE:
<221> NAME/KEY: modified_base
<222> LOCATION: (4223)..(4223)
<223> OTHER INFORMATION: a, c, t, g, unknown or other
<220> FEATURE:
<221> NAME/KEY: modified_base
<222> LOCATION: (4305)..(4305)
<223> OTHER INFORMATION: a, c, t, g, unknown or other
<220> FEATURE:
<221> NAME/KEY: modified_base
<222> LOCATION: (4438)..(4438)
<223> OTHER INFORMATION: a, c, t, g, unknown or other
<220> FEATURE:
<221> NAME/KEY: modified_base
<222> LOCATION: (4567)..(4567)
<223> OTHER INFORMATION: a, c, t, g, unknown or other
<220> FEATURE:
<221> NAME/KEY: modified_base
<222> LOCATION: (4620)..(4620)
<223> OTHER INFORMATION: a, c, t, g, unknown or other
<220> FEATURE:
<221> NAME/KEY: modified_base
<222> LOCATION: (4641)..(4641)
<223> OTHER INFORMATION: a, c, t, g, unknown or other
<220> FEATURE:
<221> NAME/KEY: modified_base
<222> LOCATION: (4710)..(4710)
<223> OTHER INFORMATION: a, c, t, g, unknown or other
<220> FEATURE:
<221> NAME/KEY: modified_base
```

```
<222> LOCATION: (4781)..(4781)
<223> OTHER INFORMATION: a, c, t, g, unknown or other
<220> FEATURE:
<221> NAME/KEY: modified_base
<222> LOCATION: (4859)..(4859)
<223> OTHER INFORMATION: a, c, t, g, unknown or other
<220> FEATURE:
<221> NAME/KEY: modified_base
<222> LOCATION: (4945)..(4945)
<223> OTHER INFORMATION: a, c, t, g, unknown or other
<220> FEATURE:
<221> NAME/KEY: modified_base
<222> LOCATION: (5022)..(5022)
<223> OTHER INFORMATION: a, c, t, g, unknown or other
<220> FEATURE:
<221> NAME/KEY: modified_base
<222> LOCATION: (5035)..(5035)
<223> OTHER INFORMATION: a, c, t, g, unknown or other
<220> FEATURE:
<221> NAME/KEY: modified_base
<222> LOCATION: (5103)..(5103)
<223> OTHER INFORMATION: a, c, t, g, unknown or other
<220> FEATURE:
<221> NAME/KEY: modified_base
<222> LOCATION: (5134)..(5134)
<223> OTHER INFORMATION: a, c, t, g, unknown or other
<220> FEATURE:
<221> NAME/KEY: modified_base
<222> LOCATION: (5200)..(5200)
<223> OTHER INFORMATION: a, c, t, g, unknown or other
<220> FEATURE:
<221> NAME/KEY: modified_base
<222> LOCATION: (5203)..(5203)
<223> OTHER INFORMATION: a, c, t, g, unknown or other
<220> FEATURE:
<221> NAME/KEY: modified_base
<222> LOCATION: (5215)..(5215)
<223> OTHER INFORMATION: a, c, t, g, unknown or other
<220> FEATURE:
<221> NAME/KEY: modified_base
<222> LOCATION: (5218)..(5218)
<223> OTHER INFORMATION: a, c, t, g, unknown or other
<220> FEATURE:
<221> NAME/KEY: modified_base
<222> LOCATION: (5236)..(5236)
<223> OTHER INFORMATION: a, c, t, g, unknown or other
<220> FEATURE:
<221> NAME/KEY: modified_base
<222> LOCATION: (5276)..(5276)
<223> OTHER INFORMATION: a, c, t, g, unknown or other
<220> FEATURE:
<221> NAME/KEY: modified_base
<222> LOCATION: (5294)..(5294)
<223> OTHER INFORMATION: a, c, t, g, unknown or other
<220> FEATURE:
<221> NAME/KEY: modified_base
<222> LOCATION: (5304)..(5304)
<223> OTHER INFORMATION: a, c, t, g, unknown or other
<220> FEATURE:
<221> NAME/KEY: modified_base
<222> LOCATION: (5671)..(5671)
<223> OTHER INFORMATION: a, c, t, g, unknown or other
<220> FEATURE:
<221> NAME/KEY: modified_base
<222> LOCATION: (5770)..(5770)
<223> OTHER INFORMATION: a, c, t, g, unknown or other
<220> FEATURE:
<221> NAME/KEY: modified_base
<222> LOCATION: (5783)..(5783)
<223> OTHER INFORMATION: a, c, t, g, unknown or other
<220> FEATURE:
<221> NAME/KEY: modified_base
<222> LOCATION: (5803)..(5803)
<223> OTHER INFORMATION: a, c, t, g, unknown or other
<220> FEATURE:
<221> NAME/KEY: modified_base
<222> LOCATION: (5809)..(5809)
<223> OTHER INFORMATION: a, c, t, g, unknown or other
<220> FEATURE:
```

```
<221> NAME/KEY: modified_base
<222> LOCATION: (5829)..(5829)
<223> OTHER INFORMATION: a, c, t, g, unknown or other
<220> FEATURE:
<221> NAME/KEY: modified_base
<222> LOCATION: (5831)..(5831)
<223> OTHER INFORMATION: a, c, t, g, unknown or other
<220> FEATURE:
<221> NAME/KEY: modified_base
<222> LOCATION: (5849)..(5849)
<223> OTHER INFORMATION: a, c, t, g, unknown or other
<220> FEATURE:
<221> NAME/KEY: modified_base
<222> LOCATION: (5856)..(5856)
<223> OTHER INFORMATION: a, c, t, g, unknown or other
<220> FEATURE:
<221> NAME/KEY: modified_base
<222> LOCATION: (5872)..(5872)
<223> OTHER INFORMATION: a, c, t, g, unknown or other
<220> FEATURE:
<221> NAME/KEY: modified_base
<222> LOCATION: (5905)..(5905)
<223> OTHER INFORMATION: a, c, t, g, unknown or other
<220> FEATURE:
<221> NAME/KEY: modified_base
<222> LOCATION: (5945)..(5945)
<223> OTHER INFORMATION: a, c, t, g, unknown or other
<220> FEATURE:
<221> NAME/KEY: modified_base
<222> LOCATION: (5955)..(5955)
<223> OTHER INFORMATION: a, c, t, g, unknown or other
<220> FEATURE:
<221> NAME/KEY: modified_base
<222> LOCATION: (5974)..(5974)
<223> OTHER INFORMATION: a, c, t, g, unknown or other
<220> FEATURE:
<221> NAME/KEY: modified_base
<222> LOCATION: (5991)..(5991)
<223> OTHER INFORMATION: a, c, t, g, unknown or other
<220> FEATURE:
<221> NAME/KEY: modified_base
<222> LOCATION: (6090)..(6090)
<223> OTHER INFORMATION: a, c, t, g, unknown or other
<220> FEATURE:
<221> NAME/KEY: modified_base
<222> LOCATION: (6227)..(6227)
<223> OTHER INFORMATION: a, c, t, g, unknown or other
<220> FEATURE:
<221> NAME/KEY: modified_base
<222> LOCATION: (6254)..(6254)
<223> OTHER INFORMATION: a, c, t, g, unknown or other
<220> FEATURE:
<221> NAME/KEY: modified_base
<222> LOCATION: (6263)..(6263)
<223> OTHER INFORMATION: a, c, t, g, unknown or other
<220> FEATURE:
<221> NAME/KEY: modified_base
<222> LOCATION: (6291)..(6291)
<223> OTHER INFORMATION: a, c, t, g, unknown or other
<220> FEATURE:
<221> NAME/KEY: modified_base
<222> LOCATION: (6307)..(6307)
<223> OTHER INFORMATION: a, c, t, g, unknown or other
<220> FEATURE:
<221> NAME/KEY: modified_base
<222> LOCATION: (6336)..(6336)
<223> OTHER INFORMATION: a, c, t, g, unknown or other
<220> FEATURE:
<221> NAME/KEY: modified_base
<222> LOCATION: (6360)..(6360)
<223> OTHER INFORMATION: a, c, t, g, unknown or other
<220> FEATURE:
<221> NAME/KEY: modified_base
<222> LOCATION: (6363)..(6363)
<223> OTHER INFORMATION: a, c, t, g, unknown or other
<220> FEATURE:
<221> NAME/KEY: modified_base
<222> LOCATION: (6367)..(6367)
<223> OTHER INFORMATION: a, c, t, g, unknown or other
```

-continued

```
<220> FEATURE:
<221> NAME/KEY: modified_base
<222> LOCATION: (6407)..(6407)
<223> OTHER INFORMATION: a, c, t, g, unknown or other
<220> FEATURE:
<221> NAME/KEY: modified_base
<222> LOCATION: (6414)..(6414)
<223> OTHER INFORMATION: a, c, t, g, unknown or other
<220> FEATURE:
<221> NAME/KEY: modified_base
<222> LOCATION: (6450)..(6450)
<223> OTHER INFORMATION: a, c, t, g, unknown or other
<220> FEATURE:
<221> NAME/KEY: modified_base
<222> LOCATION: (6458)..(6458)
<223> OTHER INFORMATION: a, c, t, g, unknown or other
<220> FEATURE:
<221> NAME/KEY: modified_base
<222> LOCATION: (6464)..(6464)
<223> OTHER INFORMATION: a, c, t, g, unknown or other
<220> FEATURE:
<221> NAME/KEY: modified_base
<222> LOCATION: (6483)..(6483)
<223> OTHER INFORMATION: a, c, t, g, unknown or other
<220> FEATURE:
<221> NAME/KEY: modified_base
<222> LOCATION: (6485)..(6485)
<223> OTHER INFORMATION: a, c, t, g, unknown or other
<220> FEATURE:
<221> NAME/KEY: modified_base
<222> LOCATION: (6488)..(6488)
<223> OTHER INFORMATION: a, c, t, g, unknown or other
<220> FEATURE:
<221> NAME/KEY: modified_base
<222> LOCATION: (6491)..(6491)
<223> OTHER INFORMATION: a, c, t, g, unknown or other
<220> FEATURE:
<221> NAME/KEY: modified_base
<222> LOCATION: (6517)..(6517)
<223> OTHER INFORMATION: a, c, t, g, unknown or other
<220> FEATURE:
<221> NAME/KEY: modified_base
<222> LOCATION: (6524)..(6524)
<223> OTHER INFORMATION: a, c, t, g, unknown or other
<220> FEATURE:
<221> NAME/KEY: modified_base
<222> LOCATION: (6556)..(6556)
<223> OTHER INFORMATION: a, c, t, g, unknown or other
<220> FEATURE:
<221> NAME/KEY: modified_base
<222> LOCATION: (6580)..(6580)
<223> OTHER INFORMATION: a, c, t, g, unknown or other
<220> FEATURE:
<221> NAME/KEY: modified_base
<222> LOCATION: (6598)..(6600)
<223> OTHER INFORMATION: a, c, t, g, unknown or other
<220> FEATURE:
<221> NAME/KEY: modified_base
<222> LOCATION: (6603)..(6603)
<223> OTHER INFORMATION: a, c, t, g, unknown or other
<220> FEATURE:
<221> NAME/KEY: modified_base
<222> LOCATION: (6609)..(6609)
<223> OTHER INFORMATION: a, c, t, g, unknown or other
<220> FEATURE:
<221> NAME/KEY: modified_base
<222> LOCATION: (6614)..(6614)
<223> OTHER INFORMATION: a, c, t, g, unknown or other
<220> FEATURE:
<221> NAME/KEY: modified_base
<222> LOCATION: (6619)..(6620)
<223> OTHER INFORMATION: a, c, t, g, unknown or other
<220> FEATURE:
<221> NAME/KEY: modified_base
<222> LOCATION: (6622)..(6622)
<223> OTHER INFORMATION: a, c, t, g, unknown or other
<220> FEATURE:
<221> NAME/KEY: modified_base
<222> LOCATION: (6628)..(6628)
```

```
<223> OTHER INFORMATION: a, c, t, g, unknown or other
<220> FEATURE:
<221> NAME/KEY: modified_base
<222> LOCATION: (6655)..(6655)
<223> OTHER INFORMATION: a, c, t, g, unknown or other
<220> FEATURE:
<221> NAME/KEY: modified_base
<222> LOCATION: (6773)..(6774)
<223> OTHER INFORMATION: a, c, t, g, unknown or other
<220> FEATURE:
<221> NAME/KEY: modified_base
<222> LOCATION: (6776)..(6779)
<223> OTHER INFORMATION: a, c, t, g, unknown or other
<220> FEATURE:
<221> NAME/KEY: modified_base
<222> LOCATION: (6782)..(6783)
<223> OTHER INFORMATION: a, c, t, g, unknown or other
<220> FEATURE:
<221> NAME/KEY: modified_base
<222> LOCATION: (6787)..(6787)
<223> OTHER INFORMATION: a, c, t, g, unknown or other
<220> FEATURE:
<221> NAME/KEY: modified_base
<222> LOCATION: (6791)..(6791)
<223> OTHER INFORMATION: a, c, t, g, unknown or other
<220> FEATURE:
<221> NAME/KEY: modified_base
<222> LOCATION: (6793)..(6793)
<223> OTHER INFORMATION: a, c, t, g, unknown or other
<220> FEATURE:
<221> NAME/KEY: modified_base
<222> LOCATION: (6804)..(6805)
<223> OTHER INFORMATION: a, c, t, g, unknown or other
<220> FEATURE:
<221> NAME/KEY: modified_base
<222> LOCATION: (6938)..(6938)
<223> OTHER INFORMATION: a, c, t, g, unknown or other
<220> FEATURE:
<221> NAME/KEY: modified_base
<222> LOCATION: (6948)..(6948)
<223> OTHER INFORMATION: a, c, t, g, unknown or other
<220> FEATURE:
<221> NAME/KEY: modified_base
<222> LOCATION: (7051)..(7051)
<223> OTHER INFORMATION: a, c, t, g, unknown or other
<220> FEATURE:
<221> NAME/KEY: modified_base
<222> LOCATION: (7184)..(7184)
<223> OTHER INFORMATION: a, c, t, g, unknown or other
<220> FEATURE:
<221> NAME/KEY: modified_base
<222> LOCATION: (7264)..(7264)
<223> OTHER INFORMATION: a, c, t, g, unknown or other
<220> FEATURE:
<221> NAME/KEY: modified_base
<222> LOCATION: (7298)..(7298)
<223> OTHER INFORMATION: a, c, t, g, unknown or other
<220> FEATURE:
<221> NAME/KEY: modified_base
<222> LOCATION: (7300)..(7301)
<223> OTHER INFORMATION: a, c, t, g, unknown or other
<220> FEATURE:
<221> NAME/KEY: modified_base
<222> LOCATION: (7331)..(7331)
<223> OTHER INFORMATION: a, c, t, g, unknown or other
<220> FEATURE:
<221> NAME/KEY: modified_base
<222> LOCATION: (7335)..(7335)
<223> OTHER INFORMATION: a, c, t, g, unknown or other
<220> FEATURE:
<221> NAME/KEY: modified_base
<222> LOCATION: (7340)..(7340)
<223> OTHER INFORMATION: a, c, t, g, unknown or other
<220> FEATURE:
<221> NAME/KEY: modified_base
<222> LOCATION: (7388)..(7388)
<223> OTHER INFORMATION: a, c, t, g, unknown or other
<220> FEATURE:
<221> NAME/KEY: modified_base
```

```
<222> LOCATION: (7396)..(7396)
<223> OTHER INFORMATION: a, c, t, g, unknown or other
<220> FEATURE:
<221> NAME/KEY: modified_base
<222> LOCATION: (7413)..(7413)
<223> OTHER INFORMATION: a, c, t, g, unknown or other
<220> FEATURE:
<221> NAME/KEY: modified_base
<222> LOCATION: (7503)..(7503)
<223> OTHER INFORMATION: a, c, t, g, unknown or other
<220> FEATURE:
<221> NAME/KEY: modified_base
<222> LOCATION: (7514)..(7514)
<223> OTHER INFORMATION: a, c, t, g, unknown or other
<220> FEATURE:
<221> NAME/KEY: modified_base
<222> LOCATION: (7561)..(7561)
<223> OTHER INFORMATION: a, c, t, g, unknown or other
<220> FEATURE:
<221> NAME/KEY: modified_base
<222> LOCATION: (7577)..(7577)
<223> OTHER INFORMATION: a, c, t, g, unknown or other
<220> FEATURE:
<221> NAME/KEY: modified_base
<222> LOCATION: (7629)..(7629)
<223> OTHER INFORMATION: a, c, t, g, unknown or other
<220> FEATURE:
<221> NAME/KEY: modified_base
<222> LOCATION: (7631)..(7631)
<223> OTHER INFORMATION: a, c, t, g, unknown or other
<220> FEATURE:
<221> NAME/KEY: modified_base
<222> LOCATION: (7755)..(7755)
<223> OTHER INFORMATION: a, c, t, g, unknown or other
<220> FEATURE:
<221> NAME/KEY: modified_base
<222> LOCATION: (7836)..(7836)
<223> OTHER INFORMATION: a, c, t, g, unknown or other
<220> FEATURE:
<221> NAME/KEY: modified_base
<222> LOCATION: (7839)..(7839)
<223> OTHER INFORMATION: a, c, t, g, unknown or other
<220> FEATURE:
<221> NAME/KEY: modified_base
<222> LOCATION: (7855)..(7856)
<223> OTHER INFORMATION: a, c, t, g, unknown or other
<220> FEATURE:
<221> NAME/KEY: modified_base
<222> LOCATION: (7887)..(7887)
<223> OTHER INFORMATION: a, c, t, g, unknown or other
<220> FEATURE:
<221> NAME/KEY: modified_base
<222> LOCATION: (7890)..(7890)
<223> OTHER INFORMATION: a, c, t, g, unknown or other
<220> FEATURE:
<221> NAME/KEY: modified_base
<222> LOCATION: (7911)..(7911)
<223> OTHER INFORMATION: a, c, t, g, unknown or other
<220> FEATURE:
<221> NAME/KEY: modified_base
<222> LOCATION: (7945)..(7945)
<223> OTHER INFORMATION: a, c, t, g, unknown or other
<220> FEATURE:
<221> NAME/KEY: modified_base
<222> LOCATION: (8009)..(8009)
<223> OTHER INFORMATION: a, c, t, g, unknown or other
<220> FEATURE:
<221> NAME/KEY: modified_base
<222> LOCATION: (8011)..(8011)
<223> OTHER INFORMATION: a, c, t, g, unknown or other
<220> FEATURE:
<221> NAME/KEY: modified_base
<222> LOCATION: (8025)..(8025)
<223> OTHER INFORMATION: a, c, t, g, unknown or other
<220> FEATURE:
<221> NAME/KEY: modified_base
<222> LOCATION: (8029)..(8034)
<223> OTHER INFORMATION: a, c, t, g, unknown or other
<220> FEATURE:
```

```
<221> NAME/KEY: modified_base
<222> LOCATION: (8053)..(8054)
<223> OTHER INFORMATION: a, c, t, g, unknown or other
<220> FEATURE:
<221> NAME/KEY: modified_base
<222> LOCATION: (8104)..(8104)
<223> OTHER INFORMATION: a, c, t, g, unknown or other
<220> FEATURE:
<221> NAME/KEY: modified_base
<222> LOCATION: (8116)..(8116)
<223> OTHER INFORMATION: a, c, t, g, unknown or other
<220> FEATURE:
<221> NAME/KEY: modified_base
<222> LOCATION: (8133)..(8133)
<223> OTHER INFORMATION: a, c, t, g, unknown or other
<220> FEATURE:
<221> NAME/KEY: modified_base
<222> LOCATION: (8149)..(8151)
<223> OTHER INFORMATION: a, c, t, g, unknown or other
<220> FEATURE:
<221> NAME/KEY: modified_base
<222> LOCATION: (8207)..(8207)
<223> OTHER INFORMATION: a, c, t, g, unknown or other
<220> FEATURE:
<221> NAME/KEY: modified_base
<222> LOCATION: (8270)..(8270)
<223> OTHER INFORMATION: a, c, t, g, unknown or other
<220> FEATURE:
<221> NAME/KEY: modified_base
<222> LOCATION: (8521)..(8521)
<223> OTHER INFORMATION: a, c, t, g, unknown or other

<400> SEQUENCE: 9
atgggtgcga gagcgtcagt attaagcggg ggaaaattag atgnatggga aaaaattcgg      60
ttaaggccgg gggggaagaa aaaatatagg ctnaaacata tagtatgggc aagcagggag     120
ctagaacgat ttgcacttaa tcctggcctt ttagagacaa cagaaggctg taannaaata     180
ataggacaac tacaancatc ccttcagaca ggatcagaag agcttaaatc attatnnaac     240
acantagtag tnctctatta tgtacatcaa angatagaan taagagacac caaggaagct     300
ttagataagc tacaggaaga acaagacaaa antcagcaaa aaacacaacn agcagcggct     360
gacaaagggg tcagtcaaaa ttaccctata gtacagaatc ttcagggca aatggtacac      420
caggctctat cacctagaac tttaaatgca tgggtaaaag taatagaaga aaggctttc      480
agcccagaag taatacccat gttttcagca ttatcagaag gggccacccc acaagattta     540
aacaccatgc taaacacagt gggggacat caagcagcca tgcaaatgtt aaaagatacc      600
atcaatgagg aagctgcaga atgggacagg ttacatccag tgcangcagg acctatccca     660
ccaggtcaga tnagagaacc tagggaagt gatatagcag gaactactag tacccttcag      720
gaacaaatag catggatgac aagcaaccca cctgtcccag taggagaaat ctataaaaga     780
tggataatcc taggattaaa taaaatagta agaatgtata gccctgtcag cattttggac     840
ataaaacaag ggccaaaaga acccttagta gactatgtag acaggttctt taaaactcta     900
agagctgagc aagctacaca ggaagtaaaa ggctggatga cagnaccctt gttggtccaa     960
aatgcgaacc cagattgtaa gaccatttta aaagcattng gaccagggc tacactagaa     1020
gaaatgatga cagcatgtca gggagtggga ggacctggcc ataaagcaag aatttttggct   1080
gaggcaatga gcnaagnaac agntacagcc ataatgatgc agaaaagcaa ctttaagggc    1140
caaanaagaa ttgttaagtg tttcaactgt ggcaaagaag gacatatagc tanaaattgc    1200
agggccccta gaaaaagggg ctgttggaaa tgtggaaagg aaggacacca aatgaaagac    1260
tgcactgana gacaggctaa ttttttaggg aaaatttggc cttccaacaa ggggaggcct    1320
ggaaattttc ttcagaacag accagagcca acagcccgc cagcagagag cttcgggtc     1380
```

```
ggagangaga taactccctc cccgaagcag gagcagaaag acaaggaacn gnatcctccc    1440
ttganttccc tcaaatcact ctttggcanc gacccntagt cacaataaaa gtagnggggc    1500
aactaaggga ggctctatta gatacagggg cagatgatac agtattagaa gatataaatt    1560
tgncaggaaa atggaaacca anaatgatag ggggaattgg aggttttatc aaagtaagac    1620
agtatgatca antacccata gaaatttgtg gacaaaaggc tataggtaca gtattagtag    1680
gncctacgcc tgtcaacata attggaagaa atatgttgac tcagattggt tgcactttaa    1740
attttccaat tagtcctatt gaaactgtac cagtaaaatt aaagccagga atggatggcc    1800
caaaggttaa acaatggcca ttgacagaag aaaaaataaa agcantaaca gaaatctgta    1860
cagagatgga aaaagaagga aaaatttcaa aaattgggcc agaaaatcca tacaatactc    1920
cagtatttgc cataaagaaa aaggacagta ctaaatggag aaaattagta gatttcagag    1980
ancttaataa aagaactcaa gattttggg aggttcaatt aggaataccA cacccTgcag    2040
ggttaaaaaa gaaaaaatca gtaacagtac tggatgtggg ggatgcatat ttttcagttc    2100
ccttagataa ggagttcagg aagtacactg cnttcaccat acctagtatc aacaatgaga    2160
caccaggaat tagatatcag tacaatgtgc ttccacaggg atggaagggg tcaccagcaa    2220
tattccaaag tagcatgaca aaaatcttag agccctttag agcaaaaaat ccagaaatag    2280
ttatctacca atacatggat gatttgtatg taggtctga cttagaaata gggcagcata    2340
ggncaaaaat agaggagtta agagaacatc tattgagatg gggatttact acaccagata    2400
aaaaacatca gaangaaccc ccatttcttt ggatggggta tgaactccat cctgacaaat    2460
ggacagtaca ggctatacaa ttgccagaca agagcagctg gactgtcaat gatatacaga    2520
agttagtggg aaaactaaat tgggcaagtc agatttatcc agggattaga gtaaagcact    2580
tatgtaaact ccttagggga gccaaagcac taacagangt agtgccactn actgcagaag    2640
cagagttaga actggcagag aacagggaaa ttctaaaaga accagtacat ggggtatatt    2700
atgacccatc aaaagattta atagcagaaa tacagaaaca agggcangan caatggacat    2760
atcaaattta tcaagancca cataaaaatc tgaaaacagg aaagtatgca anaaggangt    2820
ctgcccacac taatgatgta aaacaattaa cagaagtagt ncaaaaaata gccacagaag    2880
gcatagtaat atggggaaan gttcctaaat ttagactacc catacaaaan gaaacatggg    2940
aaanatggtg gacagagtat tggcangcca cctggattcc tgaatgggag tttgtcaata    3000
cccctcctct agtaaaatta tggtaccant tagaaacaga ncccataata ggagcagaaa    3060 cttttctatgt agatggggca gctaatagag agactaaant aggaaaagca ggatatgtta    3120
ctgacagagg aagacaaaan gttgtcnccc taactgagac aacaaatcag aagactgaat    3180
tacaagcaat tcatttagct ttgcaggact caggatcaga agtaaacata gtaacagact    3240
cacagtatgc attaggaatc attcaagcac acccagataa gagtgaatca gagttagtca    3300
accaaataat agagcaatta atacaaaagg aaanggtcta cctgtcatgg gtaccagcac    3360
ataaagggat tggaggaaat gaacaagtag ataaattagt cagtactgga atcaggaaag    3420
tactgttttt ggatgggata gataaggctc aagaagaaca tgaaaaatat cacancaatt    3480
ggagagcaat ggctagtgat tttaatctgc cacctgtagt agcaaaagaa atagtagcca    3540
gctgtgataa atgtcagcta aaaggggaag ccatgcatgg acaagtagac tgcagtccag    3600
ggatatggca attagattgt acacatttag aaggaaaaat tatcctggta gcagtccatg    3660
tagctagtgg ctatatagaa gcagaagtta tnccagcaga aacnggacag gaaacagcct    3720
```

```
acttcatact aaagttagca ggaagatggc cagtaaaaat aatacataca gacaatggca    3780
gcaatttcac cagtactgtg gttaaggcag cctgttggtg ggcaggtatc cagcaggaat    3840
ttggaattcc ctacaatccc caaagtcaag gagtagtaga atctatgaat aaagaattaa    3900
agaaaatnat aggacangta agagatcaag ctgaacatct taagacagca gtgcaaatgg    3960
cagtattcat tcacaatttt aaaagaaaag gggggattgg ggggtacagt gcagggaaa     4020 gaataataga cataatagca acagacatac aaactaaaga attacaaaaa caaattncaa    4080
aaattcaaaa ttttcgggtt tatttcaggg acagcagaga cccantttgg aaaggaccag    4140
caaagctact ctggaaaggt gaaggggcag tagtcataca agacaataat gaaataaaag    4200
tagtaccaag aagaaaagca aanatcatta gggattatgg aaaacagatg gcaggtgatg    4260
attgtgtggc aggtagacag gatgaggatt agaacatgga acagnttagt aaaacaccat    4320
atgtatgttt caaggagagc taaaggatgg ttttatagac atcactatga aagcaggcat    4380
ccaagagtaa gttcagaagt acacatccca ctagaggatg attctaaatt agtaatanta    4440
acctattggg gtctacatac aggagaaaga gattggcatt tgggtcaagg agtctccata    4500
gaatggaggc agaaaaggta taggacacaa gtagaccctg gcttggcaga ccaactaatt    4560
catctgnatt attttgattg tttttcagaa tctgccataa ggaaagccat attaggacan    4620
agagttagtc ctaggtgtaa ntatcaagca ggacataaca aggtaggatc cctacaatat    4680
ttggcactaa cagcattaat aaccccaaan aagataaagc cgcctttgcc tagtgtcagg    4740
aaactagtag aggatagatg gaacaacccc cagaagacca ngggccacag agggagccat    4800
acaatgaatg gacactagag cttttagagg agcttaagca tgaagctgtt agacattnc     4860 ctagggagtg gctccatggc ttaggacagc atatctataa cacctatggg gatacttggg    4920
agggagttga agctataata agganactgc aacaactact atttatccat ttcagaattg    4980
ggtgccatca tagcagaata ggcattattc gacaaagaag antaagaaat ggaantggta    5040
gatcctaaac tagatccctg gaaccatcca ggaagtcagc ctgagactcc ttgtaataaa    5100
tgntattgta aaaagtgttg ctttcattgc caantgtgct ttacaaggaa gggcttaggc    5160
atctcctatg gcaggaagaa gcggagacag cgacgaagan ctnctcaaag cagtnagnta    5220
catcaagatc ctgtancaaa gcagtaagta gtatatgtaa tgtcatcttt gctaanagta    5280
gtaatagcag catntatagt agcnctaata atagcaataa ttgtgtggac tatagtatat    5340
atagaatata agaaactgtt aaggcaaaaa agaataaata ggttatatga agaataaga     5400 gaaagagcag aagacagtgg caatgagagt gagggagatg cagaggaatt ggcagcactt    5460
ggggaagtgg ggccttttat tcctggggat attaataatc tgtaatgctg cagataactt    5520
gtgggtcaca gtctattatg gagtacctgt gtggaaagaa gcaaccacta ctctattttg    5580
tgcatcagat gctaaagcat atgaaagaga ggtacataat gtctgggcta catatgcctg    5640
tgtacctaca gaccccaacc cacaagaatt ngttctggga aatgtaacag aaaattttaa    5700
catgtggaaa aataacatgg tagaccagat gcatgaagat ataatcagtt tatgggatca    5760
aagcctaaan ccatgtgtaa agntaacccc actctgtgtt acnttaaant gtactgatgt    5820
taatattanc ntcactaata acaataccnc tgatancatc accctggaag ancaagggga    5880
aataaaaaac tgttctttca atatnaccac agagataaaa gataagaaga aaaagaata     5940 tgcanttttt tatanacttg atgtagtacc aatnaataat agtactacta natataggct    6000
aataagttgt aatacctcaa ccgttacaca ggcttgtcca aaggtgtcct ttgatccaat    6060
tcctatacat tattgtgctc ctgctggttn tgcgattcta aagtgtaatg ataaaaggtt    6120
```

```
caatgggaca gggttatgca ggaatgtcag cacagtacaa tgtacacatg gaattaaacc    6180
agtggtatca actcaactac tgttaaatgg cagcctagca gaagaanata taataattag    6240
atctgaaaat atcncagata atncaaaaac cataatagta cagtttaata natctgtaaa    6300
aattaantgt acaagaccca acaacaatac aagaanaagt atacgtatag gaccaggacn    6360
agnattntat gcaacaggtg agataatagg agatataaga aaggcanatt gtancattaa    6420
tggaacactg tggaatgaaa ctttaaaaan ggtagctnca gagntcaaaa accactttaa    6480
tanancanta ncatttgagc catcatcagg aggggancta gaanttacaa cacatagttt    6540
taattgtaga ggaganttt tctactgcaa cacaacagcn ctgtttaatg aaacaaannn    6600
tgnctaatnc aacnaagann anaaatgnca ctatcactct tccatgtaga ataanacaaa    6660
ttgtaaacat gtggcaaaga gtaggacgag caatgtatgc ccctcccatt gcaggaaaaa    6720
ttcagtgtaa ctcaaatatc acaggtctac tattgacaag agatggtggg aannannnna    6780
annaganaga nancctcaga cctnnagggg gagatatgag agacaattgg agaagtgaac    6840
tatataaata taaggtagta aaaattgaac cactaggagt agcacccacc aaggcaaaaa    6900
gacaagtggt gcagagagaa aaaagagcag tgggaatngg agctgtgntc cttgggttct    6960
tgggagcagc aggaagcact atgggcgcgg cgtcaataac gctgacggta caggccagac    7020
aattattgtc tggtatagtg caacagcaaa ncaatttgct gaaggctata gaagcgcaac    7080
agcatctgtt gcagctcaca gtctggggca ttaaacagct ccaggcgaga atcctggctg    7140
tggaaagata cctaaaggac caacagctcc tagggatttg ggngtgctct ggaaaactca    7200
tctgcaccac taatgtgccc tggaattcta gttggagtaa taaatctcag gatgaaattt    7260
gggnaaacat gacctggatg cagtgggaaa aagagatngn naattacaca gacacaaatt    7320
acagattaat ngaanatgcn caaaaccagc aggaaaagaa tgaacaggac ttattggcat    7380
tggacaantg ggacantctg tggagttggt ttnctataac aaactggttg tggtacataa    7440
aaatattcat aatgatagta ggaggcttga taggattaag aatagttttt gctgtgcttt    7500
ctntaataaa tagngttagg cagggatact cacctttgtc attacagacc cttatcccaa    7560
ncccgagggg acccganagg cccggaggaa tcgaagaaga aggtggagag caagacaaag    7620
acagatccnt nagattagtg agcggattct tagcacttgc ctgggacgac ctacggagcc    7680
tgtgcctctt cagctaccgc cacttgagag acttcatatt aattgcagcg aggactgtgg    7740
acaagggact gaaangggggg tgggaagtcc tcaaatatct gtggaatctc gcgcagtatt    7800
ggggtcggga actaaagaat agtgctatta gtctgnttna taccacagca atagnngtag    7860
ctgaagggac agatagaatc atagaanttn tgcaaagagc tggtagagct nttctccaca    7920
tacctagaag aataagacag ggtgntgaaa gggctttgct ataaaatggg tggcaagtgg    7980
tcaaaaagta gtatagttgg atggcctant ntaagggaaa gaatnagann nnnngcagca    8040
gaaggggtgg gannagtgtc tcaagactta gataaacatg gggcaattac aagcagcaat    8100
actngggcta ctaatnctga cttggcctgg ctngaagcgc aagaggatnn ngaagtaggt    8160
tttccagtca gacctcaggt acctttaaga ccaatgactt ataaggnagc tgtcgatctc    8220
agtcactttt taaagaaaaa ggggggactg gaagggttaa tttactccan gaaaagacaa    8280
gaaatccttg atctgtgggt ctaccacaca caaggctact ccctgattg gcagaactac    8340 acaccagggc cagggaccag atatccactg acctttggat ggtgcttcaa gctagtacca    8400
gttgatccag aggaggtaga aaaggccaat gaaggagaga acaactgttt gttacaccct    8460
```

-continued

```
atgagcctac atggaatgga ggatgaagac agggaagtgt taaagtggaa gtttgacagc      8520
ngcctagcac tgagacacat agccagagag agacatccgg agtactacaa agac            8574
```

```
<210> SEQ ID NO 10
<211> LENGTH: 9621
<212> TYPE: DNA
<213> ORGANISM: Human immunodeficiency virus
<220> FEATURE:
<221> NAME/KEY: modified_base
<222> LOCATION: (741)..(741)
<223> OTHER INFORMATION: a, c, t, g, unknown or other
<220> FEATURE:
<221> NAME/KEY: modified_base
<222> LOCATION: (865)..(865)
<223> OTHER INFORMATION: a, c, t, g, unknown or other
<220> FEATURE:
<221> NAME/KEY: modified_base
<222> LOCATION: (1428)..(1428)
<223> OTHER INFORMATION: a, c, t, g, unknown or other
<220> FEATURE:
<221> NAME/KEY: modified_base
<222> LOCATION: (2207)..(2207)
<223> OTHER INFORMATION: a, c, t, g, unknown or other
<220> FEATURE:
<221> NAME/KEY: modified_base
<222> LOCATION: (2588)..(2588)
<223> OTHER INFORMATION: a, c, t, g, unknown or other
<220> FEATURE:
<221> NAME/KEY: modified_base
<222> LOCATION: (3458)..(3458)
<223> OTHER INFORMATION: a, c, t, g, unknown or other
<220> FEATURE:
<221> NAME/KEY: modified_base
<222> LOCATION: (3746)..(3746)
<223> OTHER INFORMATION: a, c, t, g, unknown or other
<220> FEATURE:
<221> NAME/KEY: modified_base
<222> LOCATION: (3974)..(3974)
<223> OTHER INFORMATION: a, c, t, g, unknown or other
<220> FEATURE:
<221> NAME/KEY: modified_base
<222> LOCATION: (3983)..(3983)
<223> OTHER INFORMATION: a, c, t, g, unknown or other
<220> FEATURE:
<221> NAME/KEY: modified_base
<222> LOCATION: (4002)..(4002)
<223> OTHER INFORMATION: a, c, t, g, unknown or other
<220> FEATURE:
<221> NAME/KEY: modified_base
<222> LOCATION: (4445)..(4445)
<223> OTHER INFORMATION: a, c, t, g, unknown or other
<220> FEATURE:
<221> NAME/KEY: modified_base
<222> LOCATION: (5259)..(5259)
<223> OTHER INFORMATION: a, c, t, g, unknown or other
<220> FEATURE:
<221> NAME/KEY: modified_base
<222> LOCATION: (5310)..(5310)
<223> OTHER INFORMATION: a, c, t, g, unknown or other
<220> FEATURE:
<221> NAME/KEY: modified_base
<222> LOCATION: (5340)..(5340)
<223> OTHER INFORMATION: a, c, t, g, unknown or other
<220> FEATURE:
<221> NAME/KEY: modified_base
<222> LOCATION: (5900)..(5900)
<223> OTHER INFORMATION: a, c, t, g, unknown or other
<220> FEATURE:
<221> NAME/KEY: modified_base
<222> LOCATION: (6229)..(6229)
<223> OTHER INFORMATION: a, c, t, g, unknown or other
<220> FEATURE:
<221> NAME/KEY: modified_base
<222> LOCATION: (6410)..(6410)
<223> OTHER INFORMATION: a, c, t, g, unknown or other
<220> FEATURE:
<221> NAME/KEY: modified_base
```

```
<222> LOCATION: (6629)..(6629)
<223> OTHER INFORMATION: a, c, t, g, unknown or other
<220> FEATURE:
<221> NAME/KEY: modified_base
<222> LOCATION: (6631)..(6631)
<223> OTHER INFORMATION: a, c, t, g, unknown or other
<220> FEATURE:
<221> NAME/KEY: modified_base
<222> LOCATION: (6633)..(6634)
<223> OTHER INFORMATION: a, c, t, g, unknown or other
<220> FEATURE:
<221> NAME/KEY: modified_base
<222> LOCATION: (6636)..(6636)
<223> OTHER INFORMATION: a, c, t, g, unknown or other
<220> FEATURE:
<221> NAME/KEY: modified_base
<222> LOCATION: (6647)..(6647)
<223> OTHER INFORMATION: a, c, t, g, unknown or other
<220> FEATURE:
<221> NAME/KEY: modified_base
<222> LOCATION: (6651)..(6651)
<223> OTHER INFORMATION: a, c, t, g, unknown or other
<220> FEATURE:
<221> NAME/KEY: modified_base
<222> LOCATION: (6653)..(6654)
<223> OTHER INFORMATION: a, c, t, g, unknown or other
<220> FEATURE:
<221> NAME/KEY: modified_base
<222> LOCATION: (6769)..(6769)
<223> OTHER INFORMATION: a, c, t, g, unknown or other
<220> FEATURE:
<221> NAME/KEY: modified_base
<222> LOCATION: (6771)..(6772)
<223> OTHER INFORMATION: a, c, t, g, unknown or other
<220> FEATURE:
<221> NAME/KEY: modified_base
<222> LOCATION: (6779)..(6781)
<223> OTHER INFORMATION: a, c, t, g, unknown or other
<220> FEATURE:
<221> NAME/KEY: modified_base
<222> LOCATION: (6783)..(6783)
<223> OTHER INFORMATION: a, c, t, g, unknown or other
<220> FEATURE:
<221> NAME/KEY: modified_base
<222> LOCATION: (7140)..(7140)
<223> OTHER INFORMATION: a, c, t, g, unknown or other
<220> FEATURE:
<221> NAME/KEY: modified_base
<222> LOCATION: (7142)..(7142)
<223> OTHER INFORMATION: a, c, t, g, unknown or other
<220> FEATURE:
<221> NAME/KEY: modified_base
<222> LOCATION: (7238)..(7238)
<223> OTHER INFORMATION: a, c, t, g, unknown or other
<220> FEATURE:
<221> NAME/KEY: modified_base
<222> LOCATION: (7252)..(7252)
<223> OTHER INFORMATION: a, c, t, g, unknown or other
<220> FEATURE:
<221> NAME/KEY: modified_base
<222> LOCATION: (7256)..(7256)
<223> OTHER INFORMATION: a, c, t, g, unknown or other
<220> FEATURE:
<221> NAME/KEY: modified_base
<222> LOCATION: (7264)..(7264)
<223> OTHER INFORMATION: a, c, t, g, unknown or other
<220> FEATURE:
<221> NAME/KEY: modified_base
<222> LOCATION: (7394)..(7394)
<223> OTHER INFORMATION: a, c, t, g, unknown or other
<220> FEATURE:
<221> NAME/KEY: modified_base
<222> LOCATION: (7397)..(7399)
<223> OTHER INFORMATION: a, c, t, g, unknown or other
<220> FEATURE:
<221> NAME/KEY: modified_base
<222> LOCATION: (7404)..(7407)
<223> OTHER INFORMATION: a, c, t, g, unknown or other
<220> FEATURE:
```

-continued

```
<221> NAME/KEY: modified_base
<222> LOCATION: (7409)..(7409)
<223> OTHER INFORMATION: a, c, t, g, unknown or other
<220> FEATURE:
<221> NAME/KEY: modified_base
<222> LOCATION: (7566)..(7566)
<223> OTHER INFORMATION: a, c, t, g, unknown or other
<220> FEATURE:
<221> NAME/KEY: modified_base
<222> LOCATION: (8223)..(8223)
<223> OTHER INFORMATION: a, c, t, g, unknown or other
<220> FEATURE:
<221> NAME/KEY: modified_base
<222> LOCATION: (8515)..(8515)
<223> OTHER INFORMATION: a, c, t, g, unknown or other
<220> FEATURE:
<221> NAME/KEY: modified_base
<222> LOCATION: (8559)..(8559)
<223> OTHER INFORMATION: a, c, t, g, unknown or other
<220> FEATURE:
<221> NAME/KEY: modified_base
<222> LOCATION: (8858)..(8858)
<223> OTHER INFORMATION: a, c, t, g, unknown or other
<220> FEATURE:
<221> NAME/KEY: modified_base
<222> LOCATION: (8971)..(8971)
<223> OTHER INFORMATION: a, c, t, g, unknown or other
<220> FEATURE:
<221> NAME/KEY: modified_base
<222> LOCATION: (8977)..(8977)
<223> OTHER INFORMATION: a, c, t, g, unknown or other
<220> FEATURE:
<221> NAME/KEY: modified_base
<222> LOCATION: (9014)..(9014)
<223> OTHER INFORMATION: a, c, t, g, unknown or other
<220> FEATURE:
<221> NAME/KEY: modified_base
<222> LOCATION: (9258)..(9258)
<223> OTHER INFORMATION: a, c, t, g, unknown or other
<220> FEATURE:
<221> NAME/KEY: modified_base
<222> LOCATION: (9313)..(9313)
<223> OTHER INFORMATION: a, c, t, g, unknown or other
<220> FEATURE:
<221> NAME/KEY: modified_base
<222> LOCATION: (9332)..(9332)
<223> OTHER INFORMATION: a, c, t, g, unknown or other
<220> FEATURE:
<221> NAME/KEY: modified_base
<222> LOCATION: (9393)..(9393)
<223> OTHER INFORMATION: a, c, t, g, unknown or other
<220> FEATURE:
<221> NAME/KEY: modified_base
<222> LOCATION: (9532)..(9532)
<223> OTHER INFORMATION: a, c, t, g, unknown or other
<220> FEATURE:
<221> NAME/KEY: modified_base
<222> LOCATION: (9576)..(9576)
<223> OTHER INFORMATION: a, c, t, g, unknown or other
<220> FEATURE:
<221> NAME/KEY: modified_base
<222> LOCATION: (9578)..(9578)
<223> OTHER INFORMATION: a, c, t, g, unknown or other
<220> FEATURE:
<221> NAME/KEY: modified_base
<222> LOCATION: (9584)..(9584)
<223> OTHER INFORMATION: a, c, t, g, unknown or other
<220> FEATURE:
<221> NAME/KEY: modified_base
<222> LOCATION: (9598)..(9598)
<223> OTHER INFORMATION: a, c, t, g, unknown or other
<220> FEATURE:
<221> NAME/KEY: modified_base
<222> LOCATION: (9617)..(9618)
<223> OTHER INFORMATION: a, c, t, g, unknown or other
<220> FEATURE:
<221> NAME/KEY: modified_base
<222> LOCATION: (9620)..(9621)
<223> OTHER INFORMATION: a, c, t, g, unknown or other
```

<400> SEQUENCE: 10

```
acttgaccta tgggctataa taccaaagga ttcttcccag attggcagaa ctacacacca      60
gggccaggga ctagattccc actgaccctt gggtggtgct tcaaactggt accaatggat     120
ccatcagagg tagaggaagc caataaagga gagaacaaca gtctattaca ccccatctgc     180
cagcatggaa tggaggacga agacagagaa gtgctggtgt ggaaatttga cagtagccta     240
gcacggagac acatagcccg agagctgcat ccggagtact acaaagactg ctgacacaga     300
agttgctgac aagggacttt ccgcctgggg actttccagg ggaggcgcgg cctgggaggg     360
gctggggagt ggctaaccct cagaagctgc atataagcag ccgcttctcg cctgtactgg     420
gtctctcttg ttagaccaga tttgagcctg ggagctctct ggctagcagg ggaacccact     480
gcttagagcc tcaataaagc ttgccttgag tgcttcaagt agtgtgtgcc cgtctgttgt     540
gtgactctgg taactagaga tccctcagac cactctagat agtgtaaaaa tctctagcag     600
tggcgcccga acagggactt gaaagcgaaa gttaacaggg actcgaaagc gaaagttcca     660
gagaagttct ctcgacgcag gactcggctt gctgaggtgc acacagcaag aggcgagagc     720
ggcgactggt gagtacgcca naattttga ctagcggagg ctagaaggag agagatgggt     780
gcgagagcgt cagtattaag cgggggaaaa ttagatgctt gggaaaaaat tcggttgagg     840
ccaggggaa agaaaaaata tagantgaaa catttagtat gggcaagcag ggagctggag     900
agatttgcac ttaaccctga ccttttagaa acagcagaag gttgtcagca ataatgggaa     960
cagttgcaac cagctctcca gacaggaaca gaggagatta gatcattatt taatacagta    1020
gcaaccctct attgtgtaca tcaaaagata gaggtaaaag acaccaaaga agctctagag    1080
gaagtggaaa agatacaaaa gaaaagtcag caaaaaatac agcaggcagc aatggatgaa    1140
ggaaacagca gccaagtcag ccaaaattat cctatagtgc agaatgcaca agggcaaatg    1200
gtacaccagg ccatatcacc tagaacttta aatgcatggg taaaagtagt agaagaaaag    1260
gccttcagtc cagaagtaat acccatgttt tcagcattat cagaaggagc cacccccacaa    1320
gatttaaata ccatgctaaa cacagtgggg gggcatcaag cagctatgca aatgctaaag    1380
gatactatca atgaggaagc tgcagagtgg gacaggatac atccacanca ggcagggcct    1440
attccaccag gccagataag agaaccaagg ggaagtgata tagcaggaac tactagtacc    1500
ctgcaggaac aaataagatg gatgaccagc aacccaccta tcccagtggg agaaatttat    1560
aaaagatgga taatcctggg attaaataaa atagtaagaa tgtatagccc tgtcagcatt    1620
ttggacataa gacaagggcc aaaagaaccc tttagagatt atgtagatag gttctttaaa    1680
actttgagag ctgagcaagc tacacaggaa gtaaaaggct ggatgacaga caccttgttg    1740
gtccaaaatg cgaacccaga ttgtaagacc atcttaagag cattaggacc aggagctaca    1800
ctagaagaaa tgatgacagc atgtcaggga gtgggaggac ccagccataa agcaagagtt    1860
ttagctgagg caatgagcca ggcatcaggt gcagcagcag ccataatgat gcagaaaagc    1920
aatttaagg gcccaagaag aactattaag tgtttcaact gtggcaagga aggacatcta    1980
gccagaaatt gcagggcccc taggaaaaag ggctgttgga aatgtggaaa ggagggacat    2040
caaatgaaag actgcacaga gagacaggct aattttttag ggaaaatttg gccttccaac    2100
aaggggaggc cagggaattt tctccagaac aggccagagc caacagcccc acccgcagag    2160
agcttcgggt tcgagagga atagccccc tccccgaagc aggagcngaa ggaaaaggag    2220
ctatatccct tagcctccct caaatcactc tttggcagcg accctagtc acagtaaaaa    2280
```

```
tagggggaca gctaatagaa gccctattag acacaggagc agatgataca gtattagaag    2340
aaataaattt accaggaaaa tggaaaccaa aaatgatagg gggaattgga ggttttatca    2400
aagtaagaca gtatgatcaa atacttatag aaattagtgg aaaaaaggct atagggacag    2460
tattagtagg acctcacctt atcaacataa ttgggagaaa tatgttgact cagattggtt    2520
gtactttaaa ttttccaatt agtcctattg aaactgtacc agtaaaatta aagccaggaa    2580
tggatggncc aagggttaaa caatggccat tgacagaaga gaaaataaaa gcattaacag    2640
aaatttgtaa agaaatggaa aaggaaggaa aaatttcaaa aattgggcct gaaaatccat    2700
acaacactcc aatatttgcc ataagaaaaa aagacagtac taaatggaga aaattggtag    2760
atttcagaga gctcaataaa agaactcaag acttctggga ggtccaatta ggaatacctc    2820
atcccgcggg gttaaaaaag aaaaaatcag taacagtact agatgtgggg gatgcatact    2880
tttcagttcc cttagatgaa aactttagaa agtatactgc attcactata cctagtacaa    2940
ataatgagac accagggatt agatatcagt acaatgtgct tccacaggga tggaaaggat    3000
caccagcaat atttcagagt agcatgacaa aaatcttaga gccctttaga acaaaaaatc    3060
cagaaatagt gatctaccaa tacatggatg atttatatgt aggatctgac ttagaaatag    3120
ggcagcatag agcaaaaata gaggagttaa gagaacatct attgagatgg ggatttacca    3180
caccagataa aaaacatcag aaagaacctc cattcctttg gatgggatat gagctccatc    3240
ctgacaaatg gacggtacaa cctatacagc tgccagacaa ggaaagctgg actgtcaatg    3300
atatacaaaa gttagtggga aaactaaatt gggcaagtca gatttatcca gggattaaag    3360
taaagcaact atgtaaactc cttagggggg ccaaagcact aacagacata gtaccactga    3420
ctgcagaagc agaaatggaa ttggcagaga cagggganat tctaaaagaa cctgtacatg    3480
gagtctatta tgacccatca aaagaattaa tagcagaagt acagaaacaa gggctagacc    3540
aatggacata tcaaatttat caagagccat acaaaaatct gaaaacagga aaatatgcaa    3600 aaaggggggtc tgcccacact aatgatgtaa acaattaac agaagtagtg caaaaaatag    3660
ccacagagag catagtaata tggggaaaga ctcctaaatt taaactacct atacgaaaag    3720
aaacatggga agtatggtgg acagantatt ggcaggccac ctggattcct gagtgggagt    3780
ttgtcaatac ccctcctcta gtaaaattat ggtatcggtt agaaacagaa cccataccag    3840
gagcagaaac ttactatgta gatggggcag ctaataggga gacaaaatta ggaaaggcag    3900
gatatgttac tgacaaagga aaacaaaaaa ttattaccct aactgaaaca acaaaccaaa    3960
aggctgaatt acangcaatt canctagctt tgcaggactc angatcagaa gtaaacatag    4020
taacagactc acagtatgca ttaggaatca ttcaagcaca accagatagg agtgaatcag    4080
aattagtcaa tcaaataata gaacagctaa taaaaaagga aaaggtctac ctgtcatggg    4140
taccagcaca caagggaatt ggaggaaatg aacaagtaga taaattagtc agtagtggaa    4200
tcaggaaagt attatttta gatggcatag ataaagccca agaagaccat gaaagatatc    4260
acagcaattg gagagcaatg gctagtgatt ttaatctgcc acctatagta gcaaaagaaa    4320
tagtggccag ctgtgataaa tgtcagctaa aaggggaagc catgcatgga caagtagact    4380
gtagtccagg aatatggcaa ttagattgta cacatttaga aggaaaaatt atcctggtag    4440
cagtncatgt agccagtggc tatatagaag cagaagttat cccagcagaa acaggacagg    4500
aaacagcata ctttatatta aaattagcag gaaggtggcc agtaaaagta atacatacag    4560
acaatggcag caatttcacc agtgctgcag taaaggcagc atgttggtgg gcaaatatca    4620
cacaggaatt tggaattccc tacaatcccc aaagccaagg agtagtggaa tctatgaata    4680
```

```
aggaattaaa gaaaatcatc gggcaggtca gggatcaagc tgaacatctt aagacagcag    4740
tacagatggc agtattcatt cacaattta aaagaaaagg ggggattggg gggtacagtg    4800
caggggaaag aataatagac ataatagcat cagatataca aactaaagaa ctacaaaaac    4860
aaattacaaa aattcaaaat tttcgggttt attacaggga cagcagagac ccaatttgga    4920
aaggaccagc aaagctactc tggaaaggtg aaggggcagt agtaatacaa gacaataacg    4980
aaataaaggt agtaccaaga agaaaagcaa agatcattag ggattatgga aaacagatgg    5040
caggtgatga ttgtgtggca ggtagacagg atgaggatta gaacatggaa cagtttagta    5100
aaacatcata tgtatgtctc aaagaaagct aaaggctggt tttatagaca tcactatgaa    5160
agcaggcatc caaaagtaag ttcagaagta cacatcccac taggagatgc tacactagta    5220
gtaagaacat attggggtct gcatacagga gaaaaagant ggcaattggg tcatggggtc    5280
tccatagaat ggaggcagag aagatatagn acacaaatag atcctgacct agcagaccan    5340
ctgattcatc tgcattattt tgactgtttt tcagaatctg ccataaggaa agccatatta    5400
ggaaaaatag ttagtcctag gtgtgaatat caagcaggac ataataaggt aggatctcta    5460
caatatttgg cattgaaagc attagtaaca ccaacaagga caaggccacc tttgcctagt    5520
gttaggaaat taacagaaga tagatggaac aagccccaga agaccagggg ccacagagag    5580
aaccctacaa tgaatgggca ttagaactgt tagaagagct taaaaatgaa gctgttagac    5640
attttcctag gccctggctc catggcttag gacagtatat ctataacact tatggggata    5700
cttgggaagg agttgaagcc ataataagaa tactacaaca actactgttt atccatttca    5760
gaattgggtg ccaacatagc agaataggca ttactccaca gagaagagta agggatggac    5820
ccggtagatc ctaacctaga gccctggaat catccgggga gtcagcctaa aactccctgt    5880
aacaactgct attgtaaaan gtgttgctgg cattgccaag tttgctttct gaacaaaggc    5940
ttaggcatct cctatggcag gaagaagcgg aagcaccgac gaggaactcc tcagagcagt    6000
aaggatcatc aaaatcctgt accaaagcag taagtagtaa taattagtat atgtaatgca    6060
accattagaa atatctgcaa tagtaggact aatagtagca ttcatagcag ccataattgt    6120
gtggactata gtatttatag aatataggga aataagaaaa cagaaaaaaa tagaaaagtt    6180
acttgataga ataagagaaa gagcagaaga cagtggaaat gagagtgang gggatacaga    6240
ggaattggca acacttatgg aaatggggga ctttgatcct tgggttggtg ataatttgta    6300
gtgcctcaaa taacttgtgg gtcacagtct attatggggt acctgtgtgg aagatgcaa    6360 ataccactct attttgtgca tctgatgcta aagcatatag tactgaaagn cataatgtct    6420
gggctacaca tgcctgtgta cccacagacc ccaacccaca agaaatacct atggaaaatg    6480
taacagaaaa ttttaacatg tggaaaaata acatggtaga acagatgcat gaggatataa    6540
tcagtttatg ggatgaaagc ctaaagccat gtgtaaagct aaccccctctc tgtgttactt    6600 taaactgtac taatgtaacc aacaatagna ntnnntnaaca ataacantat ngnnngacaaa    6660 gaagaaataa aaaactgctc tttcaatata accacagaaa taagagataa gaagaagcaa    6720
gaatacgcgc ttttctatag acttgatgta gtaccaatta atgataatnt nnagtaatnn    6780
nantaattat aggctaataa attgtaatgt ctcaaccatt aaacaggctt gtccaaaggt    6840
aacttttgac ccaattccca tacattattg tgctccagct ggttttgcga ttttaaagtg    6900
tagggataag gagttcaatg gaacaggacc atgtaaaaat gtcagtacag tacaatgtac    6960
acatggaatt aagccagtgg tatcaactca actactgctg aatggcagtt tagcagaaga    7020
```

```
agaaataata attagatctg aaaatatcac agacaatacc aaagtcataa tagtgcagct    7080
taatgaaact atagaaatta attgtatcag acccaacaac aatacaagaa aaagtataan    7140
antcggacca ggacaagcgt tctatgcaac aggtgacata ataggagaca taagacaagc    7200
acattgtaat gttagtagaa caaaatggaa taagatgnta aagaatgtca cngcanaact    7260
aaanaaaatc tttaataaca agaacataac ctttaactca tctgcaggag gggacctaga    7320
aattacaaca catagtttca attgtagagg agaattttc tattgtaata catcaggact     7380
gtttaataat agtntgnnng tagnnnnant aatagtaata atgagactat cacactccca    7440
tgtaaaataa aacaaattgt gagaatgtgg cagagagtgg acaagcaat gtatgcccct     7500 cccatcgcag gaaacattac atgtaaatca aacattacag gactaatatt aacaagagat    7560
ggtggnaata ataatacaag tgcgactgag atcttcagac ctggaggagg agatatgaag    7620
gacaattgga gaagtgaatt atataagtat aaaacagtaa aaatcaaatc actaggagta    7680
gcacccacca gggcaaggag aagagtggtg gagagagaaa aaagagcagt tggactggga    7740
gctgtcttcc ttgggttctt aggagcagca ggaagcacta gggcgcggc gtcaataacg      7800 ctgacggtac aggtcagaca attattgtct ggcatagtgc aacagcaaag caatttgctg    7860
agggctatag aggcgcagca gcatctgttg caactcacag tctggggcat taaacagctc    7920
caggcaagag tcctggctgt ggaaagatac ctaaaggatc aacagctcct agggatttgg    7980
ggctgctctg gaaaactcat ctgcaccact aatgtgccct ggaacgctag ttggagtaat    8040
aaatcttata tgaaatttg ggataacatg acttggatag aatgggaaag ggaaattaac      8100
aattacacac aacaaatata cagcctaatt gaagaatcgc agaaccagca ggaaaagaat    8160
gaacaagact tattggcatt ggacaagtgg gcaagtttgt ggaattggtt tgacatatca    8220
aantggctat ggtatataaa aatatttata atgatagtag gaggtttaat aggtttaaga    8280
atagtttttg ctgtgctttc tatagtaaat agagttaggc agggatactc acctttgtca    8340
ttccagaccc ttacccacca ccagagggaa cccgacaggc ccggaagaat cgaagaagaa    8400
ggtggagagc aagacaaaga cagatccatt cgattagtga gcggattctt agcgcttgcc    8460
tgggacgacc tgcggagcct gtgcctcttc agctaccacc gcttgagaga cttcntcttg    8520
attgcagcga ggacagtgga acttctggga cgcagcagnc tcaagggact gagactgggg    8580
tgggaaggcc tcaaatattt gtggaatctt ctgttgtatt ggggtcggga actaaagaat    8640
agtgctatta atttgcttga tacaatagca atagcagtag ctaactggac agatagggtt    8700
atagaagtag cacaaagagc tggtagagct attctcaaca tacctacaag aataagacaa    8760
ggcttagaaa gagctttgct ataaaatggg aggcaagtgg tcaaaaagta gcatagttgg    8820
atggcctgag gtaagggaaa gaataagaca aaccccncta gcagcagaag gagtaggagc    8880
agtatctcaa gatttagcta ggcatggagc aatcacaagc agcaatacag cagccaataa    8940
tcctgattgt gcctggctgg aagcacaaga ngaggantca gaggtaggct ttccagtcag    9000
accacaggta cctntgagac caatgactta taaggctgct tttgatctca gcttctttt     9060 aaaagaaaag ggggggactgg atgggctaat ttactccaag aaaagacaag acatccttga    9120
cctgtgggtc tataatacac aaggattctt cccagattgg cagaactaca caccagggcc    9180
agggactaga ttcccactga cctttgggtg gtgcttcaaa ctagtaccaa tggatccagc    9240
agaggtagag gaagccanta aaggagaaa caacagtcta ttacacccca tctgccagca     9300
tggaatggag gangaagaca gagaagtgct gntatggaga tttgacagta gcctagcacg    9360
gagacacata gcccgagagc tgcatccgga gtnctacaaa gactgctgac acagaagttg    9420
```

```
ctgacaaagg gactttccgc ctgggacttt ccggggaggc gcggcctggg aggggctggg    9480
gagtggctaa ccctcagaag ctgcatataa gcagccgctt ctcgcctgta cngggtctct    9540
cttgttgacc agatttgagc ctgggagctc tctggntngc aggngaacca ctgcttangc    9600
ctcaataaag cttgccnngn n                                              9621

<210> SEQ ID NO 11
<211> LENGTH: 9181
<212> TYPE: DNA
<213> ORGANISM: Human immunodeficiency virus

<400> SEQUENCE: 11
ggtctctctg gttagaccag atctgagcct gggagctctc tggctaacta gggaacccac      60
tgcttaagcc tcaataaagc ttgccttgag tgcttcaagt agtgtgtgcc cgtctgttgt     120
gtgactctgg taactagaga tccctcagac cctttagtc agtgtggaaa atctctagca     180
gtggcgcccg aacagggacc tgaaagcgaa agggaaacca gaggagctct ctcgacgcag    240
gactcggctt gctgaagcgc gcacggcaag aggcgagggg cggcgactgg tgagtacgcc    300
aaaaattttg actagcggag gctagaagga gagagatggg tgcgagagcg tcagtattaa    360 gcggggaga attagatcga tgggaaaaaa ttcggttaag gccaggggga aagaaaaaat    420
ataaattaaa acatatagta tgggcaagca gggagctaga acgattcgca gttaatcctg    480
gcctgttaga acatcagaa ggctgtagac aaatactggg acagctacaa ccatcccttc    540
agacaggatc agaagaactt agatcattat ataatacagt agcaaccctc tattgtgtgc    600
atcaaaggat agagataaaa gacaccaagg aagctttaga caagatagag gaagagcaaa    660
acaaaagtaa gaaaaagca cagcaagcag cagctgacac aggacacagc aatcaggtca    720
gccaaaatta ccctatagtg cagaacatcc aggggcaaat ggtacatcag gccatatcac    780 ctagaactt aaatgcatgg gtaaagtag tagaagagaa ggctttcagc ccagaagtga    840
tacccatgtt ttcagcatta tcagaaggag ccaccccaca agatttaaac accatgctaa    900
acacagtggg gggacatcaa gcagccatgc aaatgttaaa agagaccatc aatgaggaag    960
ctgcagaatg ggatagagtg catccagtgc atgcagggcc tattgcacca ggccagatga   1020
gagaaccaag gggaagtgac atagcaggaa ctactagtac ccttcaggaa caaataggat   1080
ggatgacaaa taatccacct atcccagtag gagaaattta aaagatgg ataatcctgg   1140 gattaaataa aatagtaaga atgtatagcc ctaccagcat tctggacata agacaaggac   1200
caaaggaacc cttagagac tatgtagacc ggttctataa aactctaaga gccgagcaag   1260
cttcacagga ggtaaaaaat tggatgacag aaaccttgtt ggtccaaaat gcgaacccag   1320
attgtaagac tattttaaaa gcattgggac cagcggctac actagaagaa atgatgacag   1380
catgtcaggg agtaggagga cccggccata aggcaagagt tttggctgaa gcaatgagcc   1440
aagtaacaaa ttcagctacc ataatgatgc agagaggcaa ttttaggaac caaagaaaga   1500
ttgttaagtg tttcaattgt ggcaaagaag ggcacacagc cagaaattgc agggccccta   1560
ggaaaaaggg ctgttggaaa tgtggaaagg aaggacacca aatgaaagat tgtactgaga   1620
gacaggctaa ttttttaggg aagatctggc cttcctacaa gggaaggcca gggaattttc   1680
ttcagagcag accagagcca acagccccac cagaagagag cttcaggtct ggggtagaga   1740
caacaactcc ccctcagaag caggagccga tagacaagga actgtatcct ttaacttccc   1800
tcaggtcact ctttggcaac gacccctcgt cacaataaag ataggggggc aactaaagga   1860
```

```
agctctatta gatacaggag cagatgatac agtattagaa gaaatgagtt tgccaggaag   1920
atggaaacca aaaatgatag ggggaattgg aggttttatc aaagtaagac agtatgatca   1980
gatactcata gaaatctgtg gacataaagc tataggtaca gtattagtag gacctacacc   2040
tgtcaacata attggaagaa atctgttgac tcagattggt tgcactttaa attttcccat   2100
tagccctatt gagactgtac cagtaaaatt aaagccagga atggatggcc caaaagttaa   2160
acaatggcca ttgacagaag aaaaaataaa agcattagta gaaatttgta cagagatgga   2220
aaaggaaggg aaaatttcaa aaattgggcc tgaaaatcca tacaatactc cagtatttgc   2280
cataaagaaa aaagacagta ctaaatggag aaaattagta gatttcagag aacttaataa   2340
gagaactcaa gacttctggg aagttcaatt aggaatacca catcccgcag ggttaaaaaa   2400
gaaaaaatca gtaacagtac tggatgtggg tgatgcatat tttcagttc ccttagatga   2460 agacttcagg aagtatactg catttaccat acctagtata aacaatgaga caccagggat   2520
tagatatcag tacaatgtgc ttccacaggg atggaaagga tcaccagcaa tattccaaag   2580
tagcatgaca aaaatcttag agccttttag aaaacaaaat ccagacatag ttatctatca   2640
atacatggat gatttgtatg taggatctga cttagaaata gggcagcata gaacaaaaat   2700
agaggagctg agacaacatc tgttgaggtg gggacttacc acaccagaca aaaacatca   2760 gaaagaacct ccattccttt ggatgggtta tgaactccat cctgataaat ggacagtaca   2820
gcctatagtg ctgccagaaa aagacagctg gactgtcaat gacatacaga agttagtggg   2880
gaaattgaat tgggcaagtc agatttaccc agggattaaa gtaaggcaat tatgtaaact   2940
ccttagagga accaaagcac taacagaagt aataccacta acagaagaag cagagctaga   3000
actggcagaa aacagagaga ttctaaaaga accagtacat ggagtgtatt atgacccatc   3060
aaaagactta atagcagaaa tacagaagca ggggcaaggc caatggacat atcaaattta   3120
tcaagagcca tttaaaaatc tgaaaacagg aaaatatgca agaatgaggg gtgcccacac   3180
taatgatgta aaacaattaa cagaggcagt gcaaaaaata accacagaaa gcatagtaat   3240
atggggaaag actcctaaat ttaaactgcc catacaaaag gaaacatggg aaacatggtg   3300
gacagagtat tggcaagcca cctggattcc tgagtgggag tttgttaata cccctccctt   3360
agtgaaatta tggtaccagt tagagaaaga acccatagta ggagcagaaa ccttctatgt   3420
agatggggca gctaacaggg agactaaatt aggaaaagca ggatatgtta ctaatagagg   3480
aagacaaaaa gttgtcaccc taactgacac aacaaatcag aagactgagt tacaagcaat   3540
ttatctagct ttgcaggatt cgggattaga agtaaacata gtaacagact cacaatatgc   3600
attaggaatc attcaagcac aaccagatca aagtgaatca gagttagtca atcaaataat   3660
agagcagtta ataaaaaagg aaaaggtcta tctggcatgg gtaccagcac acaaaggaat   3720
tggaggaaat gaacaagtag ataaattagt cagtgctgga atcaggaaag tactattttt   3780
agatggaata gataaggccc aagatgaaca tgagaaatat cacagtaatt ggagagcaat   3840
ggctagtgat tttaacctgc cacctgtagt agcaaaagaa atagtagcca gctgtgataa   3900
atgtcagcta aaaggagaag ccatgcatgg acaagtagac tgtagtccag gaatatggca   3960
actagattgt acacatttag aaggaaaagt tatcctggta gcagttcatg tagccagtgg   4020
atatatagaa gcagaagtta ttccagcaga acagggcag gaaacagcat attttctttt   4080
aaaattagca ggaagatggc cagtaaaaac aatacatact gacaatggca gcaatttcac   4140
cggtgctacg gttagggccg cctgttggtg ggcgggaatc aagcaggaat ttggaattcc   4200
ctacaatccc caaagtcaag gagtagtaga atctatgaat aaagaattaa agaaaattat   4260
```

```
aggacaggta agagatcagg ctgaacatct taagacagca gtacaaatgg cagtattcat    4320
ccacaatttt aaaagaaaag gggggattgg ggggtacagt gcaggggaaa gaatagtaga    4380
cataatagca acagacatac aaactaaaga attacaaaaa caaattacaa aaattcaaaa    4440
ttttcgggtt tattacaggg acagcagaaa tccactttgg aaaggaccag caaagctcct    4500
ctggaaaggt gaaggggcag tagtaataca agataatagt gacataaaag tagtgccaag    4560
aagaaaagca aagatcatta gggattatgg aaaacagatg gcaggtgatg attgtgtggc    4620
aagtagacag gatgaggatt agaacatgga aaagtttagt aaaacaccat atgtatgttt    4680
cagggaaagc taggggatgg ttttatagac atcactatga aagccctcat ccaagaataa    4740
gttcagaagt acacatccca ctaggggatg ctagattggt aataacaaca tattggggtc    4800
tgcatacagg agaaagagac tggcatttgg gtcagggagt ctccatagaa tggaggaaaa    4860
agagatatag cacacaagta gaccctgaac tagcagacca actaattcat ctgtattact    4920
ttgactgttt ttcagactct gctataagaa aggccttatt aggacacata gttagcccta    4980
ggtgtgaata tcaagcagga cataacaagg taggatctct acaatacttg cactagcag    5040 cattaataac accaaaaaag ataaagccac ctttgcctag tgttacgaaa ctgacagagg    5100
atagatggaa caagccccag aagaccaagg gccacagagg gagccacaca atgaatggac    5160
actagagctt ttagaggagc ttaagaatga agctgttaga cattttccta ggatttggct    5220
ccatggctta gggcaacata tctatgaaac ttatggggat acttgggcag gagtggaagc    5280
cataataaga attctgcaac aactgctgtt tatccatttt cagaattggg tgtcgacata    5340
gcagaatagg cgttactcga cagaggagag caagaaatgg agccagtaga tcctagacta    5400
gagccctgga agcatccagg aagtcagcct aaaactgctt gtaccaattg ctattgtaaa    5460
aagtgttgct ttcattgcca agtttgtttc ataacaaaag ccttaggcat ctcctatggc    5520
aggaagaagc ggagacagcg acgaagagct catcagaaca gtcagactca tcaagcttct    5580
ctatcaaagc agtaagtagt acatgtaatg caacctatac caatagtagc aatagtagca    5640
ttagtagtag caataataat agcaatagtt gtgtggtcca tagtaatcat agaatatagg    5700
aaaatattaa gacaaagaaa aatagacagg ttaattgata gactaataga aagagcagaa    5760
gacagtggca atgagagtga aggagaaata tcagcacttg tggagatggg ggtggagatg    5820
gggcaccatg ctccttggga tgttgatgat ctgtagtgct acagaaaaat tgtgggtcac    5880
agtctattat ggggtacctg tgtggaagga agcaaccacc actctatttt gtgcatcaga    5940
tgctaaagca tatgatacag aggtacataa tgtttgggcc acacatgcct gtgtacccac    6000 agacccaac ccacaagaag tagtattggt aaatgtgaca gaaaatttta acatgtggaa    6060
aaatgacatg gtagaacaga tgcatgagga tataatcagt ttatgggatc aaagcctaaa    6120
gccatgtgta aaattaaccc cactctgtgt tagtttaaag tgcactgatt tgaagaatga    6180
tactaatacc aatagtagta gcgggagaat gataatggag aaggagaga taaaaaactg    6240 ctctttcaat atcagcacaa gcataagagg taaggtgcag aaagaatatg cattttttta    6300
taaacttgat ataataccaa tagataatga tactaccagc tataagttga caagttgtaa    6360
cacctcagtc attacacagg cctgtccaaa ggtatccttt gagccaattc ccatacatta    6420
ttgtgccccg gctggttttg cgattctaaa atgtaataat aagacgttca atggaacagg    6480
accatgtaca aatgtcagca cagtacaatg tacacatgga attaggccag tagtatcaac    6540
tcaactgctg ttaaatggca gtctagcaga agaagaggta gtaattagat ctgtcaattt    6600
```

```
cacggacaat gctaaaacca taatagtaca gctgaacaca tctgtagaaa ttaattgtac      6660
aagacccaac aacaatacaa gaaaagaat ccgtatccag agaggaccag ggagagcatt       6720
tgttacaata ggaaaaatag gaaatatgag acaagcacat tgtaacatta gtagagcaaa     6780
atggaataac actttaaaac agatagctag caaattaaga gaacaatttg gaaataataa     6840
aacaataatc tttaagcaat cctcaggagg ggacccagaa attgtaacgc acagttttaa     6900
ttgtggaggg gaatttttct actgtaattc aacacaactg tttaatagta cttggtttaa     6960
tagtacttgg agtactgaag ggtcaaataa cactgaagga agtgacacaa tcaccctccc    7020
atgcagaata aaacaaatta taaacatgtg gcagaaagta ggaaaagcaa tgtatgcccc    7080
tcccatcagt ggacaaatta gatgttcatc aaatattaca gggctgctat taacaagaga    7140
tggtggtaat agcaacaatg agtccgagat cttcagacct ggaggaggag atatgaggga    7200
caattggaga agtgaattat ataaatataa agtagtaaaa attgaaccat taggagtagc    7260
acccaccaag gcaaagagaa gagtggtgca gagagaaaaa agagcagtgg aataggagc     7320 tttgttcctt gggttcttgg gagcagcagg aagcactatg ggcgcagcct caatgacgct    7380
gacggtacag gccagacaat tattgtctgg tatagtgcag cagcagaaca atttgctgag    7440
ggctattgag gcgcaacagc atctgttgca actcacagtc tggggcatca agcagctcca    7500
ggcaagaatc ctggctgtgg aaagatacct aaaggatcaa cagctcctgg ggatttgggg    7560
ttgctctgga aaactcattt gcaccactgc tgtgccttgg aatgctagtt ggagtaataa    7620
atctctggaa cagatttgga atcacacgac ctggatggag tgggacagag aaattaacaa    7680
ttacacaagc ttaatacact ccttaattga agaatcgcaa aaccagcaag aaaagaatga    7740
acaagaatta ttggaattag ataaatgggc aagtttgtgg aattggttta cataacaaa     7800 ttggctgtgg tatataaaat tattcataat gatagtagga ggcttggtag gtttaagaat    7860
agtttttgct gtactttcta tagtgaatag agttaggcag ggatattcac cattatcgtt    7920
tcagacccac ctcccaaccc cgaggggacc cgacaggccc gaaggaatag aagaagaagg    7980
tggagagaga gacagagaca gatccattcg attagtgaac ggatccttgg cacttatctg    8040
ggacgatctg cggagcctgt gcctcttcag ctaccaccgc ttgagagact tactcttgat    8100
tgtaacgagg attgtggaac ttctgggacg caggggtgg gaagccctca atattggtg      8160 gaatctccta cagtattgga gtcaggaact aaagaatagt gctgttagct tgctcaatgc    8220
cacagccata gcagtagctg aggggacaga tagggttata gaagtagtac aaggagcttg    8280
tagagctatt cgccacatac ctagaagaat aagacagggc ttggaaagga ttttgctata   8340
agatgggtgg caagtggtca aaaagtagtg tgattggatg gcctactgta agggaaagaa    8400
tgagacgagc tgagccagca gcagataggg tgggagcagc atctcgagac ctggaaaaac    8460
atggagcaat cacaagtagc aatacagcag ctaccaatgc tgcttgtgcc tggctagaag    8520
cacaagagga ggaggaggtg ggttttccag tcacacctca ggtaccttta agaccaatga    8580
cttacaaggc agctgtagat cttagccact ttttaaaaga aaagggggga ctggaagggc    8640
taattcactc ccaaagaaga caagatatcc ttgatctgtg gatctaccac acacaaggct    8700
acttccctga ttagcagaac tacacaccag ggccagggt cagatatcca ctgacctttg    8760
gatggtgcta caagctagta ccagttgagc cagataagat agaagaggcc aataaaggag    8820
agaacaccag cttgttacac cctgtgagcc tgcatgggat ggatgacccg gagagagaag    8880
tgttagagtg gaggtttgac agccgcctag catttcatca cgtggcccga gagctgcatc    8940
cggagtactt caagaactgc tgacatcgag cttgctacaa gggactttcc gctggggact    9000
```

```
ttccagggag gcgtggcctg ggcgggactg gggagtggcg agccctcaga tcctgcatat      9060
aagcagctgc ttttgcctg tactgggtct ctctggttag accagatctg agcctgggag       9120
ctctctggct aactagggaa cccactgctt aagcctcaat aaagcttgcc ttgagtgctt      9180
c                                                                      9181
```

<210> SEQ ID NO 12
<211> LENGTH: 867
<212> TYPE: DNA
<213> ORGANISM: Human immunodeficiency virus

<400> SEQUENCE: 12

```
tttttagatg ggatagataa ggctcaagaa gaacatgaaa gatatcacag caattggaga        60
acaatggcta gtgattttaa tttgccacct atagtagcaa aggaaatagt agccaactgt       120
gataaatgtc aactaaaagg ggaagctatg catggacaag tagactgtag tccagggata      180
tggcaattag attgcacaca tctagaagga aaagtcatcc tggtagcagt ccacgtggcc      240
agtggatata tagaagcaga agttatccca gcagaaacag gacaggagac agcatacttt      300
ctgctaaaat tagcaggaag atggccagta aaagtaatac acacagacaa cggtagcaat      360
ttcaccagcg ctgcagttaa agcagcctgt tggtgggcca atgtccgaca ggaatttggg      420
atcccctaca atccccaaag tcaaggagta gtagaatcta tgaataagga attaagaaaa      480
atcatagggc aggtaagaga gcaagctgaa caccttaaga cagcagtaca atggcagta       540 ttcattcaca attttaaaag aaaaggggggg attgggggt acagtgcagg ggaaagaata      600
atagacataa tagcaacaga catacaaact aaagaattac aaaaacaaat tacaaaaatt      660 caaaatttc gggtttatta cagggacagc agagacccaa tttggaaagg accagcaaaa      720
ctactctgga aaggtgaagg ggcagtagta atacaagaca atagtgatat aaaagtagta     780
ccaagaagaa aagcaaagat cattagggat tatggaaaac agatggcagg tgatgattgt     840
gtggcaggta gacaggatga ggattag                                          867
```

<210> SEQ ID NO 13
<211> LENGTH: 867
<212> TYPE: DNA
<213> ORGANISM: Human immunodeficiency virus

<400> SEQUENCE: 13

```
tttttagatg gcatagataa agcccaagaa gagcatgaaa gatatcacag caattggaga        60
gcaatggcta gtgattttaa tctgccacct atagtagcaa agaaaatagt ggccagctgt      120
gataaatgtc agctaaaagg ggaagccatg catggacaag tagactgtag tccaggaata     180
tggcaattag attgtacaca tttagaagga aaaattatcc tggtagcagt ccatgtagcc     240
agtggctata tagaagcaga agttatccca gcagaaacag gacaggagac agcatacttt     300
atattaaaat tagcaggaag atggccagtg aaagtaatac acacagacaa tggcagcaat     360
ttcaccagtg ctgcagtaaa ggcagcatgt tggtgggcaa atgtcacaca agaatttgga     420
attccctaca atccccaaag ccaaggagta gtggaatcta tgaataaaga attaagaaaa     480
attatagggc aggtcaggga tcaagctgaa caccttaaga cagcagtaca gatggcagta     540
ttcattcaca attttaaaag aaaaggggggg attgggggt acagtgcagg ggaaagaata     600
atagacataa tagcatcaga tatacaaact aaagaactac aaaaacaaat tacaaaaatt     660 caaaatttc gggtttatta cagggacagc agagacccca tttggaaagg accagcaaaa     720
```

```
ctactctgga aaggtgaagg ggcagtagta atacaggaca atagtgatat aaaggtagta    780
ccaagaagaa aagcaaaaat cattaaggat tatggaaaac agatggcagg tgatgattgt    840
gtggcaggta gacaggatga ggattag                                        867
```

```
<210> SEQ ID NO 14
<211> LENGTH: 867
<212> TYPE: DNA
<213> ORGANISM: Human immunodeficiency virus

<400> SEQUENCE: 14
```

```
tttttagatg ggatagataa agctcaagaa gaacatgaaa gatatcacag caattggaga     60
gcaatggcta gtgattttaa tctgccacct atagtagcaa aggaaatagt agccagctgt    120
gataaatgtc agctaaaagg ggaagccatg catggacaag tagactgcag tccagggata    180
tggcaattag attgcacaca tctagaagga aaagtaattc tggtagcagt ccatgtagcc    240
agtggctata tagaagcaga agttatccca gcagaaacag gacaggagac agcatacttt    300
ctactaaaat tagcaggaag atggccagta aaagtagtac acacagacaa tggcagcaat    360
ttcaccagcg ctgcatttaa agcagcctgt tggtgggcaa atatccaaca ggaatttggg    420
attccctaca atccccaaag tcaaggagta gtggaatcta tgaataagga attaaagaaa    480
atcatagggc aggtaagaga gcaagctgaa caccttaaaa cagcagtaca atggcagta    540 ttcattcaca attttaaaag aaaggggggg attgggggt acagtgcagg ggaaagaata    600
atagacataa tagcaacaga catacaaact aaagaattac aaaaacaaat tacaaaaatt    660
caaaattttc gggtttatta cagggacagc agagatccaa tttggaaagg accagcaaaa    720
ctactctgga aaggtgaagg ggcagtagta atacaggaca atagtgatat aaaggtagta    780
ccaagaagaa aagcaaagat cattagggat tatggaaaac agatggcagg tgatgattgt    840
gtggcaggta gacaggatga ggattag                                        867
```

```
<210> SEQ ID NO 15
<211> LENGTH: 867
<212> TYPE: DNA
<213> ORGANISM: Human immunodeficiency virus
<220> FEATURE:
<221> NAME/KEY: modified_base
<222> LOCATION: (51)..(51)
<223> OTHER INFORMATION: a, c, t, g, unknown or other
<220> FEATURE:
<221> NAME/KEY: modified_base
<222> LOCATION: (267)..(267)
<223> OTHER INFORMATION: a, c, t, g, unknown or other
<220> FEATURE:
<221> NAME/KEY: modified_base
<222> LOCATION: (276)..(276)
<223> OTHER INFORMATION: a, c, t, g, unknown or other
<220> FEATURE:
<221> NAME/KEY: modified_base
<222> LOCATION: (310)..(310)
<223> OTHER INFORMATION: a, c, t, g, unknown or other
<220> FEATURE:
<221> NAME/KEY: modified_base
<222> LOCATION: (411)..(411)
<223> OTHER INFORMATION: a, c, t, g, unknown or other
<220> FEATURE:
<221> NAME/KEY: modified_base
<222> LOCATION: (546)..(546)
<223> OTHER INFORMATION: a, c, t, g, unknown or other
<220> FEATURE:
<221> NAME/KEY: modified_base
<222> LOCATION: (726)..(726)
<223> OTHER INFORMATION: a, c, t, g, unknown or other

<400> SEQUENCE: 15
```

```
tttttagatg ggatagataa ggctcaagaa gaacatgaaa gatatcacag naattggaga      60
gcaatggctc atgactttaa tctgccacct atagtagcaa agaaaatagt agctagctgt     120
gataaatgtc agctaaaagg ggaagccatg catggacaag tagactgtag tccaggaata     180
tggcaactag attgcacaca tctagaagga aaagttatcc tggtagcagt ccatgtagcc     240
agtggctata tagaagcaga agtcatncca gcaganacag gacaggaaac agcatacttt     300
atattaaaan tagcaggaag atggccagta aaagtaatac atacagacaa tgggcccaat     360
ttcaccagtg caacagttaa ggcagcctgt tggtgggcag gtgtccaaca ngaatttggg     420
attccctaca atccccaaag tcaaggagta gtggaatcta tgaataaaga attaaagaaa     480
atcatagggc aggtaagaga tcaagctgaa caccttaaga cagcagtaca atggcagta     540 ttcatncaca attttaaaag aaaaggggggg attgggggat acagtgcagg gaaagaata     600 atagacataa tagcaacaga tatacaaact aaagaattac aaaaacaaat tataaaaatt     660
caaaattttc gggtttatta cagggacagc agagatccaa tttggaaagg accagcaaaa     720
ctcctntgga aaggtgaagg ggcagtagta atacaagaca atagtgatat aaaggtagta     780
ccaagaagaa aagcaaagat cattagggat tatggaaaac agatggcagg tgatgattgt     840
gtggcaggta gacaggatga ggattag                                          867

<210> SEQ ID NO 16
<211> LENGTH: 867
<212> TYPE: DNA
<213> ORGANISM: Human immunodeficiency virus

<400> SEQUENCE: 16
tttttagatg gaatagataa ggcccaagaa gaacatgaga aatatcacag taattggaga     60
gcaatggcta gtgattttaa cctgccacct gtagtagcaa agaaaatagt agccagctgt     120
gataaatgtc agctaaaagg agaagccatg catggacaag tagactgtag tccaggaata     180
tggcaactag attgtacaca tttagaagga aaagttatcc tggtagcagt tcatgtagcc     240
agtggatata tagaagcaga agttattcca gcagagacag ggcaggaaac agcatacttt     300
ctcttaaaat tagcaggaag atggccagta aaaacaatac atacagacaa tggcagcaat     360
ttcaccagta ctacggttaa ggccgcctgt tggtgggcgg ggatcaagca ggaatttggc     420
attccctaca atccccaaag tcaaggagta gtagaatcta tgaataaaga attaaagaaa     480
attataggac aggtaagaga tcaggctgaa catcttaaga cagcagtaca atggcagta     540 ttcatccaca attttaaaag aaaaggggggg attgggggggt acagtgcagg ggaagaata     600 gtagacataa tagcaacaga catacaaact aaagaattac aaaaacaaat tacaaaaatt     660
caaaattttc gggtttatta cagggacagc agagatccac tttggaaagg accagcaaag     720
cttctctgga aaggtgaagg ggcagtagta atacaagata atagtgacat aaaagtagtg     780
ccaagaagaa aagcaaagat cattagggat tatggaaaac agatggcagg tgatgattgt     840
gtggcaagta gacaggatga ggattag                                          867

<210> SEQ ID NO 17
<211> LENGTH: 867
<212> TYPE: DNA
<213> ORGANISM: Human immunodeficiency virus

<400> SEQUENCE: 17
tttctagatg gaatagataa ggctcaagaa gagcatgaaa agtatcacag caattggaga     60
```

```
gcaatggcta gtgagtttaa tctgccaccc atagtagcaa agaaatagt agctagctgt      120 gataaatgtc agctaaaagg ggaagccata catggacaag tagactgtag tccagggata    180
tggcaattag attgtacaca tttagaagga aaaatcatcc tggtagcagt ccatgtagcc    240
agtggctaca tagaagcaga ggttatccca gcagaaacag gacaagaaac agcatactat    300
atactaaaat tagcaggaag atggccagtc aaagtaatac atacagacaa tggcagtaat    360
ttcaccagtg ctgcagttaa ggcagcctgt tggtgggcag gtatccaaca ggaatttgga    420
attccctaca atccccaaag tcagggagta gtagaatcca tgaataaaga attaagaaa     480 atcatagggc aggtaagaga tcaagctgag caccttaaga cagcagtaca aatggcagta    540
ttcattcaca atttaaaag aaaaggggg attgggggt acagtgcagg ggaaagaata      600
atagacataa tagcaacaga catacaaact aaagaattac aaaaacaaat tataaaaatt    660
caaaattttc gggtttatta cagagacagc agagaccta tttggaaagg accagccaaa    720
ctactctgga aaggtgaagg ggcagtagta atacaagata atagtgacat aaaggtagta    780
ccaaggagga aagcaaaaat cattaaggac tatggaaaac agatggcagg tgctgattgt    840
gtggcaggta gacaggatga agattag                                         867
```

```
<210> SEQ ID NO 18
<211> LENGTH: 867
<212> TYPE: DNA
<213> ORGANISM: Human immunodeficiency virus

<400> SEQUENCE: 18
ttcttggatg gaatagataa ggctcaagaa gaacatgaga aataccacaa caattggaga     60
gcaatggcta gtgattttaa cctgccacct gtggtagcaa agaaatagt agctagctgt    120 gataaatgtc agctaaaagg agaagccttg catggacaag tagactgtag tccaggaata    180
tggcaattag attgtacaca tttagaagga aaagttatcc tggtagcagt ccatgtagcc    240
agtggctata tagaagcaga agttattcca gcagaaacag ggcaggaaac agcctacttt    300
ctcttaaaat tagcaggaag atggccagta aaagtagtac atacagacaa tggcagcaat    360
ttcaccagcg ctgcagttaa ggccgcctgt tggtgggcag gcatcaagca ggaatttgga    420
attccctaca atccccaaag tcaaggagta gtagaatcta tgaataaaga attaagaaa     480 attataggac aggtaagaga tcaagctgaa catcttaaga cagcagtaca aatggcagta    540
ttcatccaca attttaaaag aaaaggggg attgggggt acagtgcagg ggaaagaata    600
atagacataa tagcaacaga catacaaact aaagaattac aaaaacaaat cataaaaatt    660
caaaattttc gggtttatta cagggacagc agagatccaa tttggaaagg accagcaaag    720
cttctctgga aaggtgaagg ggcagtagta atacaagaca atagtgaaat aaaggtagta    780
ccaagaagaa agtaaagat cattagggat tatggaaaac agatggcagg tgatgattgt    840
gtggcaagta gacaggatga ggattag                                         867
```

```
<210> SEQ ID NO 19
<211> LENGTH: 867
<212> TYPE: DNA
<213> ORGANISM: Human immunodeficiency virus
<220> FEATURE:
<221> NAME/KEY: modified_base
<222> LOCATION: (165)..(165)
<223> OTHER INFORMATION: a, c, t, g, unknown or other
<220> FEATURE:
<221> NAME/KEY: modified_base
<222> LOCATION: (214)..(214)
<223> OTHER INFORMATION: a, c, t, g, unknown or other
```

```
<220> FEATURE:
<221> NAME/KEY: modified_base
<222> LOCATION: (250)..(250)
<223> OTHER INFORMATION: a, c, t, g, unknown or other
<220> FEATURE:
<221> NAME/KEY: modified_base
<222> LOCATION: (285)..(285)
<223> OTHER INFORMATION: a, c, t, g, unknown or other
<220> FEATURE:
<221> NAME/KEY: modified_base
<222> LOCATION: (335)..(335)
<223> OTHER INFORMATION: a, c, t, g, unknown or other
<220> FEATURE:
<221> NAME/KEY: modified_base
<222> LOCATION: (356)..(356)
<223> OTHER INFORMATION: a, c, t, g, unknown or other
<220> FEATURE:
<221> NAME/KEY: modified_base
<222> LOCATION: (579)..(579)
<223> OTHER INFORMATION: a, c, t, g, unknown or other
<220> FEATURE:
<221> NAME/KEY: modified_base
<222> LOCATION: (632)..(632)
<223> OTHER INFORMATION: a, c, t, g, unknown or other

<400> SEQUENCE: 19
tttttagatg ggatagataa ggcacaagag gaacatgaaa aatatcacaa caattggaga      60
gcaatggcta gtgattttaa tctgccacct gtagtagcaa agaaatagt agctagctgt     120 gataagtgtc agctaaaagg ggaagccatg catggacaag tagantgtag tccaggata    180 tggcaattag attgtacaca tttagaagga aaanttatcc tggtagcagt ccatgtagct    240
agtgggtacn tagaagcaga agttatccca gcagaaacag acangaaac agcctacttc    300 atactaaagt tagcaggaag atggccagta aaaanaatac atacagacaa tggcancaat    360
ttcaccagtg ccgcggttaa ggcagcctgt tggtgggcag gtatccagca ggaatttgga    420
attccctaca accccaaag tcaaggagta gtagaatcta tgaataaaga gctaaagaag     480
atcataggac aggtaagaga tcaagctgaa catcttaaga cagcagtaca aatggcagta    540
ttcatccaca atttaaaag aaaagggggg attgggggnt acagtgcagg ggaaagaata    600
atagacataa tatcaacaga catacaaact anagaattac aaaaacaaat tataaaaatt    660
caaaatttcc gggtttatta cagggacagc agagacccag tttggaaagg accagcaaag    720
ctactctgga aaggtgaagg ggcagtagtc atacaagaca atagtgaaat aaaggtagta    780
ccaagaagaa aagcaaagat cattagggat tatggaaaac agatggcagg tgatgattgt    840
gtggcaggta gacaggatga ggattaa                                         867

<210> SEQ ID NO 20
<211> LENGTH: 867
<212> TYPE: DNA
<213> ORGANISM: Human immunodeficiency virus
<220> FEATURE:
<221> NAME/KEY: modified_base
<222> LOCATION: (50)..(50)
<223> OTHER INFORMATION: a, c, t, g, unknown or other
<220> FEATURE:
<221> NAME/KEY: modified_base
<222> LOCATION: (267)..(267)
<223> OTHER INFORMATION: a, c, t, g, unknown or other
<220> FEATURE:
<221> NAME/KEY: modified_base
<222> LOCATION: (279)..(279)
<223> OTHER INFORMATION: a, c, t, g, unknown or other
<220> FEATURE:
<221> NAME/KEY: modified_base
<222> LOCATION: (483)..(483)
<223> OTHER INFORMATION: a, c, t, g, unknown or other
<220> FEATURE:
```

```
<221> NAME/KEY: modified_base
<222> LOCATION: (492)..(492)
<223> OTHER INFORMATION: a, c, t, g, unknown or other
<220> FEATURE:
<221> NAME/KEY: modified_base
<222> LOCATION: (652)..(652)
<223> OTHER INFORMATION: a, c, t, g, unknown or other
<220> FEATURE:
<221> NAME/KEY: modified_base
<222> LOCATION: (700)..(700)
<223> OTHER INFORMATION: a, c, t, g, unknown or other
<220> FEATURE:
<221> NAME/KEY: modified_base
<222> LOCATION: (798)..(798)
<223> OTHER INFORMATION: a, c, t, g, unknown or other

<400> SEQUENCE: 20 ttttggatg ggatagataa ggctcaagaa gaacatgaaa aatatcacan caattggaga      60
gcaatggcta gtgattttaa tctgccacct gtagtagcaa agaaatagt agccagctgt    120 gataaatgtc agctaaaagg ggaagccatg catggacaag tagactgcag tccagggata    180
tggcaattag attgtacaca tttagaagga aaaattatcc tggtagcagt ccatgtagct    240
agtggctata tagaagcaga agttatncca gcagaaacng gacaggaaac agcctacttc    300
atactaaagt tagcaggaag atggccagta aaaataatac atacagacaa tggcagcaat    360
ttcaccagta ctgtggttaa ggcagcctgt tggtgggcag gtatccagca ggaatttgga    420
attccctaca atccccaaag tcaaggagta gtagaatcta tgaataaaga attaagaaa    480 atnataggac angtaagaga tcaagctgaa catcttaaga cagcagtgca aatggcagta    540
ttcattcaca attttaaaag aaaaggggg attgggggt acagtgcagg ggaaagaata    600
atagacataa tagcaacaga catacaaact aaagaattac aaaaacaaat tncaaaaatt    660
caaaattttc gggtttattt cagggacagc agagacccan tttggaaagg accagcaaag    720
ctactctgga aaggtgaagg ggcagtagtc atacaagaca ataatgaaat aaaagtagta    780
ccaagaagaa aagcaaanat cattagggat tatggaaaac agatggcagg tgatgattgt    840
gtggcaggta gacaggatga ggattag                                        867

<210> SEQ ID NO 21
<211> LENGTH: 867
<212> TYPE: DNA
<213> ORGANISM: Human immunodeficiency virus
<220> FEATURE:
<221> NAME/KEY: modified_base
<222> LOCATION: (231)..(231)
<223> OTHER INFORMATION: a, c, t, g, unknown or other

<400> SEQUENCE: 21 ttttagatg gcatagataa agcccaagaa gaccatgaaa gatatcacag caattggaga     60
gcaatggcta gtgattttaa tctgccacct atagtagcaa agaaaatagt ggccagctgt   120
gataaatgtc agctaaaagg ggaagccatg catggacaag tagactgtag tccaggaata   180
tggcaattag attgtacaca tttagaagga aaaattatcc tggtagcagt ncatgtagcc   240
agtggctata tagaagcaga agttatccca gcagaaacag gacaggaaac agcatacttt   300
atattaaaat tagcaggaag gtggccagta aaagtaatac atacagacaa tggcagcaat   360
ttcaccagtg ctgcagtaaa ggcagcatgt tggtgggcaa atatcacaca ggaatttgga   420
attccctaca atccccaaag ccaaggagta gtggaatcta tgaataagga attaagaaa   480 atcatcgggc aggtcaggga tcaagctgaa catcttaaga cagcagtaca gatgcagta   540 ttcattcaca attttaaaag aaaaggggg attgggggt acagtgcagg ggaaagaata    600
```

| atagacataa tagcatcaga tatacaaact aaagaactac aaaaacaaat tacaaaaatt | 660 |
| caaaattttc gggtttatta cagggacagc agagacccaa tttggaaagg accagcaaag | 720 |
| ctactctgga aaggtgaagg ggcagtagta atacaagaca ataacgaaat aaaggtagta | 780 |
| ccaagaagaa aagcaaagat cattagggat tatggaaaac agatggcagg tgatgattgt | 840 |
| gtggcaggta gacaggatga ggattag | 867 |

```
<210> SEQ ID NO 22
<211> LENGTH: 867
<212> TYPE: DNA
<213> ORGANISM: Human immunodeficiency virus

<400> SEQUENCE: 22
```

| ttttagatg aatagataa ggcccaagat gaacatgaga atatcacag taattggaga | 60 |
| gcaatggcta gtgattttaa cctgccacct gtagtagcaa aagaaatagt agccagctgt | 120 |
| gataaatgtc agctaaaagg agaagccatg catggacaag tagactgtag tccaggaata | 180 |
| tggcaactag attgtacaca tttagaagga aaagttatcc tggtagcagt tcatgtagcc | 240 |
| agtggatata tagaagcaga agttattcca gcagaaacag ggcaggaaac agcatatttt | 300 |
| cttttaaaat tagcaggaag atggccagta aaaacaatac atactgacaa tggcagcaat | 360 |
| ttcaccggtg ctacggttag ggccgcctgt tggtgggcgg gaatcaagca ggaatttgga | 420 |
| attccctaca atccccaaag tcaaggagta gtagaatcta tgaataaaga attaaagaaa | 480 |
| attataggac aggtaagaga tcaggctgaa catcttaaga cagcagtaca aatggcagta | 540 |
| ttcatccaca attttaaaag aaaagggggg attggggggt acagtgcagg ggaaagaata | 600 |
| gtagacataa tagcaacaga catacaaact aaagaattac aaaaacaaat tacaaaaatt | 660 |
| caaaattttc gggtttatta cagggacagc agaaatccac tttggaaagg accagcaaag | 720 |
| ctcctctgga aaggtgaagg ggcagtagta atacaagata atagtgacat aaaagtagtg | 780 |
| ccaagaagaa aagcaaagat cattagggat tatggaaaac agatggcagg tgatgattgt | 840 |
| gtggcaagta gacaggatga ggattag | 867 |

```
<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
```

| ttttcgggtt tattacagrg | 20 |

```
<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
```

| aaattcaaaa ttttcgggtt tattacaggg acagcagaga | 40 |

```
<210> SEQ ID NO 25
<211> LENGTH: 40
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 25
aaattcaaaa ttttcgggtt tattacaggg acagcagaga                               40

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aaattcaaaa ttttcgggtt tattacaggg acagcagaga                               40

<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aaattcaaaa ttttcgggtt tattacaggg acagcagaga                               40

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aaattcaaaa ttttcgggtt tattacaggg acagcagaga                               40

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aaattcaaaa ttttcgggtt tattacagag acagcagaga                               40

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aaattcaaaa ttttcgggtt tattacaggg acagcagaga                               40

<210> SEQ ID NO 31
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 31
aaattcaaaa tttccgggtt tattacaggg acagcagaga                           40

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aaattcaaaa ttttcgggtt tatttcaggg acagcagaga                           40

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aaattcaaaa ttttcgggtt tattacaggg acagcagaga                           40

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aaattcaaaa ttttcgggtt tattacaggg acagcagaaa                           40

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ttttcgggtt tattacagag ac                                              22

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cgggtctatt acagggac                                                   18

<210> SEQ ID NO 37
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 37
ggtttattac agggacagc                                                   19

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gggtttatta cagagacagc a                                                21

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cgggtttatt acagggaca                                                   19

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tggaaaacar atggcagg                                                    18

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
attagggatt atggaaaaca gatggcaggt gatgattgtg                            40

<210> SEQ ID NO 42
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
attaaggatt atggaaaaca gatggcaggt gatgattgtg                            40

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 43
attagggatt atggaaaaca gatggcaggt gatgattgtg                    40

<210> SEQ ID NO 44
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
attagggatt atggaaaaca gatggcaggt gatgattgtg                    40

<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
attagggatt atggaaaaca gatggcaggt gatgattgtg                    40

<210> SEQ ID NO 46
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
attaaggact atggaaaaca gatggcaggt gctgattgtg                    40

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
attagggatt atggaaaaca gatggcaggt gatgattgtg                    40

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
attagggatt atggaaaaca gatggcaggt gatgattgtg                    40

<210> SEQ ID NO 49
<211> LENGTH: 40
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 49
attagggatt atggaaaaca gatggcaggt gatgattgtg                40

<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
attagggatt atggaaaaca gatggcaggt gatgattgtg                40

<210> SEQ ID NO 51
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
attagggatt atggaaaaca gatggcaggt gatgattgtg                40

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
atggaaaaca aatggcagg                19

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
aaaacagatg gcaggtga                18

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tggaaaacag atggcagg                18

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 55
caaacagatg gcaggtga                                                 18

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
gtggaaaggt gaaggggcag tagt                                          24

<210> SEQ ID NO 57
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 57
aaactactct ggaaaggtga aggggcagta gtaatacaag                         40

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 58
aaactactct ggaaaggtga aggggcagta gtaatacagg                         40

<210> SEQ ID NO 59
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59
aaactactct ggaaaggtga aggggcagta gtaatacagg                         40

<210> SEQ ID NO 60
<211> LENGTH: 40
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (9)..(9)
<223> OTHER INFORMATION: a, c, t, g, unknown or other

<400> SEQUENCE: 60
aaactcctnt ggaaaggtga aggggcagta gtaatacaag                         40

<210> SEQ ID NO 61
<211> LENGTH: 40
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 61
aagcttctct ggaaaggtga aggggcagta gtaatacaag                                40

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 62
aaactactct ggaaaggtga aggggcagta gtaatacaag                                40

<210> SEQ ID NO 63
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 63
aagcttctct ggaaaggtga aggggcagta gtaatacaag                                40

<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 64
aagctactct ggaaaggtga aggggcagta gtcatacaag                                40

<210> SEQ ID NO 65
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 65
aagctactct ggaaaggtga aggggcagta gtcatacaag                                40

<210> SEQ ID NO 66
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 66
aagctactct ggaaaggtga aggggcagta gtaatacaag                                40

<210> SEQ ID NO 67
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 67
aagctcctct ggaaaggtga aggggcagta gtaatacaag          40

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 68
tctctggaaa ggtgaagggg cagt          24

<210> SEQ ID NO 69
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 69
gcaaaactac tctggaaagg tgaaggggca gtagtaatac          40

<210> SEQ ID NO 70
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 70
gcaaaactac tctggaaagg tgaaggggca gtagtaatac          40

<210> SEQ ID NO 71
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 71
gcaaaactac tctggaaagg tgaaggggca gtagtaatac          40

<210> SEQ ID NO 72
<211> LENGTH: 40
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (12)..(12)
<223> OTHER INFORMATION: a, c, t, g, unknown or other

<400> SEQUENCE: 72
gcaaaactcc tntggaaagg tgaaggggca gtagtaatac          40

<210> SEQ ID NO 73
<211> LENGTH: 40
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 73
gcaaagcttc tctggaaagg tgaaggggca gtagtaatac                              40

<210> SEQ ID NO 74
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 74
gccaaactac tctggaaagg tgaaggggca gtagtaatac                              40

<210> SEQ ID NO 75
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 75
gcaaagcttc tctggaaagg tgaaggggca gtagtaatac                              40

<210> SEQ ID NO 76
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 76
gcaaagctac tctggaaagg tgaaggggca gtagtcatac                              40

<210> SEQ ID NO 77
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 77
gcaaagctac tctggaaagg tgaaggggca gtagtcatac                              40

<210> SEQ ID NO 78
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 78
gcaaagctac tctggaaagg tgaaggggca gtagtaatac                              40

<210> SEQ ID NO 79
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 79
gcaaagctcc tctggaaagg tgaaggggca gtagtaatac                           40

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80
ctctggaaag gtgaaggggc agtg                                           24

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 81
ttggaaaggt gaaggggcag tagt                                           24

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 82
tactttggaa aggtgaaggg gcagt                                          25

<210> SEQ ID NO 83
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
ctggaaaggt gaaggggcag ttgta                                          25

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
ctggaaaggt gaaggggcag tagt                                           24

<210> SEQ ID NO 85
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 85
ttttcgggtt tattacaggg                                             20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ttttcgggtt tattacaggg                                             20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ttttcgggtt tattacaggg                                             20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ttttcgggtt tattacaggg                                             20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ttttcgggtt tattacaggg                                             20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ttttcgggtt tattacagag                                             20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 91
ttttcgggtt tattacaggg                                          20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tttccgggtt tattacaggg                                          20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ttttcgggtt tatttcaggg                                          20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ttttcgggtt tattacaggg                                          20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ttttcgggtt tattacaggg                                          20

<210> SEQ ID NO 96
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
tggaaaacag atggcagg                                            18

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
tggaaaacag atggcagg                                                  18

<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
tggaaaacag atggcagg                                                  18

<210> SEQ ID NO 99
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tggaaaacag atggcagg                                                  18

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
tggaaaacag atggcagg                                                  18

<210> SEQ ID NO 101
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tggaaaacag atggcagg                                                  18

<210> SEQ ID NO 102
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
tggaaaacag atggcagg                                                  18

<210> SEQ ID NO 103
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
tggaaaacag atggcagg                                                 18

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
tggaaaacag atggcagg                                                 18

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
tggaaaacag atggcagg                                                 18

<210> SEQ ID NO 106
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
tggaaaacag atggcagg                                                 18

<210> SEQ ID NO 107
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 107
ctggaaaggt gaagggggcag tagt                                          24

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108
ctggaaaggt gaagggggcag tagt                                          24

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109
ctggaaaggt gaaggggcag tagt                                          24

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)..(1)
<223> OTHER INFORMATION: a, c, t, g, unknown or other

<400> SEQUENCE: 110
ntggaaaggt gaaggggcag tagt                                          24

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 111
ctggaaaggt gaaggggcag tagt                                          24

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 112
ctggaaaggt gaaggggcag tagt                                          24

<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 113
ctggaaaggt gaaggggcag tagt                                          24

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 114
ctggaaaggt gaaggggcag tagt                                          24

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic -continued

```
      probe

<400> SEQUENCE: 115
ctggaaaggt gaagggggcag tagt                                          24

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 116
ctggaaaggt gaagggggcag tagt                                          24

<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 117
ctggaaaggt gaagggggcag tagt                                          24

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 118
actctggaaa ggtgaagggg cagt                                           24

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 119
actctggaaa ggtgaagggg cagt                                           24

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 120
actctggaaa ggtgaagggg cagt                                           24

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: Synthetic
      probe
```

```
<220> FEATURE:
<221> NAME/KEY: modified_base
<222> LOCATION: (4)..(4)
<223> OTHER INFORMATION: a, c, t, g, unknown or other

<400> SEQUENCE: 121
cctntggaaa ggtgaagggg cagt                                              24

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 122
tctctggaaa ggtgaagggg cagt                                              24

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 123
actctggaaa ggtgaagggg cagt                                              24

<210> SEQ ID NO 124
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 124
tctctggaaa ggtgaagggg cagt                                              24

<210> SEQ ID NO 125
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 125
actctggaaa ggtgaagggg cagt                                              24

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 126
actctggaaa ggtgaagggg cagt                                              24

<210> SEQ ID NO 127
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 127
actctggaaa ggtgaagggg cagt                                               24

<210> SEQ ID NO 128
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 128
cctctggaaa ggtgaagggg cagt                                               24

<210> SEQ ID NO 129
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
cctgccatyt gttttcca                                                      18

<210> SEQ ID NO 130
<211> LENGTH: 288
<212> TYPE: PRT
<213> ORGANISM: Human immunodeficiency virus

<400> SEQUENCE: 130
```

| | | | | | | | | | | | | | | | |
|---|---|---|---|---|---|---|---|---|---|---|---|---|---|---|---|
| Phe | Leu | Asp | Gly | Ile | Asp | Lys | Ala | Gln | Glu | Glu | His | Glu | Lys | Tyr | His |
| 1 | | | | 5 | | | | | 10 | | | | | 15 | |
| Ser | Asn | Trp | Arg | Ala | Met | Ala | Ser | Asp | Phe | Asn | Leu | Pro | Pro | Val | Val |
| | | | 20 | | | | | 25 | | | | | 30 | | |
| Ala | Lys | Glu | Ile | Val | Ala | Ser | Cys | Asp | Lys | Cys | Gln | Leu | Lys | Gly | Glu |
| | | | | 35 | | | | | 40 | | | | | 45 | |
| Ala | Met | His | Gly | Gln | Val | Asp | Cys | Ser | Pro | Gly | Ile | Trp | Gln | Leu | Asp |
| | | 50 | | | | | 55 | | | | | 60 | | | |
| Cys | Thr | His | Leu | Glu | Gly | Lys | Ile | Ile | Leu | Val | Ala | Val | His | Val | Ala |
| 65 | | | | | 70 | | | | | 75 | | | | | 80 |
| Ser | Gly | Tyr | Ile | Glu | Ala | Glu | Val | Ile | Pro | Ala | Glu | Thr | Gly | Gln | Glu |
| | | | | 85 | | | | | 90 | | | | | 95 | |
| Thr | Ala | Tyr | Phe | Leu | Leu | Lys | Leu | Ala | Gly | Arg | Trp | Pro | Val | Lys | Thr |
| | | | 100 | | | | | 105 | | | | | 110 | | |
| Ile | His | Thr | Asp | Asn | Gly | Ser | Asn | Phe | Thr | Ser | Thr | Thr | Val | Lys | Ala |
| | | | | 115 | | | | | 120 | | | | | 125 | |
| Ala | Cys | Trp | Trp | Ala | Gly | Ile | Lys | Gln | Glu | Phe | Gly | Ile | Pro | Tyr | Asn |
| | | 130 | | | | | 135 | | | | | 140 | | | |
| Pro | Gln | Ser | Gln | Gly | Val | Val | Glu | Ser | Met | Asn | Lys | Glu | Leu | Lys | Lys |
| 145 | | | | | 150 | | | | | 155 | | | | | 160 |
| Ile | Ile | Gly | Gln | Val | Arg | Asp | Gln | Ala | Glu | His | Leu | Lys | Thr | Ala | Val |
| | | | | 165 | | | | | 170 | | | | | 175 | |
| Gln | Met | Ala | Val | Phe | Ile | His | Asn | Phe | Lys | Arg | Lys | Gly | Gly | Ile | Gly |
| | | | 180 | | | | | 185 | | | | | 190 | | |
| Gly | Tyr | Ser | Ala | Gly | Glu | Arg | Ile | Val | Asp | Ile | Ile | Ala | Thr | Asp | Ile |

```
                195                 200                 205
Gln Thr Lys Glu Leu Gln Lys Gln Ile Thr Lys Ile Gln Asn Phe Arg
    210                 215                 220

Val Tyr Tyr Arg Asp Ser Arg Asp Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
                260                 265                 270

Lys Gln Met Ala Gly Asp Asp Cys Val Ala Ser Arg Gln Asp Glu Asp
                275                 280                 285

<210> SEQ ID NO 131
<211> LENGTH: 1003
<212> TYPE: PRT
<213> ORGANISM: Human immunodeficiency virus

<400> SEQUENCE: 131

Phe Phe Arg Glu Asp Leu Ala Phe Pro Gln Gly Lys Ala Arg Glu Phe
1               5                   10                  15

Ser Ser Glu Gln Thr Arg Ala Asn Ser Pro Thr Arg Arg Glu Leu Gln
                20                  25                  30

Val Trp Gly Arg Asp Asn Asn Ser Leu Ser Glu Ala Gly Ala Asp Arg
            35                  40                  45

Gln Gly Thr Val Ser Phe Ser Phe Pro Gln Ile Thr Leu Trp Gln Arg
        50                  55                  60

Pro Leu Val Thr Ile Lys Ile Gly Gly Gln Leu Lys Glu Ala Leu Leu
65                  70                  75                  80

Asp Thr Gly Ala Asp Asp Thr Val Leu Glu Glu Met Asn Leu Pro Gly
                85                  90                  95

Arg Trp Lys Pro Lys Met Ile Gly Gly Ile Gly Gly Phe Ile Lys Val
                100                 105                 110

Arg Gln Tyr Asp Gln Ile Leu Ile Glu Ile Cys Gly His Lys Ala Ile
            115                 120                 125

Gly Thr Val Leu Val Gly Pro Thr Pro Val Asn Ile Ile Gly Arg Asn
        130                 135                 140

Leu Leu Thr Gln Ile Gly Cys Thr Leu Asn Phe Pro Ile Ser Pro Ile
145                 150                 155                 160

Glu Thr Val Pro Val Lys Leu Lys Pro Gly Met Asp Gly Pro Lys Val
                165                 170                 175

Lys Gln Trp Pro Leu Thr Glu Glu Lys Ile Lys Ala Leu Val Glu Ile
                180                 185                 190

Cys Thr Glu Met Glu Lys Glu Gly Lys Ile Ser Lys Ile Gly Pro Glu
            195                 200                 205

Asn Pro Tyr Asn Thr Pro Val Phe Ala Ile Lys Lys Lys Asp Ser Thr
        210                 215                 220

Lys Trp Arg Lys Leu Val Asp Phe Arg Glu Leu Asn Lys Arg Thr Gln
225                 230                 235                 240

Asp Phe Trp Glu Val Gln Leu Gly Ile Pro His Pro Ala Gly Leu Lys
                245                 250                 255

Lys Lys Lys Ser Val Thr Val Leu Asp Val Gly Asp Ala Tyr Phe Ser
                260                 265                 270

Val Pro Leu Asp Lys Asp Phe Arg Lys Tyr Thr Ala Phe Thr Ile Pro
            275                 280                 285
```

```
Ser Ile Asn Asn Glu Thr Pro Gly Ile Arg Tyr Gln Tyr Asn Val Leu
    290             295                 300
Pro Gln Gly Trp Lys Gly Ser Pro Ala Ile Phe Gln Ser Ser Met Thr
305             310                 315                 320
Lys Ile Leu Glu Pro Phe Arg Lys Gln Asn Pro Asp Ile Val Ile Tyr
                325                 330                 335
Gln Tyr Met Asp Asp Leu Tyr Val Gly Ser Asp Leu Glu Ile Gly Gln
            340                 345                 350
His Arg Thr Lys Ile Glu Glu Leu Arg Gln His Leu Leu Arg Trp Gly
        355                 360                 365
Phe Thr Thr Pro Asp Lys Lys His Gln Lys Glu Pro Pro Phe Leu Trp
    370                 375                 380
Met Gly Tyr Glu Leu His Pro Asp Lys Trp Thr Val Gln Pro Ile Val
385                 390                 395                 400
Leu Pro Glu Lys Asp Ser Trp Thr Val Asn Asp Ile Gln Lys Leu Val
                405                 410                 415
Gly Lys Leu Asn Trp Ala Ser Gln Ile Tyr Ala Gly Ile Lys Val Lys
            420                 425                 430
Gln Leu Cys Lys Leu Leu Arg Gly Thr Lys Ala Leu Thr Glu Val Ile
        435                 440                 445
Pro Leu Thr Glu Glu Ala Glu Leu Glu Leu Ala Glu Asn Arg Glu Ile
    450                 455                 460
Leu Lys Glu Pro Val His Gly Val Tyr Tyr Asp Pro Ser Lys Asp Leu
465                 470                 475                 480
Ile Ala Glu Ile Gln Lys Gln Gly Gln Gly Gln Trp Thr Tyr Gln Ile
                485                 490                 495
Tyr Gln Glu Pro Phe Lys Asn Leu Lys Thr Gly Lys Tyr Ala Arg Met
            500                 505                 510
Arg Gly Ala His Thr Asn Asp Val Lys Gln Leu Thr Glu Ala Val Gln
        515                 520                 525
Lys Ile Ala Thr Glu Ser Ile Val Ile Trp Gly Lys Thr Pro Lys Phe
    530                 535                 540
Lys Leu Pro Ile Gln Lys Glu Thr Trp Glu Ala Trp Trp Thr Glu Tyr
545                 550                 555                 560
Trp Gln Ala Thr Trp Ile Pro Glu Trp Glu Phe Val Asn Thr Pro Pro
                565                 570                 575
Leu Val Lys Leu Trp Tyr Gln Leu Glu Lys Glu Pro Ile Val Gly Ala
            580                 585                 590
Glu Thr Phe Tyr Val Asp Gly Ala Ala Asn Arg Glu Thr Lys Leu Gly
        595                 600                 605
Lys Ala Gly Tyr Val Thr Asp Arg Gly Arg Gln Lys Val Val Ser Leu
    610                 615                 620
Thr Asp Thr Thr Asn Gln Lys Thr Glu Leu Gln Ala Ile His Leu Ala
625                 630                 635                 640
Leu Gln Asp Ser Gly Leu Glu Val Asn Ile Val Thr Asp Ser Gln Tyr
                645                 650                 655
Ala Leu Gly Ile Ile Gln Ala Gln Pro Asp Lys Ser Glu Ser Glu Leu
            660                 665                 670
Val Ser Gln Ile Ile Glu Gln Leu Ile Lys Lys Glu Lys Val Tyr Leu
        675                 680                 685
Ala Trp Val Pro Ala His Lys Gly Ile Gly Gly Asn Glu Gln Val Asp
    690                 695                 700
Lys Leu Val Ser Ala Gly Ile Arg Lys Val Leu Phe Leu Asp Gly Ile
```

```
                705                 710                 715                 720
        Asp Lys Ala Gln Glu Glu His Glu Lys Tyr His Ser Asn Trp Arg Ala
                        725                 730                 735

Met Ala Ser Asp Phe Asn Leu Pro Pro Val Ala Lys Glu Ile Val
                        740                 745                 750

Ala Ser Cys Asp Lys Cys Gln Leu Lys Gly Glu Ala Met His Gly Gln
                        755                 760                 765

Val Asp Cys Ser Pro Gly Ile Trp Gln Leu Asp Cys Thr His Leu Glu
                        770                 775                 780

Gly Lys Ile Ile Leu Val Ala Val His Val Ala Ser Gly Tyr Ile Glu
                785                 790                 795                 800

Ala Glu Val Ile Pro Ala Glu Thr Gly Gln Glu Thr Ala Tyr Phe Leu
                        805                 810                 815

Leu Lys Leu Ala Gly Arg Trp Pro Val Lys Thr Ile His Thr Asp Asn
                        820                 825                 830

Gly Ser Asn Phe Thr Ser Thr Thr Val Lys Ala Ala Cys Trp Trp Ala
                        835                 840                 845

Gly Ile Lys Gln Glu Phe Gly Ile Pro Tyr Asn Pro Gln Ser Gln Gly
                        850                 855                 860

Val Val Glu Ser Met Asn Lys Glu Leu Lys Lys Ile Ile Gly Gln Val
                865                 870                 875                 880

Arg Asp Gln Ala Glu His Leu Lys Thr Ala Val Gln Met Ala Val Phe
                        885                 890                 895

Ile His Asn Phe Lys Arg Lys Gly Gly Ile Gly Gly Tyr Ser Ala Gly
                        900                 905                 910

Glu Arg Ile Val Asp Ile Ile Ala Thr Asp Ile Gln Thr Lys Glu Leu
                        915                 920                 925

Gln Lys Gln Ile Thr Lys Ile Gln Asn Phe Arg Val Tyr Tyr Arg Asp
                        930                 935                 940

Ser Arg Asp Pro Leu Trp Lys Gly Pro Ala Lys Leu Leu Trp Lys Gly
                945                 950                 955                 960

Glu Gly Ala Val Val Ile Gln Asp Asn Ser Asp Ile Lys Val Val Pro
                        965                 970                 975

Arg Arg Lys Ala Lys Ile Ile Arg Asp Tyr Gly Lys Gln Met Ala Gly
                        980                 985                 990

Asp Asp Cys Val Ala Ser Arg Gln  Asp Glu Asp
                        995                 1000

<210> SEQ ID NO 132
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
cctgccattt gttttccat                                                    19

<210> SEQ ID NO 133
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
```
tcacctgcca tctgtttt					18

<210> SEQ ID NO 134
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
cctgccatct gttttcca					18

<210> SEQ ID NO 135
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
tcacctgcca tctgtttg					18

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
attccctaca atccccaaag					20

<210> SEQ ID NO 137
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
tacaatcccc aaagtcaagg agtagt				26

<210> SEQ ID NO 138
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
tacaatcccc aaagccaagg agtagt				26

<210> SEQ ID NO 139
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
tacaatcccc aaagtcaggg agtagt                                              26

<210> SEQ ID NO 140
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 140
acagcagtac aaatggcagt attcat                                              26

<210> SEQ ID NO 141
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 141
acagcagtac agatggcagt atacat                                              26

<210> SEQ ID NO 142
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 142
acagcagtac agatggcagt gttcat                                              26

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
attccctaca atccccaaag                                                     20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
attccctrca atcctcaaag                                                     20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
attccctaca atcctcaaag                                                     20

<210> SEQ ID NO 146
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
tacaatcccc aaagtcaagg agtagt                                          26

<210> SEQ ID NO 147
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
trcaatcctc aaagtcaagg agtagt                                          26

<210> SEQ ID NO 148
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
tacaatcccc aaagtcragg ggtagt                                          26

<210> SEQ ID NO 149
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
tacaatcctc aaagtcatgg agtagt                                          26

<210> SEQ ID NO 150
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
cacaatttta aaagaaaagg gg                                              22

<210> SEQ ID NO 151
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
casaattwta aaagaaaagg gg                                              22

```
<210> SEQ ID NO 152
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 152
acagmagtay aaatsrcagt aytyat                                              26
```